US009745614B2

(12) United States Patent
Schroeder

(10) Patent No.: US 9,745,614 B2
(45) Date of Patent: Aug. 29, 2017

(54) REDUCED REPRESENTATION BISULFITE SEQUENCING WITH DIVERSITY ADAPTORS

(71) Applicant: NuGEN Technologies, Inc., San Carlos, CA (US)

(72) Inventor: Benjamin G. Schroeder, San Mateo, CA (US)

(73) Assignee: NUGEN TECHNOLOGIES, INC., San Carlos, CA (US)

( * ) Notice: Subject to any disclaimer, the term of this patent is extended or adjusted under 35 U.S.C. 154(b) by 0 days.

(21) Appl. No.: 14/634,326

(22) Filed: Feb. 27, 2015

(65) Prior Publication Data

US 2015/0284769 A1 Oct. 8, 2015

Related U.S. Application Data

(60) Provisional application No. 61/946,617, filed on Feb. 28, 2014, provisional application No. 61/968,982, filed on Mar. 21, 2014.

(51) Int. Cl.
*C12Q 1/68* (2006.01)
*C12P 19/34* (2006.01)
*C07H 21/02* (2006.01)
*C07H 21/04* (2006.01)
*C40B 40/16* (2006.01)
*C40B 50/06* (2006.01)
*G01N 31/22* (2006.01)

(52) U.S. Cl.
CPC ......... *C12Q 1/6806* (2013.01); *C12Q 1/6827* (2013.01); *C12Q 1/6874* (2013.01)

(58) Field of Classification Search
CPC .......... C12Q 1/68; C07H 21/02; C40B 40/06; G01N 33/52
USPC ............ 435/6.1, 6.11, 91.2, 91.52; 536/23.1, 536/24.2; 422/430; 506/16, 26
See application file for complete search history.

(56) References Cited

U.S. PATENT DOCUMENTS

| | | |
|---|---|---|
| 4,362,867 A | 12/1982 | Paddock |
| 4,458,066 A | 7/1984 | Caruthers et al. |
| 4,469,863 A | 9/1984 | Ts'o et al. |
| 4,582,877 A | 4/1986 | Fairchok et al. |
| 4,876,187 A | 10/1989 | Duck et al. |
| 4,935,357 A | 6/1990 | Szybalski |
| 4,942,124 A | 7/1990 | Church |
| 4,988,617 A | 1/1991 | Landegren et al. |
| 4,996,143 A | 2/1991 | Heller et al. |
| 5,011,769 A | 4/1991 | Duck et al. |
| 5,034,506 A | 7/1991 | Summerton et al. |
| 5,035,996 A | 7/1991 | Hartley |
| 5,043,272 A | 8/1991 | Hartley |
| 5,082,830 A | 1/1992 | Brakel et al. |
| 5,090,591 A | 2/1992 | Long |
| 5,130,238 A | 7/1992 | Malek et al. |
| 5,169,766 A | 12/1992 | Schuster et al. |
| 5,171,534 A | 12/1992 | Smith et al. |
| 5,194,370 A | 3/1993 | Berninger et al. |
| 5,216,141 A | 6/1993 | Benner |
| 5,234,809 A | 8/1993 | Boom et al. |
| 5,235,033 A | 8/1993 | Summerton et al. |
| 5,242,794 A | 9/1993 | Whiteley et al. |
| 5,386,023 A | 1/1995 | Sanghvi et al. |
| 5,399,491 A | 3/1995 | Kacian et al. |
| 5,409,818 A | 4/1995 | Davey et al. |
| 5,418,149 A | 5/1995 | Gelfand et al. |
| 5,427,929 A | 6/1995 | Richards et al. |
| 5,480,784 A | 1/1996 | Kacian et al. |
| 5,494,810 A | 2/1996 | Barany et al. |
| 5,508,169 A | 4/1996 | Deugau et al. |
| 5,508,178 A | 4/1996 | Rose et al. |
| 5,510,270 A | 4/1996 | Fodor et al. |
| 5,525,471 A | 6/1996 | Zeng |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,565,340 A | 10/1996 | Chenchik et al. |
| 5,573,913 A | 11/1996 | Rosemeyer et al. |
| 5,578,832 A | 11/1996 | Trulson et al. |
| 5,589,339 A | 12/1996 | Hampson et al. |
| 5,602,240 A | 2/1997 | De Mesmaeker et al. |
| 5,637,684 A | 6/1997 | Cook et al. |

(Continued)

FOREIGN PATENT DOCUMENTS

CA 2444926 A1 11/2002
EP 0365627 B1 5/1990

(Continued)

OTHER PUBLICATIONS

Singapore exam report dated Apr. 7, 2015 for SG Application No. 11201404243W.
U.S. Appl. No. 13/980,987, filed Jul. 22, 2013, Kurn et al.
U.S. Appl. No. 14/390,012, filed Oct. 1, 2014, Armour et al.
AB Applied Biosystems. The solid 3 system enabling the next generation of science. Presentation. 2009.
Adamczyk, et al. Synthesis of a Chemiluminescent Acridinium Hydroxylamine (AHA) for the Direct Detection of Abasic Sites in DNA. Org. Lett. 1999; 1(5):779-781.

(Continued)

*Primary Examiner* — Narayan Bhat
(74) *Attorney, Agent, or Firm* — Wilson Sonsini Goodrich & Rosati

(57) ABSTRACT

Described herein are methods, compositions and kits for the generation of bisulfite-converted libraries useful for conducting reduced representation bisulfite sequencing (RRBS). The methods described herein can be employed to generate RRBS libraries in a manner that is easier and more cost-efficient than conventional RRBS methods, and can be efficiently sequenced with next generation sequencing (NGS) techniques without the need for genomic, higher diversity sequencing controls such as PhiX spike-ins.

21 Claims, 48 Drawing Sheets

(56) References Cited

U.S. PATENT DOCUMENTS

| | | |
|---|---|---|
| 5,641,658 A | 6/1997 | Adams et al. |
| 5,644,048 A | 7/1997 | Yau et al. |
| 5,665,549 A | 9/1997 | Pinkel et al. |
| 5,667,976 A | 9/1997 | Van Ness et al. |
| 5,667,979 A | 9/1997 | Berrens |
| 5,679,512 A | 10/1997 | Laney et al. |
| 5,681,726 A | 10/1997 | Huse et al. |
| 5,683,879 A | 11/1997 | Laney et al. |
| 5,688,648 A | 11/1997 | Mathies et al. |
| 5,705,628 A | 1/1998 | Hawkins |
| 5,708,154 A | 1/1998 | Smith et al. |
| 5,710,028 A | 1/1998 | Eyal et al. |
| 5,712,126 A | 1/1998 | Weissman et al. |
| 5,716,785 A | 2/1998 | Van Gelder et al. |
| 5,726,329 A | 3/1998 | Jones et al. |
| 5,750,341 A | 5/1998 | Macevicz |
| 5,759,822 A | 6/1998 | Chenchik et al. |
| 5,763,178 A | 6/1998 | Chirikjian et al. |
| 5,789,206 A | 8/1998 | Tavtigian et al. |
| 5,824,517 A | 10/1998 | Cleuziat et al. |
| 5,824,518 A | 10/1998 | Kacian et al. |
| 5,837,832 A | 11/1998 | Chee et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,945,313 A | 8/1999 | Hartley et al. |
| 5,952,176 A | 9/1999 | McCarthy et al. |
| 5,958,681 A | 9/1999 | Wetmur et al. |
| 5,965,409 A | 10/1999 | Pardee et al. |
| 5,969,119 A | 10/1999 | Macevicz |
| 5,972,618 A | 10/1999 | Bloch |
| 6,004,744 A | 12/1999 | Goelet et al. |
| 6,004,745 A | 12/1999 | Arnold, Jr. et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,056,661 A | 5/2000 | Schmidt |
| 6,077,674 A | 6/2000 | Schleifer et al. |
| 6,087,103 A | 7/2000 | Burmer |
| 6,090,553 A | 7/2000 | Matson |
| 6,090,591 A | 7/2000 | Burg et al. |
| 6,107,023 A | 8/2000 | Reyes et al. |
| 6,110,709 A | 8/2000 | Ausubel et al. |
| 6,150,112 A | 11/2000 | Weissman et al. |
| 6,159,685 A | 12/2000 | Pinkel et al. |
| 6,160,105 A | 12/2000 | Cunningham et al. |
| 6,169,194 B1 | 1/2001 | Thompson et al. |
| 6,172,208 B1 | 1/2001 | Cook |
| 6,174,680 B1 | 1/2001 | Makrigiorgos |
| 6,190,865 B1 | 2/2001 | Jendrisak et al. |
| 6,194,211 B1 | 2/2001 | Richards et al. |
| 6,197,501 B1 | 3/2001 | Cremer et al. |
| 6,197,557 B1 | 3/2001 | Makarov et al. |
| 6,210,891 B1 | 4/2001 | Nyren et al. |
| 6,225,109 B1 | 5/2001 | Juncosa et al. |
| 6,225,451 B1 | 5/2001 | Ballinger et al. |
| 6,232,104 B1 | 5/2001 | Lishanski et al. |
| 6,251,639 B1 | 6/2001 | Kurn |
| 6,262,490 B1 | 7/2001 | Hsu et al. |
| 6,270,961 B1 | 8/2001 | Drmanac |
| 6,280,935 B1 | 8/2001 | Macevicz |
| 6,287,766 B1 | 9/2001 | Nolan et al. |
| 6,287,825 B1 | 9/2001 | Weissman et al. |
| 6,291,170 B1 | 9/2001 | Van Gelder et al. |
| 6,306,365 B1 | 10/2001 | Ruoslahti et al. |
| 6,306,597 B1 | 10/2001 | Macevicz |
| 6,309,843 B1 | 10/2001 | Timms |
| 6,326,142 B1 | 12/2001 | Royer |
| 6,335,167 B1 | 1/2002 | Pinkel et al. |
| 6,339,147 B1 | 1/2002 | Lukhtanov et al. |
| 6,440,705 B1 | 8/2002 | Stanton, Jr. et al. |
| 6,449,562 B1 | 9/2002 | Chandler et al. |
| 6,582,938 B1 | 6/2003 | Su et al. |
| 6,670,461 B1 | 12/2003 | Wengel et al. |
| 6,686,156 B2 | 2/2004 | Kurn |
| 6,692,918 B2 | 2/2004 | Kurn |
| 6,770,748 B2 | 8/2004 | Imanishi et al. |
| 6,777,180 B1 | 8/2004 | Fisher et al. |
| 6,794,499 B2 | 9/2004 | Wengel et al. |
| 6,815,164 B2 | 11/2004 | Kurn |
| 6,815,167 B2 | 11/2004 | Crothers et al. |
| 6,825,011 B1 | 11/2004 | Romantchikov |
| 6,833,246 B2 | 12/2004 | Balasubramanian |
| 6,849,404 B2 | 2/2005 | Park et al. |
| 6,858,413 B2 | 2/2005 | Kurn |
| 6,913,884 B2 | 7/2005 | Stuelpnagel et al. |
| 6,917,726 B2 | 7/2005 | Levene et al. |
| 6,924,104 B2 | 8/2005 | Weissman et al. |
| 6,946,251 B2 | 9/2005 | Kurn |
| 7,001,724 B1 | 2/2006 | Greenfield |
| 7,033,764 B2 | 4/2006 | Korlach et al. |
| 7,048,481 B2 | 5/2006 | Sugata et al. |
| 7,052,847 B2 | 5/2006 | Korlach et al. |
| 7,056,676 B2 | 6/2006 | Korlach et al. |
| 7,056,716 B2 | 6/2006 | Potter et al. |
| 7,060,441 B2 | 6/2006 | Bourget et al. |
| 7,094,536 B2 | 8/2006 | Kurn |
| 7,115,400 B1 | 10/2006 | Adessi et al. |
| 7,170,050 B2 | 1/2007 | Turner |
| 7,175,982 B1 | 2/2007 | McCarthy et al. |
| 7,176,025 B2 | 2/2007 | Kurn et al. |
| 7,189,512 B2 | 3/2007 | Porat et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil |
| 7,276,720 B2 | 10/2007 | Ulmer |
| 7,294,461 B2 | 11/2007 | Kurn |
| 7,300,755 B1 | 11/2007 | Petersdorf et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,557 B2 | 4/2008 | Kurn |
| 7,354,717 B2 | 4/2008 | Kurn |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,741,463 B2 | 6/2010 | Gormley et al. |
| 7,771,934 B2 | 8/2010 | Kurn |
| 7,771,946 B2 | 8/2010 | Kurn |
| 7,803,550 B2 | 9/2010 | Makarov et al. |
| 7,846,666 B2 | 12/2010 | Kurn et al. |
| 7,846,733 B2 | 12/2010 | Kurn |
| 7,867,703 B2 | 1/2011 | Sampson et al. |
| 7,939,258 B2 | 5/2011 | Kurn et al. |
| 7,948,015 B2 | 5/2011 | Rothberg et al. |
| 7,985,565 B2 | 7/2011 | Mayer et al. |
| 8,017,335 B2 | 9/2011 | Smith |
| 8,034,568 B2 | 10/2011 | Kurn et al. |
| 8,053,192 B2 | 11/2011 | Bignell et al. |
| 8,071,311 B2 | 12/2011 | Kurn |
| 8,143,001 B2 | 3/2012 | Kurn et al. |
| 8,334,116 B2 | 12/2012 | Kurn |
| 8,465,950 B2 | 6/2013 | Kurn et al. |
| 8,492,095 B2 | 7/2013 | Kurn |
| 8,512,956 B2 | 8/2013 | Kurn et al. |
| 8,551,709 B2 | 10/2013 | Kurn et al. |
| 8,852,867 B2 | 10/2014 | Kurn et al. |

(56) References Cited

U.S. PATENT DOCUMENTS

| | | |
|---|---|---|
| 8,999,677 B1 | 4/2015 | Soldatov et al. |
| 9,175,325 B2 | 11/2015 | Kurn et al. |
| 9,175,336 B2 | 11/2015 | Soldatov et al. |
| 9,181,582 B2 | 11/2015 | Kurn |
| 9,206,418 B2 | 12/2015 | Armour |
| 2001/0000077 A1 | 3/2001 | Engelhardt et al. |
| 2001/0031739 A1 | 10/2001 | Dare |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0115088 A1 | 8/2002 | Kurn |
| 2002/0150919 A1 | 10/2002 | Weissmann et al. |
| 2002/0155451 A1 | 10/2002 | Makrigiorgos |
| 2002/0164628 A1 | 11/2002 | Kurn |
| 2002/0164634 A1 | 11/2002 | Patil et al. |
| 2002/0197639 A1 | 12/2002 | Shia et al. |
| 2003/0017591 A1 | 1/2003 | Kurn |
| 2003/0022207 A1 | 1/2003 | Balasubramanian et al. |
| 2003/0082543 A1 | 5/2003 | Su et al. |
| 2003/0087251 A1 | 5/2003 | Kurn |
| 2003/0119150 A1 | 6/2003 | Ankenbauer et al. |
| 2003/0143555 A1 | 7/2003 | Bourget et al. |
| 2003/0175780 A1 | 9/2003 | Jones |
| 2003/0180779 A1 | 9/2003 | Lofton-Day et al. |
| 2003/0186234 A1 | 10/2003 | Kurn |
| 2003/0207279 A1 | 11/2003 | Crothers et al. |
| 2003/0215926 A1 | 11/2003 | Kurn et al. |
| 2003/0224439 A1 | 12/2003 | Lafferty et al. |
| 2003/0232348 A1 | 12/2003 | Jones et al. |
| 2004/0002371 A1 | 1/2004 | Paquine et al. |
| 2004/0005614 A1 | 1/2004 | Kurn et al. |
| 2004/0023271 A1 | 2/2004 | Kurn et al. |
| 2004/0115815 A1 | 6/2004 | Li et al. |
| 2004/0137456 A1 | 7/2004 | Yokota et al. |
| 2004/0161742 A1 | 8/2004 | Dean et al. |
| 2004/0203019 A1 | 10/2004 | Kurn |
| 2004/0203025 A1 | 10/2004 | Kurn |
| 2004/0248153 A1 | 12/2004 | Dear et al. |
| 2005/0003441 A1 | 1/2005 | Kurn |
| 2005/0014192 A1 | 1/2005 | Kurn |
| 2005/0019793 A1 | 1/2005 | Kurn et al. |
| 2005/0059048 A1 | 3/2005 | Gunderson et al. |
| 2005/0064456 A1 | 3/2005 | Kurn |
| 2005/0123956 A1 | 6/2005 | Blume et al. |
| 2005/0136417 A1 | 6/2005 | Cole et al. |
| 2005/0142577 A1 | 6/2005 | Jones et al. |
| 2005/0191656 A1 | 9/2005 | Drmanac et al. |
| 2005/0191682 A1 | 9/2005 | Barone et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0024678 A1 | 2/2006 | Buzby |
| 2006/0024711 A1 | 2/2006 | Lapidus et al. |
| 2006/0035274 A1 | 2/2006 | Dong |
| 2006/0046251 A1 | 3/2006 | Sampson et al. |
| 2006/0051789 A1 | 3/2006 | Kazakov et al. |
| 2006/0068415 A1 | 3/2006 | Jones et al. |
| 2006/0216724 A1 | 9/2006 | Christians et al. |
| 2006/0263789 A1 | 11/2006 | Kincaid |
| 2006/0281082 A1 | 12/2006 | Zhu |
| 2006/0286566 A1 | 12/2006 | Lapidus et al. |
| 2006/0292597 A1 | 12/2006 | Shapero et al. |
| 2007/0031857 A1 | 2/2007 | Makarov et al. |
| 2007/0134128 A1 | 6/2007 | Korlach |
| 2007/0141604 A1 | 6/2007 | Gormley et al. |
| 2007/0224613 A1 | 9/2007 | Strathmann |
| 2007/0231823 A1 | 10/2007 | McKernan et al. |
| 2007/0238122 A1 | 10/2007 | Allbritton et al. |
| 2008/0038727 A1 | 2/2008 | Spier |
| 2008/0087826 A1 | 4/2008 | Harris et al. |
| 2008/0103058 A1 | 5/2008 | Siddiqi |
| 2008/0160580 A1 | 7/2008 | Adessi et al. |
| 2008/0176311 A1 | 7/2008 | Kurn |
| 2008/0182300 A1 | 7/2008 | Kurn |
| 2008/0194413 A1 | 8/2008 | Albert |
| 2008/0194416 A1 | 8/2008 | Chen |
| 2008/0206764 A1 | 8/2008 | Williams et al. |
| 2008/0213770 A1 | 9/2008 | Williams et al. |
| 2008/0241831 A1 | 10/2008 | Fan et al. |
| 2008/0242560 A1 | 10/2008 | Gunderson et al. |
| 2008/0286795 A1 | 11/2008 | Kawashima et al. |
| 2009/0011959 A1 | 1/2009 | Costa et al. |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0036663 A1 | 2/2009 | Kurn |
| 2009/0061425 A1 | 3/2009 | Lo et al. |
| 2009/0061439 A1 | 3/2009 | Buzby |
| 2009/0068645 A1 | 3/2009 | Sibson |
| 2009/0068655 A1 | 3/2009 | Williams |
| 2009/0068709 A1 | 3/2009 | Kurn et al. |
| 2009/0105081 A1 | 4/2009 | Rodesch et al. |
| 2009/0117573 A1 | 5/2009 | Fu et al. |
| 2009/0117621 A1 | 5/2009 | Boutell et al. |
| 2009/0124514 A1 | 5/2009 | Fu et al. |
| 2009/0127589 A1 | 5/2009 | Rothberg et al. |
| 2009/0130721 A1 | 5/2009 | Kurn et al. |
| 2009/0203085 A1 | 8/2009 | Kurn et al. |
| 2009/0203531 A1 | 8/2009 | Kurn et al. |
| 2009/0233804 A1 | 9/2009 | Kurn et al. |
| 2009/0239232 A1 | 9/2009 | Kurn et al. |
| 2009/0275486 A1 | 11/2009 | Kurn et al. |
| 2009/0280538 A1 | 11/2009 | Patel et al. |
| 2009/0298075 A1 | 12/2009 | Travers et al. |
| 2010/0015666 A1 | 1/2010 | Brenner et al. |
| 2010/0021973 A1 | 1/2010 | Makarov et al. |
| 2010/0022403 A1 | 1/2010 | Kurn et al. |
| 2010/0029511 A1 | 2/2010 | Raymond et al. |
| 2010/0105052 A1 | 4/2010 | Drmanac et al. |
| 2010/0113296 A1 | 5/2010 | Myerson |
| 2010/0129879 A1 | 5/2010 | Ach et al. |
| 2010/0137143 A1 | 6/2010 | Rothberg et al. |
| 2010/0159559 A1 | 6/2010 | Kurn et al. |
| 2010/0167954 A1 | 7/2010 | Earnshaw et al. |
| 2010/0173394 A1 | 7/2010 | Colston, Jr. et al. |
| 2010/0203597 A1 | 8/2010 | Chen et al. |
| 2010/0273219 A1 | 10/2010 | May et al. |
| 2010/0311066 A1 | 12/2010 | Kurn |
| 2010/0323348 A1 | 12/2010 | Hamady et al. |
| 2011/0015096 A1 | 1/2011 | Chiu |
| 2011/0039732 A1 | 2/2011 | Raymond et al. |
| 2011/0104785 A1 | 5/2011 | Vaidyanathan et al. |
| 2011/0105364 A1 | 5/2011 | Kurn |
| 2011/0129827 A1 | 6/2011 | Causey et al. |
| 2011/0189679 A1 | 8/2011 | Kurn et al. |
| 2011/0224105 A1 | 9/2011 | Kurn et al. |
| 2011/0288780 A1 | 11/2011 | Rabinowitz et al. |
| 2011/0294132 A1 | 12/2011 | Kurn et al. |
| 2011/0319290 A1 | 12/2011 | Raymond et al. |
| 2012/0003657 A1 | 1/2012 | Myllykangas et al. |
| 2012/0028310 A1 | 2/2012 | Kurn et al. |
| 2012/0045797 A1 | 2/2012 | Kurn et al. |
| 2012/0071331 A1 | 3/2012 | Casbon et al. |
| 2012/0074925 A1 | 3/2012 | Oliver |
| 2012/0102054 A1 | 4/2012 | Popescu et al. |
| 2012/0122701 A1 | 5/2012 | Ryan et al. |
| 2012/0149068 A1 | 6/2012 | Kurn et al. |
| 2012/0156728 A1 | 6/2012 | Li et al. |
| 2012/0157322 A1 | 6/2012 | Myllykangas et al. |
| 2012/0190587 A1 | 7/2012 | Kurn et al. |
| 2012/0220483 A1 | 8/2012 | Kurn et al. |
| 2012/0237943 A1 | 9/2012 | Soldatov et al. |
| 2012/0238738 A1 | 9/2012 | Hendrickson |
| 2012/0245041 A1 | 9/2012 | Brenner et al. |
| 2012/0270212 A1 | 10/2012 | Rabinowitz et al. |
| 2012/0283145 A1 | 11/2012 | Wang |
| 2012/0289426 A1 | 11/2012 | Roos et al. |
| 2012/0309002 A1 | 12/2012 | Link |
| 2013/0059738 A1 | 3/2013 | Leamon et al. |
| 2013/0065768 A1 | 3/2013 | Zheng et al. |
| 2013/0231253 A1 | 9/2013 | Amorese et al. |
| 2014/0038236 A1 | 2/2014 | Kurn et al. |
| 2014/0065692 A1 | 3/2014 | Kurn et al. |

(56) References Cited

U.S. PATENT DOCUMENTS

| | | |
|---|---|---|
| 2014/0038188 A1 | 6/2014 | Kurn |
| 2014/0274729 A1 | 9/2014 | Kurn et al. |
| 2014/0274731 A1 | 9/2014 | Raymond et al. |
| 2014/0274738 A1 | 9/2014 | Amorese et al. |
| 2014/0378345 A1 | 12/2014 | Hindson et al. |
| 2015/0011396 A1 | 1/2015 | Schroeder et al. |
| 2015/0017635 A1 | 1/2015 | Myllykangas et al. |
| 2015/0299767 A1 | 10/2015 | Armour et al. |
| 2016/0122756 A1 | 5/2016 | Armour |
| 2016/0130576 A1 | 5/2016 | Armour |
| 2016/0153039 A1 | 6/2016 | Amorese et al. |
| 2016/0251711 A1 | 9/2016 | Amorese et al. |
| 2016/0251712 A1 | 9/2016 | Amorese et al. |
| 2016/0265042 A1 | 9/2016 | Schroeder et al. |
| 2016/0275240 A1 | 9/2016 | Huelga et al. |

FOREIGN PATENT DOCUMENTS

| | | |
|---|---|---|
| EP | 0329822 B1 | 6/1994 |
| EP | 0667393 A2 | 8/1995 |
| EP | 0667393 A3 | 11/1995 |
| EP | 1071811 B1 | 3/2002 |
| EP | 0843735 B1 | 7/2002 |
| EP | 2272976 A1 | 1/2011 |
| EP | 2322612 A1 | 5/2011 |
| EP | 2451973 A1 | 5/2012 |
| WO | WO 92/07951 A1 | 5/1992 |
| WO | WO 93/18052 A1 | 9/1993 |
| WO | WO 94/16090 A1 | 7/1994 |
| WO | WO 96/40998 A1 | 12/1996 |
| WO | WO 97/12061 A1 | 4/1997 |
| WO | WO 97/25416 A2 | 7/1997 |
| WO | WO 97/25416 A3 | 10/1997 |
| WO | WO 98/06736 A1 | 2/1998 |
| WO | WO 98/38296 A1 | 9/1998 |
| WO | WO 98/44151 A1 | 10/1998 |
| WO | WO 99/10540 A1 | 3/1999 |
| WO | WO 99/11819 A1 | 3/1999 |
| WO | WO 99/42618 A1 | 8/1999 |
| WO | WO 00/08208 A2 | 2/2000 |
| WO | WO 00/09756 A1 | 2/2000 |
| WO | WO 00/08208 A3 | 5/2000 |
| WO | WO 00/18957 A1 | 6/2000 |
| WO | WO 00/39345 A1 | 7/2000 |
| WO | WO 00/52191 A1 | 9/2000 |
| WO | WO 00/55364 A2 | 9/2000 |
| WO | WO 00/70039 A1 | 11/2000 |
| WO | WO 01/20035 A2 | 3/2001 |
| WO | WO 01/23613 A1 | 4/2001 |
| WO | WO 01/46464 A1 | 6/2001 |
| WO | WO 01/57248 A2 | 8/2001 |
| WO | WO 01/64952 A2 | 9/2001 |
| WO | WO 00/55364 A3 | 10/2001 |
| WO | WO 01/20035 A3 | 12/2001 |
| WO | WO 02/00938 A2 | 1/2002 |
| WO | WO 01/57248 A3 | 2/2002 |
| WO | WO 02/28876 A2 | 4/2002 |
| WO | WO 02/29117 A2 | 4/2002 |
| WO | WO 02/36821 A2 | 5/2002 |
| WO | WO 02/48402 A2 | 6/2002 |
| WO | WO 02/028876 A3 | 8/2002 |
| WO | WO 02/060318 A2 | 8/2002 |
| WO | WO 02/072772 A2 | 9/2002 |
| WO | WO 02/072773 A2 | 9/2002 |
| WO | WO 02/072773 A3 | 9/2002 |
| WO | WO 02/081753 A1 | 10/2002 |
| WO | WO 02/090584 A2 | 11/2002 |
| WO | WO 01/64952 A3 | 12/2002 |
| WO | WO 03/002736 A2 | 1/2003 |
| WO | WO 03/012118 A1 | 2/2003 |
| WO | WO 02/36821 A3 | 3/2003 |
| WO | WO 03/027259 A2 | 4/2003 |
| WO | WO 02/00938 A3 | 8/2003 |
| WO | WO 02/29117 A3 | 8/2003 |
| WO | WO 02/072772 A3 | 9/2003 |
| WO | WO 02/090584 A3 | 9/2003 |
| WO | WO 03/078645 A2 | 9/2003 |
| WO | WO 02/060318 A3 | 10/2003 |
| WO | WO 03/083435 A2 | 10/2003 |
| WO | WO 03/027259 A3 | 12/2003 |
| WO | WO 03/106642 A2 | 12/2003 |
| WO | WO 03/083435 A3 | 2/2004 |
| WO | WO 03/078645 A3 | 3/2004 |
| WO | WO 02/48402 A3 | 4/2004 |
| WO | WO 2004/011665 A2 | 9/2004 |
| WO | WO 2004/092418 A2 | 10/2004 |
| WO | WO 03/106642 A3 | 11/2004 |
| WO | WO 2004/011665 A3 | 7/2005 |
| WO | WO 2005/065321 A2 | 7/2005 |
| WO | WO 2006/081222 A2 | 8/2006 |
| WO | WO 2006/086668 A2 | 8/2006 |
| WO | WO 2006/081222 A3 | 2/2007 |
| WO | WO 2007/018601 A1 | 2/2007 |
| WO | WO 2007/019444 A2 | 2/2007 |
| WO | WO 2007/030759 A2 | 3/2007 |
| WO | WO 2007/052006 A1 | 5/2007 |
| WO | WO 2007/057652 A1 | 5/2007 |
| WO | WO 2007/030759 A3 | 6/2007 |
| WO | WO 2007/136717 A1 | 11/2007 |
| WO | WO 2008/005459 A2 | 1/2008 |
| WO | WO 2008/005459 A3 | 2/2008 |
| WO | WO 2008/015396 A2 | 2/2008 |
| WO | WO 2008/033442 A2 | 3/2008 |
| WO | WO 2008/115185 A2 | 9/2008 |
| WO | WO 2008/033442 A3 | 10/2008 |
| WO | WO 2008/115185 A3 | 12/2008 |
| WO | WO 2009/053039 A1 | 4/2009 |
| WO | WO 2005/065321 A3 | 5/2009 |
| WO | WO 2009/102878 A2 | 8/2009 |
| WO | WO 2009/102896 A2 | 8/2009 |
| WO | WO 2009/112844 A1 | 9/2009 |
| WO | WO 2009/117698 A2 | 9/2009 |
| WO | WO 2009/120372 A2 | 10/2009 |
| WO | WO 2009/120374 A2 | 10/2009 |
| WO | WO 2009/120374 A3 | 12/2009 |
| WO | WO 2009/120372 A3 | 1/2010 |
| WO | WO 2010/003153 A2 | 1/2010 |
| WO | WO 2010/030683 A1 | 3/2010 |
| WO | WO 2010/039991 A2 | 4/2010 |
| WO | WO 2010/063711 A1 | 6/2010 |
| WO | WO 2010/064893 A1 | 6/2010 |
| WO | WO 2010/085715 A1 | 7/2010 |
| WO | WO 2010/115154 A1 | 10/2010 |
| WO | WO 2010/129937 A2 | 11/2010 |
| WO | WO 2011/003630 A1 | 1/2011 |
| WO | WO 2011/009941 A1 | 1/2011 |
| WO | WO 2011/019964 A1 | 2/2011 |
| WO | WO 2011/032053 A1 | 3/2011 |
| WO | WO 2011/053987 A1 | 5/2011 |
| WO | WO 2011/151777 A1 | 12/2011 |
| WO | WO 2011/156529 A2 | 12/2011 |
| WO | WO 2012/013932 A1 | 2/2012 |
| WO | WO 2012/103154 A1 | 8/2012 |
| WO | WO 2013/059740 A1 | 4/2013 |
| WO | WO 2013/059746 A1 | 4/2013 |
| WO | WO 2013/112923 A1 | 8/2013 |
| WO | WO 2013/177220 A1 | 11/2013 |
| WO | WO 2013/191775 A2 | 12/2013 |
| WO | WO 2014/144092 A1 | 9/2014 |
| WO | WO 2014/150931 A1 | 9/2014 |
| WO | WO 2015/131107 A1 | 9/2015 |

OTHER PUBLICATIONS

Adamczyk, et al. O-(Fluoresceinylmethyl) hydroxylamine (OFMHA): A Fluorescent Regent for Detection of Damaged Nucleic Acids. Bioorg. & Med. Chem. Lett. 1998; 8:3599-3602.

Adessi, et al., Solid phase DNA amplification: characterisation of primer attachment and ampflication mechanisms. Nucleic Acids Research. Oct. 15, 2000. 28:(20): e87.

(56) References Cited

OTHER PUBLICATIONS

Agilent Technologies. Agilent Technologies adds human exon kit to next-generation-sequencing target enrichment portfolio. GenomicsNews.com. Posted 2009 Sep. 23, 2009. Avaialble at http://www.genomicsnews.com/index.aspx?ID=103607&sm=Agilent%20technologies%20adds%20human%20exo. Accessed Oct. 6, 2009.

Ahmed. Sequencing of Low-Diversity Libraries. Feb. 28, 2012. http://cofactorgenomics.com/sequencing-low-diversity-libraries/.

Albert, et al. Direct selection of human genomic loci by microarray hybridization. Nat Methods. Nov. 2007;4(11):903-5. Epub Oct. 14, 2007.

Alvarado, et al. Multiplexed direct genomic selection (MDiGS): a pooled BAC capture approach for highly accurate CNV and SNP/INDEL detection. Nucleic Acids Res. Jun. 2014;42(10):e82. doi: 10.1093/nar/gku218. Epub Mar. 20, 2014.

Anisimova, et al. Isolation, characterization and molecular cloning of duplex-specific nuclease from the hepatopancreas of the kamchatka crab. *BMC Biochemistry*. May 21, 2008. 9:14 doi10.1186/1471-2091-9-14.

Antson, et al. PCR-generated padlock probes detect single nucleotide variation in genomic DNA. Nucleic Acids Res. Jun. 15, 2000;28(12):E58.

Anwar, et al. A stem-loop-mediated reverse transcription real-time PCR for the selective detection and quantification of the replicative strand of an RNA virus. Anal Biochem. May 1, 2006;352(1):120-8. Epub Feb. 17, 2006.

Archer, et al. Selective and flexible depletion of problematic sequences from RNA-seq libraries at the cDNA stage. BMC Genomics. May 26, 2014;15:401. doi: 10.1186/1471-2164-15-401.

Arraystar, Inc. Arraystar Directional RNA-seq Prep Kit (dUTP Based). Cat#: A1208. Apr. 8, 2013.

Ausubel, et al., Eds. Current Protocols in Molecular Biology. John Wiley & Sons, Inc. 1987 and updates.

Baird, et al. Rapid SNP discovery and genetic mapping using sequenced RAD markers. PLoS One. 2008;3(10):e3376.

Ballestar, et al. Methyl-CpG-binding proteins. Targeting specific gene repression. Eur J Biochem 2001; 268:1-6.

Bangs Laboratories, Inc. TechNote 205 retreived at: http:www.bangslab.com/technotes/205.pdf . Visited on Jul. 16, 2003. (8 pages).

Bashiardes, et al. Direct genomic selection. Nat Methods. Jan. 2005;2(1):63-9.

Beaucage, et al. The functionalization of oligonucleotides via phosphoramidite derivative. Tetrahedron. 1993;49(10):1925-63.

Beier, et al. HT sequencing in biomedicine—new approaches in preparing samples. *Laborwelt*. Jan. 9, 2008.

Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.

Bentley, D. R. Whole-genome re-sequencing. Curr Opin Genet Dev. Dec. 2006;16(6):545-52. Epub Oct. 18, 2006.

Bhattacharjee, et al. Complementing next generation sequencing technologies with Agilent's SureSelect DNA capture array. Agilent. Jul. 13, 2009.

Bibikova, et al. Targeted chromosomal cleavage and mutagenesis in drophila using zinc-finger nucleases genetics. *Genetics*. Jul. 2002. 161: 1169-1175.

Bioo Scientific. Illumina RNA-Seq Library Prep. Available at http://www.biooscientific.com/ProductsServices/NextGenSequencing/Illumina-Compatible/RNA-Seq.aspx. Accessed Jun. 16, 2014.

Bioo Scientific. NEXTflex RNA-Seq Kit. Available at http://www.biooscientific.com/ProductsServices/NextGenSequencing/Illumina-Compatible/RNA-Seq/NEXTflex%E2%84%A2RNA-SeqKit.aspx. Accessed Jun. 16, 2014.

Blow, N. Genomics: catch me if you can. *Nature Methods*.Jul. 2009. 6:7.539-544.

Bormann, et al. Whole methylome analysis by ultra-deep sequencing using two-base encoding. PLoS One. Feb. 22, 2010;5(2):e9320.

Borodina, et al. A strand-specific library preparation protocol for RNA sequencing. Methods Enzymol. 2011;500:79-98. doi: 10.1016/B978-0-12-385118-5.00005-0.

Boturyn, et al. A simple and Sensitive Method for in Vitro Quantitation of Abasic Sites in DNA. Chem. Res. Toxicol. 1999; 12:476-482.

Boturyn, et al. Synthesis of Fluorescent Probes for the Detection of Abasic Sites in DNA. Tetrahedron. 1997; 53(15):5485-5492.

Briggs, et al. Targeted retrieval and analysis of five Neandertal mtDNA genomes. Science. Jul. 17, 2009;325(5938):318-21. doi: 10.1126/science.1174462.

Brill, et al. Synthesis of oligodeoxynucleoside phosphorodithioates via thioamidites. J. Am. Chem. Soc. 1989;111:2321-2322.

Broude. Stem-loop oligonucleotides: a robust tool for molecular biology and biotechnology. Trends Biotechnol. Jun. 2002;20(6):249-56.

Brown, T.A. Ed. Molecular Biology, LabFax. Bios Scientific Publishers. Academic Press. 1991; pp. 147-148.

Buchman, et al. Selective RNA amplification: a novel method using dUMP-containing primers and uracil DNA glycosylase. PCR Methods Appl. Aug. 1993;3(1):28-31.

Burrows, et al. Oxidative Nucleobase Modifications Leading to Strand Scission. Chem Rev. May 7, 1998;98(3):1109-1151.

Carey, et al. Human Apurinic/Apyrimidinic Endonuclease in Processive. Biochem. 1999; 38:16553-16560.

Carlsson, et al. Screening for genetic mutations. Nature. 1996;380(6571):207.

Chan, et al. The biophysics of DNA hybridization with immobilized oligonucleotide probes. Biophys J. Dec. 1995;69(6):2243-55.

Chen, et al. Real-time quantification of microRNAs by stem-loop RT-PCR. Nucleic Acids Res. Nov. 27, 2005;33(20):e179.

Clontech Laboratories, Inc. In-Fusion SMARTer Directional cDNA Library Construction Kit User Manual. Cat. No. 634933. Copyright 2013.

CNV detection by ion semiconductor sequencing. Life Technologies. 2014.

COFACTOR genomics. Directional RNA Sequencing. Abailable at http://cofactorgenomics.com/directional-rna-sequencing. Accessed Jun. 4, 2014.

Combined search and examination report dated Apr. 24, 2013 for GB1305340.

Craig, et al. Identification of genetic variants using bar-coded multiplexed sequencing. Nat Methods. Oct. 2008;5(10):887-93.

Croucher, et al. A simple method for directional transcriptome sequencing using Illumina technology. Nucleic Acids Res. Dec. 2009;37(22):e148.

Dahl, et al. Multigene amplification and massively parallel sequencing for cancer mutation discovery. Proc Natl Acad Sci U S A. May 29, 2007;104(22):9387-92. Epub May 17, 2007.

Dahl, et al. Multiplex amplification enabled by selective circularization of large sets of genomic DNA fragments. Nucleic Acids Res. Apr. 28, 2005;33(8):e71.

Dempcy, et al. Synthesis of a thymidyl pentamer of deoxyribonucleic guanidine and binding studies with DNA homopolynucleotides. Proc Natl Acad Sci USA. 1995;92(13):6097-101.

Derisi, et al. Use of cDNA microarray to analyse gene expression patterns in human cancer. Nature Genetics. 1996; 14:457-460.

Diagnosing problems with phasing and pre-phasing on Illumina platforms. Loman Labs. Nov. 21, 2013. http://nickloman.github.io/high-throughput%20sequencing/2013/11/21/diagnosing-problems-with-phasing-and-pre-phasing-on-illumina-platforms/.

Dressman, et al., Transforming single DNA molecules into fluorescent magnetic particles for detection and enumeration of genetic variations. Proc Natl Sci USA. Jul. 22, 2003. 100(15): 8817-8822.

Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.

Egholm, et al. Peptide nucleic acids (PNA) oligonucleotide analogues with an achiral peptide backbone. J. Am. Chem. Soc. 1992;114:1895-1897.

Egholm, et al. PNA hybridizes to complementary oligonucleotides obeying the Watson-Crick hydrogen-bonding rules. Nature. 1993;365(6446):566-8.

(56) References Cited

OTHER PUBLICATIONS

Erlanger, et al. Antibodies Specific for Ribonucleosides and Ribonucleotides and Their Reaction With DNA. Proc Natl Acad Sci USA. 1964; 52:68-74.

Esteller. Cancer epigenomics: DNA methylomes and histone-modification maps. Nat Rev Genet. Apr. 2007;8(4):286-98. Epub Mar. 6, 2007.

European office action dated Apr. 1, 2011 for Application No. 03771533.1.

European search report and opinion dated Nov. 28, 2013 for EP Application No. 11793123.8.

European search report and search opinion dated Apr. 3, 2013 for Application No. 10808789.1.

European search report dated Oct. 18, 2007 for Application No. 3771533.1.

European search report dated Feb. 12, 2010 for Application No. 7810169.8.

European search report dated Mar. 29, 2010 for Application No. 4815722.6.

Fadrosh, et al. An improved dual-indexing approach for multiplexed 16S rRNA gene sequencing on the Illumina MiSeq platform. Microbiome. Feb. 24, 2014;2(1):6. doi: 10.1186/2049-2618-2-6.

Fahy, et al., Self-sustained sequence replication (3 SR): an isothermal transcription-based amplication system alternative to PCR. Genome Res. 1991. 1:25-33.

Faircloth, et al. Not all sequence tags are created equal: designing and validating sequence identification tags robust to indels. PLoS One. 2012;7(8):e42543. doi: 10.1371/journal.pone.0042543. Epub Aug. 10, 2012.

Feinberg, et al. Hypomethylation distinguishes genes of some human cancers from their normal counterparts. Nature. Jan. 6, 1983;301(5895):89-92.

Fodor, et al. Light-Directed, spatially addressable parallel chemical synthesis. 1991; 251: 767-773.

Franca, et al. Optimizing a qPCR gene expression quantification assay for S. epidermidis biofilms: a comparison between commercial kits and a customized protocol. PLoS One. 2012;7(5):e37480. doi: 10.1371/journal.pone.0037480. Epub May 21, 2012.

Frank. Barcrawl and Bartab: software tools for the design and implementation of barcoded primers for highly multiplexed DNA sequencing. BMC Bioinformatics. Oct. 29, 2009;10:362.

Fredriksson, et al. Multiplex amplification of all coding sequences within 10 cancer genes by Gene-Collector. Nucleic Acids Res. 2007;35(7):e47. Epub Feb. 22, 2007.

Freeman, et al. Fundamentals of DNA Hybridization Arrays for Gene Expression Analysis. BioTechniques. Nov. 2000; 29:1042-1044, 1046, 1048-1055.

Freshney, R.I. ed. (1987). *Animal Cell Culture*. IRL Press: Oxford, pp. vii-xii (Table of Contents Only.).

Fujiwara, et al. Direct probing: covalent attachment of probe DNA to double-stranded target DNA. Nucleic Acids Res. Dec. 15, 1998;26(24):5728-33.

Fullwood, et al. Next-generation DNA sequencing of paired-end tags (PET) for transcriptome and genome analyses. *Genome Research Open Access*. 2009. Available at http://genome.cshlp.org/content/19/4/521.long. Accessed Oct. 6, 2009.

Gait, M.J., Ed. 1984 . Oligonucleotide Synthesis: A Practical Approach. IRL Press: Oxford, pp. vii-xii (Table of Contents).

Gertz, et al. Transposase mediated construction of RNA-seq libraries. Genome Res. Jan. 2012;22(1):134-41. doi: 10.1101/gr.127373.111. Epub Nov. 29, 2011.

Ghosh, S.S. Synthesis of 5'-Oligonucleotide Hydrazide Derivatives and Their Use in Preparation of Enzyme-Nucleic Acid Hybridization Probes. Anal. Biochem. 1989; 178:43-51.

Gnirke, et al. Solution hybrid selection with ultra-long oligonucleotides for massively parallel targeted sequencing. Nature Biotechnology. Feb. 2009; 27(2):182-9.

Gu, et al. Partitioning the c. elegans genome by nucleosome modification, occupancy, and position. Online Aug. 25, 2009. http://www.springerlink.com/content/r0gw044155823242/fulltext.pdf. Accessed Oct. 6, 2009.

Gu, et al. Preparation of reduced representation bisulfate sequencing libraries for genome-scale DNA methylation profiling. Nat Protoc. Apr. 2011;6(4):468-81. doi: 10.1038/nprot.2010.190. Epub Mar. 18, 2011.

Haraguchi, et al. Synthesis and characterization of oligodeoxynucleotides containing formamidopyrimidine lesions and nonhydrolyzable analogues. J Am Chem Soc. Apr. 3, 2002;124(13):3263-9.

Heimgartner, et al.Polyacrylic Polyhydrazides as Reagents for Detection of Glycoproteins. Anal. Biochem. 1989; 181:182-189.

Hodges, et al. Genome-wide in situ exon capture for selective resequencing. Nat Genet. Dec. 2007;39(12):1522-7. Epub Nov. 4, 2007.

Hodges, et al. Hybrid selection of discrete genomic intervals on custom-designed microarrays for massively parallel sequencing. *Nat. Protoc*. 2009; 4(6): 960-974.

Hollis, et al. Structural studies of human alkyladenine glycosylase and *E. coli* 3- methyladenine glycosylase.Mutat Res. 2000; 460(3-4):201-10.

Horn, et al. Solid supported hydrolysis of apurinic sites in synthetic oligonucleotides for rapid and efficient purification on reverse-phase cartridges. Nucl. Acids Res. 1988; 16:11559-11571.

Hottiger, et al. Strand displacement activity of the human immunodeficiency virus type 1 reverse transcriptase heterodimer and its individual subunits. J Biol Chem. Jan. 14, 1994;269(2):986-91.

Huber, et al. Processing of the primer for plus strand DNA synthesis by human immunodeficiency virus 1 reverse transcriptase. J Biol Chem. Jun. 25, 1990;265(18):10565-73.

Ide, et al. Synthesis and Damage Specificity of a Novel Probe for the Detection of Abasic Sites in DNA. Biochem. 1993; 32:8276-8283.

illumina Inc. Directional mRNA-Seq Sample Preparation—Application to prepare directional (strand specific) sample from mRNA. Oct. 2010.

International Preliminary Examination Report mailed on Mar. 22, 2006 for PCT Patent Application No. PCT/US03/15825 filed May 19, 2003, 9pages.

International search report and written opinion dated Jan. 27, 2012 for PCT Application No. US2011/039683.

International search report and written opinion dated Feb. 12, 2013 for PCT/US2012/061218.

International search report and written opinion dated Feb. 24, 2011 for PCT Application No. US10/55137.

International search report and written opinion dated Apr. 16, 2013 for PCT Application No. US2013/023278.

International search report and written opinion dated May 10, 2012 for PCT Application No. US2012/22448.

International search report and written opinion dated Jul. 15, 2014 for PCT Application No. US2014/028356.

International search report and written opinion dated Jul. 29, 2014 for PCT Application No. US2014/24581.

International search report and written opinion dated Oct. 18, 2013 for PCT Application No. US2013/032606.

International search report and written opinion dated Dec. 3, 2010 for PCT Application No. US10-45384.

International search report dated Jan. 2, 2008 for PCT Application No. US2007/15409.

International search report dated Jun. 14, 2005 for PCT Application No. US 2003/015825.

International search report dated Jul. 9, 2008 for PCT Application No. US2004/043710.

Jenkins, et al. The biosynthesis of carbocyclic nucleosides. Chem. Soc. Rev. 1995;169-176.

Jones, et al. The epigenomics of cancer. Cell. Feb. 23, 2007;128(4):683-92.

Kaboev, et al. PCR hot start using primers with the structure of molecular beacons (hairpin-like structure). Nucleic Acids Res. Nov. 1, 2000;28(21):E94.

(56) References Cited

OTHER PUBLICATIONS

Karata, et al. Construction of a circular single-stranded DNA template containing a defined lesion. DNA Repair (Amst). Jul. 4, 2009;8(7):852-6.
Karow. New Capture Method Enables MPI Team to Sequence Five Neandertal Mitochondrial Genomes. GenomeWeb. Jul. 21, 2009. https://www.genomeweb.com/sequencing/new-capture-method-enables-mpi-team-sequence-five-neandertal-mitochondrial-genom.
Kawarada, et al. Antibodies Specific for Methylated DNA Elicited in Rabbits Recognize only a Single Strand Region of DNA Containing 7-Methylguanine Tohuku. J Exp Med. 1986; 149:151-161.
Khrapko, et al. A method for DNA sequencing by hybridization with oligonucleotide matrix. DNA Sequence- J. DNA Sequencing and Mapping. 1991; 1:375-388.
Kiedrowski, et al. Parabolic growth of a self-replicating hexadeoxynucleotide bearing a 3'-5'-phosphoamidate linkage. Angew. Chem. Intl. Ed. English 1991;30:423-426.
Kim, et al. Evidence for thiol-dependent production of oxygen radicals by 4-methyl-5-pyrazinyl-3H-1,2-dithiole-3-thione (oltipraz) and 3H-1,2-dithiole-3-thione: possible relevance to the anticarcinogenic properties of 1,2-dithiole-3-thiones. Chem Res Toxicol. Mar. 1997;10(3):296-301.
Koshkin, et al. LNA (Locked Nucleic Acid): An RNA mimic forming exceedingly stable LNA:LNA duplexes. J. Am. Chem. Soc. 1998; 120:13252-3.
Kow, et al. Detection of Abasic Sites and Oxidative DNA Base Damage Using an ELISA-like Assay. Methods. 2000; 22:164-169.
Kozich, et al. Development of a dual-index sequencing strategy and curation pipeline for analyzing amplicon sequence data on the MiSeq Illumina sequencing platform. Appl Environ Microbiol. Sep. 2013;79(17):5112-20. doi: 10.1128/AEM.01043-13. Epub Jun. 21, 2013.
Krishnakumar, et al. A comprehensive assay for targeted multiplex amplification of human DNA sequences. Proc Natl Acad Sci U S A. Jul. 8, 2008;105(27):9296-301. doi: 10.1073/pnas.0803240105. Epub Jul. 2, 2008.
Krueger, et al. Bismark: a flexible aligner and methylation caller for Bisulfite-Seq applications. Bioinformatics. Jun. 1, 2011;27(11):1571-2. doi: 10.1093/bioinformatics/btr167. Epub Apr. 14, 2011.
Krueger, et al. Large scale loss of data in low-diversity illumina sequencing libraries can be recovered by deferred cluster calling. PLoS One. Jan. 28, 2011;6(1):e16607. doi: 10.1371/journal.pone.0016607.
Krueger. Loss of data in low-diversity libraries can be recovered by deferred cluster calling. Poster Jan. 29, 2011. http://seqanswers.com/forums/showthread.php?t=9150.
Kubo, et al. A Novel Sensitive, and Specific Assay for Abasic Sites, the Most Commonly Produced DNA Lesion. Biochem. 1992; 31:3703-3708.
Kumar, et al. A High-Throughput Method for Illumina RNA-Seq Library Preparation. Front Plant Sci. Aug. 28, 2012;3:202. doi: 10.3389/fpls.2012.00202. eCollection 2012.
Kurn. Method for generation of double stranded cDNA from RNA targets useful for global amplification, sequencing or other quantification of short RNA in a sample. Mar. 21, 2010. 1-5.
Laird. Principles and challenges of genomewide DNA methylation analysis. Nat Rev Genet. Mar. 2010;11(3):191-203. doi: 10.1038/nrg2732.
Lao, et al. Real time PCR profiling of 330 human micro-RNAs. Biotechnol J. Jan. 2007;2(1):33-5.
LC Sciences. Targeted sequencing—sample enrichment service. 2009. Available at www.lcsciences.com/products/genomics/targeted_sequencing/targeted_sequencing.html . Accessed Oct. 6, 2009.
LC Sciences. Technology—Massively parallel oligonucleotide and peptide synthesis on a micrchip based on the uParaflo microfluidic technology. Available at www.lcsciences.com/support/technology/technology.html. Accessed Oct. 6, 2009.
LC Sciences. Oligonucleotide mixture. OligoMix. 2009. Available at www.lcsciences.com/products/genomics/oligomix/oligomix_detail.html. Accessed Oct. 6, 2009.
Leamon, et al., a Massively parallel Pico TiterPlate based platform for discrete picoliter-scale polymerase chaine reactions [abstract]. Electrophoresis. Nov. 24, 2003(21) 3769-77.
Lefrancois, et al. Efficient yeast ChIP-Seq using multiplex short-read DNA sequencing. BMC Genomics. Jan. 21, 2009;10:37.
Lennon, et al. A scalable, fully automated process for construction of sequence-ready barcoded libraries for 454. Genome Biol. 2010;11(2):R15.
Leonard. What is a reliable method for multiplexing more than 384 samples on a MiSeq run? Posted Aug. 19, 2013. http://www.researchgate.net/post/What_is_a_reliable_method_for_multiplexing_more_than_384_samples_on_a_MiSeq_run2.
Letsinger, et al. Cationic oligonucletides. J. Am Chem. Soc. 1988; 110:4470-4471.
Letsinger, et al. Effects of pendant groups at phosphorus on binding properties of d-ApA analogues. Nucleic Acids Res. 1986;14(8):3487-99.
Letsinger, et al. Phosphoramidate analogs of oligonucleotides. J Org Chem. 1970;35(11):3800-3.
Levin, et al. Comprehensive comparative analysis of strand-specific RNA sequencing methods. Nat Methods. Sep. 2010;7(9):709-15. doi: 10.1038/nmeth.1491. Epub Aug. 15, 2010.
Lhomme, et al. Abasic DNA Structure reactivity and recognition. Biopolymers. 1999; 52(2): 65-83.
Lindahl, T. An N-Glycosidase from *Escherichia coli* That Releases Free Uracil from DNA Containing Deaminated Cytosine Residues. Proc Natl. Acad. Sci. USA 1974; 71(9):3649-3653.
Lizardi, et al., Mutation detection and single-molecule counting using isothermal rolling-circle amplification. *Nature Genetics*. 1998 Jul. 1998.19:(3):225-32.
Lockhart, et al. Expression monitoring by hybridization to high-density oligonucleotide arrays. Nature Biotechnology. 1996; 14:1675-1680.
Mag, et al. Synthesis and selective cleavage of an oligodeoxynucleotide containing a bridged internucleotide 5'-phosphorothioate linkage. Nucleic Acids Res. 1991;19(7):1437-41.
Makrigiogos, G. Fluorescent Labeling of Abasic Sites: A Novel Methodology to Detect Closely-Spaced Damage Sites in DNA. Int. J. Radiat. Biol. 1998: 74(1):99-109.
Marchuk, et al. Construction of T-vectors, a rapid and general system for direct cloning of unmodified PCR products. Nucleic Acids Res. Mar. 11, 1991; 19(5): 1154.
Mardis, E. New strategies and emerging technologies for massively parallel sequencing: applications in medical research. Online Apr. 17, 2009. *Genome Med*. 2009: 1(4); 40. Available at www.ncbinlm.nih.gov/pmc/aricles/PMC2684661/?tool=pubmed. Accessed Oct. 22, 2009.
Mardis. Next-Generation DNA Sequencing Methods. The Annual Review of Genomics and Human Genetics. 2008; 9:387-402.
Margulies, et al. Genome sequencing in microfabricated high-density picolitre reactors [abstract]. *Nature*. Sep. 15, 2005; 437 (7057): 376-80. Epub Jul. 31, 2005.
Maskos, et al. Oligonucleotide hybridisations on glass supports: a novel linker for oligonucleotide synthesis and hybridization properties of oligonucleotides synthesised in Situ. Nucl. Acids. Res. 20(7):1679-1684.
Maulik, et al. Novel Non-isotopic Detection of MutY Enzyme-recognized Mismatches in DNA Via Ultrasensitive Detection of Aldehydes. Nucl. Acids. Res. 1999: 27(5):1316-1322.
McCarthy, et al. Inducible repair of O-alkylated DNA pyrimidines in *Escherichia coli*. EMBO J. 1984; 3(3):545-50.
McClure, et al. Bovine exome sequence analysis and targeted SNP genotyping of recessive fertility defects BH1, HH2, and HH3 reveal a putative causative mutation in SMC2 for HH3. PLoS One. Mar. 25, 2014;9(3):e92769. doi: 10.1371/journal.pone.0092769. eCollection 2014.
McHugh, et al. Novel Regents for Chemical Cleavage at Abasic Sites and UV Photoproducts in DNA. Nucl. Acids. Res. 23(10): 1664-1670.

(56) References Cited

OTHER PUBLICATIONS

Meier, et al. Peptide nuclieic acids (PNAs)—Unusual properties of nonionic oligonucleotide analogues. Chem. Int. Ed. Engl. 1992;31:1008-1010.
Meissner, et al. Reduced representation bisulfate sequencing for comparative high-resolution DNA methylation analysis. Nucleic Acids Res. Oct. 13, 2005;33(18):5868-77. Print 2005.
Metzker, M. Sequencing technologies—the next generation. Nat Rev Genet. Jan. 2010;11(1):31-46. Epub Dec. 8, 2009.
Meuzelaar, et al. MegaPlex PCR: a strategy for multiplex amplification. Nat Methods. Oct. 2007;4(10):835-7. Epub Sep. 16, 2007.
Meyer, et al. Parallel tagged sequencing on the 454 platform. Nat Protoc. 2008;3(2):267-78. doi: 10.1038/nprot.2007.520.
Meyer, et al. Targeted high-throughput sequencing of tagged nucleic acid samples. Nucleic Acids Res. 2007;35(15):e97.
Mitchell, et al. Circulating microRNAS as stable blood-based markers for cancer detection. Proc Natl Acad Sci U S A. Jul. 29, 2008;105(30):10513-8. Epub Jul. 28, 2008.
Mitra, et al. Oxidative DNA cleavage by the antitumor antibiotic leinamycin and simple 1,2-dithiolan-3-one 1-oxides: Evidence for thiol-dependent conversion of molecular oxygen to DNA-cleaving oxygen radicals mediated by polysulfides. Journal of the American Chemical Society. 1997; vol. 119(48):11691-11692.
Mitra, et al., In situ localized amplification and contact replication of many individual DNA moecules. Nucleic Acids Research. 1999. 27:(24); e34.
Mizugaki, et al. Preparation of a monoclonal antibody specific for 5-methyl-2' deoxycytidine and its application for the detection of DNA methylation levels in human peripheral blood cells. Biol Pharm Bull. 1996; 19(12):1537-1540.
Molecular Probe Handbook Section 3.2 obtained from website at: http://www.probes.com/handbook/print/0302.html (Copyright© 1996-2003 by Molecular Probes, Inc.) Visited on Aug. 13, 2003. (18 pages).
Mullis, K.B et al., Eds. (1994). PCR: Polymerase Chain Reaction. Birkhauser: Boston, pp. xv-xvii (Table of Contents).
Myllykangas, et al. Efficient targeted resequencing of human germline and cancer genomes by oligonucleotide-selective sequencing. Nat Biotechnol. Oct. 23, 2011;29(11):1024-7. doi: 10.1038/nbt.1996.
Nakamura, et al. Highly Sensitive Apurinic/Apyrimidinic site Assay Can Detect Spontaneous and Chemically Induced Depurination Under Physiological Conditions. Cancer Res. 1998; 58:222-225.
Nayak, et al. Functional architecture of T7 RNA polymerase transcription complexes. *J Mol Biol*. Aug. 10, 2007; 371(2): 490-500.
Nedderman, et al. Cloning and expression of human G/T mismatch-specific thymine-DNA glycosylase. J Biol Chem. 1996; 271(22):12767-74.
New England BioLabs Inc. NEBNext® Ultra™ Directional RNA Library Prep Kit for Illumina®. Available at https://www.neb.com/products/e7420-nebnext-ultra-directional-rna-library-prep-kit-for-illumina. Accessed Jun. 4, 2014.
Nextera® Rapid Capture Enrichment Low-Plex Pooling Guidelines. Technical Note: DNA Analysis. 2014. http://www.illumina.com/content/dam/illumina-marketing/documents/products/technotes/technote-nextera-rapid-capture-low-plex-pooling-guidelines.pdf.
Neylon, et al. Chemical and biochemical strategies for the randomization of protein encoding DNA sequences: library construction methods for directed evolution. Nucleic Acids Res. Feb. 27, 2004;32(4):1448-59. Print 2004.
Ng, et al. Targeted capture and massively parallel sequencing of 12 human exomes. *Nature*. Sep. 10, 2009. 461, 272-276. http://www.nature.com/nature/journal/v461/n7261/full/nature08250.html. Accessed Oct. 6, 2009.
Nikolaev, et al. Detection of genomic variation by selection of a 9Mb DNA region and high throughput sequencing. *PLoS One*. Aug. 17, 2009. 4(8): e6659.
Nugen, Inc. Ovation Biotin RNA Amplification and Labeling System User Guite. Catalog #2300-12. Published 2004.

Nugen, Inc. Technical Report #1. The Ovation Biotin System Validation for Use with Affymetrix GeneChip Arrays. Published 2004.
O'Shannessy, et al. Immobilization of Glycoconjugates by Their Oligosaccharides: Use of Hydrazido-Derivatized Matrices. Anal. Biochem. 1990; 191:1-8.
Ochman, et al. Genetic applications of an inverse polymerase chain reaction. Genetics. Nov. 1998;120(3):621-3.
Office action dated Jan. 16, 2013 for U.S. Appl. No. 12/938,112.
Office action dated Feb. 5, 2014 for U.S. Appl. No. 13/750,768.
Office action dated Feb. 8, 2012 for EP Application No. 07810169.8.
Office action dated Feb. 17, 2011 for U.S. Appl. No. 12/305,633.
Office action dated Feb. 28, 2013 for U.S. Appl. No. 13/156,294.
Office action dated Mar. 1, 2010 for U.S. Appl. No. 10/441,663.
Office action dated Mar. 7, 2007 for U.S. Appl. No. 10/441,663.
Office action dated Mar. 9, 2015 for CN Application No. 201380006942.4.
Office action dated Apr. 16, 2014 for U.S. Appl. No. 13/239,226.
Office action dated May 16, 2011 for U.S. Appl. No. 11/948,784.
Office action dated May 25, 2006 for U.S. Appl. No. 10/441,663.
Office action dated Jun. 6, 2012 for U.S. Appl. No. 10/441,663.
Office action dated Jun. 19, 2013 for U.S. Appl. No. 12/855,611.
Office action dated Jun. 27, 2013 for U.S. Appl. No. 12/938,112.
Office action dated Jun. 30, 2008 for U.S. Appl. No. 11/026,280.
Office action dated Jul. 5, 2007 for U.S. Appl. No. 10/441,663.
Office action dated Jul. 8, 2009 for U.S. Appl. No. 10/441,663.
Office action dated Jul. 13, 2007 for U.S. Appl. No. 11/026,280.
Office action dated Jul. 15, 2008 for U.S. Appl. No. 10/441,663.
Office action dated Aug. 18, 2010 for U.S. Appl. No. 12/305,633.
Office action dated Sep. 5, 2013 for U.S. Appl. No. 13/156,294.
Office action dated Sep. 9, 2010 for U.S. Appl. No. 10/441,663.
Office action dated Sep. 18, 2006 for U.S. Appl. No. 10/441,663.
Office action dated Sep. 24, 2009 for U.S. Appl. No. 10/441,663.
Office action dated Sep. 24, 2014 for U.S. Appl. No. 13/239,226.
Office action dated Sep. 25, 2014 for U.S. Appl. No. 13/750,768.
Office action dated Oct. 9, 2013 for U.S. Appl. No. 12/938,112.
Office action dated Oct. 14, 2010 for U.S. Appl. No. 11/948,784.
Office action dated Nov. 7, 2012 for U.S. Appl. No. 13/411,170.
Office action dated Nov. 13, 2012 for U.S. Appl. No. 12/855,611.
Office action dated Dec. 5, 2008 for U.S. Appl. No. 10/441,663.
Office action dated Dec. 17, 2007 for U.S. Appl. No. 10/441,663.
Okou, et al. Microarray-based genomic selection for high-throughput resequencing. Nat Methods. Nov. 2007;4(11):907-9. Epub Oct. 14, 2007.
Olson, M. Enrichment of super-sized resequencing targets from the human genome. Nat Methods. Nov. 2007;4(11):891-2.
Openwetware. Directional-RNAseq Prep. Available at http://openwetware.org/wiki/Directional-RNAseq_Prep. Accessed Jun. 4, 2014.
Pabinger, et al. A survey of tools for variant analysis of next-generation genome sequencing data. Brief Bioinform. Mar. 2014;15(2):256-78. doi: 10.1093/bib/bbs086. Epub Jan. 21, 2013.
Pang, et al. Use of modified nucleotides and uracil-DNA glycosylase (UNG) for the control of contamination in the PCR-based amplification of RNA. Molecular and Cellular Probes. 1992; 6:251-256.
Parameswaran, et al. A pyrosequencing-tailored nucleotide barcode design unveils opportunities for large-scale sample multiplexing. Nucleic Acids Res. 2007;35(19):e130.
Parkhomchuk, et al. Transcriptome analysis by strand-specific sequencing of complementary DNA. Nucleic Acids Res. Oct. 2009;37(18):e123.
Pauwels, et al. Biological activity of new 2-5A analogues. Chemica Scripta. 1986;26:141-9.
Pease, et al. A rapid, directional RNA-seq library preparation workflow for Illumina [reg] sequencing. Nature Methods. 2012; 9, No. 3.
Pease, et al. Light-generated oligonucleotide arrays for rapid DNA sequence analysis. Proc. Natl. Acad. Sci. USA 1994; 91:5022-5026.
Pease, et al. Rapid, directional RNA-seq library preparation kits for formalin-fixed paraffin-embedded RNA. Nature Methods. 2012; 9: Published online Sep. 27, 2012.

(56) References Cited

OTHER PUBLICATIONS

Pei, et al. Site-specific cleavage of duplex DNA by semisynthetic nuclease via triple-helix formation. *Pro. Natl. Acad. Sci. USA*. Dec. 1990 87: 9858-9862.
Peng, et al. Kamchatka crab duplex-specific nuclease-mediated transcriptome subtraction method for identifying long cDNAs of differentially expressed genes. *Analytical Biochemistry*. Jan. 15, 2008. 372:2, 148-155. (abstract).
Pierce, et al. Linear-after-the-exponential polymerase chain reaction and allied technologies. Real-time detection strategies for rapid, reliable diagnosis from single cells. Methods Mol Med. 2007;132:65-85.
Pollack, et al. Genome-wide analysis of DNA copy-number changes using cDNA microarrays. Nature Genet. 1999; 23:41-46.
Porreca, et al. Multiplex amplification of large sets of human exons. Nat Methods. Nov. 2007;4(11):931-6. Epub Oct. 14, 2007.
Prashar, et al. Analysis of differential gene expression by display of 3' end restriction fragments of cDNAs. Proc Natl Acad Sci U S A. Jan. 23, 1996;93(2):659-63.
Proudnikov, et al. Chemical methods of DNA and RNA fluorescent labeling. Nucleic Acids Res. Nov. 15, 1996;24(22):4535-42.
Ramsahoye, et al. Non-CpG methylation is prevalent in embryonic stem cells and may be mediated by DNA methyltransferase 3a. Proc Natl Acad Sci U S A. May 9, 2009;97(10):5237-42.
Ranasinghe, et al. Fluorescence based strategies for genetic analysis. Chem Commun (Camb). Nov. 28, 2005;(44):5487-502. Epub Sep. 30, 2005.
Rawls, R. Optimistic about antisense. Promising clinical results and chemical strategies for further improvements delight antisense drug researchers. C & E News. Jun. 2, 1997; 35-59.
Riley, et al. A novel, rapid method for the isolation of terminal sequences from yeast artificial chromosome (YAC) clones. Nucleic Acids Res. May 25, 1990;18(10):2887-90.
Roberts, R. Restriction enzymes at NEB: over 30 years of innovation, the discovery, cloning and engineering of these essential reagents. *NEB Expression*. Winter. 2008. vol. 2.4. Available at www.neb.com/nebecomm/tech_reference/restriction_enzymes/feature_article_innovation.asp. Accessed Aug. 16, 2010.
Robertson. DNA methylation and human disease. Nat Rev Genet. Aug. 2005;6(8):597-610.
Roche Company. 454 life sciences, applications—sequence capture targeted region. http://www.454.com/applications/sequence-capture-targeted-region.asp. Accessed Oct. 6, 2009.
Saiki, et al. Analysis of enzymatically amplified beta-globin and HLA-DQ alpha DNA with allele-specific oligonucleotide probes. Nature. Nov. 13-19, 1986;324(6093):163-6.
Sambrook, J. et al., Eds. (1989). *Molecular Cloning: A Laboratory Manual*. 2nd Edition, Cold Spring Harbor Laboratory Press, pp. xi-xxxviii (Table of Contents).
Sanders, et al. Targeting individual subunits of the FokI restriction endonuclease to specific DNA strands, *Nucleic Acids Research*. Apr. 2009. Nucleic Acids Res. 37:(7):2105-15.
Sanghvi, et al. ed. Chapters 2 and 3, ASC Symposium Series 580—Carbohydrates Modifications in Antisense Research. American Chemical Society. Washington, DC. 1994.
Sanghvi, et al. ed. Chapters 6 and 7, ASC Symposium Series 580—Carbohydrates Modifications in Antisense Research. American Chemical Society. Washington, DC. 1994.
Sano, et al. Detection of heavy methylation in human repetitive DNA subsets by a monoclonal antibody against 5-methylcytosine. Biochim Biophys Acta. 1988; 951(1):157-65.
Sartori, et al. A novel uracil-DNA glycosylase with broad substrate specificity and an unusual active site. EMBO J. 2002; 21(12):3182-91.
Sawai, et al. Synthesis and properties of oligoadenylic acids containing 2'-5' phosphoramide linkage. Chem. Lett. 1984; 805-808.
Schena, et al. Parallel human genome analysis: microarray-based espression monitoring of 1000 genes. Proc Natl. Acad. Sci. USA Biochemistry. 1996; 93:10614-10619.

Schena, et al. Quantitative monitoring of gene expression patterns with a complementary DNA microarray. Science. 1995; 270:467-470.
Schmid, et al. Chic and chec: genomic mapping of chromatin proteins. *Molecular Cell*. 2004. 16, no1, pp. 147-157. (abstract).
SEQanswers. MiSeq cluster generation problems. Posted Mar. 17, 2012. http://seqanswers.com/forums/showthread.php?t=18499.
SEQanswers. Sequencing a Low diversity library on the HiSeq. Posted Nov. 18, 2011. http://seqanswers.com/forums/showthread.php?t=18499.
Shalon, et al. Parallel human genome analysis: microarray system for analyzing complex DNA samples using two-color fluorescent probe hybridization. Genome Res. 1996; 6:639-645.
Shida, et al. Cleavage of Single-and double-Stranded DNAs Containing an Abasic Residue by *Escherichia coli* Exonuclease III (AP Endonuclease VI) Nucl. Acids. Res. 1996; 24(22):4572-4576.
Singapore written opinion dated Mar. 17, 2015 for SG Application No. 11201401628W.
Slupphaug, et al. Low incorporation of dUMP by some thermostable DNA polymerases may limit their use in PCR amplifications. Anal. Biochem. 1993; 211:164-169.
Sohail, et al. Human activation-induced cytidine deaminase causes transcription-dependent, strand-biased C to U deaminations. Nucleic Acids Res. 2003; 31(12):299-04.
Soni, et al. Progress toward ultrafast DNA sequencing using solid-state nanopores. Clin Chem. Nov. 2007;53(11):1996-2001. Epub Sep. 21, 2007.
Sprinzl, et al. Enzymatic incorporation of ATP and CTP analogues into the 3' end of tRNA. Eur J Biochem. Dec. 1997;81(3):579-89.
Srivastava, et al. Mammalian Abasic Site Base Excision Repair. Identification of the Reaction Sequence and Rate-Determining Steps. J. Biol. Chem. 1998; 273(33):21203-21209.
Stemmer, et al. Single-step assembly of a gene and entire plasmid from large numbers of oligodeoxyribonucleotides. Gene. Oct. 16, 1995;164(1):49-53.
Stephpens, et al. Automating sequence-based detection and genotyping of SNPs from diploid samples. Nat Genet. Mar. 2006;38(3):375-81. Epub Feb. 19, 2006.
Steullet, et al. Clevage of Abasic Sites in DNA by Intercalator-amines. Bioorganic and Medicinal Chem. 1999; 7:2531-2540.
Stratagene catalog, Gene Characterizatin Kits. 1988 p. 39.
Sugiyama, et al. Chemistry of thermal degradation of abasic sites in DNA. Mechanistic investigation on thermal DNA stand clevage of alkylated DNA. Chem. Res. Toxicol. 1994; 1:673-683.
Summerer, D. Enabling technologies of genomic-scale sequence enrichment for targeted high-throughput sequencing. *Genomics*Dec. 2009;94(6):363-8 (abstract).
Summerer, et al. Microarray-based muticycle-enrichment of genomic subsets for targeted next-generation sequencing. Accepted Jun. 18, 2009. Available at www.ncbi.nlm.nih.gov/pubmed/19638418. Accessed Oct. 6, 2009.
Timblin, et al. Application for PCR technology to subtractive cDNA cloning: identification of genes expressed specifically in murine plasmacytoma cells. Nucleic Acids Res. Mar. 25, 1990;18(6):1587-93.
Tong, et al. Detection of restriction enzyme-digested target DNA by PCR amplification using a stem-loop primer: application to the detection of hypomethylated fetal DNA in maternal plasma. Clin Chem. Nov. 2007;53(11):1906-14. Epub Sep. 27, 2007.
Turner, et al. Methods for genomic partitioning. Annu Rev Genomics Hum Genet. 2009;10:263-84. doi: 10.1146/annurev-genom-082908-150112.
Vairapandi, et al. Partial purification and characterization of human 5- methylcytosine-DNA glycosylase. Oncogene. 1996; 13(5):933-8.
Vairapandi, et al. Human DNA-demethylating activity: a glycosylase associated with RNA and PCNA. J Cell Biochem. 2000; 79(2):249-60.
Varkonyi-Gasic, et al. Protocol: a highly sensitive RT-PCR method for detection and quantification of microRNAs. Plant Methods. Oct. 12, 2007;3:12.

(56) References Cited

OTHER PUBLICATIONS

Varley, et al. Nested Patch PCR enables highly multiplexed mutation discovery in candidate genes. Genome Res. Nov. 2008;18(11):1844-50. doi: 10.1101/gr.078204.108. Epub Oct. 10, 2008.
Vincent, et al. Helicase-dependent isothermal DNA amplification. EMBO Rep. Aug. 2004;5(8):795-800. Epub Jul. 9, 2004.
Vos, et al. AFLP: a new technique for DNA fingerprinting. Nucleic Acids Res. Nov. 11, 1995;23(21):4407-14.
Walker, et al., Strand displacement amplification-an isothermal, in vitro DNA amplifcation technique. Nucleic Acids Resarch. 1991. 20(7): 1691-1696.
Westburg. Fast, Directional RNA-Seq Library Prep. Abailable at http://www.westburg.eu/lp/rna-seq-library-preparation. Accessed on Jun. 4, 2014.
Westin, et al., Anchored multiplex amplification on a microelectronic chip array. Nature Biotechnology. Feb. 18, 2000(2):199-204.
Wikipedia. ABI solid sequencing. Http://en.wikipedia.org/wild/ABI_Solid_Sequencing. Last modified Oct. 4, 2009. Accessed Oct. 22, 2009.
Wikipedia. DNA sequencing. Alailable at http://en.wikipedia.org/wiki/Next-generation_sequencing. Last modified Oct. 8, 2009. Accessed Oct. 22, 2009.
Wilchek, et al. Labeling Glycoconjugates with Hydrazide Reagents. Methods Enzymol. 1987; 138:429-442.
Wolffe, et al. DNA demethylation. Proc Natl Acad Sci USA. 1999; 96(11):5894-6.
Wu, et al. Phasing Amplicon Sequencing for Robust Microbial Community Analysis. I-2630. 2014. http://www.asmonlineeducation.com/php/asm2014abstracts/data/papers/I-2630.htm.
Xiao, et al. Sequential amplification of flanking sequences by Y-shaped adaptor dependent extension using multiple templates. Zhi Wu Sheng Li Yu Fen Zi Sheng Wu Xue Xue Bao (Journal of Plant Physiology and Molecular Biology). Feb. 2007;33(1):85-90.
Young, et al. A new strategy for genome assembly using short sequence reads and reduced representation libraries. Genome Res. Feb. 2010;20(2):249-56. doi: 10.1101/gr.097956.109.
Zalipsky, S. Functionalized Poly(ethylene glycol) for Preparation of Biologically Relevant Congugates. Bioconjugate Chem. 1995; 6:150-165.
Zang, et al. DNA alkylation by leinamycin can be triggered by cyanide and phosphines. Bioorg Med Chem Lett. Jun. 18, 2001;11(12):1511-5.
Zhang, et al. Multiplex sequencing on the SOLID platform with 10, 16, or 96 barcodes. 2009 Life technologies. www3.appliedbiosystems.com/cms/groups/mcb_marketing/documents/generaldocuments/cms_065528.pdf.
Zheng, et al. Titration-free 454 sequencing using Y adapters. Nat Protoc. Aug. 18, 2011;6(9):1367-76. doi: 10.1038/nprot.2011.369.
Zhu, et al. Overexpression of 5-methylcytosine DNA glycosylase in human embryonic kidney cells EcR293 demethylates the promoter of a hormone-regulated reporter gene. Proc Natl Acad Sci USA. 2001; 98(9):5031-6.
Zhu, et al. 5-Methylcytosine DNA glycosylase activity is also present in the human MBD4 (G/T mismatch glycosylase) and in a related avian sequence. Nucleic Acids Res. 2000; 28(21):4157-65.
Zhulidov, et al. Simple cDNA normalization using kamchatka crab duplex=specific nuclease. *Nucleic Acids Research*. Online Feb. 18, 2004. 32:3 e37.
Ziller, et al. Genomic distribution and inter-sample variation of non-CpG methylation across human cell types. PLoS Genet. Dec. 2011;7(12):e1002389. doi: 10.1371/journal.pgen.1002389. Epub Dec. 8, 2011.
U.S. Appl. No. 14/778,564, filed Sep. 16, 2015, Amorese et al.
U.S. Appl. No. 14/836,936, filed Aug. 26, 2015, Amorese et al.
U.S. Appl. No. 14/877,075, filed Oct. 7, 2015, Kurn.
U.S. Appl. No. 14/920,254, filed Oct. 22, 2015, Armour.
Beaucage et al. Deoxynucleoside Phosphoramidites-A New Class of Key Intermediates for Deoxypolynucleotide Synthesis. Tetrahedron Letters. 1981;22(20):1859-1862.
Brown, et al. Chemical synthesis and cloning of a tyrosine tRNA gene. Methods Enzymol. 1979;68:109-51.
Gundmundsson, et al. Genome-wide association and replication studies identify four variants associated with prostate cancer susceptibility. Nat Genet. Oct. 2009;41(10):1122-6. doi: 10.1038/ng.448. Epub Sep. 20, 2009.
Narang, et al. Improved phosphotriester method for the synthesis of gene fragments. Methods Enzymol. 1979;68:90-8.
Out, et al. Deep sequencing to reveal new variants in pooled DNA samples. Hum Mutat. Dec. 2009;30(12):1703-12. doi: 10.1002/humu.21122.
Turner, et al. Massively parallel exon capture and library-free resequencing across 16 genomes. Nat Methods. May 2009;6(5):315-6. doi: 10.1038/nmeth.f.248. Epub Apr. 6, 2009.
Voelkerding, et al. Next-generation sequencing: from basic research to diagnostics. Clin Chem. Apr. 2009;55(4):641-58. doi: 10.1373/clinchem.2008.112789. Epub Feb. 26, 2009.
U.S. Appl. No. 14/991,340, filed Jan. 8, 2016, Schroeder et al.
U.S. Appl. No. 14/995,882, filed Jan. 14, 2016, Amour.
Callow, et al. Selective DNA amplification from complex genomes using universal double-sided adapters. Nucleic Acids Res. Jan. 28, 2004;32(2):e21.
European search report and opinion dated Jul. 23, 2015 for EP Application No. 13740653.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Office action dated Jul. 9, 2015 for U.S. Appl. No. 14/211,261.
Office action dated Jul. 15, 2015 for U.S. Appl. No. 13/750,768.
Office action dated Jul. 15, 2015 for U.S. Appl. No. 13/938,059.
Shendure, et al. Accurate multiplex polony sequencing of an evolved bacterial genome. Science. Sep. 9, 2005;309(5741):1728-32. Epub Aug. 4, 2005.
Shendure, et al. Accurate multiplex polony sequencing of an evolved bacterial genome. Science. Sep. 9, 2005;309(5741):1728-32. Epub Aug. 4, 2005. Supplemental Materials. 41 pages.
Bower, et al. Targeted rapid amplification of cDNA ends (T-RACE)—an improved RACE reaction through degradation of non-target sequences. Nucleic Acids Res. Nov. 2010;38(21):e194. doi: 10.1093/nar/gkq816. Epub Sep. 15, 2010.
Chen, et al. BisQC: an operational pipeline for multiplexed bisulfate sequencing. BMC Genomics. Apr. 16, 2014;15:290. doi: 10.1186/1471-2164-15-290.
Chenchik, et al. Full-length cDNA cloning and determination of mRNA 5' and 3' ends by amplification of adaptor-ligated cDNA. Biotechniques. Sep. 1996;21(3):526-34.
European search report and opinion dated May 22, 2015 for EP Application No. 12842163.3.
International search report and written opinion dated Jun. 18, 2015 for PCT/US2015/018112.
Office action dated Jun. 2, 2016 for U.S. Appl. No. 13/750,768.
Rothberg, et al. An integrated semiconductor device enabling non-optical genome sequencing. Nature. Jul. 20, 2011;475(7356):348-52. doi: 10.1038/nature10242. With supplemental information.
U.S. Appl. No. 15/154,414, filed May 13, 2016, Armour et al.
Gu, et al. Depletion of Abundant Sequences by Hybridization (DASH): using Cas9 to remove unwanted high-abundance species in sequencing libraries and molecular counting applications. Genome Biology. 2016; 17:41. Doi: 10.1186/s13059-016-09045.
Oyola, et al. Efficient Depletion of Host DNA Contamination in Malaria Clinical Sequencing. J. Clin. Microbiol. Mar. 2013; 51(3):745-751.
Gerrish, et al. Tailed pooled suppression subtractive hybridization (PSSH) adaptors do not alter efficiency. Antonie Van Leeuwenhoek. Nov. 2010;98(4):573-9. doi:.10.1007/s10482-010-9465-x. Epub Jun. 8, 2010.
Olivarius, et al. High-throughput verification of transcriptional starting sites by Deep-RACE. Biotechniques. Feb. 2009;46(2):130-2. doi: 10.2144/000113066.
Levesque-Sergerie, et al. Detection limits of several commercial reverse transcriptase enzymes: impact on the low- and high-abundance transcript levels assessed by quantitative RT-PCR. BMC Mol Biol. Oct. 22, 2007;8:93.

(56) References Cited

OTHER PUBLICATIONS

Office action dated Apr. 4, 2016 for U.S. Appl. No. 14/995,882.
Office action dated Apr. 7, 2016 for U.S. Appl. No. 14/390,012.
U.S. Appl. No. 15/047,448, filed Feb. 18, 2016, Huelga et al.
Zhang, et al. Copy number variation in human health, disease, and evolution. Annu Rev Genomics Hum Genet. 2009;10:451-81. doi:10.1146/annurev genom.9.081307.164217.
Bodi, et al. Comparison of Commercially Available Target Enrichment Methods for Next-Generation Sequencing. J Biomol Tech. Jul. 2013; 24(2): 73-86.
European search report and opinion dated Jan. 29, 2016 for EP Application No. 13806978.
International search report and written opinion dated Feb. 5, 2016 for PCT/US2015/047053.
Ovation® Target Enrichment System. User guide. Nugen. 2016. 45 pages.
Watson, et al. Cloning and assembly of PCR products using modified primers and DNA repair enzymes. Biotechniques. Nov. 1997;23(5):858-62, 864.
U.S. Appl. No. 14/990,339, filed Jan. 7, 2016, Amorese et al.
Office action dated Apr. 3, 2015 for CN Application No. 2012800608251.
Ganova-Raeva, et al. Primer Extension Enrichment Reaction (PEER): a new subtraction method for identification of genetic differences between biological specimens. Nucleic Acids Research. 2006; 34(11):e76.
Notice of allowance dated Jul. 28, 2015 for U.S. Appl. No. 13/643,056.
Froussard. A random-PCR method (rPCR) to construct whole cDNA library from low amounts of RNA. Nucleic Acids Res. Jun. 11, 1992;20(11):2900.
Office action dated Oct. 30, 2015 for U.S. Appl. No. 13/750,768.
Office action dated Nov. 4, 2015 for U.S. Appl. No. 14/030,761.
Tucker, et al. Massively parallel sequencing: the next big thing in genetic medicine. Am J Hum Genet. Aug. 2009;85(2):142-54. doi: 10.1016/j.ajhg.2009.06.022.
Vater, et al. Short bioactive Spiegelmers to migraine-associated calcitonin gene-related peptide rapidly identified by a novel approach: tailored-SELEX. Nucleic Acids Res. Nov. 1, 2003;31(21):e130.
Zhong, et al. High-throughput Alumina strand-specific RNA sequencing library preparation. Cold Spring Harb. Protoc.; 2011; 940-949. doi:10.1101/pdb.prot5652.
Amorese, et al. Improved pathogen sequencing of host-pathogen RNA-sequence. AGBT 2016. Advances in Genome Biology Technology Conference. Feb. 10, 2016. Orlando, FL. Nugen Technologies. Poster Presentation. 2 pages.
Li, et al. Targeted depletion of host reads in host-pathogen mixed RNA-seq libraries. Advances in Genome Biology Technology Conference. Feb. 11, 2016. Orlando, FL. Nugen Technologies. Poster. 1 page.
Notice of allowance dated Jan. 5, 2017 for U.S. Appl. No. 13/750,768.
Office Action dated Oct. 31, 2016 for European Application 13806978.6.
Bradford, et al. A comparison of massively parallel nucleotide sequencing with oligonucleotide microarrays for global transcription profiling. BMC Genomics. May 5, 2010;11:282. doi: 10.1186/1471-2164-11-282.
European search report and opinion dated Sep. 1, 2016 for EP Application No. 14764629.3
Hurd, et al. Advantages of next-generation sequencing versus the microarray in epigenetic research. Brief Funct Genomic Proteomic. May 2009;8(3):174-83.d doi: 10-1093/bfgp/elp013.Epub Jun. 17, 2009.
Lefrancois, et al., Efficient yeast CHIP-seq using multiplex short-read DNA sequencing. BMC Genomics. 2009; 10(37).
Office Action dated Sep. 8, 2016 for U.S. Appl. No. 14/390,012.
Stewart, et al. Complete MHC Haplotype Sequencing for Common Disease Gene Mapping. Genome Res. Jun. 2004;14(6):1176-87. Epub May 12, 2004.
Office Action dated Mar. 15, 2017 for U.S. Appl. No. 14/390,012.

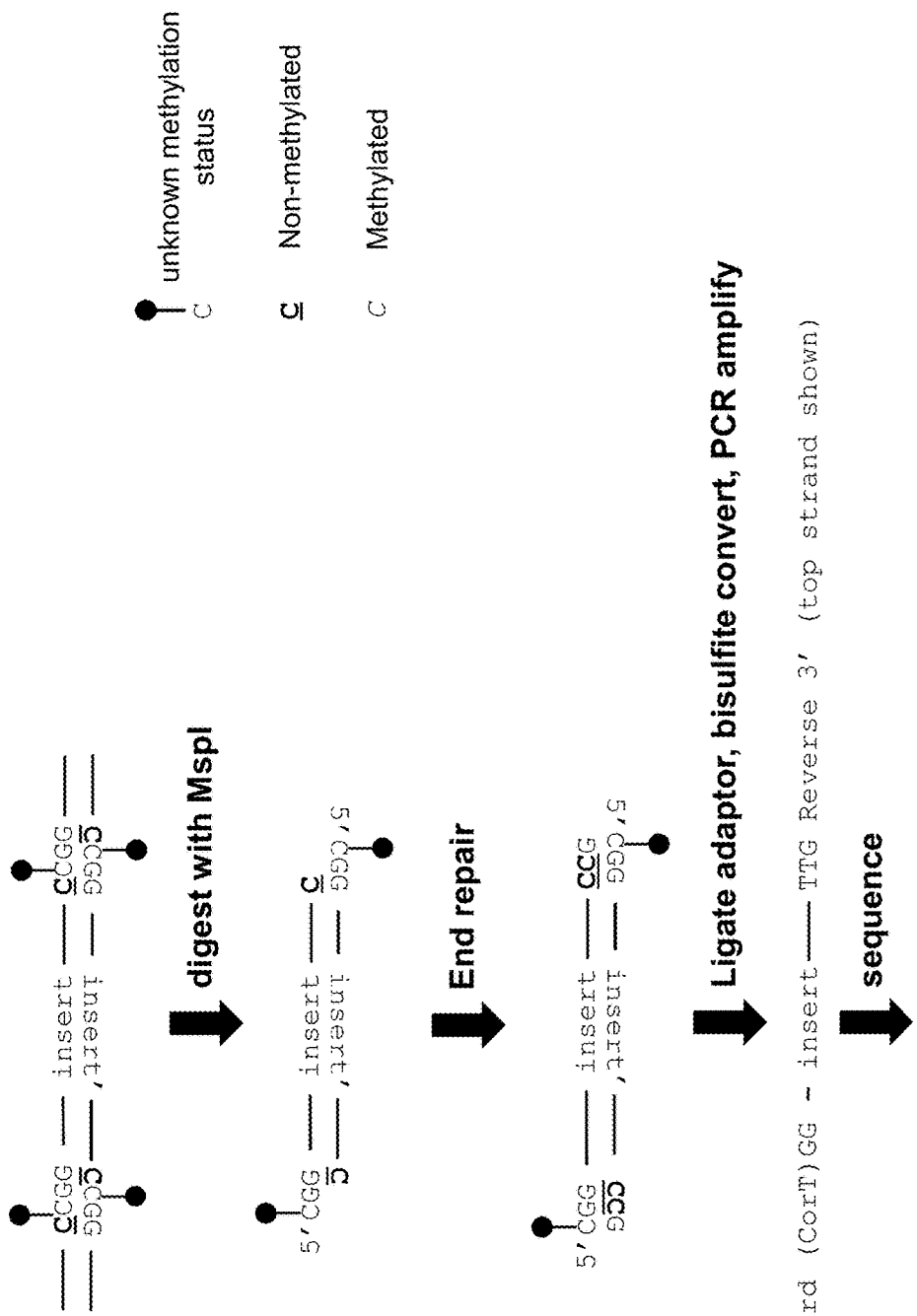

FIG. 2A

```
Ben383    /5Biosg/CGHHHAGATCGGAAGAG/3ddC/    (H = A,C, or T, (no G))
Ben384    /5Biosg/CGHHAGATCGGAAGAG/3ddC/
Ben385    /5Biosg/CGHAGATCGGAAGAG/3ddC/
Ben341    /5Biosg/CGAGATCGGAAGAG/3ddC/

R01446    CAAGCAGAAGACGGCATACGTGATCTGGTTGTGACTGGAGTTCTGACGTGCTCTTCCGATCT
```

FIG. 2B

1. Anneal

```
                    R01446 →
5'-CAAGCAGAAGACGGCATACGTGATCTGGTTGTGACTGGAGTTCTGACGTGCTCTTCCGATCT
                                                    ddC/GAGAAGGCTCTTCGTGCAGTCAGTTCTGAGGTCAGTGTAGCTAGGTGCTAGCAGAAGCGACGAAHHHGC/gsoiB5
                                                                                                            ← Ben383
```

2. Extend with D mix (dATP, dGTP, dTTP (no dCTP))    (D = T, G, or A, (no C))

```
                    R01446 →
5'-CAAGCAGAAGACGGCATACGTGATCTGGTTGTGACTGGAGTTCTGACGTGCTCTTCCGATCTDDD
                                                    ddC/GAGAAGGCTCTTCGTGCAGTCAGTTCTGAGGTCAGTGTAGCTAGGTGCTAGCAGAAGCGACGAAHHHGC/gsoiB5
                                                                                                            ← Ben383
```

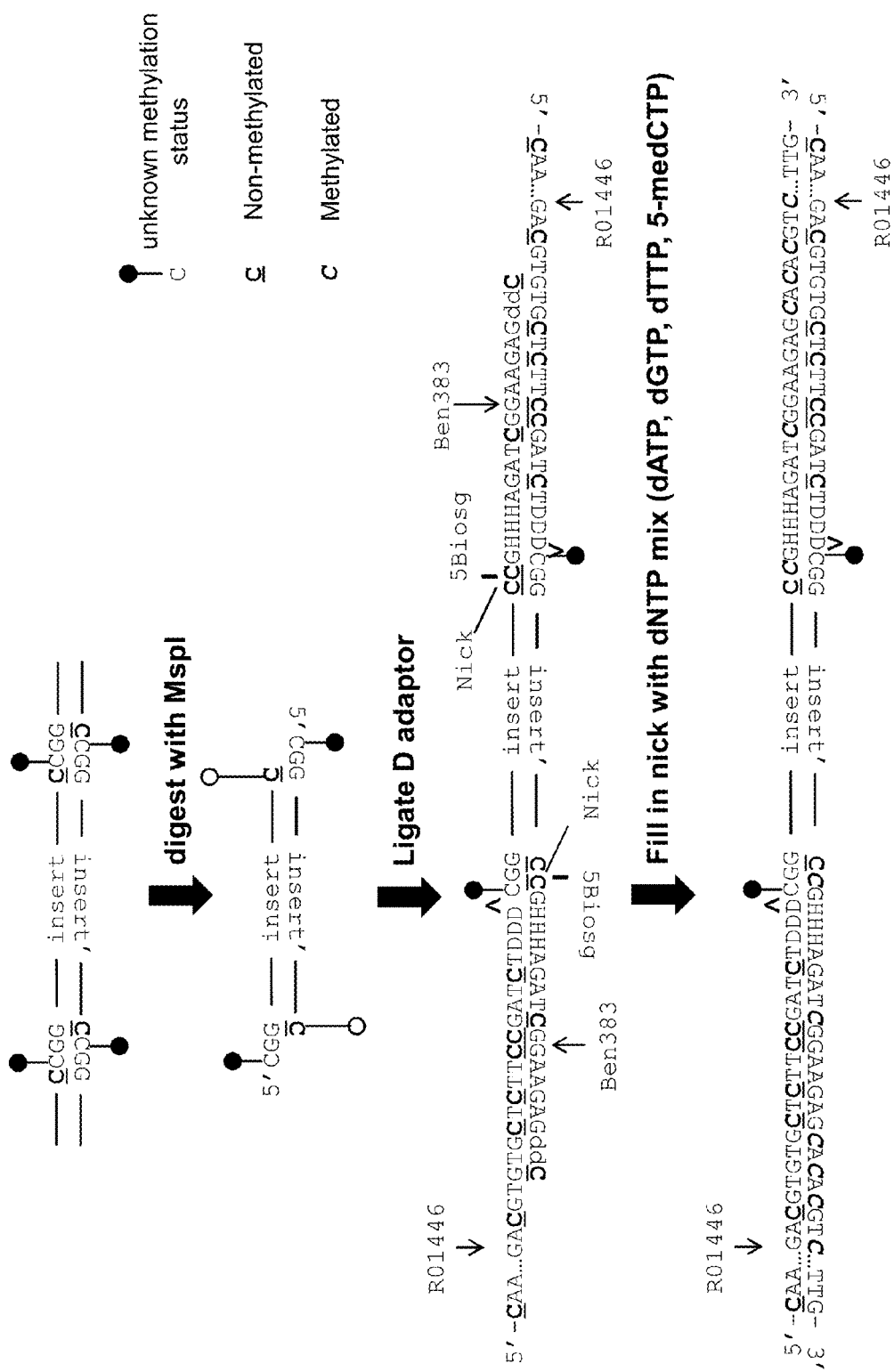

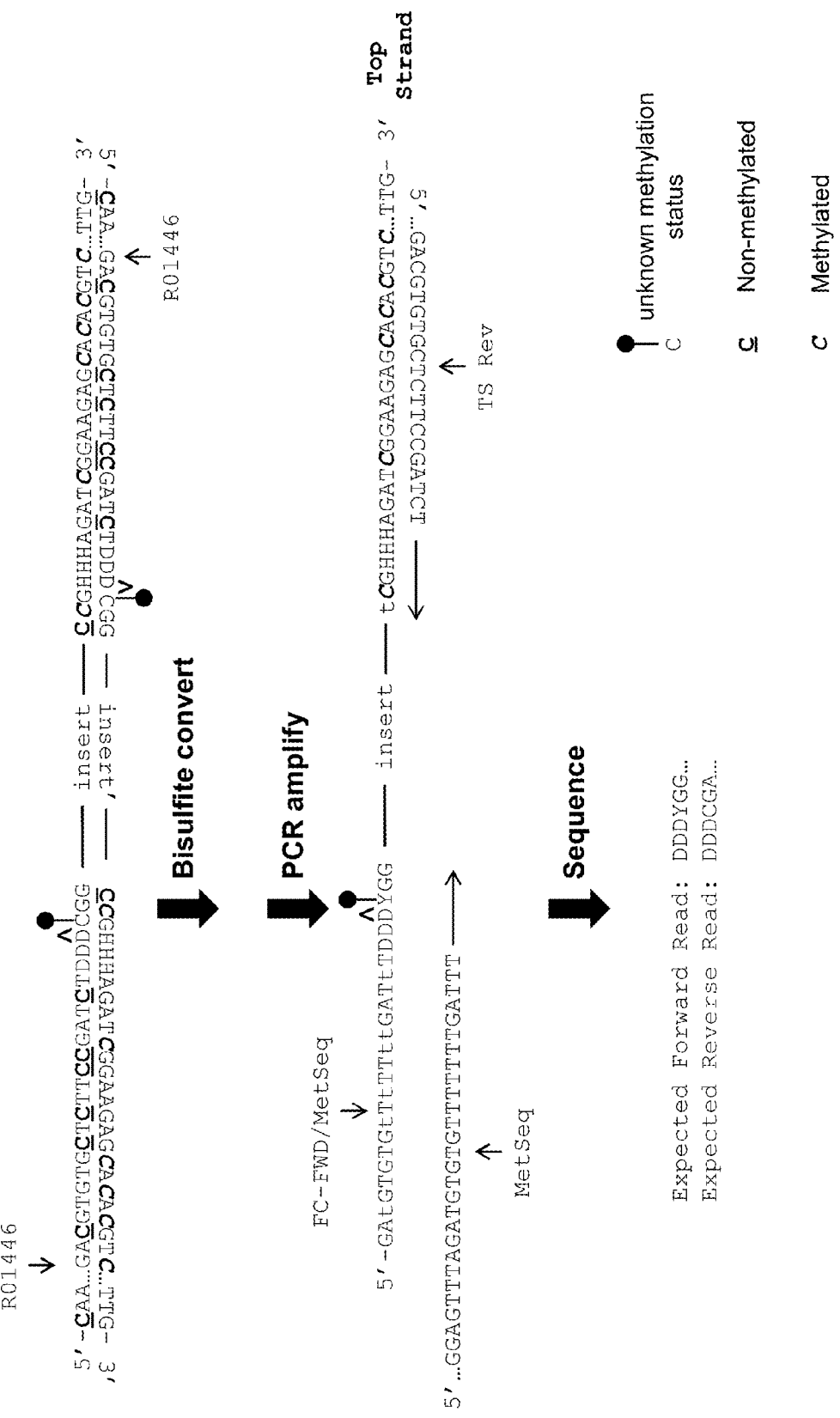

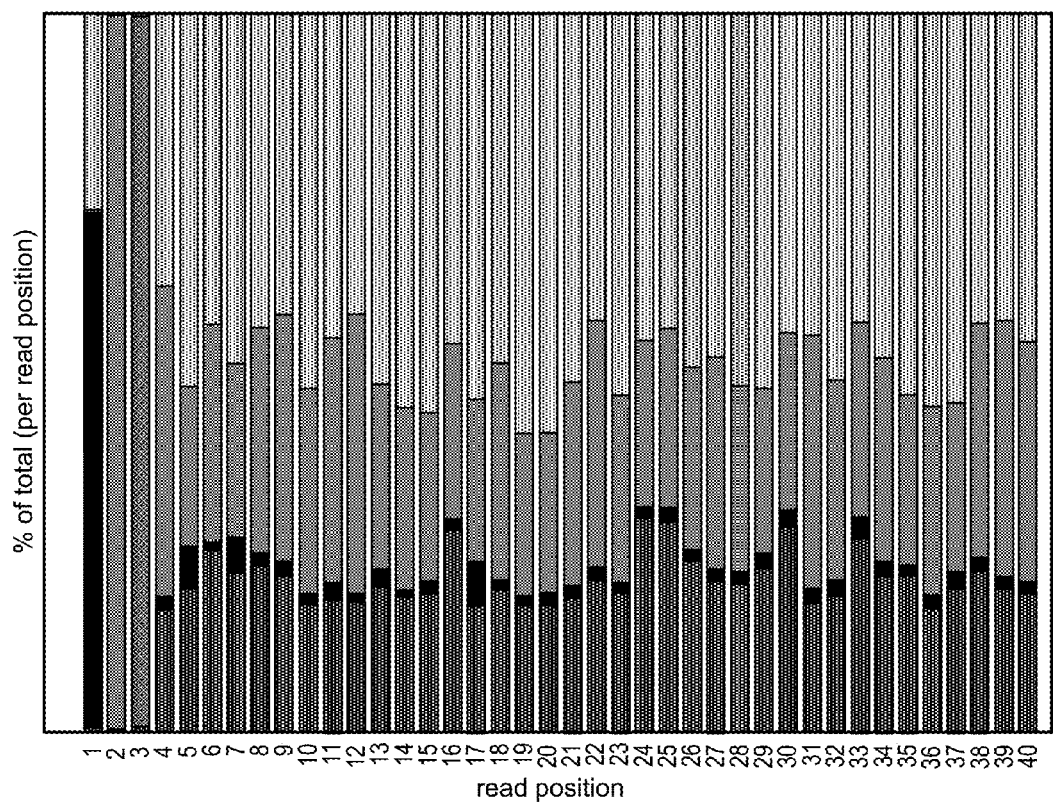

FIG. 8

DR Rev Helper Style Ed3 BC
R01450 mix4    MIX    5

H = A, C, or T
D = A, G, or T
Y = C or T
B = C, G, or T

Expected Forward Read
sum of:
YGG...
DYGG...
DDYGG...
DDDYGG...
NNNNNN...

Expected Reverse Read
sum of:
CGA...
DCGA...
DDCGA...
DDDCGA...
NNNNNN...

Expected Forward Read
sum of:
YGG...
DYGG...
DDYGG... (if don't have DDDYGG)
NNBNN.. (missing A at position 3)

FIG. 10
40+6+25 run
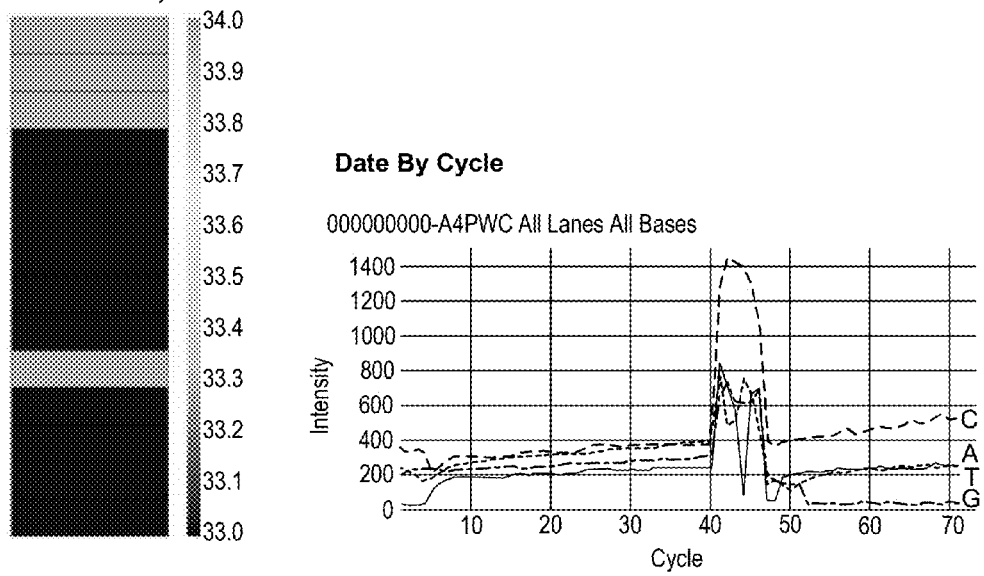
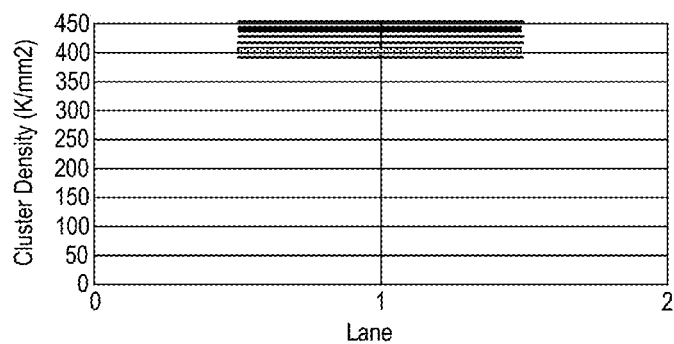

FIG. 10
(Continued)
QScore Distribution
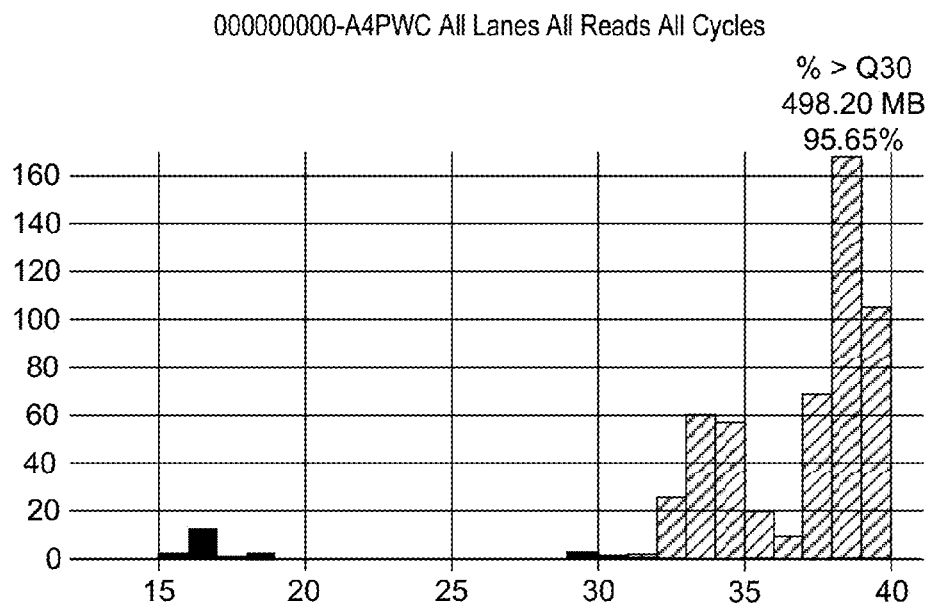
QScore Heatmap
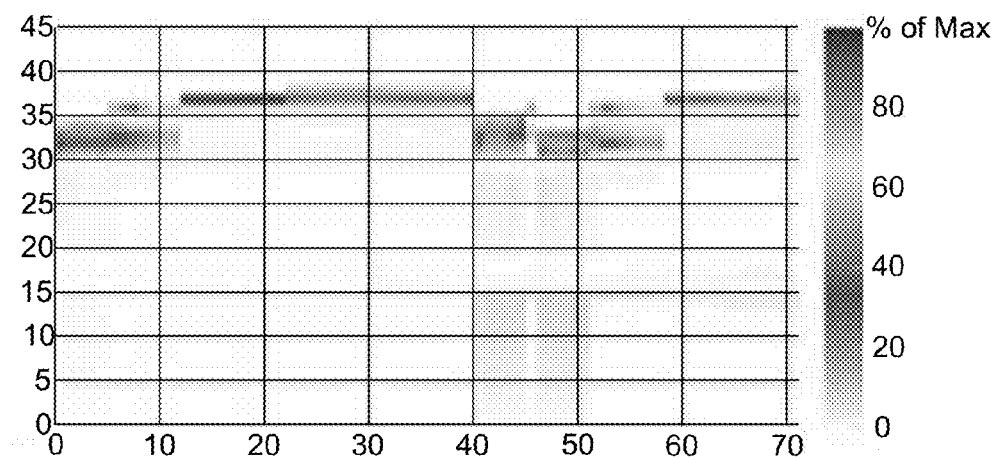

FIG. 14
40+6+25 run
Flowcell Chart
000000000-A3BVR Cycle 1 Base A
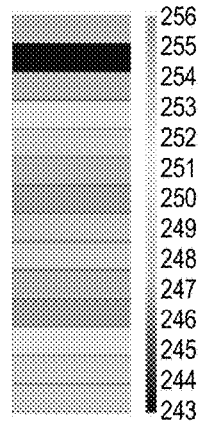
Date By Cycle
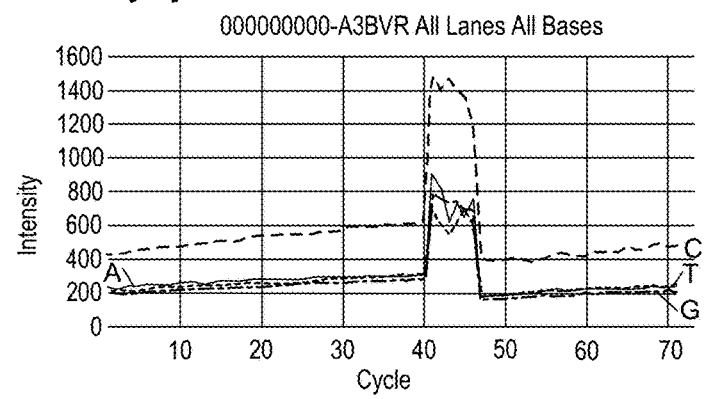
Date By Lane
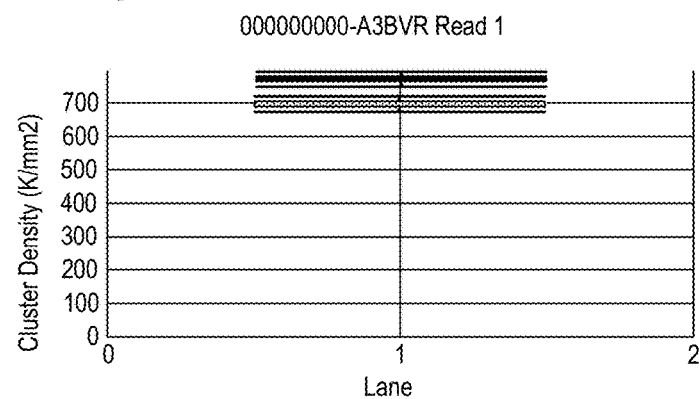

FIG. 14
(Continued)
QScore Distribution
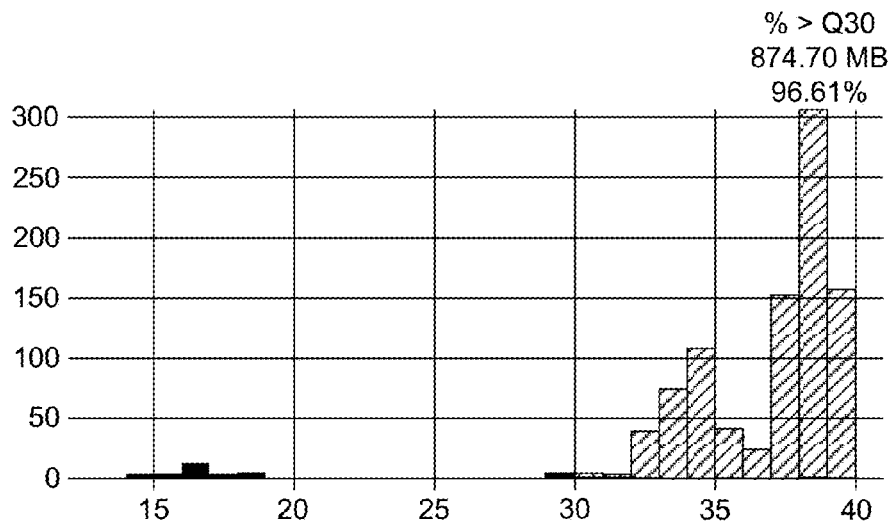
QScore Heatmap
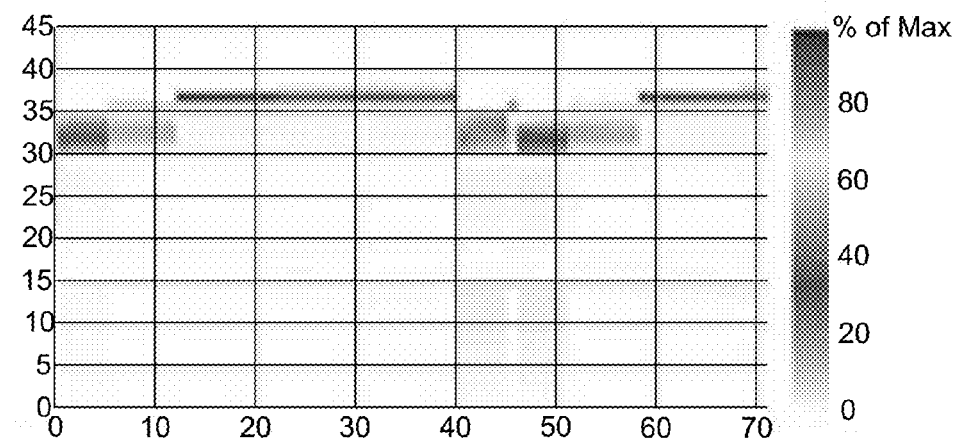

Adaptors at each end can be different lengths.

H = A, C, or T
D = A, G, or T
Y = C or T

FC-FWD/MetSeq 5'-...GAtGTGTGtTTTtGAttTDDDYGG —— insert —— tCGHHHAGATCGGAAGAGCACGTC...TTG-3'
MetSeq 5'...GGAGTTTAGATGTGTGTTTTTTGATTT Forward Read
Within the 6nt at 5' end, look for YGG and trim the 0-3 D's before it:
YGG..insert    (what if YGG not found?)
DYGG..insert   (what to do with non-D bases?)
DDYGG..insert.
DDDYGG..insert (but in this case, DDD can = TGG, so how to tell if adaptor or real insert?)

Within the 6nt at 3' end (after adaptor trimming is done), look for TCG and trim it and the 0-3 H's after it:
insert..TCGHHH
insert..TCGHH
insert..TCGH
insert..TCG
It's OK if TCG not found, the MspI fragment can be larger than the read length.
If TCG not found, look for TC at 3' end and remove it, and if TC not found, look for T at 3' end and remove it.

properly trimmed Forward read:     c   Methylated
5' YGG...insert...

FIG. 18B

Adaptors at each end can be different lengths.

H = A, C, or T
D = A, G, or T
Y = C or T
R = A or G

FC-FWD/MetSeq 5'-...GAtGTGTGtT*TTttGAtTtDDDYGG —— insert —— tCGHHHAGATCGGAAGAGCACACGTC...TTG-3'
                                                                  LGLYGGCLLGLLCGLLCGGALC"""GACGTTGGCTCTCTTCGGATC TS Rev 5' GACGTTGGCTCTCTTCGGATC"""GAG 5'

Reverse Read
Within the 6nt at 5' end, look for CGA and trim the 0-3 D's and the CGA (since this contains no genomic info other than it's an MspI site):
CGA..insert
DCGA..insert
DDCGA..insert
DDDCGA..insert Within the 6nt at 3' end (after adaptor trimming is done), look for CCR and trim the 0-3 H's after it:
insert..CCRHHH
insert..CCRHH
insert..CCRH
insert..CCR
It's OK if CCR is not found, the MspI fragment can be larger than the read length.

→ properly trimmed Reverse read:
5' insert...(may or may not end in CCR, depending on the MspI fragment size and readlength)

c  Methylated

FIG. 19

D0 = 1
D1 = 3
D2 = 3x3 = 9
D3 = 3x3x3 = 27 total diversity = 40

FIG. 20

| Sample | ng | Sequences analysed in total | Mapping efficiency | No alignments | Did not map uniquely. | CT/CT. | CT/GA. | mCG | mCHG | mCHH | Total CpGs analysed |
|---|---|---|---|---|---|---|---|---|---|---|---|
| NA19238 | 400 | 28,467,191 | 59.58% | 7.52% | 32.91% | 8,464,806 | 8,495,775 | 28.6% | 0.5% | 0.3% | 47,208,201 |
| NA19238 | 100 | 27,239,653 | 58.42% | 6.94% | 34.64% | 7,944,860 | 7,968,954 | 32.7% | 0.5% | 0.3% | 42,071,026 |
| NA19238 | 25 | 26,732,815 | 58.28% | 6.81% | 34.92% | 7,774,534 | 7,804,757 | 34.9% | 0.5% | 0.4% | 39,632,176 |
| NA19238 | 6.25 | 28,820,811 | 57.86% | 7.09% | 35.05% | 8,324,948 | 8,351,549 | 34.9% | 0.6% | 0.4% | 42,654,227 |
| NA19238 | 1.56 | 25,889,539 | 57.46% | 7.46% | 35.08% | 7,425,771 | 7,451,201 | 34.5% | 0.6% | 0.5% | 38,504,765 |
| IMR90 | 100 | 27,431,639 | 59.94% | 6.59% | 33.47% | 8,213,675 | 8,228,851 | 30.5% | 0.5% | 0.3% | 44,343,781 |
| IMR90 | 100 | 29,671,768 | 59.59% | 6.75% | 33.67% | 8,833,296 | 8,846,892 | 31.0% | 0.5% | 0.3% | 47,371,339 |
| WGBS | 50 | 21,577,677 | 75.66% | 6.5% | 17.8% | 8,161,875 | 8,163,270 | 76.7% | 1.2% | 1.2% | 5,495,435 |

FIG. 21

| | Sample | ng | Ave CpG per Read Total | Ave CpG per Uniquely Aligned Read |
|---|---|---|---|---|
| RRBS | NA19238 | 400 | 1.66 | 2.78 |
| | NA19238 | 100 | 1.54 | 2.64 |
| | NA19238 | 25 | 1.48 | 2.54 |
| | NA19238 | 6.25 | 1.48 | 2.56 |
| | NA19238 | 1.56 | 1.49 | 2.59 |
| | IMR90 | 100 | 1.62 | 2.70 |
| | IMR90 | 100 | 1.60 | 2.68 |
| | WGBS | 50 | 0.25 | 0.34 |

FIG. 22

| Sample | ng | CpG Islands | | | CpG Shores | | | Promoters | | |
|---|---|---|---|---|---|---|---|---|---|---|
| | | 1x depth | 5x depth | 20x depth | 1x depth | 5x depth | 20x depth | 1x depth | 5x depth | 20x depth |
| NA19238 | 400 | 1,504,475 | 1,266,783 | 667,786 | 656,096 | 461,332 | 170,336 | 1,664,663 | 1,324,874 | 660,439 |
| NA19238 | 100 | 1,476,388 | 1,260,019 | 432,222 | 659,484 | 482,788 | 110,350 | 1,647,854 | 1,334,295 | 430,005 |
| NA19238 | 25 | 1,450,314 | 1,236,153 | 306,773 | 654,881 | 486,022 | 89,159 | 1,524,751 | 1,318,058 | 312,095 |
| NA19238 | 6.25 | 1,436,633 | 1,228,801 | 399,082 | 644,323 | 479,246 | 125,823 | 1,603,990 | 1,306,739 | 408,945 |
| NA19238 | 1.56 | 1,374,221 | 1,149,018 | 345,608 | 596,378 | 436,296 | 107,778 | 1,516,399 | 1,215,205 | 353,982 |
| IMR90 | 100 | 1,463,177 | 1,257,887 | 552,607 | 653,059 | 472,682 | 145,786 | 1,625,626 | 1,323,880 | 546,676 |
| IMR90 | 100 | 1,469,576 | 1,272,816 | 619,104 | 658,688 | 483,909 | 170,471 | 1,636,068 | 1,343,959 | 615,871 |
| insilico 40nt SE 40-300bp | | 1,213,017 | | | 507,061 | | | 1,305,452 | | |
| insilico 40nt SE all sizes | | 1,665,942 | | | 852,847 | | | 2,025,019 | | |

FIG. 24

TABLE 1 | Comparison of genome-wide DNA methylation profiling technologies*.

| | RRBS | MeDIP-seq | MethylCap-seq/MBD-seq | WGBS | Infinium 27K |
|---|---|---|---|---|---|
| Method for enriching CpGs | CCGG/MspI | Anti-mC antibody | mC-binding protein | N/A | Predefined set |
| Genomic DNA input | 0.01-0.3 µg | 0.3-5 µg | 1-3 µg | 5 µg | 0.5-1 µg |
| Maximum resolution (bp) | 1 | >100 | >100 | 1 | 1 |
| Theoretical genomic coverage | 10% | 100% | 100% | 100% | 0.1% |
| Actual coverage (≥10 reads^) | 9% | 9% | 14% | 76% | 0.1% |
| Illumina reads per sample | ~10 million | ~50 million | ~50 million | >500 million | Microarray based |

RRBS is appropriate for analysis of small amounts of DNA, e.g., from FACS-purified cell populations or embryonic tissue. Analysis of clinical samples in FFPE tissues or laser-microdissected tissue material, studies with a focus on CpG islands and gene promoters (while also sampling a sizable percentage of other genomic elements), studies investigating small effects (e.g., for non-cancer diseases, or environmental effects) that require high sequencing depth and many samples, to achieve sufficient sensitivity and reproducibility across several labs. mC methylation. ^Adapted from reference 31. *Quantitative measurement of DNA methylation requires a minimum number of overlapping reads. Very deep sequencing is necessary to achieve the same read coverage per CpG as RRBS (which is the key determinant of method sensitivity and accuracy).

| | Class | CpG Island | CpG shores | Promoters | Enhancers | Coding Exons | Introns |
|---|---|---|---|---|---|---|---|
| Genome-wide | # regions in Class | 27,718 | 45,494 | 82,145 | 1,339 | 377,744 | 404,405 |
| | Average Size | 764.1 | 2,225.6 | 2,334.9 | 1,522.2 | 165.6 | 6,422.8 |
| | Total # CpG | 2,089,538 | 2,287,717 | 4,148,299 | 22,160 | 1,951,024 | 26,571,158 |
| | CpG per Kbp | 97.3 | 20.9 | 20.3 | 11.4 | 28.7 | 14.0 |
| | Stranded CpG | 4,179,076 | 4,575,434 | 8,296,598 | 44,320 | 3,902,048 | 53,142,316 |
| RRBS | 100nt SE | 2,187,671 | 1,003,815 | 2,431,738 | 3,860 | 984,468 | 5,022,090 |
| | 50nt SE | 1,452,825 | 606,959 | 1,564,822 | 2,578 | 629,482 | 2,786,556 |
| | 40nt SE | 1,213,017 | 507,061 | 1,305,452 | 2,270 | 528,990 | 2,277,500 |

RRBS analysis considers 40-300bp Msp I fragments and assumes 0% methyl-C and 100% bisulfite conversion.

1 CpG = 2 "Stranded CpG" measurements

FIG. 26
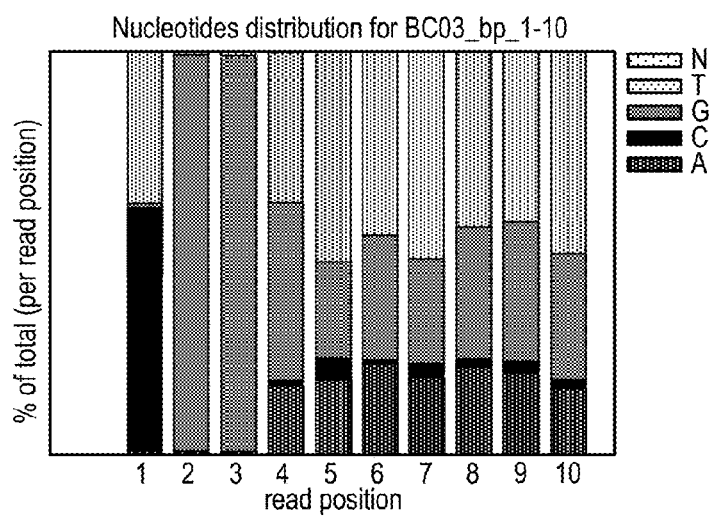
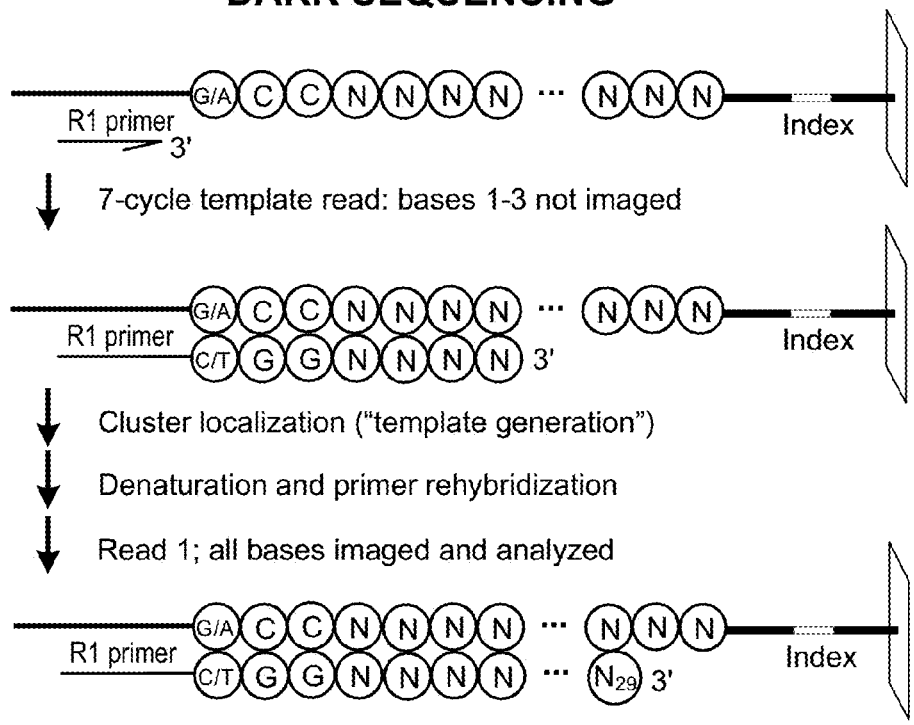

FIG. 35

*D and R bases comprise DNA sequence derived from library construction

| | | | |
|---|---|---|---|
| 0 diversity bases added | 5' | YGG(BCO) | BCO = Bisulfite-Converted Original genomic strand |
| 1 diversity base added | 5' | DYGG(BCO) | Y = C or T, depending on methylation status |
| 2 diversity bases added | 5' | DDYGG(BCO) | D = A, G, or T |
| 3 diversity bases added | 5' | RDDYGG(BCO) | R = A or G |

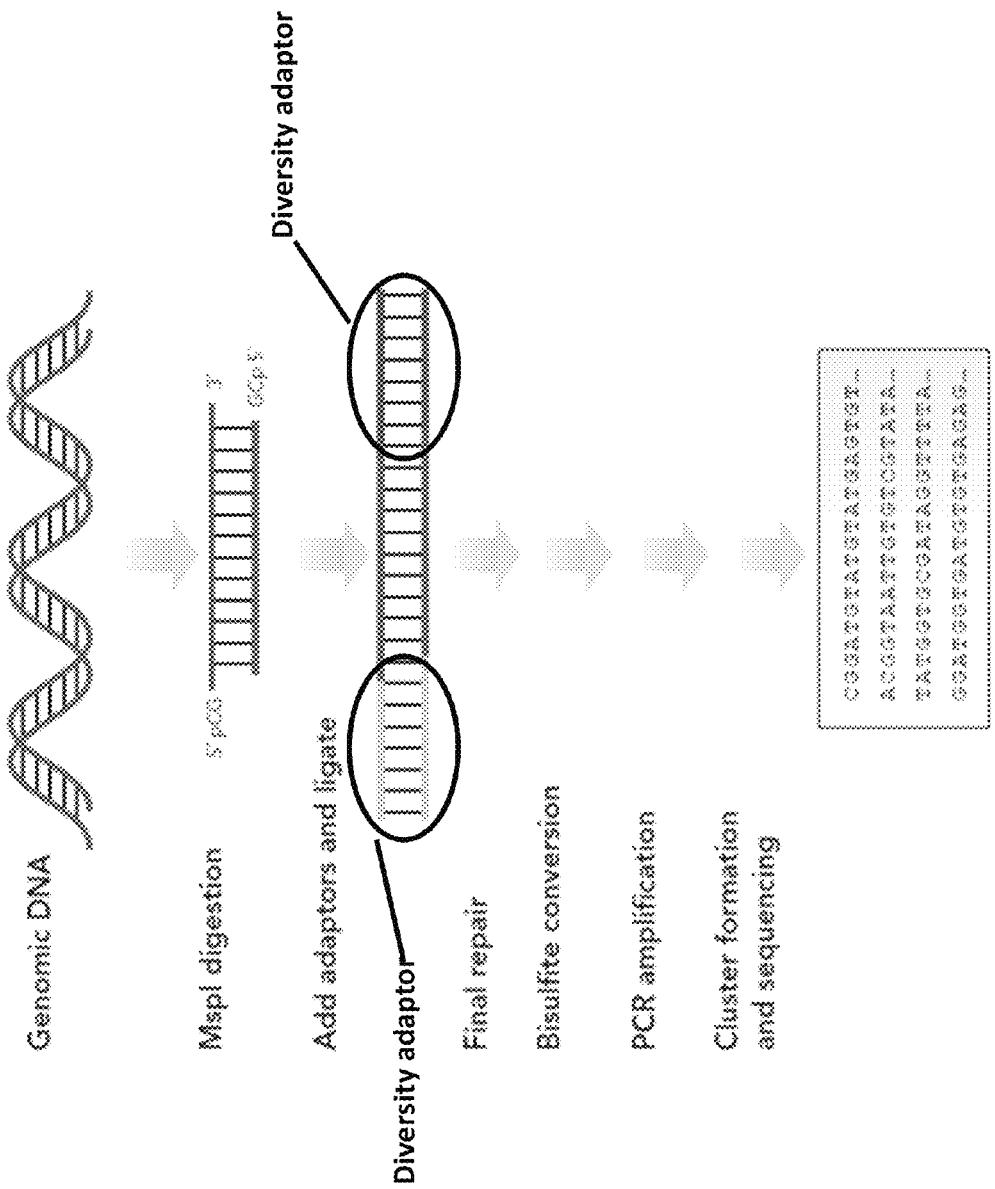

SEQUENCE LISTING

```
<160> NUMBER OF SEQ ID NOS: 32

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaatcaaaaa aac                                                        13

<210> SEQ ID NO 2
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 rddcggagtt                                                              10

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aagggccghh y                                                            11

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 aactccghhy                                                              10

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
rddcggccct t                                                            11

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 rddyggagtt                                                              10

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aagggtcghh y                                                            11

<210> SEQ ID NO 8
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 8 aactccrhhy                                                          10

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
rddcgaccct t                                                        11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
rddcgaccct t                                                        11

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 aactccrhhy                                                          10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 aagggtcghh                                                          10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 ddcgaccctt                                                          10

<210> SEQ ID NO 14
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: 5' Biotin
<220> FEATURE:
<221> NAME/KEY: modified_base
<222> LOCATION: (18)..(18)
<223> OTHER INFORMATION: dideoxycytosine

<400> SEQUENCE: 14
cghhhagatc ggaagagc                                                        18

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Biotin
<220> FEATURE:
<221> NAME/KEY: modified_base
<222> LOCATION: (17)..(17)
<223> OTHER INFORMATION: dideoxycytosine

<400> SEQUENCE: 15
cghhagatcg gaagagc                                                         17

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Biotin
<220> FEATURE:
<221> NAME/KEY: modified_base
<222> LOCATION: (16)..(16)
<223> OTHER INFORMATION: dideoxycytosine

<400> SEQUENCE: 16
cghagatcgg aagagc                                                          16

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Biotin
<220> FEATURE:
<221> NAME/KEY: modified_base
<222> LOCATION: (15)..(15)
<223> OTHER INFORMATION: dideoxycytosine

<400> SEQUENCE: 17
cgagatcgga agagc                                                           15

<210> SEQ ID NO 18
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 18
caagcagaag acggcatacg tgatctggtt gtgactggag ttctgacgtg tgctcttccg    60
atct                                                                64

<210> SEQ ID NO 19
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
caagcagaag acggcatacg tgatctggtt gtgactggag ttctgacgtg tgctcttccg    60 atctddd                                                             67

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gacgtgtgct cttccgatct dddcgg                                        26

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccghhhagat cggaagagc                                                19

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Methylated nucleotide
<220> FEATURE:
<221> NAME/KEY: modified_base
<222> LOCATION: (11)..(11)
<223> OTHER INFORMATION: Methylated nucleotide
<220> FEATURE:
<221> NAME/KEY: modified_base
<222> LOCATION: (19)..(19)
<223> OTHER INFORMATION: Methylated nucleotide
<220> FEATURE:
<221> NAME/KEY: modified_base
<222> LOCATION: (21)..(21)
<223> OTHER INFORMATION: Methylated nucleotide
<220> FEATURE:
<221> NAME/KEY: modified_base
<222> LOCATION: (23)..(23)
<223> OTHER INFORMATION: Methylated nucleotide
<220> FEATURE:
<221> NAME/KEY: modified_base
<222> LOCATION: (26)..(26)

<223> OTHER INFORMATION: Methylated nucleotide

<400> SEQUENCE: 22 ccghhagat cggaagagca cacgtc                                    26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatgtgtgtt tttttgattt dddygg                                   26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Methylated nucleotide
<220> FEATURE:
<221> NAME/KEY: modified_base
<222> LOCATION: (11)..(11)
<223> OTHER INFORMATION: Methylated nucleotide
<220> FEATURE:
<221> NAME/KEY: modified_base
<222> LOCATION: (19)..(19)
<223> OTHER INFORMATION: Methylated nucleotide
<220> FEATURE:
<221> NAME/KEY: modified_base
<222> LOCATION: (21)..(21)
<223> OTHER INFORMATION: Methylated nucleotide
<220> FEATURE:
<221> NAME/KEY: modified_base
<222> LOCATION: (23)..(23)
<223> OTHER INFORMATION: Methylated nucleotide
<220> FEATURE:
<221> NAME/KEY: modified_base
<222> LOCATION: (26)..(26)
<223> OTHER INFORMATION: Methylated nucleotide

<400> SEQUENCE: 24 tcghhagat cggaagagca cacgtc                                    26

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gacgtgtgct cttccgatct                                          20

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggagtttaga tgtgtgtttt tttgattt                                              28

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (21)..(23)
<223> OTHER INFORMATION: May or may not be present

<400> SEQUENCE: 27
gatgtgtgtt tttttgattt dddygg                                                26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: Methylated nucleotide
<220> FEATURE:
<221> NAME/KEY: misc_feature
<222> LOCATION: (4)..(6)
<223> OTHER INFORMATION: May or may not be present
<220> FEATURE:
<221> NAME/KEY: modified_base
<222> LOCATION: (11)..(11)
<223> OTHER INFORMATION: Methylated nucleotide
<220> FEATURE:
<221> NAME/KEY: modified_base
<222> LOCATION: (19)..(19)
<223> OTHER INFORMATION: Methylated nucleotide
<220> FEATURE:
<221> NAME/KEY: modified_base
<222> LOCATION: (21)..(21)
<223> OTHER INFORMATION: Methylated nucleotide
<220> FEATURE:
<221> NAME/KEY: modified_base
<222> LOCATION: (23)..(23)
<223> OTHER INFORMATION: Methylated nucleotide
<220> FEATURE:
<221> NAME/KEY: modified_base
<222> LOCATION: (26)..(26)
<223> OTHER INFORMATION: Methylated nucleotide

<400> SEQUENCE: 28
tcghhhagat cggaagagca cacgtc                                                26

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cggatgtatg tatgagtgt                                                        19

<210> SEQ ID NO 30
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 30
acggtaattg tgtcgtata                                                19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tatggtgcga taggtttta                                                19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggatggtgat gtgtgagag                                                19
```

REDUCED REPRESENTATION BISULFITE SEQUENCING WITH DIVERSITY ADAPTORS

CROSS-REFERENCE

This application claims the benefit of U.S. Provisional Application No. 61/946,617, filed on Feb. 28, 2014, and U.S. Provisional Application No. 61/968,982, filed on Mar. 21, 2014, each of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Mar. 27, 2015, is named 25115-764.201_SL.txt and is 9,982 bytes in size.

BACKGROUND

DNA methylation is an epigenetic modification that can occur at the C5 position of cytosine residues. In mammals, 5-methylcytosine can appear in the CpG dinucleotide context (Ramsahoye et al., *Proc Natl Acad Sci USA* 97:5237-5242, 2000). Recent data suggests that approximately 25% of all cytosine methylation identified in stem cells can occur in non-CpG context (see Ziller et al., *PLoS Genet.* 7 (12): e1002389, 2011). Although CpG dinucleotides can be underrepresented in the genome, stretches of sequences known as CpG islands can exist that are rich in CpG dinucleotides. These CpG islands can be associated with promoter regions and span several hundred nucleotides or more.

Epigenomics, i.e., the study of the complete set of epigenetic modifications on the genetic material of a cell, has revealed that epigenetic modifications (e.g., DNA methylation) can play a role in mammalian development and disease. For example, DNA methylation is implicated in embryonic development, genomic imprinting and X-chromosome inactivation through regulation of transcriptional activity, chromatin structure and chromatin stability (Robertson, *Nat Review Genet* 6:597-610, 2005). Increased DNA methylation (hypermethylation) at promoter regions of genes can be associated with transcriptional silencing, whereas decreased methylation (hypomethylation) at promoter regions can be associated with increased gene activity. Aberrant methylation patterns can be associated with various human pathologies, including tumor formation and progression (Feinberg and Fogelstein, *Nature* 301:89-92, 1983; Esteller, *Nat Review Genet* 8: 286-298, 2007; and Jones and Paylin, *Cell* 128:683-692, 2007). Therefore, analysis of DNA methylation status across the human genome can be of interest.

Methods for measuring DNA methylation at specific genomic loci include, for example, immunoprecipitation of methylated DNA, methyl-binding protein enrichment of methylated fragments, digestion with methylation-insensitive restriction enzymes, and bisulfite conversion followed by Sanger sequencing (reviewed in Laird, *Nat Review Genet* 11: 191-203, 2010). Bisulfite treatment can convert unmethylated cytosine residues into uracils (the readout of which can be thymine after amplification with a polymerase). Methylcytosines can be protected from conversion by bisulfite treatment to uracils. Following bisulfite treatment, methylation status of a given cytosine residue can be inferred by comparing the sequence to an unmodified reference sequence.

Techniques have been developed for profiling methylation status of the whole genome, i.e. the methylome, at a single-base resolution using high throughput sequencing technologies. Bisulfite conversion of genomic DNA combined with next generation sequencing (NGS), or BS-seq, is one strategy. Because of the high cost still associated with genome-wide methylation sequencing, variations of BS-seq technology that enable genome partitioning to enrich for regions of interest can be used. One such variation is reduced representation BS-seq (RRBS), which can involve digestion of a DNA sample with a methylation-insensitive restriction endonuclease that has CpG dinucleotide as a part of its recognition site, followed by bisulfite sequencing of the selected fragments (Meissner et al., *Nucleic Acids Res.* 33(18):5868-5877, 2005). RRBS provides less coverage than whole genome bisulfite sequencing, but allows the researcher to obtain quantitative DNA methylation information across many features with approximately 50-fold fewer sequencing reads, resulting in substantial sequencing cost reduction. Since the RRBS technique was first described (Meissner, et al. (2005) *Nucleic Acids Res* 33(18):5868), there have been many enhancements and improvements (see for example, Boyle, et al. (2012) *Genome Biol* 13:R92). The current approach utilizes the methylation insensitive restriction enzyme MspI, which recognizes CCGG. As a result of partial fragmentation during bisulfite conversion, PCR, and efficiency of cluster generation, only a subset of these fragments, typically under 300 bp in length, can be sequenced. However these smaller fragments are derived from genomic DNA that has a high frequency of MspI sites and therefore a high frequency of potential CpG methylation sites. This is how RRBS can achieve reduced representation. One feature of RRBS can be that all forward reads start with either TGG or CGG. This feature can create a lack of color balance that can be problematic for some NGS sequencers. For example, the complete lack of color balance at bases 2 and 3 can make these samples very challenging for both Illumina MiSeq and HiSeq instruments. The methods, compositions and kits provided herein can allow RRBS libraries to be generated easily and sequenced more efficiently by increasing the diversity of nucleotide bases sequenced during the initial cycles of sequencing. The increased diversity can increase the efficiency and accuracy of cluster identification by sequencers during certain types of next generation sequencing applications (e.g., Illumina based sequencing by synthesis).

SUMMARY

In one aspect, provided herein is a method for increasing diversity of sequences at ends of a plurality of polynucleotides in a sample, the method comprising introducing a pool of oligonucleotide sequences to 3' ends of the plurality of polynucleotides, a. wherein each oligonucleotide sequence in the pool of oligonucleotide sequences comprises a sequence complementary to a sequencing primer, b. wherein the pool of oligonucleotide sequences comprises a first sequence, wherein a terminal 3' nucleotide base of the sequencing primer is capable of annealing to a terminal 5' nucleotide base of the first sequence, wherein following introduction the 5' end of the first sequence is adjacent to a 3' end of a polynucleotide from the plurality of polynucleotides, c. wherein the pool of oligonucleotide sequences comprises a second sequence, wherein the second sequence terminates at its 5' end with an additional base relative to the 5' end of the first sequence, wherein following introduction the 5' end of the second sequence is adjacent to a 3' end of a polynucleotide from the plurality of polynucleotides; d. wherein the pool of oligonucleotide sequences comprises a third sequence, wherein the third sequence terminates at its 5' end with two additional bases relative to the 5' end of the first sequence, wherein following introduction the 5' end of the third sequence is adjacent to a 3' end of a polynucleotide from the plurality of polynucleotides; e. wherein the pool of oligonucleotide sequences comprises a fourth sequence, wherein the fourth sequence terminates at its 5' end with three additional bases relative to the 5' end of the first sequence, wherein following introduction the 5' end of the fourth sequence is adjacent to a 3' end of a polynucleotide from the plurality of polynucleotides; and f. wherein the introducing generates a plurality of oligonucleotide-polynucleotide complexes, thereby increasing diversity of sequences at ends of the plurality of polynucleotides. In some cases, the sample is a whole genome sample. In some cases, the sample comprises a polynucleotide library. In some cases, the method further comprises fragmenting the polynucleotides prior to introducing the pool of oligonucleotide sequences to the 3' ends of the plurality of polynucleotides. In some cases, the fragmenting is performed by contacting the polynucleotides with an enzyme. In some cases, the enzyme is a restriction enzyme. In some cases, the restriction enzyme is a methylation insensitive restriction enzyme. In some cases, the methylation insensitive restriction enzyme is MspI. In some cases, the additional base of the second sequence is an adenine, thymine, or cytosine base. In some cases, each of the two additional bases of the third sequence is an adenine, thymine, or cytosine base. In some cases, a 3' most base of the three additional bases of the fourth sequence comprises a thymine or cytosine base, and each of the two other bases of the three additional bases of the fourth sequence comprises an adenine, thymine, or cytosine base. In some cases, each oligonucleotide sequence in the pool of oligonucleotide sequences is within a strand of a duplexed adaptor. In some cases, the duplexed adaptor is a partial duplexed adaptor comprising a short strand and a long strand. In some cases, the duplexed adaptor is a partial duplexed adaptor comprising two strands of equal length. In some cases, the short strand is a non-ligation strand of the duplexed adaptor, and the long strand is a ligation strand of the duplexed adaptor. In some cases, the non-ligation strand comprises a 5' overhang. In some cases, the 5' overhang comprises two bases. In some cases, the two bases are 3'-GC-5'. In some cases, the introducing comprises a ligation reaction. In some cases, the ligation reaction comprises cohesive end ligation. In some cases, the ligation reaction comprises blunt end ligation. In some cases, the plurality of polynucleotides are strands of double-stranded nucleic acids, wherein each 5' end of the double-stranded nucleic acids comprises a ligation end and each 3' end comprises a non-ligation end, wherein each of the non-ligation ends of the double-stranded nucleic acid comprises part of the polynucleotide sequence. In some cases, the 3'-GC-5' of the non-ligation strand of the duplexed adaptor anneals to a 5'-CG-3' sequence of the ligation end of the double-stranded sequence comprising the polynucleotide sequence. In some cases, the 3'-GC-5' of the non-ligation strand of the duplexed adaptor is 5' to the terminal 5' nucleotide base of the first sequence. In some cases, the 3'-GC-5' of the non-ligation strand of the duplexed adaptor is 5' to the additional base of the second sequence relative to the 5' end of the first sequence. In some cases, the 3'-GC-5' of the non-ligation strand of the duplexed adaptor is 5' to the two additional bases of the third sequence relative to the 5' end of the first sequence. In some cases, the 3'-GC-5' of the non-ligation strand of the duplexed adaptor is 5' to the three additional bases of the fourth sequence relative to the 5' end of the first sequence. In some cases, the ligation strand is capable of ligating to a 5' end of the plurality of polynucleotides, and wherein a nick is formed between the non-ligation strand and the end of the plurality of polynucleotides. In some cases, the method further comprises an extending step, wherein the non-ligation end of the plurality of polynucleotides is extended using a polymerase in the presence of a mixture of dNTPs using the ligation strand of the adaptor as template, thereby introducing the pool of oligonucleotide sequences to the 3' ends of the plurality of polynucleotides. In some cases, the ligation strand of each adaptor duplex in the pool comprise cytosine analogs resistant to bisulfite treatment and the mixture of dNTPs comprises dATP, dTTP, dGTP, and dCTP, whereby the extending generates the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, the ligation strand of each adaptor duplex in the pool of adaptor duplexes comprise cytosine bases sensitive to bisulfite treatment and the mixture of dNTPs comprises dATP, dTTP, dGTP, and a dCTP analog resistant to bisulfite treatment, whereby the extending generates the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, each oligonucleotide sequence in the pool of oligonucleotide sequences is a primer, wherein the pool of oligonucleotide sequences comprises the primer and a complement thereof. In some cases, the introducing comprises an amplification reaction. In some cases, the amplification reaction comprises polymerase chain reaction. In some cases, each of the primers in the pool comprises cytosine bases sensitive to bisulfite treatment, wherein the amplification is conducted in the presence of a mixture of dNTPs comprising dATP, dTTP, dGTP, and a dCTP analog resistant to bisulfite treatment, thereby generating the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, each of the primers in the pool of primers comprises cytosine analogs resistant to bisulfite treatment, wherein the amplification is conducted in the presence of a mixture of dNTPs comprising dATP, dTTP, dGTP, and dCTP, thereby generating the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, the cytosine analog resistant to bisulfite treatment is 5-methylcytosine, 5-hydroxymethylcytosine, or 5-propynylcytosine. In some cases, the cytosine analog resistant to bisulfite treatment is 5-methylcytosine. In some cases, the method further comprises amplifying the plurality of oligonucleotide sequence-polynucleotide complexes, wherein the amplifying comprises solid-phase nucleic acid amplification to generate a plurality of clusters, wherein each cluster represents a plurality of copies of each of the plurality of oligonucleotide sequence-polynucleotide complexes. In some cases, the method further comprises treating the plurality of oligonucleotide sequence-polynucleotides complexes with bisulfite prior to the amplification, wherein the treating generates a plurality of oligonucleotide sequence-polynucleotide complexes comprising non-complementary ends. In some cases, the treating with bisulfite prior to amplification generates the sequence complementary to a sequencing primer in each oligonucleotide sequence in the pool of oligonucleotide sequences comprises. In some cases, the method further comprises sequencing each of the plurality of clusters, wherein the sequencing comprises hybridizing the sequencing primer to the sequence complementary to a sequencing primer, and conducting sequencing by synthesis. In some cases, the introducing of the pool of oligonucleotide sequences to the polynucleotides improves identification of each of the plurality of clusters generated from the plurality of oligonucleotide sequence-polynucleotide complexes relative to the identification of each cluster from a plurality of clusters generated from the plurality of polynucleotides not introduced to the pool of oligonucleotide sequences. In some cases, the sequencing comprises paired-end sequencing.

In one aspect, provided herein is a method for generating a bisulfite converted library, the method comprising: a. introducing a pool of oligonucleotide sequences to each end of a plurality of polynucleotides from a sample, i. wherein each oligonucleotide sequence in the pool of oligonucleotide sequences comprises a sequence complementary to a sequencing primer and a sequence element adjacent to the sequence complementary to a sequencing primer, ii. wherein the pool of oligonucleotide sequences comprises a first sequence, wherein the first sequence terminates at its 3' end with the sequence element, wherein following ligation the 3' end of the sequence element is adjacent to a 5' end of a polynucleotide from the plurality of polynucleotides, iii. wherein the pool of oligonucleotide sequences comprises a second sequence, wherein the second oligonucleotide sequence terminates at its 3' end with an additional base relative to the 3' end of the first sequence, wherein following ligation the 3' end of the second sequence is adjacent to a 5' end of a polynucleotide from the plurality of polynucleotides; iv. wherein the pool of oligonucleotide sequences comprises a third sequence, wherein the third sequence terminates at its 3' end with two additional bases relative to the 3' end of the first sequence, wherein following ligation the 3' end of the third sequence is adjacent to a 5' end of a polynucleotide from the plurality of polynucleotides; v. wherein the pool of oligonucleotide sequences comprises a fourth sequence, wherein the fourth sequence terminates at its 3' end with three additional bases relative to the 3' end of the first sequence, wherein following ligation the 3' end of the fourth sequence is adjacent to a 5' end of a polynucleotide from the plurality of polynucleotides; vi. wherein the introducing generates a plurality of oligonucleotide sequence-polynucleotide complexes; and b. treating the plurality of oligonucleotide sequence-polynucleotide complexes with bisulfite, thereby generating a bisulfite converted polynucleotide library. In some cases, the sample is a whole genome sample. In some cases, the sample comprises a polynucleotide library. In some cases, the method further comprises fragmenting the polynucleotides prior to introducing the pool of oligonucleotide sequences to the 3' ends of the plurality of polynucleotides. In some cases, the fragmenting is performed by contacting the polynucleotides with an enzyme. In some cases, the enzyme is a restriction enzyme. In some cases, the restriction enzyme is a methylation insensitive restriction enzyme. In some cases, the methylation insensitive restriction enzyme is MspI. In some cases, the additional base of the second sequence is an adenine, thymine, or guanine base. In some cases, each of the two additional bases of the third sequence is an adenine, thymine, or guanine base. In some cases, a 5' most base of the three additional bases of the fourth sequence comprises an adenine or guanine base, and each of the two other bases of the three additional bases of the fourth sequence comprises an adenine, thymine, or guanine base. In some cases, each oligonucleotide sequence in the pool of oligonucleotide sequences is within a strand of a duplexed adaptor. In some cases, the duplexed adaptor is a partial duplexed adaptor. In some cases, the strand is a ligation strand of the duplexed adaptor. In some cases, the non-ligation strand comprises a 5' overhang. In some cases, the 5' overhang comprises two bases. In some cases, the two bases are 3'-GC-5'. In some cases, the introducing comprises a ligation reaction. In some cases, the ligation reaction comprises cohesive end ligation. In some cases, the ligation reaction comprises blunt end ligation. In some cases, the plurality of polynucleotides are double-stranded nucleic acids, wherein each 5' end of the double-stranded nucleic acids comprises a ligation end and each 3' end comprises a non-ligation end. In some cases, each duplexed adaptor in the pool comprises a ligation strand and a non-ligation strand, wherein the ligation strand is capable of ligating to the ligation end of the plurality of polynucleotides, and wherein a nick is formed between the non-ligation strand and the non-ligation end of the plurality of polynucleotides. In some cases, the method further comprises an extending step, wherein the non-ligation end of the plurality of polynucleotides is extended using a polymerase in the presence of a mixture of dNTPs using the ligation strand of the adaptor as template, thereby introducing the pool of oligonucleotide sequences to the 3' ends of the plurality of polynucleotides. In some cases, the ligation strand of each adaptor duplex in the pool comprise cytosine analogs resistant to bisulfite treatment and the mixture of dNTPs comprises dATP, dTTP, dGTP, and dCTP, whereby the extending generates the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, the ligation strand of each adaptor duplex in the pool of adaptor duplexes comprise cytosine bases sensitive to bisulfite treatment and the mixture of dNTPs comprises dATP, dTTP, dGTP, and a dCTP analog resistant to bisulfite treatment, whereby the extending generates the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, each oligonucleotide sequence in the pool of oligonucleotide sequences is within a primer, wherein the pool of oligonucleotide sequences comprises the primer and a complement thereof. In some cases, the introducing comprises an amplification reaction. In some cases, the amplification reaction comprises polymerase chain reaction. In some cases, each of the primers in the pool comprises cytosine bases sensitive to bisulfite treatment, wherein the amplification is conducted in the presence of a mixture of dNTPs comprising dATP, dTTP, dGTP, and a dCTP analog resistant to bisulfite treatment, thereby generating the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, each of the primers in the pool of primers comprises cytosine analogs resistant to bisulfite treatment, wherein the amplification is conducted in the presence of a mixture of dNTPs comprising dATP, dTTP, dGTP, and dCTP, thereby generating the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, the cytosine analog resistant to bisulfite treatment is 5-methylcytosine, 5-hydroxymethylcytosine, or 5-propynylcytosine. In some cases, the cytosine analog resistant to bisulfite treatment is 5-methylcytosine. In some cases, the method further comprises amplifying the plurality of amplifying the plurality of oligonucleotide sequence-polynucleotide complexes. In some cases, the amplifying comprises solid-phase nucleic acid amplification to generate a plurality of clusters, wherein each cluster represents a plurality of copies of each of the plurality of oligonucleotide sequence-polynucleotide complexes. In some cases, the method further comprises treating the plurality of oligonucleotide sequence-polynucleotides complexes with bisulfite prior to the amplification, wherein the treating generates a plurality of oligonucleotide sequence-polynucleotide complexes comprising non-complementary ends. In some cases, the sequence complementary to a sequencing primer in one end of the plurality of oligonucleotide sequence-polynucleotide complexes comprising non-complementary ends is complementary to a reverse read sequencing primer, and wherein the sequence complementary to a sequencing primer in an opposite end of the non-complementary ends in the plurality of oligonucleotide sequence-polynucleotide complexes comprising non-complementary ends is complementary to a forward read sequencing primer. In some cases, the method further comprises sequencing each of the plurality of clusters, wherein the sequencing comprises hybridizing the sequencing primer to the sequence complementary to a sequencing primer, and conducting sequencing by synthesis, wherein the introducing of the pool of oligonucleotide sequences to the polynucleotides improves identification of each of the plurality of clusters generated from the plurality of oligonucleotide sequence-polynucleotide complexes relative to the identification of each cluster from a plurality of clusters generated from the plurality of polynucleotides not introduced to the pool of oligonucleotide sequences. In some cases, the sequence element comprises a barcode, a universal sequence, a linker sequence, or a random sequence.

In one aspect, provided herein is a kit comprising a pool of oligonucleotide sequences, a. wherein each oligonucleotide sequence in the pool of oligonucleotide sequences comprises a sequence complementary to a sequencing primer, b. wherein the pool of oligonucleotide sequences comprises a first oligonucleotide sequence, wherein a terminal 3' nucleotide base of the sequencing primer is capable of annealing to a terminal 5' nucleotide base of the first oligonucleotide sequence, c. wherein the pool of oligonucleotide sequences comprises a second oligonucleotide sequence, wherein the second oligonucleotide sequence terminates at a 5' end with an additional base relative to the 5' end of the first oligonucleotide sequence; d. wherein the pool of oligonucleotide sequences comprises a third oligonucleotide sequence, wherein the third oligonucleotide sequence terminates at a 5' end with two additional bases relative to the 5' end of the first oligonucleotide sequence; and e. wherein the pool of oligonucleotide sequences comprises a fourth oligonucleotide sequence, wherein the fourth oligonucleotide sequence terminates at a 5' end with three additional bases relative to the 5' end of the first oligonucleotide sequence. In some cases, each oligonucleotide sequence in the pool of oligonucleotide sequences is within a primer, wherein the pool of oligonucleotide sequences comprises the primer and a complement thereof. In some cases, the primer comprises cytosine analogs resistant to bisulfite conversion. In some cases, the primer comprises cytosine bases sensitive to bisulfite conversion. In some cases, each oligonucleotide sequence in the pool of oligonucleotide sequences is within a strand of a duplexed adaptor. In some cases, each duplexed adaptor in the pool comprises a ligation strand and a non-ligation strand. In some cases, the ligation strand and the non-ligation strand of each of duplexed adaptor in the pool comprise cytosine bases sensitive to bisulfite treatment. In some cases, the kit further comprises a mixture of dNTPs comprising dATP, dTTP, dGTP, and a dCTP analog resistant to bisulfite treatment. In some cases, the ligation strand and the non-ligation strand of each of duplexed adaptor in the pool comprise cytosine analogs resistant to bisulfite treatment. In some cases, the kit further comprises a mixture of dNTPs comprising dATP, dTTP, dGTP, and a dCTP analog sensitive to bisulfite treatment. In some cases, the kit further comprises a restriction enzyme. In some cases, the restriction enzyme is MspI. In some cases, the kit further comprises a DNA polymerase. In some cases, the DNA polymerase comprises exonuclease activity. In some cases, the DNA polymerase comprises strand displacement activity. In some cases, the non-ligation strand comprises a block at a 5' and 3' end, whereby the non-ligation strand is enzymatically unreactive. In some cases, the block at the 5' end comprises a biotin moiety. In some cases, the block at the 3' end comprises a dideoxy residue. In some cases, the cytosine analog resistant to bisulfite treatment is 5-methylcytosine, 5-hydroxymethylcytosine, or 5-propynylcytosine. In some cases, the cytosine analog resistant to bisulfite treatment is 5-methylcytosine.

In one aspect, provided herein is a method for analyzing sequence reads, the method comprising: a. generating a plurality of sequence reads, wherein the generating comprises conducting sequencing by synthesis on a plurality of clusters, wherein each cluster of the plurality of clusters comprises copies of one oligonucleotide sequence-polynucleotide from a plurality of oligonucleotide sequence-polynucleotides, wherein the sequencing by synthesis comprises hybridizing a sequencing primer to sequence complementary to the sequencing primer present in each cluster of the plurality of clusters, wherein the plurality of clusters are produced from solid-phase nucleic acid amplification of the plurality of oligonucleotide sequence-polynucleotides, wherein each of the plurality of oligonucleotide sequence-polynucleotides comprises a single nucleotide base extender sequence, a dinucleotide base extender sequence, a trinucleotide base extender sequence or no nucleotide base extender sequence between the sequence complementary to the sequencing primer of an oligonucleotide sequence and an end of a polynucleotide; and b. analyzing each of the plurality of sequence reads, wherein the analyzing comprises trimming or removing the extender sequence in silico from each of the plurality of sequence reads. In some cases, the plurality of oligonucleotide sequence-polynucleotides are generated by introducing a pool of oligonucleotide sequences to 3' ends of the plurality of polynucleotides from a sample, a. wherein each oligonucleotide sequence in the pool of oligonucleotide sequences comprises a sequence complementary to a sequencing primer, b. wherein the pool of oligonucleotide sequences comprises a first sequence, wherein a terminal 3' nucleotide base of the sequencing primer is capable of annealing to a terminal 5' nucleotide base of the first sequence, wherein following introduction the 5' end of the first sequence is adjacent to a 3' end of a polynucleotide from the plurality of polynucleotides, c. wherein the pool of oligonucleotide sequences comprises a second sequence, wherein the second sequence terminates at its 5' end with an additional base relative to the 5' end of the first sequence comprising the single nucleotide base extender, wherein following introduction the 5' end of the second sequence is adjacent to a 3' end of a polynucleotide from the plurality of polynucleotides; d. wherein the pool of oligonucleotide sequences comprises a third sequence, wherein the third sequence terminates at its 5' end with two additional bases relative to the 5' end of the first sequence comprising the dinucleotide base extender, wherein following introduction the 5' end of the third sequence is adjacent to a 3' end of a polynucleotide from the plurality of polynucleotides; e. wherein the pool of oligonucleotide sequences comprises a fourth sequence, wherein the fourth sequence terminates at its 5' end with three additional bases relative to the 5' end of the first sequence comprising the trinucleotide base extender, wherein following introduction the 5' end of the fourth sequence is adjacent to a 3' end of a polynucleotide from the plurality of polynucleotides; and f. wherein the introducing generates a plurality of oligonucleotide-polynucleotide complexes, thereby increasing diversity of sequences at ends of the plurality of polynucleotides. In some cases, the sample is a whole genome sample. In some cases, the sample comprises a polynucleotide library. In some cases, the method further comprises fragmenting the polynucleotides prior to introducing the pool of oligonucleotide sequences to the 3' ends of the plurality of polynucleotides. In some cases, the fragmenting is performed by contacting the polynucleotides with an enzyme. In some cases, the enzyme is a restriction enzyme. In some cases, the restriction enzyme is a methylation insensitive restriction enzyme. In some cases, the methylation insensitive restriction enzyme is MspI. In some cases, the additional base of the second sequence is an adenine, thymine, or cytosine base. In some cases, each of the two additional bases of the third sequence is an adenine, thymine, or cytosine base. In some cases, a 3' most base of the three additional bases of the fourth sequence comprises a thymine or cytosine base, and each of the two other bases of the three additional bases of the fourth sequence comprises an adenine, thymine, or cytosine base. In some cases, each oligonucleotide sequence in the pool of oligonucleotide sequences is within a strand of a duplexed adaptor. In some cases, the duplexed adaptor is a partial duplexed adaptor comprising a long strand and a short strand. In some cases, the short strand is a non-ligation strand of the duplexed adaptor and the long strand is a ligation strand. In some cases, the non-ligation strand comprises a 5' overhang. In some cases, the 5' overhang comprises two bases. In some cases, the two bases are 3'-GC-5'. In some cases, the introducing comprises a ligation reaction. In some cases, the ligation reaction comprises cohesive end ligation. In some cases, the ligation reaction comprises blunt end ligation. In some cases, the plurality of polynucleotides are strands of double-stranded nucleic acids, wherein each 5' end of the double-stranded nucleic acids comprises a ligation end and each 3' end comprises a non-ligation end, wherein each of the non-ligation ends of the double-stranded nucleic acid comprises part of the polynucleotide sequence. In some cases, the 3'-GC-5' of the non-ligation strand of the duplexed adaptor anneals to a 5'-CG-3' sequence of the ligation end of the double-stranded sequence comprising the polynucleotide sequence. In some cases, the 3'-GC-5' of the non-ligation strand of the duplexed adaptor is 5' to the terminal 5' nucleotide base of the first sequence. In some cases, the 3'-GC-5' of the non-ligation strand of the duplexed adaptor is 5' to the additional base of the second sequence relative to the 5' end of the first sequence. In some cases, the 3'-GC-5' of the non-ligation strand of the duplexed adaptor is 5' to the two additional bases of the third sequence relative to the 5' end of the first sequence. In some cases, the 3'-GC-5' of the non-ligation strand of the duplexed adaptor is 5' to the three additional bases of the fourth sequence relative to the 5' end of the first sequence. In some cases, each duplexed adaptor in the pool comprises a ligation strand and a non-ligation strand, wherein the ligation strand is capable of ligating to a 5' end of the plurality of polynucleotides, and wherein a nick is formed between the non-ligation strand and the 3' end of the plurality of polynucleotides. In some cases, the method further comprises an extending step, wherein the 3' end of the plurality of polynucleotides is extended using a polymerase in the presence of a mixture of dNTPs using the ligation strand of the adaptor as template, thereby introducing the pool of oligonucleotide sequences to the 3' ends of the plurality of polynucleotides. In some cases, the ligation strand of each adaptor duplex in the pool comprise cytosine analogs resistant to bisulfite treatment and the mixture of dNTPs comprises dATP, dTTP, dGTP, and dCTP, whereby the extending generates the plurality of oligonucleotide-polynucleotide complexes, wherein each of the plurality of oligonucleotide-polynucleotide complexes comprises complementary ends, wherein one end comprises cytosine bases sensitive to bisulfite treatment, while the opposite end comprises cytosine analogs resistant to bisulfite treatment. In some cases, the ligation strand of each adaptor duplex in the pool of adaptor duplexes comprise cytosine bases sensitive to bisulfite treatment and the mixture of dNTPs comprises dATP, dTTP, dGTP, and a dCTP analog resistant to bisulfite treatment, whereby the extending generates the plurality of oligonucleotide-polynucleotide complexes, wherein each of the plurality of oligonucleotide-polynucleotide complexes comprises complementary ends, wherein one end comprises cytosine bases sensitive to bisulfite treatment, while the opposite end comprises cytosine analogs resistant to bisulfite treatment. In some cases, each oligonucleotide in the pool of oligonucleotides is a primer, wherein the pool of oligonucleotides comprises the primer and a complement thereof. In some cases, the introducing comprises an amplification reaction. In some cases, the amplification reaction comprises polymerase chain reaction. In some cases, each of the primers in the pool comprises cytosine bases sensitive to bisulfite treatment, wherein the amplification is conducted in the presence of a mixture of dNTPs comprising dATP, dTTP, dGTP, and a dCTP analog resistant to bisulfite treatment, thereby generating the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, each of the primers in the pool of primers comprises cytosine analogs resistant to bisulfite treatment, wherein the amplification is conducted in the presence of a mixture of dNTPs comprising dATP, dTTP, dGTP, and dCTP, thereby generating the plurality of oligonucleotide sequence-polynucleotide complexes, wherein each of the plurality of oligonucleotide sequence-polynucleotide complexes comprises complementary ends, wherein one end comprises cytosine bases sensitive to bisulfite treatment, while the opposite end comprises cytosine analogs resistant to bisulfite treatment. In some cases, the cytosine analog resistant to bisulfite treatment is 5-methylcytosine, 5-hydroxymethylcytosine, or 5-propynylcytosine. In some cases, the method further comprises treating the plurality of oligonucleotide sequence-polynucleotides complexes with bisulfite prior to the amplification, wherein the treating generates a plurality of oligonucleotide sequence-polynucleotide complexes comprising non-complementary ends. In some cases, the treating with bisulfite prior to amplification generates the sequence complementary to a sequencing primer in each oligonucleotide sequence in the pool of oligonucleotide sequences comprises. In some cases, the generating the plurality of sequence reads comprises paired-end sequencing.

In one aspect, provided herein is a method for increasing diversity of sequences at ends of a plurality of polynucleotide fragments in a library, the method comprising: a. fragmenting polynucleotides to generate polynucleotide fragments; b. ligating a pool of adaptor sequences to 3' ends of the plurality of polynucleotide fragments, wherein each adaptor sequence in the pool of adaptor sequences comprises a sequence complementary to a sequencing primer, wherein a 3' end of the sequencing primer anneals at least four bases from the 5' end of the adaptor sequence, and wherein each of four different types of nucleotide bases are present in each of the at least three terminal nucleotides at the 5' ends of the adaptors, thereby increase diversity of sequences at ends of the plurality of polynucleotide fragments.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features described herein are set forth with particularity in the appended claims. A better understanding of the features and advantages described herein will be obtained by reference to the following detailed description that sets forth illustrative embodiments, in which the principles described herein are utilized, and the accompanying drawings of which:

FIG. 1 illustrates the basic principle of RRBS. Nucleic acid Library inserts (or genomic DNA) is digested with MspI, bisulfite converted (a chemical reaction that converts non-methylated C to U, but leaves 5-mC unreacted), and sequenced. C in the sequence indicates the presence of 5-mC at that position. Note how the first base of every sequence contains a methylation measurement.

FIG. 2A-B illustrates a method for generating the diversity adapters used in the methods provided herein. FIG. 2A illustrates a long strand of nucleotides (R01446 (SEQ ID NO: 18)) and 4 different short strands (i.e., Ben383 (SEQ ID NO: 14), Ben384 (SEQ ID NO: 15), Ben385 (SEQ ID NO: 16), and Ben341 (SEQ ID NO: 17)) such that each short strand comprises a stretch of 12 nucleotides that comprise bases complementary to the long strand (R01446). FIG. 2B illustrates the method used to generate a diversity adaptor using the long strand (R01446 (SEQ ID NOS 18 and 19, respectively, in order of appearance)) and a representative short strand (Ben383 (SEQ ID NO: 14)) from FIG. 2A.

FIG. 3 illustrates an alternative method for generating an RRBS library. FIG. 3 discloses SEQ ID NOS 20, 21, 21, 20, 20, 22, 22, 20, 20 22, 22, 20 and 23-26, respectively, in order of appearance.

FIG. 7A-B illustrates the sequencing results of forward reads (FIG. 7A) and reverse reads (FIG. 7B) for sequencing an RRBS library generated using diversity-adapters comprising no "D" bases.

FIG. 8 illustrates expected sequencing reads (forward and reverse reads) for sequencing an RRBS library with a pool of diversity-adapters comprising a variable number of "D" bases. The expected forward or reverse reads can be from N to NNNNNN bases in the first 6 sequencing cycles, wherein an N base can be an H, D, Y or B base.

FIG. 10 illustrates the sequencing results for sequencing an RRBS library with a 5-plex pool of diversity-adapters comprising a variable number of "D" bases, wherein the sequencing was performed without using a PhiX control as described in Example 2.

FIG. 14 illustrates the sequencing results for sequencing a blood sample using a 16 plex sequencing system (e.g., Ovation® Blood Seq Library System) as described in Example 2.

FIG. 16 illustrates a run summary for the sequencing reactions performed in FIG. 10.

FIG. 17 illustrates a run summary for the sequencing reactions performed in FIG. 14.

FIG. 18A-C illustrates proposed rules for trimming diversity "D" bases in silico from sequence reads from nucleic acid inserts generated with mixed diversity-Adaptor sequences comprising 0 to 3 "D" bases (D0-D3). FIG. 18A illustrates a first rule. FIG. 18A discloses SEQ ID NOS 23, 24 and 26, respectively, in order of appearance. FIG. 18B illustrates a second rule. FIG. 18B discloses SEQ ID NOS 23-25, respectively, in order of appearance. FIG. 18C illustrates a third rule. FIG. 18C discloses SEQ ID NOS 27, 28 and 25, respectively, in order of appearance.

FIG. 19 illustrates the total theoretical diversity possible for introducing to the ends of a polynucleotide upon introduction of a pool of diversity adaptors comprising diversity-adapters comprising 0 to 3 "D" bases (D0-D3).

FIG. 20 illustrates total CpGs analyzed using the modified RRBS methods provided herein in comparison to Whole Genome Bisulfite Sequencing (WGBS).

FIG. 21 illustrates a comparison of the average CpG per read and average CpG per uniquely aligned read between the modified RRBS method as provided herein vs. WGBS.

FIG. 22 illustrates the feature coverage using the modified RRBS as provided herein.

FIG. 24 illustrates a comparison between RRBS and other DNA methylation profiling technologies.

FIG. 26 illustrates an example of a dark sequencing approach used that can be used separately or in conjunction with RRBS.

FIG. 35 illustrates types of sequence diversity added to the beginning of forward reads in RRBS libraries generated using diversity adaptors with 0, 1, 2, or 3 diversity "D" bases.

FIG. 38 illustrates an overview of the RRBS library preparation process described in Example 6. FIG. 38 discloses SEQ ID NOS 29-32, respectively, in order of appearance.

DETAILED DESCRIPTION

I. Overview

Figure 4A:
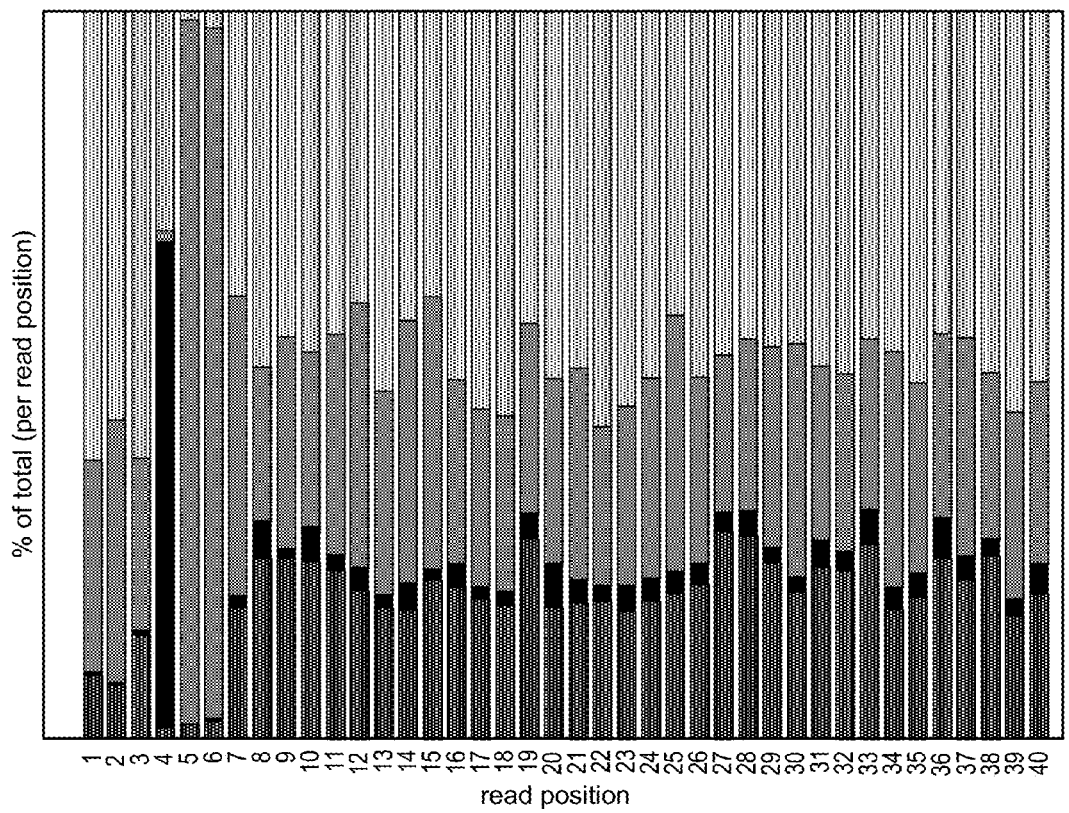
FIG. 4A-B illustrates the sequencing results of forward reads (FIG. 4A) and reverse reads (FIG. 4B) for sequencing an RRBS library generated using diversity-adapters comprising 3 "DDD" bases.
Figure 4B:
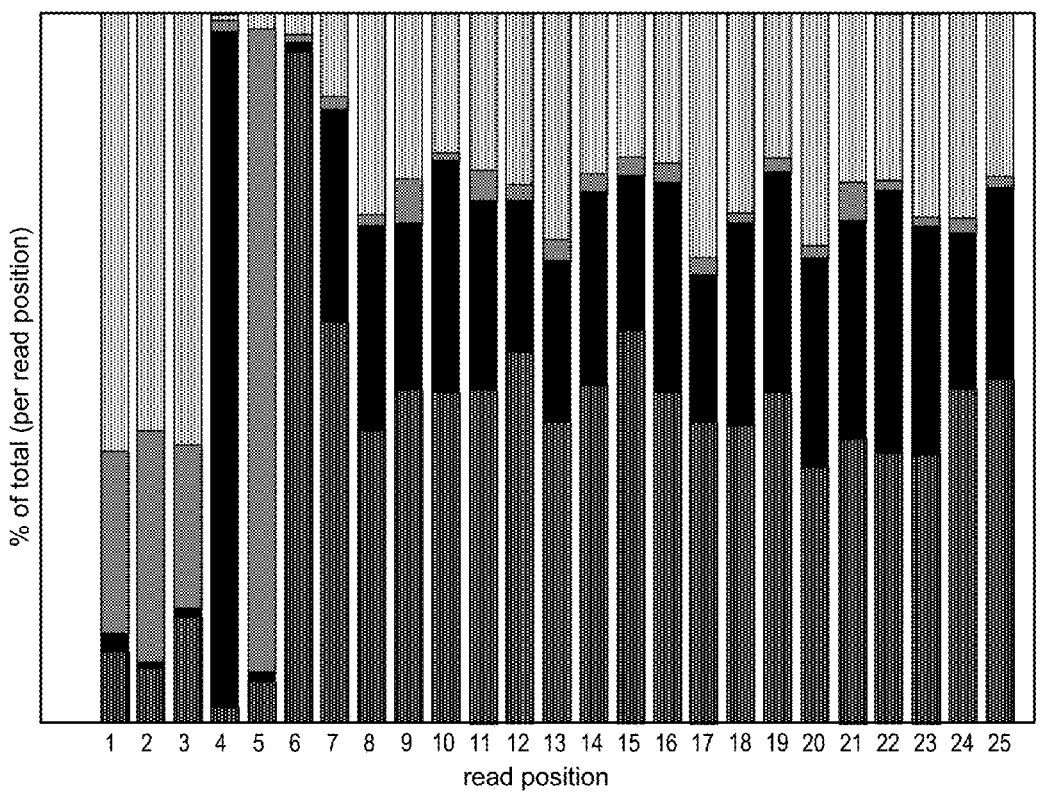
Figure 5A:
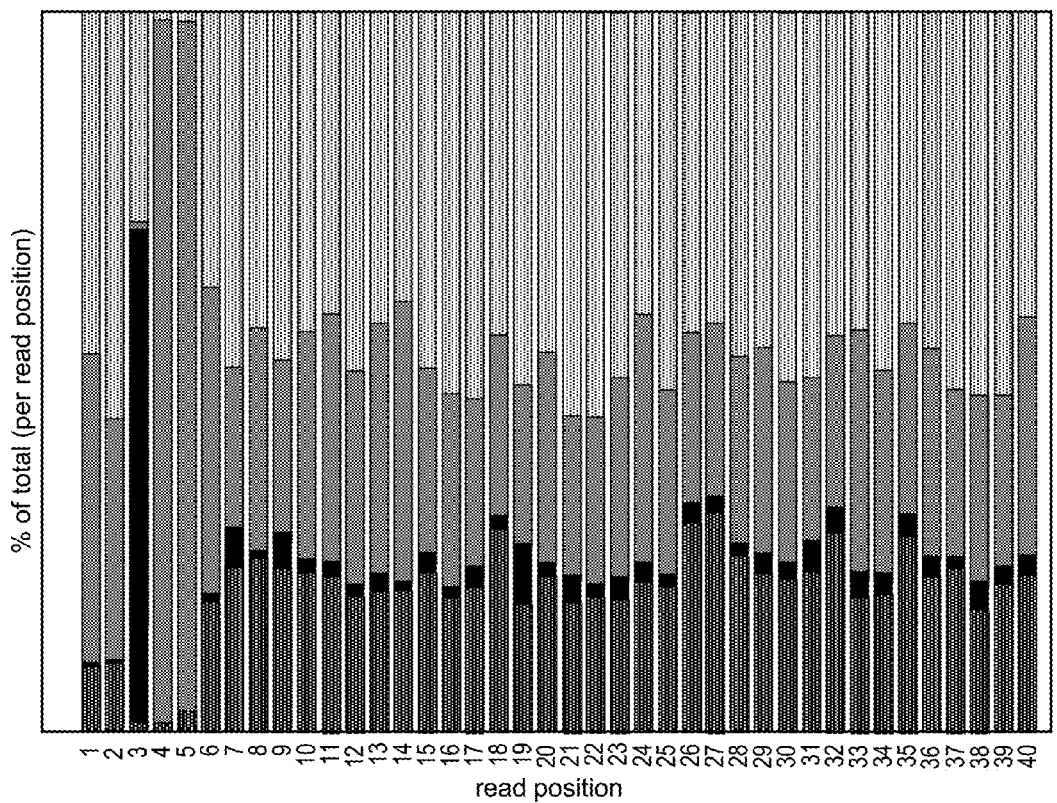
FIG. 5A-B illustrates the sequencing results of forward reads (FIG. 5A) and reverse reads (FIG. 5B) for sequencing an RRBS library generated using diversity-adapters comprising 2 "DD" bases.
Figure 5B:
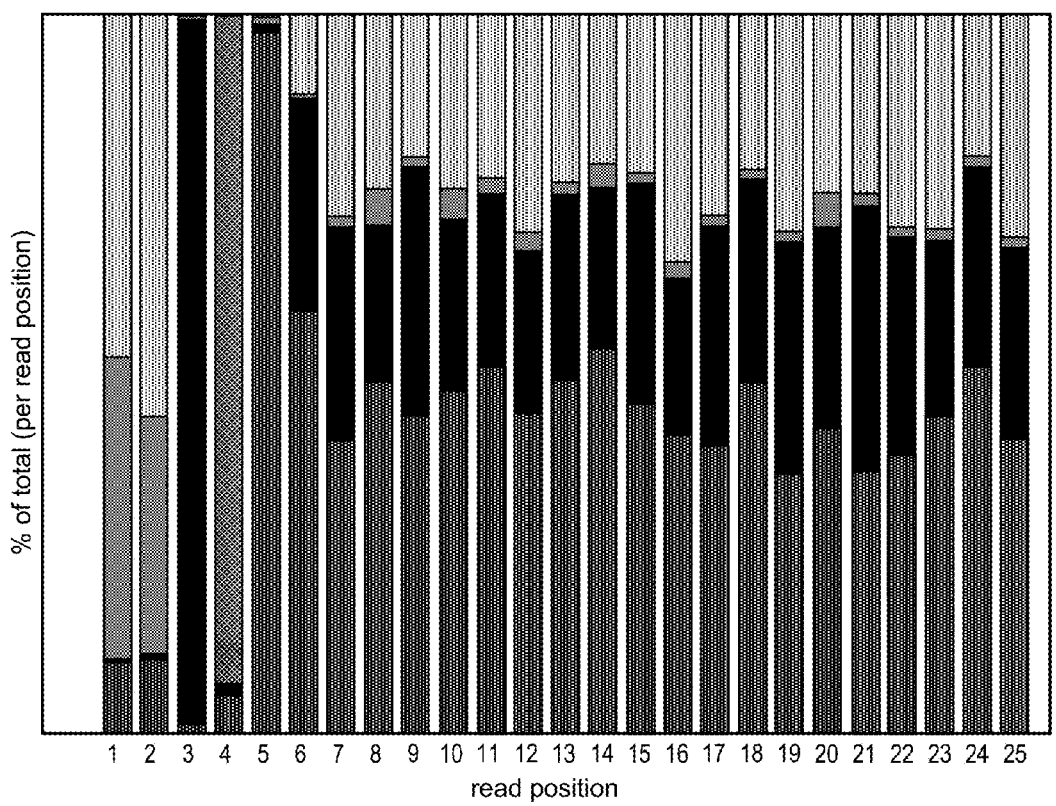
Figure 6A:
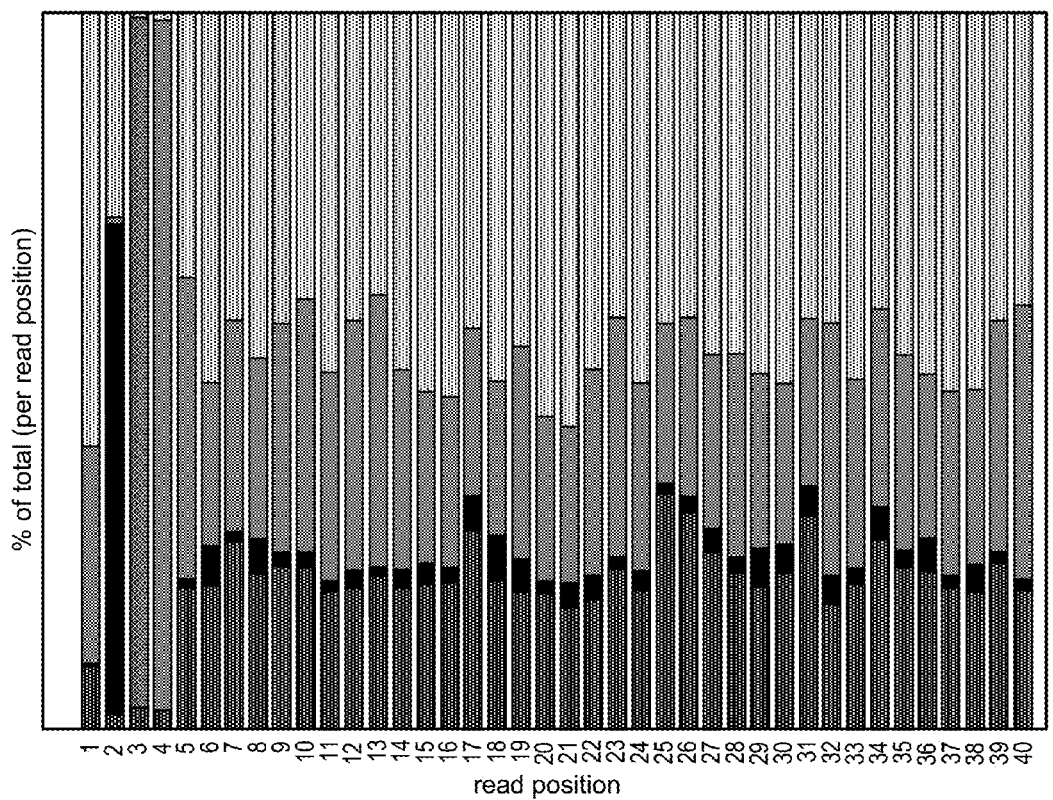
FIG. 6A-B illustrates the sequencing results of forward reads (FIG. 6A) and reverse reads (FIG. 6B) for sequencing an RRBS library generated using diversity-adapters comprising a single "D" base.
Figure 6B:
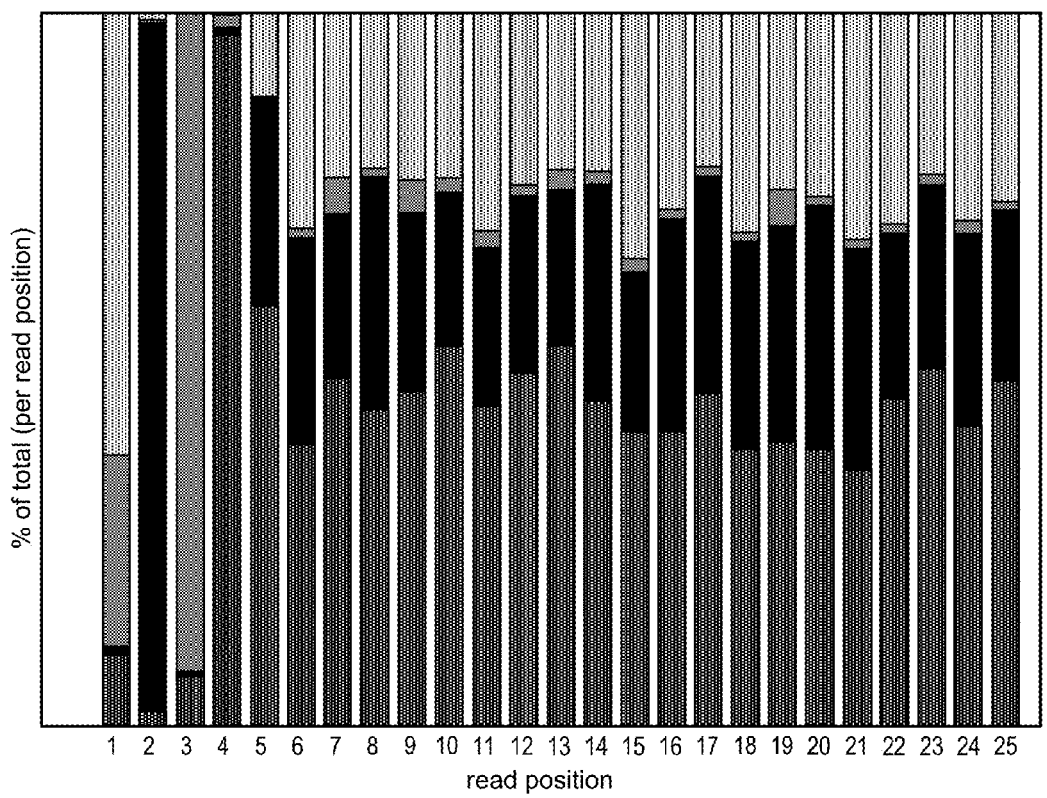
Figure 7B:
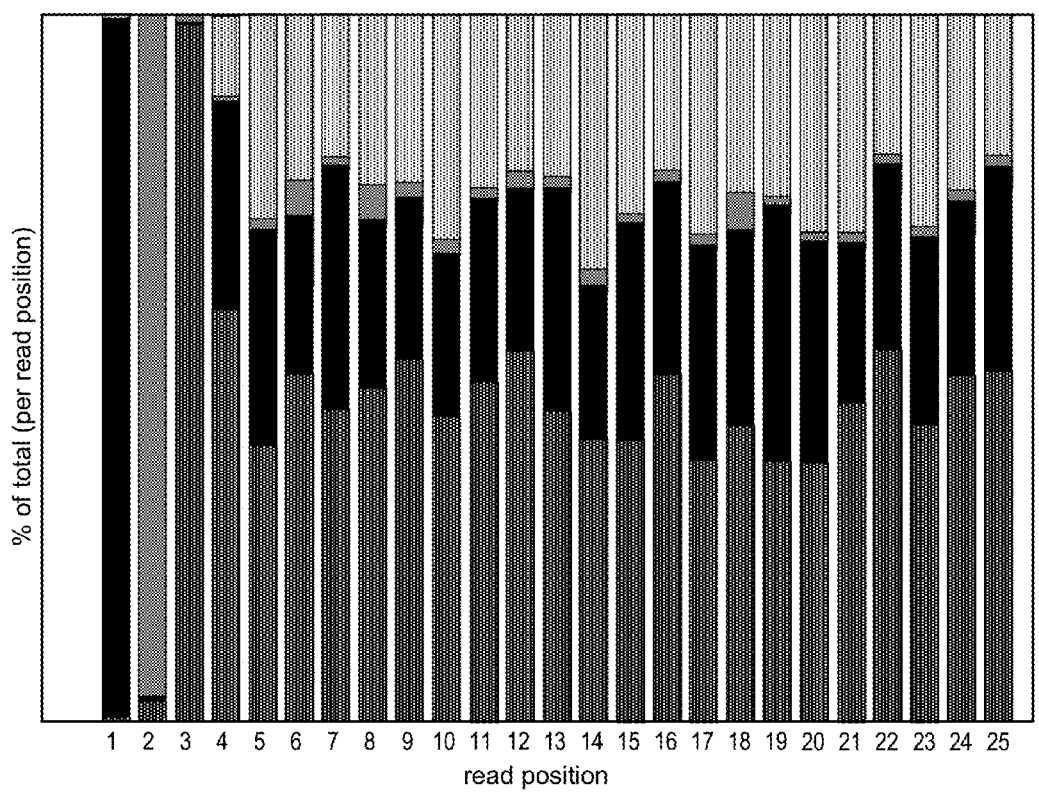

Provided herein are methods, compositions, and kits for introducing sequence diversity into genomic regions comprising low sequence diversity. The genomic regions comprising low sequence diversity can be highly conserved genomic regions between organisms (e.g., 16s rRNA sequences between microbial species). The genomic regions comprising low sequence diversity can be repetitive sequences within a genome (e.g., CpG islands within mammalian genomes). The methods described herein can introduce sequence diversity into genomic regions comprising low sequence diversity by introducing oligonucleotide sequence to one or both ends of a polynucleotide. The introduction can be through ligation (e.g., blunt-end or cohesive-end) using adaptors such that the adaptors comprise the oligonucleotide sequence introduced to one or both ends of the polynucleotide. The introduction can through amplification of a target sequence in a polynucleotide (e.g., genomic region) using primers such that the primers comprise the oligonucleotide sequence introduced to one or both ends of the polynucleotide. The primers can comprise sequence complementary to a target sequence in a nucleic acid as well as the oligonucleotide sequence. The oligonucleotide sequence can be present in the primer as a tail such that it is non-complementary to the target sequence. In general, the oligonucleotide sequence can comprise sequence complementary to a sequencing primer, one or more barcodes, universal sequence, random sequence, and/or sequence useful for introducing sequence diversity at one or both ends of a polynucleotide (e.g., extender sequence as provided herein). The oligonucleotide sequence can be configured such that sequence complementary to a sequencing primer is immediately adjacent to the end of the polynucleotide upon introduction (i.e., through amplification or ligation) of the oligonucleotide sequence complementary to a sequencing primer. In some cases, the oligonucleotide sequence further comprises an extender sequence such that the sequence complementary to a sequencing primer precedes the extender sequence such that, upon introduction, the extender sequence is immediately adjacent to the end of the polynucleotide.

In the methods, compositions and kits provided herein, the extender sequence in an oligonucleotide sequence as described herein can be a variable number of nucleotides in length. The extender sequence can be less than, more than, or about 0, 1, 2, 3, 4, 5, 6, 7, 8, 9, 10, 11, 12, 13, 14, 15, 16, 17, 18, 19 nucleotides in length. In some cases, the extender sequence is a single nucleotide in length. In some cases, the extender sequence is two nucleotides in length. In some cases, the extender sequence is three nucleotides in length. In some cases, an additional sequence element is present in the oligonucleotide sequence such that the additional sequence is located between the sequence complementary to a sequencing primer and the extender sequence such that upon introduction the extender sequence is immediately adjacent to the end of the polynucleotide and is followed by the additional sequence element which is followed by the sequence complementary to a sequencing primer. In some cases, the oligonucleotide sequence can comprise one or more additional sequence elements such that the one or more additional sequence elements are not located between the sequence complementary to a sequencing primer and an extender sequence such that the one or more additional sequence elements precedes the sequence complementary to a sequencing primer. In this case, upon introduction of the oligonucleotide sequence to one or both ends of a polynucleotide, the extender sequence is immediately adjacent to the end of the polynucleotide and is followed by the sequence complementary to a sequencing primer which is followed by the one or more additional sequence elements. In some cases, the oligonucleotide sequence can comprise a plurality of additional sequence elements such that one of the plurality of additional sequence elements is located between the sequence complementary to a sequencing primer and the extender sequence while one or more additional sequence elements of the plurality of additional sequence elements are not located between the sequence complementary to a sequencing primer and an extender sequence. The one or more additional sequence elements of the plurality of additional sequence elements precede the sequence complementary to a sequencing primer. In this case, upon introduction of the oligonucleotide sequence to one or both ends of a polynucleotide, the extender sequence is immediately adjacent to the end of the polynucleotide and is followed in succession by one of the plurality of additional sequence elements, the sequence complementary to a sequencing primer and the one or more additional sequence elements of the plurality of additional sequence elements.

An additional sequence element can be one or more barcodes, universal adaptor sequence, linker sequence, and/or random sequence. The sequencing primer can be a custom sequencing primer or can be a sequencing primer compatible with a commercially available NGS sequencing system.

The polynucleotides can be in a sample. The sample can be any sample as provided herein. The polynucleotides can be fragmented prior to the introduction of an oligonucleotide sequence as described herein. Fragmentation can be mechanical (e.g., sonication) or chemical (e.g., enzymatic) as provided herein.

Following introduction of the oligonucleotide sequence to the ends of a polynucleotide, the resulting oligonucleotide sequence-polynucleotide complex can be amplified. In some cases, oligonucleotide sequence is introduced to both ends of a polynucleotide, and subsequent amplification is performed using primers directed to complementary sequence in the oligonucleotide sequences introduced to the ends of the polynucleotide. The primers used for amplification can introduce further sequence elements to the oligonucleotide sequence-polynucleotide complex formed after introduction of the oligonucleotide sequence. The sequence elements introduced during amplification can be barcode(s) or sequence complementary to a capture probe on a solid surface. The solid surface can be a bead or planar surface (e.g., flow cell). The amplification can be a solid-state amplification (e.g., cluster amplification) that generates a cluster comprising a plurality of copies of the oligonucleotide sequence-polynucleotide complex. The methods provided herein can further comprise sequencing the amplified oligonucleotide-polynucleotide complexes. An extender sequence can be a barcode, universal sequence, linker sequence, or random sequence.

In the methods, compositions and kits provided herein, the extender sequence in an oligonucleotide sequence as described herein can comprise any of the four canonical nucleotide bases (i.e., thymine, adenine, cytosine, or guanine) found in DNA. The nucleotide base composition of a nucleotide in an extender sequence can be selected such that the nucleotide base composition can differ from the nucleotide base composition at an end of a polynucleotide to which the extender sequence can be introduced, whereby the presence of one or more nucleotides from the extender sequence at the end of the polynucleotide can serve to increase sequence read length as well as nucleotide base diversity. The increase based diversity can aid identification of individual clusters as well as maintain accurate label detection in NGS sequencing systems that use cluster based sequencing by synthesis (e.g., Illumina).

The methods, compositions, and kits provided herein can comprise a pool of oligonucleotide sequences as described herein. The pool of oligonucleotide sequences can be a pool of adaptors comprising the oligonucleotide sequence as described herein. The pool of adaptors comprising the oligonucleotide sequence can be introduced to one or both ends of a plurality of polynucleotides through ligation (e.g., blunt end or cohesive end). The pool of oligonucleotide sequences can be a pool of primers comprising the oligonucleotide sequence as described herein. The pool of primers comprising the oligonucleotide sequence can be introduced to one or both ends of a plurality of polynucleotides through amplification (e.g., isothermal or PCR). The pool of oligonucleotide sequences can comprise sets of oligonucleotide sequences such that each set comprises either no extender sequence or an extender sequence of a length that differs from the length of an extender sequence in a separate set of oligonucleotide sequences within the pool of oligonucleotide sequences. The length of an extender sequence in a set of oligonucleotide sequences in a pool of oligonucleotide sequences can be 0, 1, 2, 3, 4, 5, 6, 7, 8, 9, 10 or more nucleotides.

In some cases, a pool of oligonucleotide sequences comprises a first set of oligonucleotide sequences that do not comprise an extender sequence, a second set of oligonucleotide sequences that comprise an extender sequence comprising a single nucleotide, a third set of oligonucleotide sequences that comprise an extender sequence comprising two nucleotides, and a fourth set of oligonucleotide sequences that comprise an extender sequence comprising three nucleotides. Each oligonucleotide sequence within the pool of oligonucleotide sequences can comprise the same sequence complementary to a sequencing primer as described herein. The nucleotide base composition of each nucleotide in an extender sequence comprising more than one nucleotides can be identical or different. The nucleotide base composition of each nucleotide in an extender sequence comprising more than one nucleotide can be known or randomly assigned as provided herein.

Figure 31:
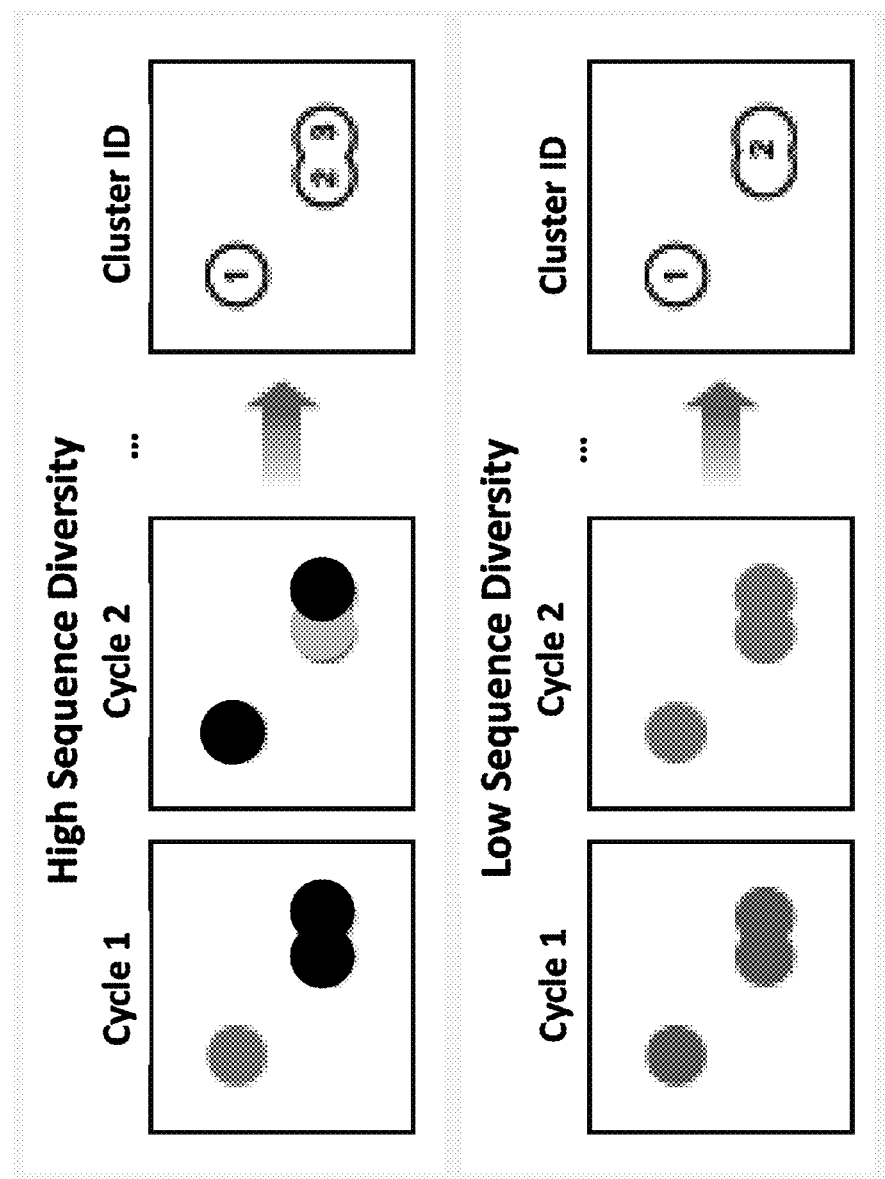
FIG. 31 illustrates cluster identification requires sequence diversity. The Illumina software identifies clusters over the first several cycles of sequencing. During sequencing of normal, high diversity clusters (top), overlapping clusters can be distinguished because they are different colors. If overlapping clusters contain the same sequence (bottom), they can be mistaken as a single cluster.

In some cases, the methods, compositions, and kits provided herein are useful for generating bisulfite converted nucleic acid libraries with increased sequence diversity at the ends of nucleic acid inserts within the library. The bisulfite converted libraries can be reduced representation bisulfite sequencing (RRBS) libraries. Such libraries can be useful, for example, for determining the methylation status across a genome, or alternatively, for determining the methylation status at given genomic loci. The RRBS libraries generated by the methods, compositions, and kits provided herein can be useful for determining the methylation status of CpG islands in polynucleotides derived from whole genome samples. The whole genome samples can be from eukaryotic cells (e.g., mammalian cells). The methods can produce RRBS libraries that can be more efficiently sequenced by current NGS sequencers (e.g., Illumina sequencers), and in some embodiments, without the need for spiking in a genomic, higher-diversity sample nucleic acids (e.g. PhiX control library). The method for generating an RRBS library can comprise enzymatically fragmenting a nucleic acid (polynucleotide) such that a plurality of nucleic acids fragments comprising substantially similar nucleotide compositions at the ends or termini of each fragment are generated. In some cases, the method comprises fragmenting the nucleic acid with a methylation sensitive restriction enzyme such as, for example, MspI. In some cases, a pool of adaptors is ligated to the 5' ends of each nucleic acid fragment in the plurality of nucleic acid fragments such that each nucleic acid fragment comprises double stranded sequence and the ligation generates a plurality of adaptor-ligated nucleic acid fragments. The pool of adaptors can comprise adaptors that share a sequence complementary to a sequencing primer as well as a first set of adaptors comprising no extender sequence, a second set comprising a single nucleotide extender sequence, a third set comprising a dinucleotide extender sequence, and a fourth set comprising a trinucleotide extender sequence. In some cases, the nucleotide base composition of the extender sequences in a pool of adaptors comprising extender sequence are chosen such that the base composition differs for the nucleotide base composition at the end of the nucleic fragment to which the extender sequence is appended. In some cases, the single nucleotide in first set of adaptors can comprises a thymine, guanine, or adenine base, while the each nucleotide in the dinucleotide of the second set can comprise a thymine, guanine, or adenine base and two of the three nucleotides in the trinucleotide of the third set can be a thymine, guanine, or adenine base, while the third nucleotide can be guanine or adenine. As provided herein, the extender sequence can be used to increase sequence diversity between the sequencing primer and the end of a library nucleic acid insert. In some cases, the adaptor-ligated nucleic acid fragments are subjected to an extension reaction as provided herein followed by denaturation and bisulfite treatment, whereby the bisulfite treatment generates adaptor-ligated nucleic acid fragment comprising non-complementary adaptor sequence on opposite ends. The non-complementary adaptor sequences can subsequently be utilized to amplify and/or sequence each adaptor-ligated nucleic acid fragment. The amplification can be solution phase and/or solid-state amplification. In some cases, the plurality of adaptor-ligated nucleic acid fragments are PCR amplified followed by solid-state amplification to generate clusters such that each cluster comprises thousands of copies of an adaptor-ligated nucleic acid fragment form the plurality of adaptor-ligated nucleic acid fragments. The presence of extender sequence in the plurality of adaptor-ligated nucleic acid fragments can increase the ability of NGS sequencers (e.g., Illumina) to successfully identify and discern between neighboring clusters formed by solid-state amplification during sequencing of the clusters (e.g., as illustrated in FIG. 31).

Provided herein are methods for generating adaptors comprising extender sequences for use in the generation of bisulfite converted nucleic acid libraries (e.g., RRBS libraries). Adaptors comprising extender sequences can also be referred to as diversity adaptors.

Provided herein are in silico methods for filtering and trimming the extender sequence present in sequences reads produced from sequencing nucleic acids or polynucleotides comprising extender sequence as generated through the methods provided herein. The in silico methods can comprise trimming away any oligonucleotide sequence (e.g., adaptor sequence) that may be present on the 3' ends of reads using publically available trimming algorithms (e.g., Trim Galore). In some cases, the trimming script or algorithm can remove adaptor sequence such as adaptor sequence associated with a specific sequencing platform (e.g., Illumina adaptor sequence) and/or any nucleotide bases whose quality score is below a set quality score (Q-score) threshold. In some cases, the Q-score threshold is set at 30, 20, or 10 such that any Q-score below said threshold is trimmed or removed from analysis by the script or algorithm. Once the oligonucleotide sequence (e.g., adaptor sequence) is trimmed away, a custom python script can remove any reads that do not contain the known end sequence of the library insert. In RRBS libraries generated through fragmentation via MspI digestion, the python script can remove any reads that do not contain an MspI site signature, YGG (Y=cytosine of thymine bases), at the 5' end. For paired end data an MspI site signature can be required at 5' ends of both sequences. Following filtering and trimming, all reads should begin with YGG, where Y is C or T, 5 bases can be trimmed from every read (6 bases are trimmed for paired-end to prevent alignment issues). If YGG is not found in the first 6 bases, the read is discarded.

Provided herein are methods for identifying and removing duplicate sequence reads following NGS sequencing. In some cases, an oligonucleotide sequence introduced to one or both ends of a polynucleotide comprises additional sequence elements upstream of a sequence complementary to a sequencing primer relative to an end of a polynucleotide to which the oligonucleotide sequence has been appended. In some cases, the additional sequence elements comprise a barcode and a stretch of random nucleotides immediately adjacent thereto. In some cases, the stretch of random nucleotides is 6 nucleotides in length. The methods provided herein can utilize an in silico analysis to discriminate between true duplicates produced during amplification (e.g., PCR). The analysis can utilize in silico algorithms in order to utilize information provided by the unique stretch of random nucleotides to discriminate between true PCR duplicates and independent adaptor ligated-nucleic acid fragments. In some cases, the algorithm for removing duplicate sequence reads uses sequence reads recovered from an index read. The index read can provide sequence data or reads comprising the barcode(s) and the random sequence located adjacent to the barcode(s). In order to read the inserted random sequence adjacent to the barcode(s) during an index read, the cycle number of the index read can be increased by the number of nucleotide bases present in the inserted random sequence. For example, the barcode can be 6 nucleotides and the random sequence can be 6 nucleotides and the index read can be a total of 12 cycles.

II. Adaptors

In one aspect provided herein is a method for increasing sequence diversity at the ends of polynucleotides that comprise conserved sequence at one or both ends with other polynucleotides using adaptors comprising extender sequence as described herein. The adaptor comprising an extender sequence can be used in the methods described herein to increase the sequence diversity at one or both ends of a polynucleotide by appending the adaptor comprising the extender sequence to one or both ends of the polynucleotide. The increased sequence diversity can aid an NGS sequencer in determining the sequence of each polynucleotide in a group of polynucleotides that share identical or substantially similar nucleotide base compositions at their end or ends when conducting NGS sequencing using NGS methods and systems that generate and identify clusters of individual polynucleotides during sequencing (e.g., Illumina, SOLiD). As a result, an adaptor comprising extender sequence as described herein can be referred to as a diversity adaptor and each nucleotide and its corresponding nucleotide base can be referred to as a diversity base.

FIG. 35 illustrates the DNA sequence derived from a bisulfite converted library constructed using diversity adaptors such that following introduction of the diversity adaptors to the ends of DNA polynucleotides, the library comprises polynucleotides with either no diversity bases (i.e., 0 diversity bases added) derived from the diversity adaptor, one diversity base (i.e., 1 diversity base added) derived from the diversity adaptor, two diversity bases (i.e., 2 diversity bases added) derived from the diversity adaptor, or three diversity bases (i.e., 3 diversity "3" bases added) derived from the diversity adaptor. The number of diversity bases added can be variable and can be tailored to the type of library being constructed (e.g., 16S rRNA libraries, RRBS libraries, etc.). The diversity bases in a diversity adaptor can be "D" bases such that a "D" base can be an adenine, thymine, or guanine such as in FIGS. 2A-B, 3, 4A-B, 5A-B, 6A-B, 7A-B, 8, 9A-B, 18A-B and 35. The diversity bases in a diversity adaptor can be "R" bases such that an "R" base can be an adenine or guanine such as in FIGS. 18B and 35. The complement of a "D" or an "R" base can be an "H" base. In some cases, an "H" base is a complement of a "D" base such that the "H" base can be a thymine when the "D" base is an adenine, an adenine when the "D" base is a thymine, or a cytosine when the "D" base is guanine. In some cases, an "H" base is a complement of an "R" base such that the "H" base can be a thymine when the "R" base is an adenine or a cytosine when the "R" base is guanine. In some cases, each diversity base in a diversity adaptor is a "D" base. In some cases, each base in a diversity adaptor is an "R" base. Each diversity base in a diversity adaptor comprising more than one diversity base can be either a "D" base or an "R" base. In some cases, a pool of diversity adaptors is used in a method herein, wherein the pool comprises diversity adaptors comprising no diversity bases, diversity adaptors comprising 1 "D" base, diversity adaptors comprising 2 "D" bases, and diversity adaptors comprising 1 R base and 2 D bases. The diversity adaptor with 1 R base and two D bases can have the R base at the 5', middle, or 3' position.

Figure 32:
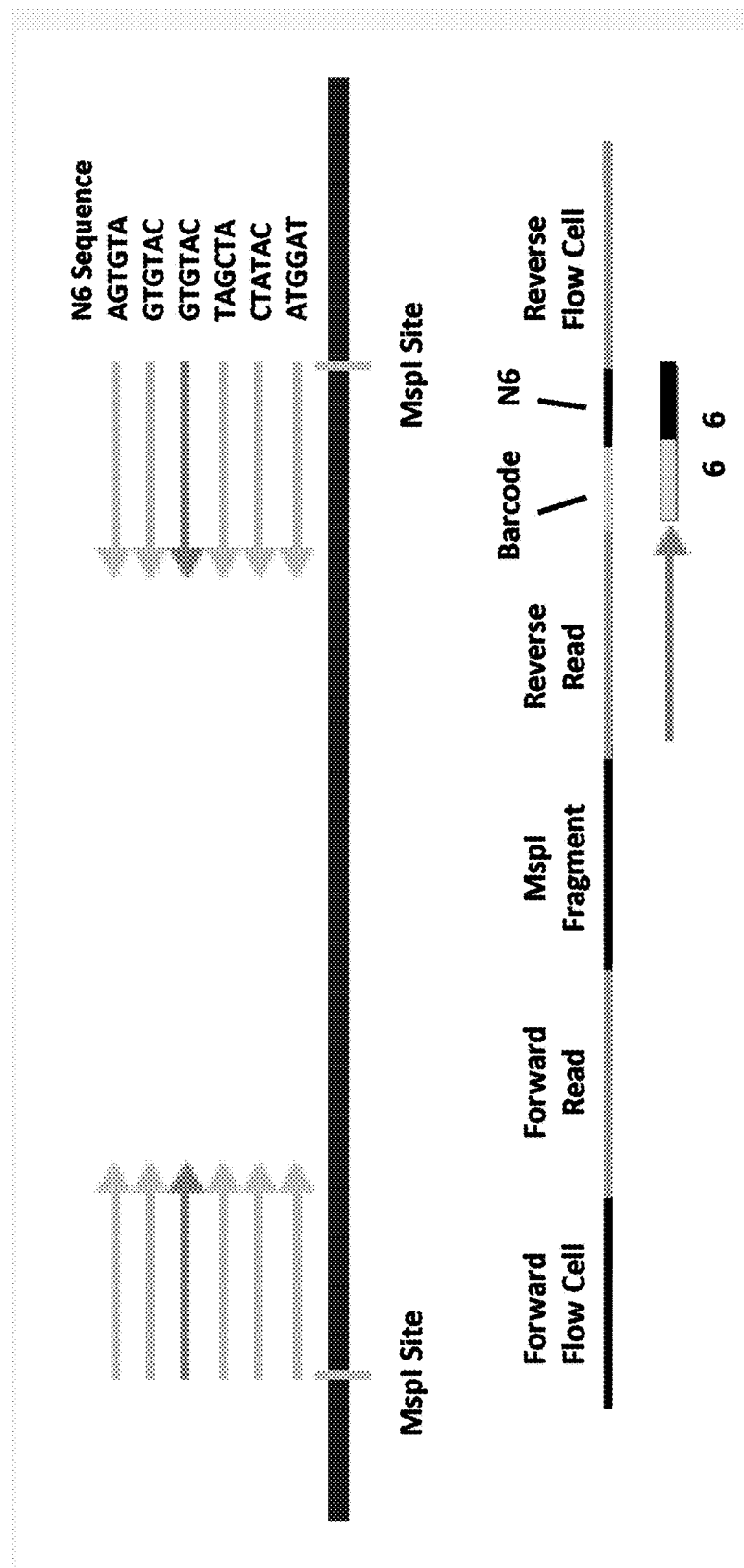
FIG. 32 illustrates random N6 sequence adjacent to the barcode that can be used to mark PCR duplicates for in silico removal.
Figure 37:
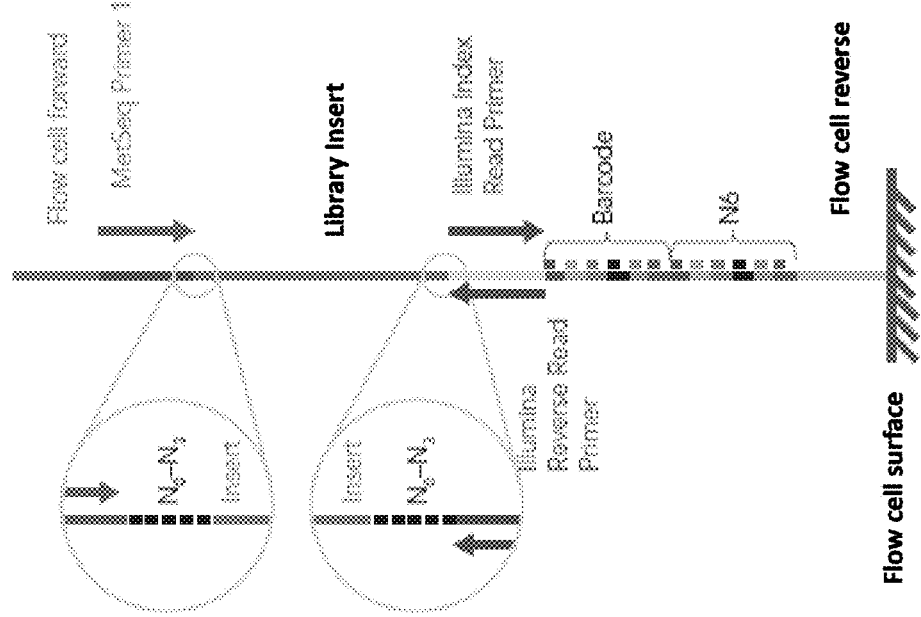
FIG. 37 illustrates a schematic of a nucleic acid insert from an RRBS library generated using the library preparation process provided herein

In some cases, the diversity bases can be added to the ends of target polynucleotides as shown in FIG. 35, using primers comprising said diversity bases or complements thereof instead of adaptors, whereby the introduction is performed using polymerase extension reactions (e.g., PCR). The primers can be designed to target specific sequences in a polynucleotide such as specific genomic regions (e.g., 16S rRNA sequences in microbial species) such that the primers comprise tails that comprise the diversity bases (i.e., extender sequences) or complements thereof. The adaptors comprising diversity base(s) (i.e., extender sequence) can be designed such that the diversity base or bases are immediately adjacent to sequence derived from a polynucleotide or polynucleotide insert from a library. In other words, the diversity base or bases are the first non-target sequence polynucleotide base or bases present at the junction of a complex comprising a target sequence from a polynucleotide and non-target sequence derived sequence. Also as provided herein, the adaptor comprising diversity bases can comprise a sequence or complement thereof that is capable of hybridizing a sequencing primer and this sequence or complement thereof can be located adjacent to the diversity base or bases such that the diversity base or bases are the bases initially sequenced in a sequencing reaction. In some cases, there can also be additional sequence elements located between the sequence or complement thereof that is capable of hybridizing a sequencing primer and the diversity base or bases such as barcodes (e.g., inline barcodes), universal sequence, or random sequence. In some cases, the additional sequence elements (e.g., barcode(s), universal sequence and/or random sequence) can be located after the sequence or complement thereof that is capable of hybridizing a sequencing primer and distal to the diversity base or bases. In some cases, the additional sequence elements (e.g., barcode(s), universal sequence and/or random sequence) can be located after the sequence or complement thereof that is capable of hybridizing a sequencing primer and distal to the diversity base or bases as well as between the sequence or complement thereof that is capable of hybridizing a sequencing primer and the diversity base or bases such as barcodes (e.g., inline barcodes), universal sequence, or random sequence. An example of a polynucleotide library insert generated to possess one or more additional sequence elements after the sequence that is capable of hybridizing a sequencing primer and therefore distal to the end of the polynucleotide library insert is shown in FIGS. 32 and 37. The insert generated in FIGS. 32 and 37 can be generated by introducing an adaptor or primer as provided herein.

As provided herein, the polynucleotide to which the adaptor attached can be a nucleic acid fragment generated using any fragmentation method known in the art. The fragmentation method can be one described herein such as enzymatic fragmentation. The nucleic acid fragment can be double stranded and the adaptor can be attached to both ends of the double stranded nucleic acid fragment. The term "adaptor", as used herein, can refer to an oligonucleotide of known sequence or an oligonucleotide comprising a portion or portions of known sequence, the ligation of which to a target polynucleotide or a target polynucleotide strand of interest enables the generation of amplification-ready products of the target polynucleotide or the target polynucleotide strand of interest. Various adaptor designs can be envisioned. Various ligation processes and reagents are known in the art and can be useful for carrying out the methods described herein. For example, blunt end ligation can be employed. Similarly, a single dA nucleotide can be added to the 3'-end of a double-stranded, blunted DNA product, by a polymerase lacking 3'-exonuclease activity and can anneal to an adaptor comprising a dT overhang (or the reverse). This design allows the hybridized components to be subsequently ligated (e.g., by T4 DNA ligase). Other ligation strategies and the corresponding reagents known in the art and kits and reagents for carrying out efficient ligation reactions are commercially available (e.g, from New England Biolabs, Roche).

In some embodiments, an adaptor comprises a duplex adaptor. In some cases, an adapter comprises a partial duplex adaptor. The partial duplex adaptor can be a forked adaptor. The forked adaptor can be a forked adaptor available from a commercial source and comprise known sequence. The forked adaptor can be compatible with specific NGS sequencing systems that utilize cluster amplification (e.g., Illumina forked adaptors for Illumina based sequencing by synthesis). The forked adaptors can comprise a duplex region where a first strand and a second strand share complementary sequence. The duplex region can be of varying length. The duplex region can be 1, 2, 3, 4, 5, 6, 7, 8, 9, 10, 15, 20, 25, 30 or more nucleotides in length. Outside of the duplex region, the forked adaptor can have single stranded non-complementary regions such that the first strand comprises a 5' single stranded region that is non-complementary to a 3' single-stranded region of the second strand. In some cases, one or more cytosine bases in the forked adaptor can be substituted with a cytosine analog resistant to bisulfite treatment. These types of forked adaptors can be useful in the generation of RRBS libraries using the methods provided herein. In some cases, the cytosine analog is 5-methylcytosine. In some cases, the cytosine analog is 5-hydroxymethylcytosine. In some cases, the cytosine analog is 5-propynylcytosine. The 3' and 5' ends of the duplex region of a forked adaptor used in the methods, compositions, and kits herein can comprise no or one or more bases of extender sequence (i.e., diversity bases) as described herein or complements thereof. In some cases, ligation of a forked adaptor as provided herein to both ends of a double stranded polynucleotide can generate forked adaptor-ligated polynucleotide complexes comprising non-complementary adaptor sequence on the 5' and 3' ends of each strand of the double stranded polynucleotide. The non-complementary sequence can be useful for further manipulation and downstream processing of the ligated polynucleotide complexes (e.g., PCR amplification, solid-state amplification, and/or sequencing).

In some cases, the partial duplex adaptor useful in the methods, compositions and kits provided herein can comprise a long strand and a short strand wherein the short strand comprises sequence complementary to the long strand. The short strand can hybridize completely with the long strand. The short strand can hybridize to a portion of the long strand, and thereby comprise either a 5' or 3' overhang. In some cases, an adaptor for use in the methods provided herein comprises a partial duplex adaptor as shown in FIG. 2A-B or 3. In some cases, an adapter for use in the methods described herein comprises a partial duplex adapter wherein the long strand comprises adaptor sequence comprising one or more sequence elements, while the short strand comprises sequence complementary to a portion of the sequence of the long strand as well as an overhang complementary to sequence in an overhang found in a nucleic acid following cleavage of said nucleic acid.

The nucleic acid can be cleaved by a restriction endonuclease (RE). The RE can be any restriction endonuclease described herein. In some cases, the RE is MspI.

In some cases, an adaptor for use in the methods provided herein comprises a ligation strand and a non-ligation strand. In some cases, an adaptor for use in the methods provided herein comprises a partial duplex wherein the long strand comprises a ligation strand, and a short strand comprises a non-ligation strand.

In some cases, an adaptor (e.g., diversity adaptor) for use in the methods provided herein comprises one or more identifier sequences. The one or more identifier sequences can be present in a long strand and/or a short strand of a partial duplex diversity adaptor as provided herein. The one or more identifier sequences can be present in a ligation strand and/or a non-ligation strand of a partial duplex diversity adapter as provided herein. The identifier sequence can be a barcode sequence, a flow cell sequence, and/or an index sequence. In some cases, the index sequence is a Truseq primer sequence compatible with the NGS platform produced by Illumina. In some cases, the 3' and/or 5' ends of the non-ligation strand comprise a blocking group or moiety and are enzymatically unreactive. The blocking group or moiety can be a dideoxynucleotide (ddCMP, ddAMP, ddTMP, or ddGMP), various modified nucleotides (e.g. phosphorothioate-modified nucleotides), or non-nucleotide chemical moieties. In some cases, the blocking group comprises a nucleotide analog that comprises a blocking moiety. The blocking moiety can mean a part of the nucleotide analog that inhibits or prevents the nucleotide analog from forming a covalent linkage to a second nucleotide or nucleotide analog. For example, in the case of nucleotide analogs having a pentose moiety, a reversible blocking moiety can prevent formation of a phosphodiester bond between the 3' oxygen of the nucleotide and the 5' phosphate of the second nucleotide. Reversible blocking moieties can include phosphates, phosphodiesters, phosphotriesters, phosphorothioate esters, and carbon esters, in some cases, a blocking moiety can be attached to the 3' position or 2' position of a pentose moiety of a nucleotide analog. A reversible blocking moiety can be removed with a deblocking agent. The 3' end of the non-ligation strand can be modified to comprise a blocking group, for example, a dideoxynucleotide (ddCMP, ddAMP, ddTMP, or ddGMP) to prevent polymerase extension. The blocking group at the 3' end of the non-ligation strand can be a nucleotide terminator. In some cases, the block at the 3' end of the non-ligation strand comprises a terminal dideoxycytosine. The 5' end of the non-ligation strand can be modified to comprise a blocking group. The blocking group at the 5' end of the non-ligation strand can be a spacer (C3 phosphoramidite, triethylene glycol (TEG), photo-cleavable, hexa-ethyleneglycol), inverted dideoxy-T, biotin, thiol, dithiol, hexanediol, digoxigenin, an azide, alkynes, or an amino modifier. The biotin blocking group can be photo-cleavable biotin, biotin-triethylene glycol (TEG), biotin-dT, desthiobiotin-TEG, biotin-azide, or dual biotin. In some cases, the block at the 5' end of the non-ligation strand comprises a biotin moiety. In some cases, the 5' end of the non-ligation strand does not comprise a 5' phosphate. The 5' end can be removed by treatment with an enzyme. The enzyme can be a phosphatase. In some cases, the 5' end of the non-ligation strand is dephosphorylated by treatment with alkaline phosphatase. In some cases, the 5' end of the non-ligation strand does comprise a 5' phosphate, wherein the 3' end of the polynucleotide lacks a free 3' hydroxyl. In some cases, the non-ligation strand comprises a block at the 3' end comprising terminal dideoxycytosine and a block at the 5' end comprising a biotin moiety. In some cases, one or more cytosine bases in the ligation strand of a duplex adaptor can be substituted with a cytosine analog resistant to bisulfite treatment. The ligation strand comprising the one or more cytosine analogs resistant to bisulfite treatment can be the long strand in a partial duplex adaptor as provided herein. In some cases, one or more cytosine bases in the non-ligation strand of a duplex adaptor can be substituted with a cytosine analog resistant to bisulfite treatment. The non-ligation strand comprising the one or more cytosine analogs resistant to bisulfite treatment can be the short strand in a partial duplex adaptor as provided herein. These types of duplex or partial duplex adaptors can be useful in the generation of RRBS libraries using the methods provided herein. In some cases, the cytosine analog is 5-methylcytosine. In some cases, the cytosine analog is 5-hydroxymethylcytosine. In some cases, the cytosine analog is 5-propynylcytosine.

Provided herein is a method for generating the diversity adaptors useful for generating RRBS nucleic acid libraries comprising increased sequence diversity as provided herein. FIG. 2A-B illustrates a method for generating the diversity adaptors useful in the methods, compositions, and kits proved herein. FIG. 2A shows a long strand of nucleotides (R01446) and 4 different short strands (i.e., Ben383, Ben384, Ben385, and Ben341) such that each short strand comprises stretch of 12 nucleotides that comprise bases complementary to the 3' end of the long strand (R01446). Each of the four short strands differ in their 5' end sequences such that Ben341 comprises a 5'-CG-3' dinucleotide, while Ben385 comprises an additional H base 3' to the 5'-CG-3' dinucleotide, Ben384 an additional two H bases 3' to the 5'-CG-3' dinucleotide, and Ben383 an additional three H bases 3' to the 5'-CG-3' dinucleotide. The H bases in the short strands can be either and adenine (A), cytosine (C), or thymine (T). FIG. 2B illustrates the method used to generate a diversity adaptor using the long strand (R01446) and a representative short strand (Ben383) from FIG. 2A, although it should be noted that any of the four short strands can be substituted for the Ben383 short strand in FIG. 2B. Each of the short strands (Ben383, 384, 385, or 341) in FIG. 2A comprise a 5' terminal GC sequence with a Biosg label on the terminal cytosine residue, while the 3' terminus comprises a terminal 3' dideoxy cytosine residue.

In FIG. 2B, the long strand of nucleotides (R01446) can be annealed to a short strand of nucleotides (Ben383) such that a partial duplex is formed. The partial duplex can comprise a duplex region and a 5' overhang on both ends of the duplex, wherein both the long strand (R01446) and the short strand (Ben383) contribute sequence to the 5' overhang on the opposite strand. The 5' overhang comprising sequence from the short strand of the partial duplex can comprise a 5' terminal GC sequence with a Biosg label on the terminal cytosine residue, while the 3' terminus comprises a terminal 3' dideoxy cytosine residue. Additionally, the 5' overhang from the short strand comprises three "H" bases. If Ben384 were used in the method illustrated in FIG. 2B, the 5' overhang would further comprise two H bases, Ben385 would comprise one H base, and Ben341 would comprise no H bases. The "H" bases can be either an adenosine, cytosine or thymine residue, but cannot be a guanine residue. As shown in FIG. 2B, following annealing, the partial duplex adapter can be subjected to an extension reaction using a dNTP mix containing only dATP, dGTP, and dTTP (i.e., no dCTP), whereby a partial duplex adapter comprising a 5' overhang comprising at least one "H" (e.g., R01446 hybridized to Ben 383, 384, or 385) is extended to produce a partial duplex adapter containing a two base 5' overhang with the sequence GC at one end. In some cases, the diversity adaptors generated in FIG. 2B are ligated to polynucleotides fragmented with MspI. The diversity adaptors generated in FIG. 2B can be mixed into a single pool thereby comprising a mixture of diversity adaptors comprising 0, 1, 2, or 3 D bases (D0-D3) and ligated to the MspI polynucleotide fragments. In some cases, the MspI polynucleotide fragments were separated into different pools, wherein a first pool was ligated to diversity adaptors with no D bases (D0), a second pool was ligated to diversity adapters with one D base (D1), a third pool was ligated diversity adapters comprising two D bases (D2), a fourth pool was ligated to adapters comprising three D bases (D3), and a fifth pool was ligated to a mixture of D0, D1, D2, and D3 diversity adapters. The methods illustrated in FIG. 2A-B can be used to generate diversity adaptors useful for ligating to polynucleotide fragments generated by digestion with any restriction enzyme. In these cases, the nucleotide base compositions of the non-H base overhang can be adjusted to be complementary to overhang sequence produced by enzymatic digestion, while the base identity of the H bases can be altered to so as to be distinguishable from the recognition sequence of the restriction enzyme used to generate the site upon sequencing of the fragments. In some cases, diversity adaptors or pools of diversity adaptors can be ligated to polynucleotide ends using blunt end ligation. The ends of the polynucleotide can be blunt due to digestion with an enzyme that generates blunt ends, or can be blunted using an end repair reaction as described herein and known in the art. In some cases, the diversity adaptors are configured such that each strand is capable of ligation to an end of a polynucleotide. In some cases, the diversity adaptors where both strands are ligation capable differ in that one strand comprises cytosine analogs resistant to bisulfite treatment, while the complementary strand comprises cytosine bases sensitive to bisulfite treatment such that bisulfite treatment of polynucleotides comprising said diversity adaptors ligated thereto generate polynucleotides comprising non-complementary termini.

III. Polynucleotides, Oligonucleotides, Primers, Samples, and Nucleotides

A bisulfite converted polynucleotide library (e.g., reduced representation bisulfite library) can be generated from a polynucleotide obtained from a source of polynucleotides. The polynucleotides can be single-stranded or double stranded. In some cases, the polynucleotide is DNA. The DNA can be obtained and purified using standard techniques in the art and include DNA in purified or unpurified form. The DNA can be mitochondrial DNA, cell-free DNA, complementary DNA (cDNA), or genomic DNA. In some cases, the polynucleotide is genomic DNA. The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can derived from one or more of chromosome 1, 2, 3, 4, 5, 6, 7, 8, 9, 10, 11, 12, 13, 14, 15, 16, 17, 18, 19, 20, 21, 22, X, or Y. In some cases, the DNA is double-stranded DNA. In some cases, the double-stranded DNA is genomic DNA. In some cases, the DNA is cDNA. In some cases, the cDNA is double-stranded cDNA. In some cases, the cDNA is derived from RNA, wherein the RNA is subjected to first strand synthesis followed by second strand synthesis. The RNA can be obtained and purified using standard techniques in the art and include RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA or ncRNA can include snoRNAs, microRNAs, siRNAs, piRNAs and long nc RNAs. First strand synthesis can be performed using any number of RNA dependent DNA polymerases known in the art.

The source of polynucleotides for use in the methods described herein can be a sample comprising the polynucleotides. The polynucleotides can be isolated from the sample and purified by any of the methods known in the art for purifying the nucleic acid from the sample. The sample can be derived from a non-cellular entity comprising polynucleotides (e.g., a virus) or from a cell-based organism (e.g., member of archaea, bacteria, or eukarya domains). In some cases, the sample is obtained from a swab of a surface, such as a door or bench top.

The sample can from a subject, e.g., a plant, fungi, eubacteria, archeabacteria, protest, or animal. The subject can be an organism, either a single-celled or multi-cellular organism. The subject can be cultured cells, which can be primary cells or cells from an established cell line, among others. The sample can be isolated initially from a multicellular organism in any suitable form. The animal can be a fish, e.g., a zebrafish. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. The human can be an infant, child, teenager, adult, or elderly person. The female can be pregnant, suspected of being pregnant, or planning to become pregnant.

The sample can be from a subject (e.g., human subject) who is healthy. In some cases, the sample is taken from a subject (e.g., an expectant mother) at at least 4, 5, 6, 7, 8, 9, 10, 11, 12, 13, 14, 15, 16, 17, 18, 19, 20, 21, 22, 23, 24, 25, or 26 weeks of gestation. In some cases, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs).

The sample can be from a subject who has a specific disease, disorder, or condition, or is suspected of having (or at risk of having) a specific disease, disorder or condition. For example, the sample can be from a cancer patient, a patient suspected of having cancer or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient.

The sample can be from a subject who is known or suspected to have a genetic disease, disorder or condition. The sample can be from a subject who is known or suspected to have gene silencing, imprinting, X-chromosome inactivation, phenotypic variation or genetic disease susceptibility. In some cases, the subject is known to be wild-type or mutant for a gene, or portion of a gene, e.g., CFTR, Factor VIII (F8 gene), beta globin, hemachromatosis, G6PD, neurofibromatosis, GAPDH, beta amyloid, or pyruvate kinase gene. In some cases, the status of the subject is either known or not known, and the subject is tested for the presence of a mutation or genetic variation of a gene, e.g., CFTR, Factor VIII (F8 gene), beta globin, hemachromatosis, G6PD, neurofibromatosis, GAPDH, beta amyloid, or pyruvate kinase gene.

The sample can be aqueous humour, vitreous humour, bile, whole blood, blood serum, blood plasma, breast milk, cerebrospinal fluid, cerumen, enolymph, perilymph, gastric juice, mucus, peritoneal fluid, saliva, sebum, semen, sweat, tears, vaginal secretion, vomit, feces, or urine. The sample can be obtained from a hospital, laboratory, clinical or medical laboratory. The sample can be taken from a subject.

The sample can comprise nucleic acid. The sample can comprise a whole genome, and thus be considered a whole genome sample. The sample can be a nucleic acid or polynucleotide library. The nucleic acid can be, e.g., mitochondrial DNA, genomic DNA, mRNA, siRNA, miRNA, cRNA, single-stranded DNA, double-stranded DNA, single-stranded RNA, double-stranded RNA, tRNA, rRNA, or cDNA. The sample can comprise cell-free nucleic acid. The sample can be a cell line, genomic DNA, cell-free plasma, formalin fixed paraffin embedded (FFPE) sample, or flash frozen sample. A formalin fixed paraffin embedded sample can be deparaffinized before nucleic acid is extracted. The sample can be from an organ, e.g., heart, skin, liver, lung, breast, stomach, pancreas, bladder, colon, gall bladder, brain, etc. Nucleic acids can be extracted from a sample by means available to one of ordinary skill in the art.

The sample can be processed to render it competent for fragmentation, ligation, denaturation, and/or amplification. Exemplary sample processing can include lysing cells of the sample to release nucleic acid, purifying the sample (e.g., to isolate nucleic acid from other sample components, which can inhibit enzymatic reactions), diluting/concentrating the sample, and/or combining the sample with reagents for further nucleic acid processing. In some examples, the sample can be combined with a restriction enzyme, reverse transcriptase, or any other enzyme of nucleic acid processing.

The methods described herein can be used for analyzing or detecting one or more target polynucleotides. The term polynucleotide, or grammatical equivalents, can refer to at least two nucleotides covalently linked together. A polynucleotide described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469, 863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some cases. The polynucleotides can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

"Unmodified nucleotide" or "unmodified dNTP" can refer to the four deoxyribonucleotide triphosphates dATP (deoxyadenosine triphosphate), dCTP (deoxycytidine triphosphate), dGTP (deoxyguanosine triphosphate) and dTTP (deoxythymidine triphosphate) that can normally be used as building blocks in the synthesis of DNA.

"Modified nucleotide," "modified dNTP," or "nucleotide analog," can refer to any molecule suitable for substituting one corresponding unmodified nucleotide. The modified nucleotide or dNTP render the polynucleotide more or less susceptible to degradation or alteration by a suitable degrading or altering agent. In some cases, the modified nucleotide substitutes for cytosine, which in its unmodified state undergoes conversion to uracil when subjected to bisulfite treatment. In some cases, the modified nucleotide substituting for cytosine is 5-methylcytosine. In some cases, the modified nucleotide substituting for cytosine is 5-hydroxymethylcytosine. In some cases, the modified nucleotide is 5-propynylcytosine.

As used herein, "oligonucleotide" can refer to a polynucleotide chain, typically less than 200 residues long, most typically between 15 and 100 nucleotides long, but also intended to encompass longer polynucleotide chains. Oligonucleotides may be single- or double-stranded. The terms "primer", and "oligonucleotide primer", as used herein, can refer to an oligonucleotide capable of hybridizing to a complementary nucleotide sequence.

As used herein, "hybridization"/"hybridizing" and "annealing" can be used interchangeably and refer to the pairing of complementary nucleic acids or sequences within nucleic acids. "Primer", as used herein, can refer to an oligonucleotide, generally with a free 3' hydroxyl group, that is capable of hybridizing with a template (such as a target polynucleotide or target sequence within a polynucleotide, target DNA, target RNA or a primer extension product) and is also capable of promoting polymerization of a polynucleotide complementary to the template. A primer may contain a non-hybridizing sequence that constitutes a tail of the primer. A primer may still be hybridizing to a target even though its sequences are not fully complementary to the target. In some cases, a first and/or second primer used to amplify a nucleic acid or polynucleotide fragment comprising diversity sequences on the 5' and/or 3' ends generated by the methods as provided herein further comprise one or more identifier sequences. In some cases, the identifier sequences comprise a non-hybridizable tail on the first and/or second primer. The identifier sequence can be a barcode sequence, a flow cell sequence, and/or an index sequence. In some cases, the index sequence is a Truseq primer sequence compatible with the next generation sequencing (NGS) platform produced by Illumina. In some cases, the first and/or second primer can bind to a solid surface. The solid surface can be a planar surface or a bead. The planar surface can be the surface of a chip, microarray, well, or flow cell. In some cases, the first and/or second primer comprises one or more sequence elements wherein products of the amplification reaction (i.e. amplification products) bind to a solid surface, whereby the one or more sequences elements are complementary to one or more capture probes attached to a solid surface.

The primers described herein can generally be oligonucleotides that are employed in an extension reaction by a polymerase along a template (such as a target polynucleotide or target sequence within a polynucleotide, target DNA, target RNA or a primer extension product), such as in PCR or cDNA synthesis, for example. An oligonucleotide primer can be a synthetic polynucleotide that is single stranded, containing a sequence at its 3'-end that is capable of hybridizing with a sequence of a target polynucleotide. Normally, the 3' region of the primer that hybridizes with the target nucleic acid has at least 80%, 90%, 95%, 100%, complementarity to a sequence or primer binding site.

In some cases, one or more primers can be used in the methods provided herein to generate nucleic acid libraries comprising increased diversity relative to the same nucleic acid libraries being generated without the increased diversity. The primers used to generate the nucleic acid libraries comprising increased diversity can comprise extender sequence diversity sequence as provided herein. The primers can comprise sequence complementary to a target sequence in a polynucleotide as well as sequence that is non-complementary to the target sequence. The non-complementary sequence can be a tail and can comprise one or more diversity bases or extender sequence as described herein. The primers comprising one or more diversity bases can be introduced to one or more ends of the target sequence from a polynucleotide using a polymerase extension reaction (e.g., PCR) as provided herein. The primers comprising diversity base(s) (i.e., extender sequence) can be designed such that the diversity base or bases are immediately adjacent to the target sequence derived from a polynucleotide following introduction. In other words, the diversity base or bases are the first non-target sequence polynucleotide base or bases present at the junction of a complex comprising a target sequence from a polynucleotide and non-target sequence derived sequence. Also as provided herein, the primers comprising diversity bases can comprise a sequence or complement thereof that is capable of hybridizing a sequencing primer and this sequence or complement thereof can be located adjacent to the diversity base or bases such that the diversity base or bases are the bases initially sequenced in a sequencing reaction. In some cases, there can also be additional sequence elements located between the sequence or complement thereof that is capable of hybridizing a sequencing primer and the diversity base or bases such as barcodes (e.g., inline barcodes), universal sequence, index sequence, or random sequence. In some cases, the additional sequence elements (e.g., barcode(s), universal sequence and/or random sequence) can be located after the sequence or complement thereof that is capable of hybridizing a sequencing primer and distal to the diversity base or bases. In some cases, the additional sequence elements (e.g., barcode(s), universal sequence and/or random sequence) can be located after the sequence or complement thereof that is capable of hybridizing a sequencing primer and distal to the diversity base or bases as well as between the sequence or complement thereof that is capable of hybridizing a sequencing primer and the diversity base or bases such as barcodes (e.g., inline barcodes), universal sequence, or random sequence. In some cases, the primers comprising diversity bases used in the methods provided herein can be used to generate low diversity libraries such as 16S rRNA libraries or RRBS libraries such that the low diversity libraries comprise increased diversity versus low diversity libraries generated without the use of primers comprising diversity bases. The primers comprising diversity bases can be mixed into a single pool thereby comprising a mixture of primers comprising diversity bases of varying lengths, wherein some of the primers in the pool comprise no diversity bases, while some comprise 1 diversity bases, some comprise 2 diversity bases, some comprise 3 diversity bases, some comprise 4 diversity bases, some comprise 5 diversity bases, some comprise 6 diversity bases, some comprise 7 diversity bases, some comprise 8 diversity bases, some comprise 9 diversity bases, some comprise 10 diversity bases, some comprise 11 diversity bases, and some comprise 12 diversity bases. Each primer in the pool of primers can comprise sequence complementary to the same target sequence. Each primer in the pool of primers can further comprise sequence that can be hybridized by a sequencing primer or a primer that can introduce a common sequencing primer target sequence. The single pool of primers comprising diversity bases of varying lengths can be introduced to a target sequence (e.g., 16S rRNA) present in polynucleotides from multiple samples. As described herein, the diversity bases in a primer comprising diversity bases can be "D" bases, "R" bases, complements of "D" bases, or complements of "R" bases or combinations thereof.

"Complementary", as used herein, can refer to complementarity to all or only to a portion of a sequence. The number of nucleotides in the hybridizable sequence of a specific oligonucleotide primer can be such that stringency conditions used to hybridize the oligonucleotide primer can prevent excessive random non-specific hybridization. In some cases, the number of nucleotides in the hybridizing portion of the oligonucleotide primer can be at least as great as the defined sequence on the target polynucleotide that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 of 12 to about 200 nucleotides, usually about 10 to about 50 nucleotides. In general, the target polynucleotide can be larger than the oligonucleotide primer or primers as described previously.

In some cases, the identity of the investigated target polynucleotide sequence is known, and hybridizable primers can be synthesized precisely according to the antisense sequence of the aforesaid target polynucleotide sequence. In other cases, when the target polynucleotide sequence is unknown, the hybridizable sequence of an oligonucleotide primer is a random sequence. Oligonucleotide primers comprising random sequences may be referred to as "random primers", as described below. In yet other cases, an oligonucleotide primer such as a first primer or a second primer comprises a set of primers such as for example a set of first primers or a set of second primers. In some cases, the set of first or second primers may comprise a mixture of primers designed to hybridize to a plurality (e.g. 2, 3, 4, about 6, 8, 10, 20, 40, 80, 100, 125, 150, 200, 250, 300, 400, 500, 600, 800, 1000, 1500, 2000, 2500, 3000, 4000, 5000, 6000, 7000, 8000, 10,000, 20,000, 25,000, 30,000, 40,000, 50,000, 60,000, 70,000, 80,000, 90,000, 100,000 or more) of target sequences. In some cases, the plurality of target sequences may comprise a group of related sequences, random sequences, a whole transcriptome or fraction (e.g. substantial fraction) thereof, or any group of sequences such as mRNA.

"Barcode" can refer to a known polynucleotide sequence that allows some feature of a polynucleotide with which the barcode is associated to be identified. In some cases, the feature of the polynucleotide to be identified is the sample from which the polynucleotide is derived. In some cases, barcodes are at least 3, 4, 5, 6, 7, 8, 9, 10, 11, 12, 13, 14, 15, or more nucleotides in length. In some cases, barcodes are shorter than 10, 9, 8, 7, 6, 5, or 4 nucleotides in length. A oligonucleotide (e.g., primer or adaptor) can comprise about, more than, less than, or at least 1, 2, 3, 4, 5, 6, 7, 8, 9, or 10 different barcodes. In some cases, barcodes associated with some polynucleotides are of different length than barcodes associated with other polynucleotides. Barcodes can be of sufficient length and comprise sequences that can be sufficiently different to allow the identification of samples based on barcodes with which they are associated. In some cases, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some cases, each barcode in a plurality of barcodes differ from every other barcode in the plurality at at least three nucleotide positions, such as at least 3, 4, 5, 6, 7, 8, 9, 10, or more positions. In some cases, an oligonucleotide (e.g., adaptor or primer) comprises at least one of a plurality of barcode sequences. In some cases, barcodes for a second oligonucleotide (e.g., adaptor or primer) are selected independently from barcodes for a first oligonucleotide (e.g., adaptor or primer). In some cases, first oligonucleotides (e.g., adaptor or primer) and second oligonucleotides (e.g., adaptor or primer) having barcodes are paired, such that oligonucleotides (e.g., adaptors or primers) of the pair comprise the same or different one or more barcodes. In some cases, the methods described herein further comprise identifying the sample from which a target polynucleotide is derived based on a barcode sequence to which the target polynucleotide is joined. A barcode can comprise a oligonucleotide sequence that when joined to a target polynucleotide serves as an identifier of the sample from which the target polynucleotide was derived.

"Extender sequence" can refer to a stretch of nucleotides that can vary in length and base composition and can serve to increase the distance between the 3' end of a sequencing primer hybridized to a sequence complementary to the sequencing primer and the first nucleotide of a target sequence in a polynucleotide to be read during a nucleotide sequencing reaction. "Extender sequence" can be used interchangeably with "diversity sequence" or "diversity base."

As provided herein, the sequence complementary to the sequencing primer and the extender sequence can be appended or introduced to the first nucleotide of a target sequence in a polynucleotide through ligation or amplification such that the extender sequence is immediately upstream of the first base with respect to the direction of sequencing and thus will be sequenced prior to the first base. The extender sequence can be 1, 2, 3, 4, 5, 6, 7, 8, 9, 10, 11, 12, 13, 14, 15, 16, 17, 18, 19, 20 or more nucleotides in length. In some cases, the extender sequence and the sequence complementary to a sequencing primer are present in the same oligonucleotide sequence. As provided herein, the oligonucleotide sequence can be present in a primer or adaptor. The extender sequence and the sequence complementary to a sequencing primer can be immediately adjacent to each other or can be separated by a stretch of nucleotides. The stretch of nucleotides can be an additional sequence element. The additional sequence element can be one or more barcodes as provided herein, universal sequence, linker sequence, or random sequence. The nucleotide base composition of each nucleotide in an extender sequence comprising more than one nucleotide can be identical or different. The nucleotide base composition of each nucleotide in an extender sequence can be randomly assigned. The nucleotide base composition of each nucleotide in an extender sequence can be semi-randomly assigned such that each nucleotide in an extender sequence (or diversity sequence) can only comprise 2 or 3 of the four possible canonical bases (i.e., thymine, guanine, cytosine, or adenine) such that one or two specific bases can be excluded. The nucleotide base composition of each nucleotide in an extender sequence can have a 25% chance of being one of the four unmodified bases (i.e., thymine, guanine, cytosine, or adenine). The nucleotide base composition of each nucleotide in an extender sequence can be the same nucleotide base. The nucleotide base composition of an extender sequence comprising more than one nucleotide can be constructed such that one or more nucleotide positions can have a fixed base composition, while the remaining nucleotides can have a randomly or semi-randomly assigned base composition as described herein.

RNA-dependent DNA polymerases for use in the methods and compositions provided herein can be capable of effecting extension of a primer according to the methods provided herein. Accordingly, an RNA-dependent DNA polymerase can be one that is capable of extending a nucleic acid primer along a nucleic acid template that is comprised at least predominantly of ribonucleotides. Suitable RNA-dependent DNA polymerases for use in the methods, compositions, and kits provided herein include reverse transcriptases (RTs). RTs are well known in the art. Examples of RTs include, but are not limited to, Moloney murine leukemia virus (M-MLV) reverse transcriptase, human immunodeficiency virus (HIV) reverse transcriptase, rous sarcoma virus (RSV) reverse transcriptase, avian myeloblastosis virus (AMV) reverse transcriptase, rous associated virus (RAV) reverse transcriptase, and myeloblastosis associated virus (MAV) reverse transcriptase or other avian sarcoma-leukosis virus (ASLV) reverse transcriptases, and modified RTs derived therefrom. See e.g. U.S. Pat. No. 7,056,716. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a RT which lacks or has substantially reduced RNase H activity. RTs devoid of RNase H activity are known in the art, including those comprising a mutation of the wild type reverse transcriptase where the mutation eliminates the RNase H activity. Examples of RTs having reduced RNase H activity are described in US20100203597. In these cases, the addition of an RNase H from other sources, such as that isolated from E. coli, can be employed for the degradation of the starting RNA sample and the formation of the double stranded cDNA. Combinations of RTs can also contemplated, including combinations of different non-mutant RTs, combinations of different mutant RTs, and combinations of one or more non-mutant RT with one or more mutant RT.

DNA-dependent DNA polymerases for use in the methods and compositions provided herein can be capable of effecting extension of a primer according to the methods provided herein. Accordingly, a DNA-dependent DNA polymerase can be one that is capable of extending a nucleic acid primer along a first strand cDNA in the presence of the RNA template or after selective removal of the RNA template. Exemplary DNA dependent DNA polymerases suitable for the methods provided herein include but are not limited to Klenow polymerase, with or without 3'-exonuclease, Bst DNA polymerase, Bca polymerase, .phi.29 DNA polymerase, Vent polymerase, Deep Vent polymerase, Taq polymerase, T4 polymerase, and E. coli DNA polymerase 1, derivatives thereof, or mixture of polymerases. In some cases, the polymerase does not comprise a 5'-exonuclease activity. In other cases, the polymerase comprises 5' exonuclease activity. In some cases, the primer extension can be performed using a polymerase comprising strong strand displacement activity such as for example Bst polymerase. In other cases, the primer extension can be performed using a polymerase comprising weak or no strand displacement activity. One skilled in the art can recognize the advantages and disadvantages of the use of strand displacement activity during the primer extension step, and which polymerases can be expected to provide strand displacement activity (see e.g., New England Biolabs Polymerases). For example, strand displacement activity can be useful in ensuring whole transcriptome coverage during the random priming and extension step. Strand displacement activity can further be useful in the generation of double stranded amplification products during the priming and extension step. Alternatively, a polymerase which comprises weak or no strand displacement activity can be useful in the generation of single stranded nucleic acid products during primer hybridization and extension that can be hybridized to the template nucleic acid.

In some cases, the double stranded products generated by the methods described herein can be end repaired to produce blunt ends for the adapter ligation applications described herein. Generation of the blunt ends on the double stranded products can be generated by the use of a single strand specific DNA exonuclease such as for example exonuclease 1, exonuclease 7 or a combination thereof to degrade overhanging single stranded ends of the double stranded products. Alternatively, the double stranded products can be blunt ended by the use of a single stranded specific DNA endonuclease for example but not limited to mung bean endonuclease or 51 endonuclease. Alternatively, the double stranded products can be blunt ended by the use of a polymerase that comprises single stranded exonuclease activity such as for example T4 DNA polymerase, any other polymerase comprising single stranded exonuclease activity or a combination thereof to degrade the overhanging single stranded ends of the double stranded products. In some cases, the polymerase comprising single stranded exonuclease activity can be incubated in a reaction mixture that does or does not comprise one or more dNTPs. In other cases, a combination of single stranded nucleic acid specific exonucleases and one or more polymerases can be used to blunt end the double stranded products of the primer extension reaction. In still other cases, the products of the extension reaction can be made blunt ended by filling in the overhanging single stranded ends of the double stranded products. For example, the fragments can be incubated with a polymerase such as T4 DNA polymerase or Klenow polymerase or a combination thereof in the presence of one or more dNTPs to fill in the single stranded portions of the double stranded products. Alternatively, the double stranded products can be made blunt by a combination of a single stranded overhang degradation reaction using exonucleases and/or polymerases, and a fill-in reaction using one or more polymerases in the presence of one or more dNTPs.

In another embodiment, the adapter ligation applications described herein can leave a nick between a non-ligation strand of the adapters and a strand of the double stranded product. In these instances, a gap repair or fill-in reaction can be used to append the double stranded product with the sequence complementary to the ligation strand of the adapter. Gap repair can be performed with any number of DNA dependent DNA polymerase described herein. In some cases, gap repair can be performed with a DNA dependent DNA polymerase with strand displacement activity. In some cases, gap repair can be performed using a DNA dependent DNA polymerase with weak or no strand displacement activity. In some cases, the ligation strand of the adapter can serve as the template for the gap repair or fill-in reaction. In some cases, gap repair can be performed using Taq DNA polymerase.

Various ligation processes and reagents are known in the art and can be useful for carrying out the methods provided herein. For example, the NuGEN Ovation® Ultralow Methyl-Seq Library System can be used. In some cases, blunt end ligation is employed. Similarly, a single dA nucleotide can be added to the 3'-end of the double-stranded DNA product, by a polymerase lacking 3'-exonuclease activity and can anneal to an adaptor (e.g., diversity adaptor as provided herein) comprising a dT overhang (or the reverse). This design can allow the hybridized components to be subsequently ligated (e.g., by T4 DNA ligase). Other ligation strategies and the corresponding reagents known in the art can be employed and kits and reagents for carrying out efficient ligation reactions are commercially available (e.g, from New England Biolabs, Roche) and can be used for the methods provided herein.

"Bisulfite" as used herein can encompass all types of bisulfites, such as sodium bisulfite that are capable of chemically converting a cytosine (C) to a uracil (U) without chemically modifying a methylated cytosine and therefore can be used to differentially modify a DNA sequence based on the methylation status of the DNA.

"Low diversity" can refer to a polynucleotide. For example, the methods, compositions, and kits described herein can be used with pools of polynucleotides that have low diversity at one or more positions at one or both ends of polynucleotides in the pool. A "position" can be a single nucleotide, or 2 or more nucleotides. A "position" can be 1, 2, 3, 4, 5, 6, 7, 8, 9, 10, 11, 12, 13, 14, 15, 16, 17, 18, 19, or 20 nucleotides in length. A "position" can be a nucleotide sequence repeat such as CpG or a conserved region of a gene.

A polynucleotide can have low diversity at a position among polynucleotides if the position among polynucleotides has only one, two, or three nucleotide bases out of the four canonical DNA nucleotide bases. In some cases, a polynucleotide can have low diversity at a position among polynucleotides if it lacks one of the types of nucleotide bases present in the polynucleotide. For example, a pool of polynucleotides can one type of nucleotide base, e.g., only A, only T, only C, or only G at a position in the polynucleotides in the pool. In some cases, a pool of polynucleotides has only two types of polynucleotides at a position, e.g., only A or C, only A or G, only A or T, only C or T, only G or T, or only C or G. In some cases, a pool of polynucleotides has only three types of polynucleotides at a position, e.g., only A, C, and G; only A, C, and T; only C, T, and G.

In some cases, a pool of polynucleotides can have low diversity at a position if all types of nucleotide bases (e.g., A, T, C, and G) are at the position among polynucleotides in the pool, but the percentage of polynucleotides with one, two, or three types of bases at the position is low. For example, a pool of polynucleotides can have all four canonical bases found in DNA at the position, but one of the types of nucleotide bases is present at that position in less than 10%, 9%, 8%, 7%, 6%, 5%, 4%, 3%, 2%, or 1% of the polynucleotides. For example, a pool polynucleotides can have A, T, C, and G at a position, where 50% of polynucleotides have an A at the position, 20% have a T at the position, 20% have a C at the position, and only 10% have a G at the position.

In some cases, a pool of polynucleotides can have all four canonical bases found in DNA at a position among the polynucleotides in the pool, but each of two of the types of nucleotide bases is present at that position in less than 10%, 9%, 8%, 7%, 6%, 5%, 4%, 3%, 2%, or 1% of the polynucleotides. For example, a pool polynucleotides can have A, T, C, and G at a position, where 50% of polynucleotides have an A at the position, 40% have a T at the position, 5% have a C at the position, and 5% have a G at the position.

A pool of polynucleotides can have low diversity at a position if all four canonical bases found in DNA are at the position among the polynucleotides in the pool, but each of three of the types of nucleotide bases is present at that position in less than 10%, 9%, 8%, 7%, 6%, 5%, 4%, 3%, 2%, or 1% of the polynucleotides. For example, a pool polynucleotides can have A, T, C, and G at a position, where 94% of polynucleotides have an A at the position, 2% have a T at the position, 2% have a C at the position, and 2% have a G at the position.

A pool of polynucleotides can have any of the characteristics of a position described herein at 1, 2, 3, 4, 5, 6, 7, 8, 9, 10 or more positions. A pool of polynucleotides can have any of the characteristics of a position described herein at 1, 2, 3, 4, 5, 6, 7, 8, 9, 10 or more positions immediately 5' to base that anneals to the 3' end of a primer, e.g., a sequencing primer. A pool of polynucleotides can have any of the characteristics of a position described herein at 1, 2, 3, 4, 5, 6, 7, 8, 9, 10 or more positions immediately 5' to base that anneals to the 3' end of a primer, e.g., a sequencing primer.

In some cases, a pool of polynucleotides with low diversity at one or both ends is generated using restriction enzyme. In some cases the restriction enzyme has a palindromic recognition sequence. In some cases, a recognition site comprises a methylation site. In some cases, a palindromic recognition site comprises a methylation site. For example, a pool of polynucleotides can be generated by using the restriction enzyme MspI, which can have the recognition sequence CCGG, where CG can be a methylation site.

In some cases, a pool of polynucleotides with low sequence diversity is generated using an amplification based method, for example, polymerase chain reaction (PCR).

IV. Methods of Fragmentation

The methods provided herein can comprise fragmenting a polynucleotide to produce polynucleotide fragments. In some cases, the polynucleotides are double-stranded and fragmentation of the polynucleotides generates double stranded polynucleotide fragments. In some cases, fragmentation can be achieved through methods known in the art. Fragmentation can be through physical fragmentation methods and/or enzymatic fragmentation methods. Physical fragmentation methods can include nebulization, sonication, and/or hydrodynamic shearing. In some cases, the fragmentation can be accomplished mechanically comprising subjecting the nucleic acid to acoustic sonication. In some cases, the fragmentation comprises treating the nucleic acid with one or more enzymes under conditions suitable for the one or more enzymes to generate breaks in the double-stranded nucleic acid. Examples of enzymes useful in the generation of nucleic acid fragments include sequence specific and non-sequence specific nucleases. Non-limiting examples of nucleases include DNase I, Fragmentase, restriction endonucleases, variants thereof, and combinations thereof. Reagents for carrying out enzymatic fragmentation reactions are commercially available (e.g, from New England Biolabs). For example, digestion with DNase I can induce random double-stranded breaks in DNA in the absence of $Mg^{++}$ and in the presence of $Mn^{++}$. In some cases, fragmentation comprises treating DNA with one or more restriction endonucleases. Fragmentation can produce fragments having 5' overhangs, 3' overhangs, blunt ends, or a combination thereof. In some cases, such as when fragmentation comprises the use of one or more restriction endonucleases, cleavage of the DNA leaves overhangs having a predictable sequence. In some cases, the methods provided herein are used on to generate nucleic acid libraries from polynucleotides fragmented by digestion with restriction enzymes. In some cases, the method includes the step of size selecting the fragments via standard methods known in the art such as column purification or isolation from an agarose gel.

In some cases, the methods, compositions, and kits provided herein are used to generate a reduced representation bisulfite sequencing (RRBS) library. An initial step in the generation of an RRBS library (see FIG. 1, FIG. 3, or FIG. 36) can comprise fragmenting a polynucleotide or a sample comprising polynucleotides by treating the polynucleotide or sample comprising polynucleotides with a methylation insensitive restriction enzyme. The methylation insensitive restriction enzyme can be AatII, AccB7I, AccIII, Acc65I, ApaI, AvaI, BanII, BbuI, BclI, BamHI, BalI, BglII, Bsp1286I, BssHII, BstEII, BstOI, BstXI, ClaI, CaspI, Csp45I, DdeI, Eco47III, EcoRI, HaeIII, HhaI, HincII, HindIII, KpnI, MboII, MluI, MspI, NarI, NdeII, NruI, PstI, PvuII, SacI, ScaI, SinI, SnaBI, SphI, StuI, TaqI, XbaI, XhoII, or XmaI. In some cases, fragmenting a polynucleotide or a sample comprising polynucleotides comprises treating the polynucleotide or the sample comprising polynucleotides with MspI, thereby generating polynucleotide fragments comprising a 5'-CG-3" overhang at each end. The polynucleotides treated with MspI can be from mammalian sources, whereby the CCGG recognition site of MspI is not methylated at the first cytosine residue.

In some cases, the polynucleotide, for example DNA, can be fragmented into a population of fragmented polynucleotides of one or more specific size range(s). In some cases, the fragments can have an average length from about 10 to about 10,000 nucleotides or base pairs. In some cases, the fragments have an average length from about 50 to about 2,000 nucleotides or base pairs. In some cases, the fragments have an average length from about 100 to about 2,500, about 10 to about 1000, about 10 to about 800, about 10 to about 500, about 50 to about 500, about 50 to about 250, or about 50 to about 150 nucleotides or base pairs. In some cases, the fragments have an average length less than 10,000 nucleotides or bp, less than 7,500 nucleotides or bp, less than 5,000 nucleotides or bp, less than 2,500 nucleotides or bp, less than 2,000 nucleotides or bp, less than 1,500 nucleotides or bp, less than 1,000 nucleotides or bp, less than 500 nucleotides or bp, less than 400 nucleotides or bp, less than 300 nucleotides or bp, less than 200 nucleotides or bp, or less than 150 nucleotides or bp. In some cases, the polynucleotide fragments have an average length of about, more than, less than, or at least 10, 20, 30, 40, 50, 60, 70, 80, 90, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3500, 4000, 4500, 5000, 5500, 6000, 6500, 7000, 7500, 8000, 8500, 9000, 9500, or 10,000 nucleotides or base pairs.

In some cases, polynucleotide fragments generated by fragmentation are subjected to end repair. End repair can include the generation of blunt ends, non-blunt ends (i.e. sticky or cohesive ends), or single base overhangs such as the addition of a single dA nucleotide to the 3'-end of the double-stranded nucleic acid product by a polymerase lacking 3'-exonuclease activity. In some cases, end repair is performed on the double stranded polynucleotide fragments to produce blunt ends wherein the ends of the polynucleotide fragments contain 5' phosphates and 3' hydroxyls. End repair can be performed using any number of enzymes and/or methods known in the art. An overhang can comprise about, more than, less than, or at least 1, 2, 3, 4, 5, 6, 7, 8, 9, 10, 11, 12, 13, 14, 15, 16, 17, 18, 19, or 20 nucleotides.

In some cases, the polynucleotide fragments are captured using a binding agent directed against an epigenetic modification within the sequence of the polynucleotide fragments. The epigenetic modification can be methylation. In some cases, the double stranded polynucleotide fragments are captured using a binding agent directed against 5-methylcytosine residues in the double-stranded polynucleotide fragments. The binding agent can be an antibody, or the binding domain of a protein directed against 5-methylcytosine residues. The protein can be a methyl-CpG-binding domain (MBD) protein. The MBD protein can be methyl-CpG-binding domain protein 1, 2, 4, or MECP2. In some cases, the double stranded polynucleotide fragments are captured using the binding domain of MBD2. In some cases, the double stranded polynucleotide fragments are captured using the binding domain of MECP2.

V. Methods of Amplification

The methods, compositions and kits described herein can be useful to generate amplification-ready products for downstream applications such as massively parallel sequencing (i.e. next generation sequencing methods) or hybridization platforms. As provided herein, the method, compositions and kits can be used to generate nucleic acid library (e.g., bisulfite converted libraries) such that each nucleic acid insert in the library comprises non-complementary sequence in opposing termini. Primer pairs comprising primers designed to target the non-complementary sequence can be used to amplify the nucleic acid inserts of a nucleic acid library prepared using the methods provided herein using the methods of amplification as provided herein. Methods of amplification are well known in the art. In some embodiments, the amplification is exponential, e.g. in the enzymatic amplification of specific double stranded sequences of DNA by a polymerase chain reaction (PCR). In other embodiments the amplification method is linear. In other embodiments the amplification method is isothermal. Examples of PCR techniques that can be used include, but are not limited to, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), bridge PCR, picotiter PCR, digital PCR, droplet digital PCR, and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA), single primer isothermal amplification (SPIA, see e.g. U.S. Pat. No. 6,251,639), Ribo-SPIA, or a combination thereof. Other amplification methods that can be used herein include those described in U.S. Pat. Nos. 5,242,794; 5,494,810; 4,988,617; and 6,582,938. Amplification of target nucleic acids can occur on a bead. In other embodiments, amplification does not occur on a bead. Amplification can be by isothermal amplification, e.g., isothermal linear amplification. A hot start PCR can be performed wherein the reaction is heated to 95° C. for two minutes prior to addition of the polymerase or the polymerase can be kept inactive until the first heating step in cycle 1. Hot start PCR can be used to minimize nonspecific amplification. Other strategies for and aspects of amplification are described in U.S. Patent Application Publication No. 2010/0173394 A1, published Jul. 8, 2010, which is incorporated herein by reference. In some cases, the amplification methods can be performed under limiting conditions such that only a few rounds of amplification (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.), such as for example as is commonly done for cDNA generation. The number of rounds of amplification can be about 1-30, 1-20, 1-15, 1-10, 5-30, 10-30, 15-30, 20-30, 10-30, 15-30, 20-30, or 25-30.

Techniques for amplification of target and reference sequences are known in the art and include the methods described in U.S. Pat. No. 7,048,481. Briefly, the techniques can include methods and compositions that separate samples into small droplets, in some instances with each containing on average less than about 5, 4, 3, 2, or one target nucleic acid molecule (polynucleotide) per droplet, amplifying the nucleic acid sequence in each droplet and detecting the presence of a target nucleic acid sequence. In some cases, the sequence that is amplified is present on a probe to the genomic DNA, rather than the genomic DNA itself. In some cases, at least 200, 175, 150, 125, 100, 90, 80, 70, 60, 50, 40, 30, 20, 10, or 0 droplets have zero copies of a target nucleic acid.

PCR can involve in vitro amplification based on repeated cycles of denaturation, oligonucleotide primer annealing, and primer extension by thermophilic template dependent polynucleotide polymerase, which can result in the exponential increase in copies of the desired sequence of the polynucleotide analyte flanked by the primers. In some cases, two different PCR primers, which anneal to opposite strands of the DNA, can be positioned so that the polymerase catalyzed extension product of one primer can serve as a template strand for the other, leading to the accumulation of a discrete double stranded fragment whose length is defined by the distance between the 5' ends of the oligonucleotide primers.

LCR uses a ligase enzyme to join pairs of preformed nucleic acid probes. The probes can hybridize with each complementary strand of the nucleic acid analyte, if present, and ligase can be employed to bind each pair of probes together resulting in two templates that can serve in the next cycle to reiterate the particular nucleic acid sequence.

SDA (Westin et al 2000, Nature Biotechnology, 18, 199-202; Walker et al 1992, Nucleic Acids Research, 20, 7, 1691-1696), can involve isothermal amplification based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Some aspects of the methods described herein can utilize linear amplification of nucleic acids or polynucleotides. Linear amplification can refer to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some cases, the amplification is exponential, e.g. in the enzymatic amplification of specific double stranded sequences of DNA by a polymerase chain reaction (PCR). In other embodiments the amplification method is linear. In other embodiments the amplification method is isothermal.

VI. Generation of Bisulfite Converted Libraries

In one aspect, a method is provided for generating a directional, bisulfite-converted nucleic acid library using duplex-forming adaptors comprising diversity bases or extender sequence as described herein. The nucleic acid library generated using the duplex-forming adapters comprising diversity bases can maintain directional (strandedness) information of the original nucleic acid sample. In some cases, the original nucleic acid is DNA. In some cases, the DNA is double-stranded DNA. In some cases, the double-stranded DNA is genomic DNA. In some cases, the nucleic acid or polynucleotide is from a whole genome sample. In some cases, the methods provided herein comprise generating a plurality of bisulfite converted libraries. One of the plurality of bisulfite converted libraries can be generated using a duplex-forming adaptor lacking diversity bases, while others of the plurality of bisulfite converted libraries can be generated using a duplex-forming adaptor comprising a variable number of diversity bases. One of the others of the plurality of bisulfite converted libraries can be generated using a duplex-forming adaptor comprising 1 diversity base. One of the others of the plurality of bisulfite converted libraries can be generated using a duplex-forming adaptor comprising 2 diversity bases. One of the others of the plurality of bisulfite converted libraries can be generated using a duplex-forming adaptor comprising 3 diversity bases.

As provided herein, the diversity base or bases can be introduced to adjacent to the first nucleotide of sequence derived from the polynucleotide to which it is attached such that the diversity base is sequenced immediately prior to the sequencing of the polynucleotide to which it is attached. In some cases, each of the plurality of bisulfite converted libraries can comprises a polynucleotide comprising the same or substantially similar sequence across at least a portion of each polynucleotide. Each of the plurality of bisulfite converted libraries comprising the polynucleotide comprising the same or substantially similar sequence across at least a portion of each polynucleotide sequence can be pooled and subsequently processed (e.g., amplified and/or solid-state amplified) and sequenced in parallel. In some cases, the bisulfite converted libraries can be generated using the method described herein by introducing (e.g., ligating) a pool of adaptors comprising adaptors comprising no diversity bases as well as adaptors comprising a varying number of diversity bases as described herein to a sample comprising polynucleotides comprising the same or substantially similar sequence across at least a portion of each polynucleotide sequence. The sequencing can be performed using a commercially available NGS system such as Illumina. The presence of diversity bases can aid in cluster determination in sequencing systems such as Illumina sequencing which can suffer from poor cluster identification in sequencing samples with low sequence diversity in their initial nucleotide bases as shown in FIG. 31.

Figure 36:
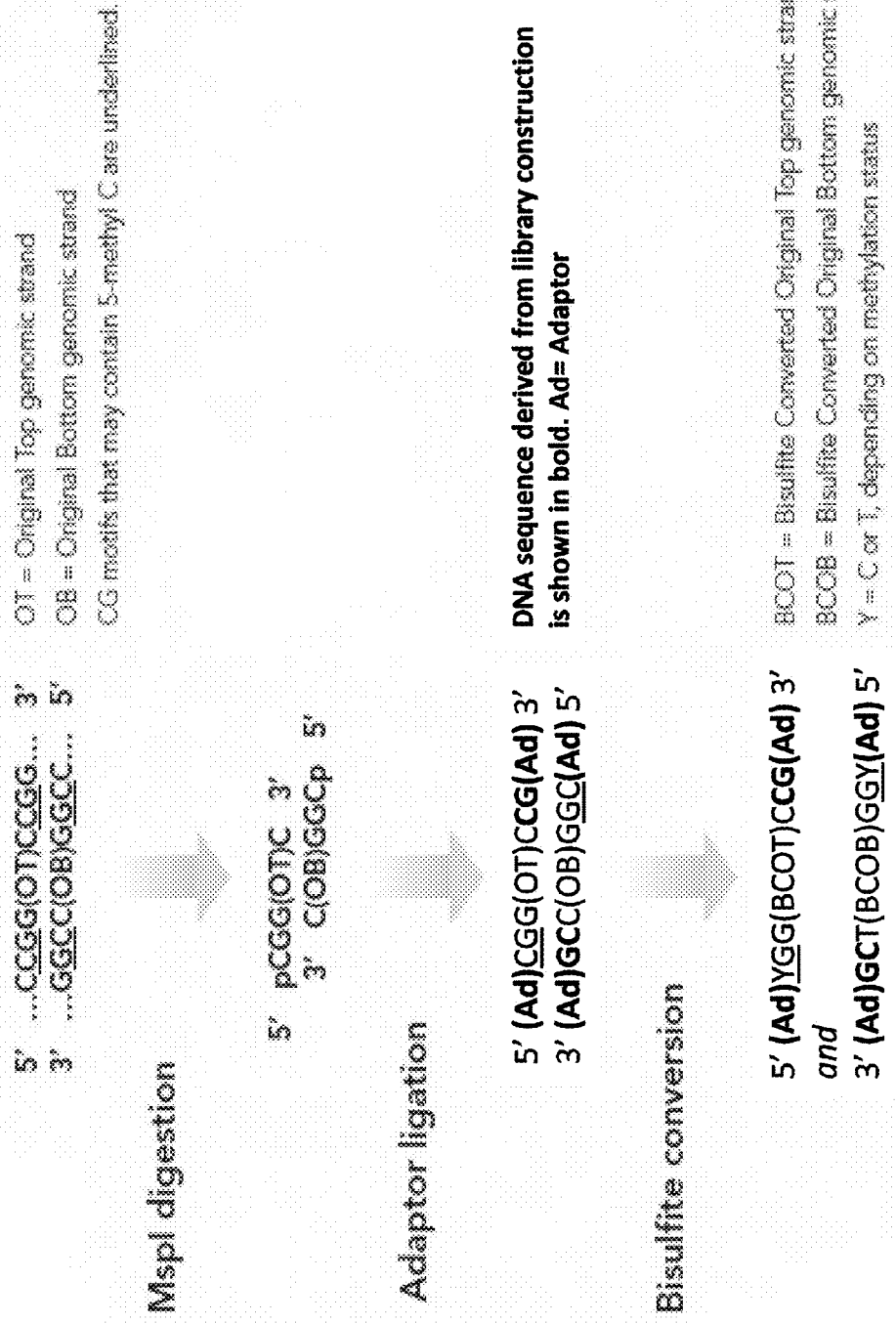
FIG. 36 illustrates the process of generating an RRBS library using MspI digestion and diversity adaptors lacking diversity bases.

The method can comprise fragmenting a double stranded polynucleotide to produce double stranded polynucleotide fragments. In some cases, fragmentation can be achieved through methods known in the art. In some cases, fragmentation can be achieved through methods known in the art and provided herein. In some cases, the fragmentation comprises treating the nucleic acid with one or more enzymes under conditions suitable for the one or more enzymes to generate breaks in the double-stranded nucleic acid. In some cases, fragmentation comprises treating DNA with one or more restriction endonucleases. Fragmentation can produce fragments having 5' overhangs, 3' overhangs, blunt ends, or a combination thereof. In some cases, such as when fragmentation comprises the use of one or more restriction endonucleases, cleavage of the DNA leaves overhangs having a predictable sequence. In some cases, the method includes the step of size selecting the fragments via standard methods known in the art such as column purification or isolation from an agarose gel. In some cases, the methods provided herein are used to generate RRBS libraries such that a sample comprising polynucleotides is fragmented using a methylation insensitive enzyme such as MspI in order to generate fragments with a predictable 5'-CG-3' overhang and subsequently introduced (e.g., through ligation) to an adaptor as shown in FIGS. 1, 3 and 36.

In some cases, polynucleotide fragments generated by fragmentation are subjected to end repair. End repair can include the generation of blunt ends, non-blunt ends (i.e. sticky or cohesive ends), or single base overhangs such as the addition of a single dA nucleotide to the 3'-end of the double-stranded nucleic acid product by a polymerase lacking 3'-exonuclease activity. In some cases, end repair is performed on the double stranded nucleic acid fragments to produce blunt ends wherein the ends of the polynucleotide fragments contain 5' phosphates and 3' hydroxyls. End repair can be performed using any number of enzymes and/or methods known in the art. An overhang can comprise about, more than, less than, or at least 1, 2, 3, 4, 5, 6, 7, 8, 9, 10, 11, 12, 13, 14, 15, 16, 17, 18, 19, or 20 nucleotides.

In some cases, double stranded polynucleotide fragments are captured using a binding agent directed against an epigenetic modification within the sequence of the polynucleotide fragments. The epigenetic modification can be methylation. In some cases, the double stranded polynucleotide fragments are captured using a binding agent directed against 5-methylcytosine residues in the double-stranded polynucleotide fragments. The binding agent can be an antibody, or the binding domain of a protein directed against 5-methylcytosine residues. The protein can be a methyl-CpG-binding domain (MBD) protein. The MBD protein can be methyl-CpG-binding domain protein 1, 2, 4, or MECP2. In some cases, the double stranded polynucleotide fragments are captured using the binding domain of MBD2. In some cases, the double stranded polynucleotide fragments are captured using the binding domain of MECP2.

The method can further comprise ligating an adapter comprising either no diversity bases or a variable number of diversity bases as provided herein to the double-stranded polynucleotide fragments. Ligation can be blunt end ligation or sticky or cohesive end ligation. In some cases, the ligation is performed using cohesive end ligation as shown in FIG. 3. The ligation can be performed with any of the enzymes known in the art for performing ligation (e.g. T4 DNA ligase). The adapter can be any type of adapter known in the art including, but not limited to, a conventional duplex or double stranded adapter. The adapter can comprise DNA, RNA, or a combination thereof. The adapters can be about, less than about, or more than about 10, 15, 20, 25, 30, 35, 40, 45, 50, 55, 60, 65, 70, 75, 80, 90, 100, or 200 nucleotides in length. The adapters can be a duplex adaptor, partial duplex adaptor, a forked adaptor or single stranded adaptor. In some cases, the adapter is a duplex adapter. In some cases, the duplex adapters comprises about, less than about, or more than about 10, 15, 20, 25, 30, 35, 40, 45, 50, 55, 60, 65, 70, 75, 80, 90, 100, or 200 nucleotides in length. In some cases, the adapter is a partial duplex adapter, wherein the adapter comprises a long strand and a short strand. In some cases, a partial duplex adapter has overhangs of about, more than, less than, or at least 1, 2, 3, 4, 5, 6, 7, 8, 9, 10, 11, 12, 13, 14, 15, 16, 17, 18, 19, or 20 nucleotides. In some cases, the overhang is a 5' overhang. In some cases, the overhang is a 3' overhang. In some cases, the partial duplex adapter comprises a 5' and 3' overhang. In some cases, the adapter comprises duplexed sequence. In some cases, the adapters comprise about, more than, less than, or at least 5, 6, 7, 8, 9, 10, 12, 12, 13, 14, 15, 16, 17, 18, 19, 20, 21, 22, 23, 24, 25, 30, 35, 40, 45, 50, 55, 60, 65, 70, 75, 80, 90, 100, 200, or more of base paired or duplexed sequence. In some cases, the adapter comprises a single stranded adapter. In some cases, a single-stranded adapter comprises about, more than, less than, or at least 10, 15, 20, 25, 30, 35, 40, 45, 50, 55, 60, 65, 70, 75, 80, 90, 100, or 200 nucleotides in length. In some cases, the single-stranded adapter forms a stem-loop or hairpin structure. In some cases, the stem of the hairpin adapter is about, less than about, or more than about 1, 2, 3, 4, 5, 6, 7, 8, 9, 10, 11, 12, 13, 14, 15, 20, 25, 30, 35, 40, 45, 50, 75, 100, or more nucleotides in length. In some cases, the loop sequence of a hairpin adapter is about, less than about, or more than about 5, 10, 15, 20, 25, 30, 35, 40, 45, 50, or more nucleotides in length. The adapter can further comprise known or universal sequence and, thus, allow generation and/or use of sequence specific primers for the universal or known sequence. In some cases, an adapter comprises one or more barcodes. In some cases, the one or more barcodes are in a stem and/or a loop.

In some cases, an adapter is marked via incorporation of at least one modified dNTP. In some cases, the modified dNTP comprises a nucleotide analog resistant to conversion by treatment with a converting agent. The nucleotide analog can be a cytosine analog. The converting agent can be any biological, biochemical, and/or chemical agent capable of altering the base composition of a dNTP. In some cases, the converting agent is a chemical. In some cases, the converting agent is the chemical compound bisulfite or sodium bisulfite. In some cases, the adapter comprises a cytosine analog resistant to conversion by bisulfite treatment. In some cases, the long strand of a partial duplex adapter comprises cytosine analog residues in place of cytosine residues, which are protected from bisulfite conversion, while the short strand of the partial duplex adapter does not comprise cytosine analog residues in place of cytosine residues. In some cases, the short strand of a partial duplex adapter comprises cytosine analog residues in place of cytosine residues, which are protected from bisulfite conversion, while the long strand of the partial duplex adapter does not comprise cytosine analog residues in place of cytosine residues. In some cases, both the long and short strand of a partial duplex adapter comprises cytosine analog residues in place of cytosine residues. In some cases, the cytosine analog is 5-methylcytosine. In some cases, the cytosine analog is 5-hydroxymethylcytosine. In some cases, the cytosine analog is 5-propynylcytosine. A strand can comprise a modified cytosine at about, more than, less than, or at least every 1, 2, 3, 4, 5, 6, 7, 8, 9, 10, 15, 20, 25, 30, 40, 50, 65, 75, 85, 90, 95, 100, 110, 120, 130, 140, 150, 160, 170, 180, 190, 200, 225, or 250 nucleotides. In some cases, ligation of an adapter to a double stranded polynucleotide is by blunt end ligation. In some cases, ligation of an adapter to a double stranded polynucleotide is by cohesive or sticky end ligation, wherein an overhang in the adapter hybridizes to an overhang in the double stranded polynucleotide comprising complementary sequence such as shown in FIG. 3. In some cases, an adapter comprising a modified dNTP (e.g. a cytosine analog resistant to bisulfite treatment) comprises a ligation strand or first strand capable of ligation to a 5' end of the polynucleotide fragments and a non-ligation strand or second strand incapable of ligation to either end of the polynucleotide fragments. In some cases, the duplex adapter is a partial duplex adapter, wherein the adapter comprises a long strand and a short strand, and wherein the long strand is the ligation strand or first strand, while the short strand is the non-ligation strand or second strand. In some cases, the partial duplex has strands of unequal length. In some cases, the partial duplex comprises an overhang at one end of the adapter and a blunt end at another end of the adapter. The overhang can be at the 3' end or the 5' end. In some cases, the partial duplex comprises an overhang at each end of the adapter. The overhang can be of equal length or unequal length. In some cases, the 5' end of the ligation strand does not comprise a 5' phosphate group. In some cases, the 5' end of the ligation strand does comprise a 5' phosphate, wherein the 3' end of the polynucleotide lacks a free 3' hydroxyl.

In some cases, the 3' and/or 5' ends of the non-ligation strand comprise a blocking group and are enzymatically unreactive. The blocking group or moiety on the 3' and/or 5' end can be any blocking group or moiety as described herein and/or known in the art. In some cases, the block at the 5' end of the non-ligation strand comprises a biotin moiety. In some cases, the 5' end of the non-ligation strand does not comprise a 5' phosphate. The 5' end can be removed by treatment with an enzyme. The enzyme can be a phosphatase. In some cases, the 5' end of the non-ligation strand is dephosphorylated by treatment with alkaline phosphatase. In some cases, the 5' end of the non-ligation strand does comprise a 5' phosphate, wherein the 3' end of the polynucleotide lacks a free 3' hydroxyl. In some cases, the non-ligation strand comprises a block at the 3' end comprising terminal dideoxycytosine and a block at the 5' end comprising a biotin moiety. In some cases, distinct adapters as described herein are ligated to a 5' end of a double strand polynucleotide.

In some cases, the adapter is a hairpin adapter comprising a stem-loop, wherein both strands of the stem comprise a modified dNTP (e.g. a cytosine analog resistant to bisulfite treatment). In some cases, the stem-loop adapter comprises a ligation or first strand and a non-ligation or second strand as described herein. In some cases, the 3' end of the stem comprises the ligation strand, while the 5' end of the stem comprises the non-ligation strand. In some cases, the 5' end of the stem does not comprise a 5' phosphate. In some cases, the 5' end of the stem comprises a 5' phosphate, while the 3' ends of the double strand polynucleotide lacks a free 3' hydroxyl. In some cases, the 5' end of the stem comprises a blocking group. The blocking group can be any of the blocking groups described herein. In some cases, the stem comprises an overhang. The overhang can be a 5' overhang or a 3' overhang and can comprise DNA, RNA, or both. A stem-loop adapter can be ligated to a double stranded polynucleotide by the methods described herein. In some cases, a stem loop adapter comprises a replication block. The replication block can be a non-replicable base or region in the loop or in a region of the stem adjacent to the loop comprising abasic sites. The replication block can comprise an inverted repeat. Abasic sites can be generated in the stem-loop by any of the methods known in the art, which can include, but is not limited to, incorporation of dUTP during generating of the adapter followed by treatment with dU-glycosylase (which is also referred to as Uracyl-DNA Glycosylase or UDG). In some cases, the replication block is removable or cleavable.

In some cases, the adapter comprises a ligation or first strand as described herein, and a non-ligation or second strand, wherein the non-ligation or second strand comprises RNA residues. In some cases, the adapter comprises a ligation or first strand as described herein, and a non-ligation or second strand, wherein the ligation or first strand comprises RNA residues.

In some cases, the ligation of an adapter to a first strand of a double stranded polynucleotide fragments creates a nick or break in the backbone between the non-ligation strand of the adapter and the 3' end of the second strand of the double-stranded polynucleotide fragments, wherein the non-ligation strand is not joined to the 3' end of the second strand of the polynucleotide fragments. In this case, the 5' end of the ligation strand does not comprise a 5' phosphate group. Further to this case, ligation of an adapter to the polynucleotide fragment can generate a polynucleotide fragment comprising the ligation strand comprising a cytosine analog joined to a first and second 5' end of the polynucleotide fragments. In some cases, the 5' end of the ligation strand comprises a 5' phosphate group, and the 3' ends of the polynucleotide fragment lacks a free 3' hydroxyl. Further to this case, ligation of an adapter to the polynucleotide fragment can generate a polynucleotide fragment comprising the ligation strand comprising a cytosine analog joined to a first and second 5' end of the polynucleotide fragments.

The method can further comprise performing an extension reaction. The extension reaction can be performed using any number of methods known in the art including, but not limited to, the use of a DNA dependent DNA polymerase with strand displacement activity or a DNA polymerase with exonuclease activity and all four dNTPs (i.e. dATP, dTTP, dCTP, and dGTP), wherein the dNTPs are unmodified. In some cases, adaptors (e.g., duplex or partial duplex) as described herein comprising cytosine analogs resistant to bisulfite treatment in a ligation strand as well as no or one or more diversity bases are ligated to a polynucleotide and further subject to an extension reaction that is performed with a DNA polymerase and unmodified dNTPs (i.e. dATP, dTTP, dCTP, and dGTP). In some cases, adaptors (e.g., duplex or partial duplex) as described herein comprising cytosine bases sensitive to bisulfite treatment in a ligation strand as well as no or one or more diversity bases are ligated to a polynucleotide and further subject to an extension reaction that is performed with a DNA polymerase and a dNTP mixture comprising dATP, dTTP, dGTP, and a dCTP analog resistant to bisulfite treatment. In some cases, the extension reaction extends the 3' ends of the polynucleotide fragments, whereby a non-ligation strand of an adapter is removed. The non-ligation strand can be removed by being displaced, degraded, or denatured. In some cases, the non-ligation strand of the joined adapter is removed by heat denaturation, and the 3' ends of the polynucleotide fragment are extended with a polymerase without strand displacement activity. In some cases, the melting temperature of the non-ligation strand bound to the ligation strand can be lower than the melting temperature of the two strands of the polynucleotide fragment to which the ligation strand of the adapter is joined. In some cases, the non-ligation strand is displaced by a polymerase comprising strand displacement activity during extension of the 3' ends of the double stranded polynucleotide fragment. In some cases, the adapter is a hairpin adapter and the extension reaction displaces the non-ligation strand of the stem. In some cases, the displaced strand of the stem adapter remains connected to the ligation strand of the stem via the loop. In some cases, the loop comprises a cleavage site for an enzyme (i.e. restriction endonuclease). In some cases, the cleavage site is within a replication block. In some cases, the cleavage site is cleaved, thereby removing the non-ligation strand of the stem. In these cases, the ligation strand of the stem can comprise the modified nucleotide (i.e. nucleotide with cytosine analog resistant to bisulfite treatment). In some cases, the ligation strand serves as the template, wherein the extension reaction generates sequence complementary to the ligation strand. In some cases a single adapter is ligated to the 5' ends of the double stranded polynucleotide fragment, whereby extension of the 3' ends of the polynucleotide fragment generates polynucleotide fragments comprising complementary adapter sequences at the 3' and 5' ends. In some cases, the adapter ligated to the polynucleotide fragments comprises a non-ligation strand comprising RNA thereby forming a DNA/RNA heteroduplex with the ligation strand, wherein the extension reaction extends the 3' ends of the polynucleotide fragments following degradation of the RNA in the non-ligation strand using an agent capable of degrading RNA in a DNA/RNA heteroduplex. The agent can be an enzyme. The enzyme can be RNase H. In this embodiment, the ligation or first strand serves as the template, wherein the extension reaction generates sequence complementary to the ligation or first strand, thereby generating polynucleotide fragments comprising complementary adapter sequences at the 3' and 5' ends.

In some cases, the duplex adapter is a partial duplex adapter, wherein the adapter comprises a long strand and a short strand, wherein both the long strand and the short strand are capable of ligation. In some cases, the long strand comprises a modified dNTP (e.g. a cytosine analog resistant to bisulfite treatment). In some cases, the short strand comprises a modified dNTP (e.g. a cytosine analog resistant to bisulfite treatment). In these cases, the partial duplex adapter comprises a 5' overhang and a blunt end, or both a 5' and 3' overhang. In order to reduce the formation of primer dimers, the 3' end of the short arm of the adapter can comprise a blocking group and can be enzymatically unreactive. The blocking group can be any of the blocking groups described herein. In some cases, the short arm of the adapter comprises a reversible blocking group, wherein the reversible blocking group can be removed following ligation of the adapter to the double stranded polynucleotide. In some cases, unligated adapter is removed by washing and/or degradation following ligation and prior to removal of the reversible blocking group. In some cases, the method can further comprise performing an extension reaction. The extension reaction can be performed using any number of methods known in the art including, but not limited to, the use of a DNA dependent DNA polymerase with strand displacement activity and all four dNTPs (i.e. dATP, dTTP, dCTP, and dGTP), wherein the dNTPs are unmodified. In some cases, the extension reaction is performed with a DNA polymerase and unmodified dNTPs (i.e. dATP, dTTP, dCTP, and dGTP). In some cases, the extension reaction extends the 3' ends of short strand of the adapters ligated to the ends of the double stranded polynucleotide fragments, thereby generating polynucleotide fragments comprising complementary adapter sequences at the 3' and 5' ends. The cytosine analog resistant to bisulfite treatment can be 5-methylcytosine, 5-hydroxymethylcytosine or 5-propynylcytosine.

In some cases, double stranded polynucleotide fragments comprising adapter sequence at the 3' and 5' ends are captured prior to treatment with a converting agent. In some cases, the double stranded polynucleotide fragments are captured using a binding agent directed against modified dNTPs in the double-stranded polynucleotide fragments with adapters. The modified dNTP can be a modified dCTP comprising a cytosine analog. The cytosine analog can be 5-methylcytosine, 5-hydroxymethylcytosine or 5-propynylcytosine. The binding agent can be an antibody, or the binding domain of a protein directed against a cytosine analog. In some cases, the binding domain is directed against 5-methylcytosine residues. The binding domain can be from a methyl-CpG-binding domain (MBD) protein. The MBD protein can be methyl-CpG-binding domain protein 1, 2, 4, or MECP2. In some cases, the double stranded polynucleotide fragments are captured using the binding domain of MBD2. In some cases, the double stranded polynucleotide fragments are captured using the binding domain of MECP2. In some cases, one or both strands of the adapter sequence on the end(s) of the double stranded polynucleotide fragments comprise a cytosine analog other than 5-methylcytosine, wherein the double stranded polynucleotide fragments are captured using the binding domain of a methyl-CpG-binding domain (i.e. MBD2 or MECP2). The cytosine analog other than 5-methylcytosine can be 5-hydroxymethylcytosine or 5-propynylcytosine.

In some cases, the method further comprises a denaturing step, wherein the polynucleotide fragments comprising adaptor sequences at the 3' and 5' ends are denatured. Denaturation can be achieved using any of the methods known in the art which can include, but are not limited to, heat denaturation, and/or chemical denaturation. Heat denaturation can be performed by raising the temperature of the reaction mixture to be above the melting temperature of the polynucleotide fragments comprising adapter sequence at both ends. The melting temperature can be about, more than, less than, or at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, 85, 86, 87, 88, 89, 90, 91, 92, 93, 94, or 95 degrees C. The temperature can be raised above the melting temperature by about, more than, less than, or at least 1, 2, 3, 4, 5, 6, 7, 8, 9, or 10 degrees C. Chemical denaturation can be performed using bases (i.e. NaOH), and/or competitive denaturants (i.e. urea, or formaldehyde). In some cases, denaturation generates single stranded polynucleotide fragments comprising complementary adaptor sequence at the 3' and 5' ends such that the juncture between the fragments and the adaptors comprise one or more diversity bases. In some cases, denaturation generates single stranded polynucleotides fragments comprising distinct adapter sequence at the 3' and 5' ends such that the juncture between the fragments and the adaptors comprise one or more diversity bases.

In some cases, single stranded polynucleotide fragments comprising adapter sequence at the 3' and 5' ends are captured prior to treatment with a converting agent. In some cases, the polynucleotide fragments are captured by a binding agent directed against one or more modified dNTPs present in the adapter sequence. In some cases, the modified dNTP is a nucleotide base analog. In some cases, the binding agent is a binding protein. In some cases, the binding protein is an antibody directed against the modified dNTP. In some cases, the binding protein is an antibody directed against the modified dNTP, wherein the modified dNTP is a nucleotide analog. In some cases, the single stranded polynucleotide fragments comprising adapter sequence at the 3' and 5' ends are captured prior to treatment with a bisulfite. In some cases, the nucleic acid fragments (polynucleotides) are captured by a binding agent directed against one or more elements present in the adapter sequence. In some cases, the one or more elements comprise a cytosine analog. In some cases, the cytosine analog is 5-methylcytosine. In some cases, the binding agent is a 5-methylcytosine binding protein. In some cases, the binding protein is an anti-5-methylcytosine antibody. In some cases, 5-methylcytosine capture is performed prior to bisulfite treatment, wherein the cytosine analog resistant to bisulfite treatment is a cytosine analog other than 5-methylcytosine. In some cases, the cytosine analog can be 5-hydroxymethylcytosine or 5-propynylcyotsine. The one or more elements can be introduced during the extension reaction. In some cases, a modified nucleotide can be incorporated during the extension reaction, wherein the modified nucleotide contains a tag. The tag can be a biotin moiety. In some cases, the binding agent is avidin, streptavidin, or an anti-biotin antibody.

Following denaturation, and optional capture by a binding agent, the single-stranded polynucleotide fragments comprising adapter sequence at the 3' and 5' ends can be treated with a converting agent. In some cases, treatment of the single-stranded polynucleotide fragments with a converting agent alters the sequence of the complement of the ligation strand as well as the first and second strands of the double stranded polynucleotide fragment, while leaving the sequence of the ligation or first strand unchanged. In some cases, a single adapter is ligated to the 5' ends of the polynucleotide fragments, whereby treatment with a converting agent generates single stranded polynucleotide fragments comprising non-complementary sequence at the 5' and 3' ends. In some cases, distinct adapters are ligated to the 5' ends of the polynucleotide fragments, whereby treatment with a converting agent generates single stranded polynucleotide fragments wherein the non-ligation strands of the distinct adapters is altered to be non-complementary to the ligation strands of the distinct adapters. In some embodiments, the sequence of the ligation or first strand of the adapter marks the 5' end of the polynucleotide fragments, thereby maintaining the strandedness of the polynucleotide fragment and thus providing information on directionality.

In some cases, the single-stranded nucleic acid fragments are treated with a converting agent wherein the converting agent is bisulfite. In some cases, treatment of the single-stranded polynucleotide fragments converts cytosine residues in the polynucleotide fragment and the complement of the ligation or first strand to uracil residues while the cytosine analogs in the ligation or first strand are resistant to conversion. In some cases, treatment of the single stranded polynucleotide fragments with bisulfite generates single stranded polynucleotide fragments comprising non-complementary adapter sequence at the 5' and 3' ends. In some cases, the sequence of the ligation strand of the adapter unaltered by bisulfite treatment marks the 5' end of the polynucleotide fragments, thereby maintaining the strandedness of the polynucleotide fragment and thus providing information on directionality. In some cases, distinct adapters are ligated to the 5' ends of the polynucleotide fragments, whereby treatment with a bisulfite generates single stranded polynucleotide fragments wherein cytosine residues in the non-ligation strands of the distinct adapters are converted to uracil residues, whereby the sequence of the non-ligation strand is no longer complementary to the ligation strands of the distinct adapters.

In some cases, the method further comprises amplifying the single-stranded polynucleotide fragments comprising adapter sequences at the 3' and 5' ends. In some cases, amplification of the single-stranded polynucleotide fragments comprising adapter sequence at the 3' and 5' ends generates directional polynucleotide libraries. In some cases, one end of the polynucleotide fragment marks the orientation of the original polynucleotide strand to which it is appended due to its resistance to conversion by the converting agent, whereby the sequence in said end is resistant to conversion to a different sequence by treatment with the converting agent. In some cases, amplification of the single-stranded polynucleotide fragments comprising adapter sequence at the 3' and 5' ends generates directional polynucleotide libraries wherein one end of the polynucleotide fragments marks the orientation of the original polynucleotide strand to which it is appended due to its resistance to conversion by bisulfite treatment. In some cases, the cytosine residues present in said end are resistant to conversion to uracil residues by bisulfite treatment.

In some cases, amplifying the single stranded polynucleotide fragments comprising adapter sequence at the 3' and 5' ends comprises the use of a first primer and a second primer. In some cases, the first primer is directed against sequence complementary to the ligation or first strand of an adapter altered following treatment with a converting agent. In some cases, the second primer is directed against sequence complementary to the ligation or first strand of an adapter, wherein the ligation or first strand to which said complementary sequence is complementary is not altered by treatment with the converting agent. In some cases, the converting agent is bisulfite, whereby treatment with bisulfite converts cytosine residues in the sequence complementary to the ligation or first strand to uracil residues. In some cases, the first primer is directed against sequence complementary to the ligation or first strand of the adapter comprising uracil residues following bisulfite treatment. In some cases, the second primer is directed against sequence complementary to the ligation or first strand of the adapter, wherein the ligation or first strand to which said complementary sequence is complementary to does not contain uracil residues following bisulfite treatment. The single stranded polynucleotide fragments comprising adapter sequence at the 3' and 5' ends can represent a first strand of a double stranded polynucleotide fragment or a second strand of a double stranded polynucleotide fragment.

In some cases, a single adapter is ligated to the 5' ends of the polynucleotide, whereby the first and second strands can comprise non-complementary sequence following treatment with the converting agent (e.g., bisulfite treatment). In some cases, distinct adapters are ligated to the 5' ends of the polynucleotide fragments, whereby treatment with bisulfite generates single stranded polynucleotide fragments from a first strand of a double stranded polynucleotide fragment or a second strand of a double stranded polynucleotide fragment, wherein cytosine residues in the non-ligation strands of the distinct adapters are converted to uracil residues. In these cases, the sequence of the non-ligation strand is no longer complementary to the ligation strands of the distinct adapters. Amplifying the single stranded polynucleotide fragments comprising adapter sequence at the 3' and 5' ends can produce amplification products from either or both of the first and second strand of the double stranded polynucleotide fragment following treatment with the converting agent (i.e. bisulfite). In some cases, the first and/or second primer further comprises one or more identifier sequences. In some cases, the identifier sequences comprise a non-hybridizable tail on the first and/or second primer. The identifier sequence can be a barcode sequence, a flow cell sequence, and/or an index sequence. In some cases, the index sequence is a Truseq primer sequence compatible with the next generation sequencing platform produced by Illumina. In some cases, the first and/or second primer can bind to a solid surface. The solid surface can be a planar surface or a bead. The planar surface can be the surface of a chip, microarray, well, or flow cell. In some cases, the first and/or second primer comprises one or more sequence elements products of the amplification reaction (i.e. amplification products) to a solid surface, wherein the one or more sequences are complementary to one or more capture probes attached to a solid surface.

In some cases, methods for generating a polynucleotide library using modified duplex-forming adapters described herein further comprise determining the methylation status of the input double stranded polynucleotide. In some cases, the input polynucleotide is genomic DNA and the amplification of single-stranded polynucleotide fragments comprising non-complementary sequence at the 3' and 5' ends is followed by sequencing. The non-complementary sequence at the 3' ends of the single-stranded polynucleotide fragments can be complementary to reverse read sequencing primers, while the 5' ends of the single-stranded polynucleotide fragments can be complementary to forward read sequencing primers. This differentially complementarity to forward and reverse sequencing primers can result from the bisulfite treatment differentially affecting the sequence of the 3' and 5' ends based on the presence or absence of cytosine analogs resistant to bisulfite treatment in the 3' and 5' ends as described herein. Further to this embodiment, the methylation status of the genomic DNA can be determined by comparing the sequence obtained from the sequencing of the single-stranded polynucleotide fragments comprising non-complementary sequence at the 3' and 5' ends representing either or both of the first and second strand of the double stranded polynucleotide following treatment with converting agent (i.e. bisulfite treatment) generated by the methods described herein against a reference sequence. The reference sequence can be the sequence of the genomic DNA (either or both strands) not subjected to alteration by treatment with the converting agent. The comparing can be performed on a computer. The comparing can be done on a computer using a sequence alignment tool or program. The sequence alignment tool or program can map bisulfite treated sequencing reads to a genome of interest and perform methylation calls. The bisulfite sequencing mapping tool can be the Bismark program. In some cases, the comparing comprises performing a nucleotide alignment between the sequence obtained from the sequencing of the single-stranded DNA fragments comprising non-complementary sequence at the 3' and 5' ends generated by the methods described herein with a reference sequence on a computer using any of the nucleotide alignment programs known in the art (e.g. Bismark). In some cases, the methods described herein can be used to determine the methylation status of a specific locus or region of genomic DNA or the entire genome (i.e. the methylome). In some cases, following bisulfite treatment, the methylation status of a given cytosine residue is inferred by comparing the sequence to an unmodified reference sequence.

Sequencing can be any method of sequencing, including any of the next generation sequencing (NGS) methods described herein. In some cases, the NGS method comprises sequencing by synthesis. In some embodiments, sequencing is performed with primers directed against known or universal sequence introduced into the nucleic acid fragments by the adapter ligated to the nucleic acid fragments. In some cases, the primers used for sequencing are directed against adapter sequence unaltered by treatment with a converting agent. In some cases, primers used for sequencing are directed against adapter sequence altered by treatment with a converting agent. The converting agent can be bisulfite, wherein bisulfite treatment converts cytosine residues to uracil residues. In some cases, the sequencing primers are directed against adapter sequence comprising thymine residues following bisulfite treatment and amplification. In some cases, the sequencing primers are directed against adapter sequence wherein the adapter sequence is resistant to conversion by bisulfite treatment. In this embodiment, the adapter sequence to which the sequencing primers are directed does not comprise thymine residues following bisulfite treatment and amplification. In some cases, sequencing is performed with primers directed against identifier sequence introduced into the polynucleotide fragments by the first and/or second primer used to amplify single-stranded polynucleotide fragments comprising non-complementary sequence at the 3' and 5' ends. The identifier sequence can be a barcode sequence, a flow cell sequence, and/or index sequence. In some cases, the index sequence is a Truseq primer sequence compatible with the next generation sequencing platform produced by Illumina.

Figure 23:
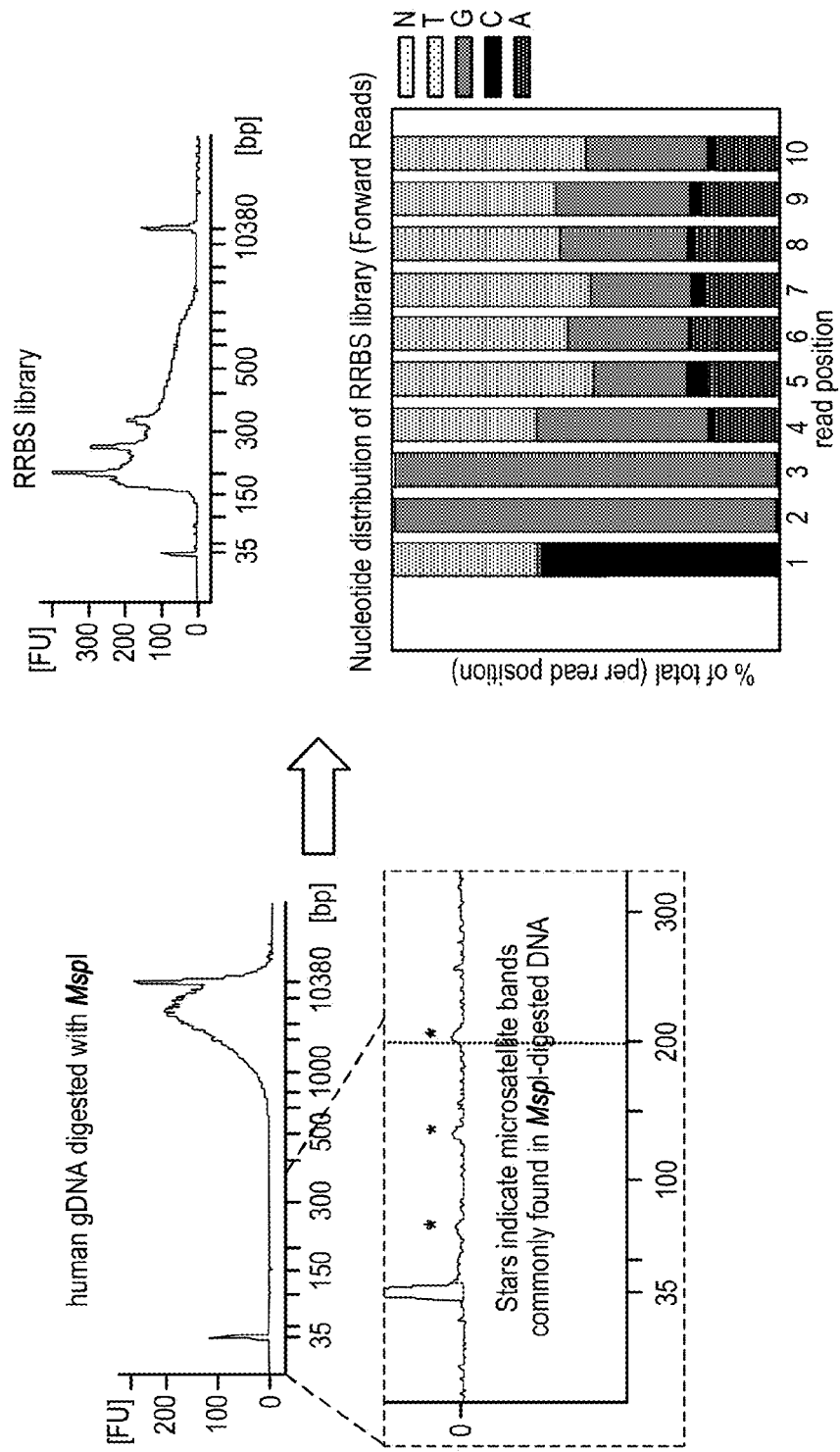
FIG. 23 illustrates bioanalyzer traces of MspI-digested human genomic DNA (left), and the resulting RRBS sequencing library (top right) including an example of the nucleotide distribution (Forward Reads) obtained using said method (bottom right).
Figure 25:
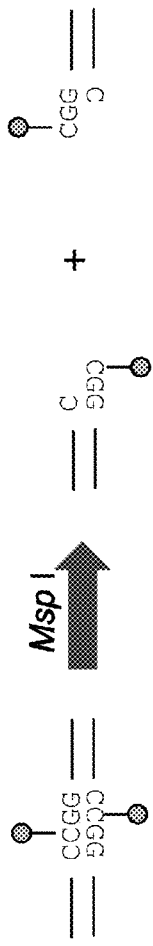
FIG. 25 illustrates a comparison of the in silico assignment of CpGs into classes for RRBS vs. whole genome bisulfite sequencing.

As described herein, the methods, compositions and kits provided herein can be used to generate reduced representation bisulfite (RRBS) libraries. As shown in FIG. 23, generation of an RRBS library can result in representation of about 1% of the genome that is enriched for 40-300 bp fragments comprising microsatellite bands and aid in silico assignment of CpG sites into genomic classes using far less sequencing than can be required using whole genome bisulfite sequencing approach as shown in FIG. 25. A comparison of RRBS library generation with other DNA methylation profiling technologies (FIG. 24), as reproduced from Gu et al. *Nature Protocols.* 6(4): 468-481 (2011), which is herein incorporated by reference in its entirety, reveals that RRBS provides about 9% actual genomic coverage at a resolution of 1 bp with an input of only 0.01-0.3 μg. However, as described herein, RRBS can sometimes create a lack of color balance that can be an issue for some sequencing platforms. The methods, compositions, and kits provided herein can be used to eliminate or substantially reduce these issues.

Figure 27A:
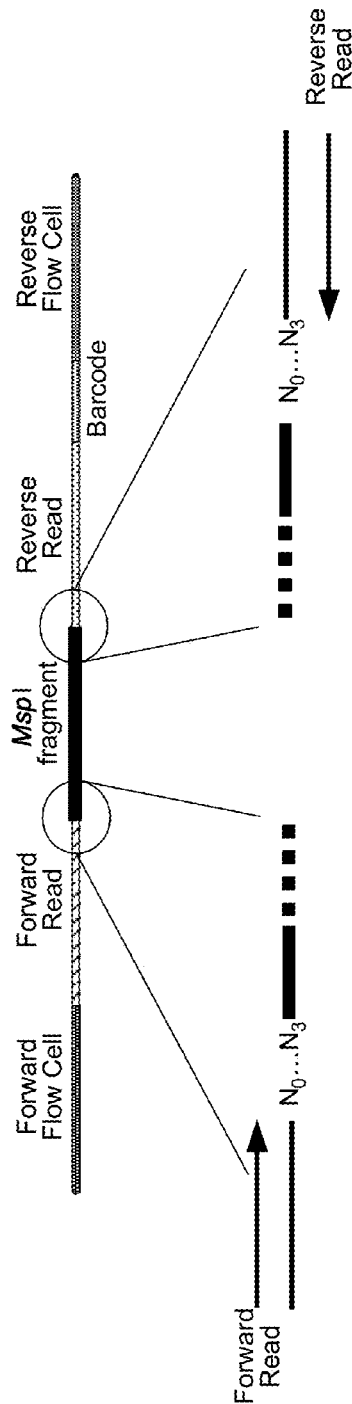
FIG. 27A illustrates a polynucleotide insert from an RRBS generated using diversity adapters as provided herein.
Figure 27B:
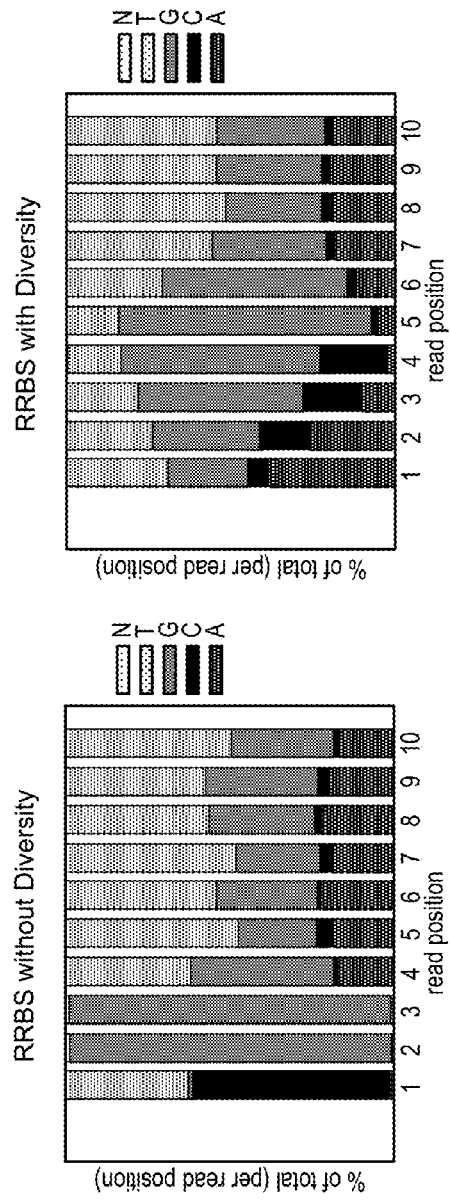
FIG. 27B illustrates the increased color balance in the initial sequence reads of an RRBS library generated using diversity adapters as provided herein and comprising polynucleotide inserts as shown in FIG. 27A.

A schematic exemplary of an embodiment of the methods described herein for generating an RRBS library using partial duplex-forming adapters comprising diversity bases is shown in FIG. 3. The method can comprise digesting a double stranded polynucleotide (e.g., genomic DNA) at one or more recognition sites for a methylation insensitive restriction endonuclease (RE). In some cases, the one or more recognition sites comprise the sequence "CCGG", and the methylation insensitive RE is MspI. The methylation insensitive restriction enzyme can be DpnII, HpaII, SalI-HF®, ScrFI, and the recognition site can be any recognition site recognized by said restriction endonucleases. Cleavage with the RE produces one or more polynucleotide fragments with or without overhangs. As shown in FIG. 3, cleavage with MspI generates a double-stranded polynucleotide fragment comprising a 5' overhang dinucleotide comprising 5'-CG-3'. A pool of diversity adaptors as shown in FIG. 2A-B can be appended to the double stranded polynucleotide generated by cleavage with MspI. The appending can be through ligation. Ligation can be performed with any ligation method known in the art. The ligation can be cohesive end ligation such as shown in FIG. 3. For illustrative purposes, ligation of a single diversity adaptor to both ends of the MspI cleaved double stranded polynucleotide is shown. The cleaved polynucleotide can be ligated on each end by a diversity adaptor comprising a different number of diversity bases than on an opposite end of the same cleaved polynucleotide. The diversity adapter in FIG. 3 comprises a short strand whose 5' end comprises a terminal "CG" dinucleotide which immediately follows three 'H' nucleotides, which can be either a adenine (A), cytosine (C), or thymine (T) base, but cannot be a guanine (G) base. The long strand of the diversity adaptor terminates with a "DDD" trinucleotide comprising all "D" bases, wherein the "DDD" is the complement of the HHH triplet on the short strand and, therefore can be an A, G, or T base, but cannot be a C base. The long strand of the diversity adapter comprises non-methylated cytosine residues. In some cases, the long strand of the diversity adaptor can comprise cytosine analogs resistant to bisulfite treatment. In some cases, the cytosine analog resistant to bisulfite treatment is 5-methyl-cytosine. As can be seen in FIG. 2A-B, the short strand can comprise 0, 1, 2, or 3 "H" bases, and thus, the long strand can comprise either 0, 1, 2, or 3 "D" bases. FIG. 2A-B also illustrates that the short strand comprises both a 5' (e.g., Biosg), and 3' (e.g., ddC) group. One or both groups can serve to block ligation and/or extension of the short strand. Following ligation of the diversity adapters in FIG. 3, the 3' ends of the polynucleotide fragments can be extended in the presence of a nucleotide mixture comprising dTTP, dGTP, dATP, and 5-methyl dCTP using the long strand of the diversity adapter as template. Extension can produce polynucleotide fragments comprising the long strand diversity adapter sequence comprising non-methylated cytosine residues at the 5' end and sequence complementary to the long strand diversity adapter sequence comprising methylated cytosine residues at the 3' end. In some cases, the long strand of the diversity adaptor comprises 5-methylcytosine and following ligation of the diversity adapters in FIG. 3, the 3' ends of the polynucleotide fragments can be extended in the presence of a nucleotide mixture comprising dTTP, dGTP, dATP, and dCTP using the long strand of the diversity adapter as template. Thus, extension can produce polynucleotide fragments comprising the long strand diversity adapter sequence comprising methylated cytosine residues at the 5' end and sequence complementary to the long strand diversity adapter sequence comprising non-methylated cytosine residues at the 3' end. In some cases, both the long strand and the short strand of the diversity adaptor comprises 5-methylcytosines and can ligate to each end of the MspI digested polynucleotide and following ligation of the diversity adapters, the 3' ends of the short strand of the D-adaptor can be extended in the presence of a nucleotide mixture comprising dTTP, dGTP, dATP, and dCTP using the long strand of the diversity adapter as template. Thus, extension can produce polynucleotide fragments comprising the long strand diversity adapter sequence comprising methylated cytosine residues at the 5' end and sequence complementary to the long strand diversity adapter sequence comprising non-methylated cytosine residues at the 3' end. In some cases, both the long strand and the short strand of the diversity adaptor comprises non-methylated cytosines and can ligate to each end of the MspI digested polynucleotide and following ligation of the diversity adapters, the 3' ends of the short strand of the diversity adaptor can be extended in the presence of a nucleotide mixture comprising dTTP, dGTP, dATP, and 5-methyl dCTP using the long strand of the diversity adapter as template. Thus, extension can produce polynucleotide fragments comprising the long strand diversity adapter sequence comprising non-methylated cytosine residues at the 5' end and sequence complementary to the long strand diversity adapter sequence comprising methylated cytosine residues at the 3' end. 5-methyl cytosine in the diversity adaptor and/or the reaction mixture used for extension can be substituted with any cytosine analog resistant to bisulfite treatment known in the art. The cytosine analog can be 5-hydroxymethylcytosine. The cytosine analog can be 5-propynlcytosine. The polynucleotide fragment resulting from digestion with MspI and ligation with one or more diversity adaptors to each end can be denatured and then subjected to bisulfite treatment as shown in FIG. 3. In some cases, fragments of a desired size are selected prior to bisulfite treatment and PCR amplification by running the fragments comprising the adapters in a gel and size selecting. Bisulfite treatment can generate single stranded polynucleotide fragments comprising non-complementary diversity adaptor sequence at each terminus. As shown in FIG. 3, bisulfite treatment can generates single-stranded polynucleotide fragments comprising long strand diversity adapter sequence at the 5' end wherein each cytosine residue has been converted to a uracil, and sequence which remains complementary to the long strand of the diversity adapter sequence present in the fragment prior to treatment at the 3' end. Any non-methylated cytosine residues present in the polynucleotide fragment between the adapter sequence can also be converted to uracil residues. Following bisulfite treatment, the fragments can be subjected to PCR using primers directed to the adapter sequences following conversion. PCR amplification can generate polynucleotide fragments with distinct adapter sequences on each end. The "D," "R," and "H" bases present in the diversity adapters can retain their original base identity following bisulfite treatment and subsequent amplification. The resultant bisulfite converted library can be further subjected to sequencing. Sequencing can be performed by any of the known next generation sequencing platforms. As can be seen in FIG. 3, sequencing the RRBS library generated by the method depicted in FIG. 3 can generate predictable forward and reverse reads in the initial cycles. The long strand of the adapter can further comprise additional sequence elements such as barcodes and/or random sequence. Additional sequence elements can also be introduced to RRBS nucleic acid inserts through amplification of the inserts with primers comprising the additional sequence elements. The additional sequence elements can be one or more barcodes, random sequence, and/or flow cell sequences that can be used to hybridize and thus capture an insert on a solid surface for subsequent solid-phase amplification. FIG. 27A illustrates a polynucleotide insert from an RRBS generated using diversity adapters as provided herein. FIG. 37 illustrates a polynucleotide insert from an RRBS generated using diversity adapters as provided herein that is subsequently attached to a solid surface. The solid surface can be a flow cell surface or a bead. As shown in FIG. 37, a capture probe on a flow cell surface can be used to capture (via hybridization) a library insert such as the one shown in FIG. 27A. The "N" in FIG. 37 or FIG. 27A can be a D base or a mixture of D and H bases as described herein. FIG. 27B illustrates the increased color balance in the initial sequence reads of an RRBS library generated using diversity adapters as provided herein and comprising polynucleotide inserts as shown in FIG. 27A. The increased sequence diversity (as shown in FIG. 27B by the increase in nucleotide base composition in the initial sequencing cycles) present in one or more polynucleotide inserts from an RRBS library generated using diversity adaptors can serve to substantially lower levels of genomic, higher diversity control libraries (e.g., PhiX control libraries) typically employed when sequencing RRBS libraries. The amount of higher diversity control libraries can be reduced by about, more than, or less than 1%, 5%, 10%, 20%, 30%, 40%, 50%, 60%, 70%, 80%, 90%, 95%, or 99%. The amount of higher diversity control libraries can be reduced by about 1-5%, 5-10%, 10-20%, 30-40%, 40-50%, 50-60%, 60-70%, 70-80%, 80-90%, 90-95% or 95-99%. The amount of higher diversity control libraries can be reduced by between 1-5%, 5-10%, 10-20%, 30-40%, 40-50%, 50-60%, 60-70%, 70-80%, 80-90%, 90-95% or 95-99%. FIG. 19 illustrates the total theoretical diversity possible for introducing to the ends of a polynucleotide upon introduction of a pool of diversity adaptors comprising diversity adapters comprising 0 to 3 "D" bases (D0-D3).

In some cases, no genomic, higher diversity control libraries (e.g., PhiX control libraries) are required to be added or spiked into sequencing reactions from the RRBS libraries generated by the methods provided herein.

In some cases, the methods depicted in FIG. 3 for generating RRBS libraries can be combined with a dark sequencing approach as illustrated in FIG. 26 (see Boyle et al., *Genome Biology.* 13 (R92):1-10 (2012), which is herein incorporated by reference in its entirety), which can serve to further reduce a lack of color balance. In some cases, the methods depicted in FIG. 3 for generating RRBS libraries can be combined with spiking in a high diversity control library (e.g., Phi X) during sequencing, which can serve to further reduce a lack of color balance.

The method depicted in FIG. 3 and described herein can also be used in the context of generating whole genome bisulfite sequencing libraries from samples spanning a 100-fold range of inputs, down to as little as 1 ng of genomic DNA. Library performance metrics such as mapping, complexity, and 5-methylC content can be altered using the methods provided herein. In some cases, the methods provided herein improve Library performance metrics. The Library performance metrics can be mapping, complexity, and 5-methylC content.

VII. Downstream Applications

The methods and compositions disclosed herein can be efficiently and cost-effectively utilized for downstream analyses, such as next generation sequencing or hybridization platforms, with minimal loss of biological material of interest. The methods described herein can be useful for generating high throughput reduced representation sequencing libraries from bisulfite-converted DNA, for methylation analysis at specific regions across the genome or methylome.

For example, the methods described herein can be useful for sequencing by the method commercialized by Illumina, as described U.S. Pat. Nos. 5,750,341; 6,306,597; and 5,969,119. Directional (strand-specific) cDNA libraries are prepared using the methods described herein, and the selected single-stranded nucleic acid is amplified, for example, by PCR. The resulting nucleic acid can then be denatured and the single-stranded amplified polynucleotides can be randomly attached to the inside surface of flow-cell channels. Unlabeled nucleotides can be added to initiate solid-phase bridge amplification to produce dense clusters of double-stranded DNA. To initiate the first base sequencing cycle, four labeled reversible terminators, primers, and DNA polymerase can be added. After laser excitation, fluorescence from each cluster on the flow cell can be imaged. The identity of the first base for each cluster can then be recorded. Cycles of sequencing are performed to determine the fragment sequence one base at a time. The identity of the bases of the first few cycles (4-5) can then be used to discern separate clusters and facilitate sequencing of individual clusters. Additionally, clusters that share identical or substantially similar sequences at one or more ends as other clusters can experience problems with focusing of the laser and subsequent detection of fluorescence when sequencing such clusters in parallel due to the presence of the same base at each cycle. In some cases, the introduction of one or more diversity bases allows clear identification of individual clusters. For library inserts comprising low diversity portions at one or more ends of the inserts, the introduction of diversity bases at the low diversity ends can allow identification of individual clusters and allow different nucleotide bases to be incorporated in each cycle between inserts with identical or substantially similar sequences at their ends. The incorporation in each cycle of different bases between inserts with identical or substantially similar sequences at their ends can facilitate enhanced laser focusing during each sequencing cycle and thus accurate sequencing of individual clusters.

In some embodiments, the methods described herein are useful for preparing target polynucleotides for sequencing by the sequencing by ligation methods commercialized by Applied Biosystems (e.g., SOLiD sequencing). In other embodiments, the methods are useful for preparing target polynucleotides for sequencing by synthesis using the methods commercialized by 454/Roche Life Sciences, including but not limited to the methods and apparatus described in Margulies et al., Nature (2005) 437:376-380 (2005); and U.S. Pat. Nos. 7,244,559; 7,335,762; 7,211,390; 7,244,567; 7,264,929; and 7,323,305. In other embodiments, the methods are useful for preparing target polynucleotide(s) for sequencing by the methods commercialized by Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In other embodiments, the methods are useful for preparing target polynucleotide(s) for sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764.

Another example of a sequencing technique that can be used in the methods described herein is nanopore sequencing (see e.g. Soni G V and Meller A. (2007) *Clin Chem* 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows can be sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Another example of a sequencing technique that can be used in the methods described herein is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When one or more nucleotides are incorporated by DNA polymerase, protons (hydrogen ions) are released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

Another example of a sequencing technique that can be used in the methods described herein is DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adapters (Ad1) can be attached to the ends of the fragments. For example, DNA can be fragmented with MspI and size selected to a mean length of about 500 bp. Adapters (Ad1) can be attached to the ends of the fragments. The adapters can be used to hybridize to anchors for sequencing reactions. DNA with adapters bound to each end can be PCR amplified. The adapter sequences can be modified so that complementary single strand ends bind to each other forming circular DNA. The adapter sequences can be further modified so that they comprise diversity bases. In some cases, the adaptors comprise a pool of adaptors such that some of the adaptors in the pool comprise no diversity bases, some adaptors comprise 1 diversity base, some adaptors comprise 2 diversity bases, and some comprise 3 diversity bases. The DNA can be methylated to protect it from cleavage by a type IIS restriction enzyme used in a subsequent step. An adapter (e.g., the right adapter) can have a restriction recognition site, and the restriction recognition site can remain non-methylated. The non-methylated restriction recognition site in the adapter can be recognized by a restriction enzyme (e.g., AcuI), and the DNA can be cleaved by AcuI 13 bp to the right of the right adapter to form linear double stranded DNA. A second round of right and left adapters (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Ad1 adapter. A restriction enzyme (e.g., AcuI) can be applied, and the DNA can be cleaved 13 bp to the left of the Ad1 to form a linear DNA fragment. A third round of right and left adapter (Ad3) can be ligated to the right and left flank of the linear DNA, and the resulting fragment can be PCR amplified. The adapters can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adapters (Ad4) can be ligated to the DNA, the DNA can be amplified (e.g., by PCR), and modified so that they bind each other and form the completed circular DNA template. Rolling circle replication (e.g., using Phi 29 DNA polymerase) can be used to amplify small fragments of DNA. The four adapter sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamethyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adapter sequences can be determined.

In some cases, the sequencing technique can comprise paired-end sequencing in which both the forward and reverse template strand can be sequenced. In some cases, the sequencing technique can comprise mate pair library sequencing. In mate pair library sequencing, DNA can be fragments, and 2-5 kb fragments can be end-repaired (e.g., with biotin labeled dNTPs). The DNA fragments can be circularized, and non-circularized DNA can be removed by digestion. Circular DNA can be fragmented and purified (e.g., using the biotin labels). Purified fragments can be end-repaired and ligated to sequencing adapters.

In some cases, a sequence read is about, more than about, less than about, or at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, or 3000 bases. In some cases, a sequence read is about 10 to about 50 bases, about 10 to about 100 bases, about 10 to about 200 bases, about 10 to about 300 bases, about 10 to about 400 bases, about 10 to about 500 bases, about 10 to about 600 bases, about 10 to about 700 bases, about 10 to about 800 bases, about 10 to about 900 bases, about 10 to about 1000 bases, about 10 to about 1500 bases, about 10 to about 2000 bases, about 50 to about 100 bases, about 50 to about 150 bases, about 50 to about 200 bases, about 50 to about 500 bases, about 50 to about 1000 bases, about 100 to about 200 bases, about 100 to about 300 bases, about 100 to about 400 bases, about 100 to about 500 bases, about 100 to about 600 bases, about 100 to about 700 bases, about 100 to about 800 bases, about 100 to about 900 bases, or about 100 to about 1000 bases.

The number of sequence reads from a sample can be about, more than about, less than about, or at least about 100, 1000, 5,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, or 10,000,000.

The depth of sequencing of a sample can be about, more than about, less than about, or at least about 1×, 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×, 71×, 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×, 95×, 96×, 97×, 98×, 99×, 100×, 110×, 120×, 130×, 140×, 150×, 160×, 170×, 180×, 190×, 200×, 300×, 400×, 500×, 600×, 700×, 800×, 900×, 1000×, 1500×, 2000×, 2500×, 3000×, 3500×, 4000×, 4500×, 5000×, 5500×, 6000×, 6500×, 7000×, 7500×, 8000×, 8500×, 9000×, 9500×, or 10,000×. The depth of sequencing of a sample can about 1× to about 5×, about 1× to about 10×, about 1× to about 20×, about 5× to about 10×, about 5× to about 20×, about 5× to about 30×, about 10× to about 20×, about 10× to about 25×, about 10× to about 30×, about 10× to about 40×, about 30× to about 100×, about 100× to about 200×, about 100× to about 500×, about 500× to about 1000×, about 1000×, to about 2000×, about 1000× to about 5000×, or about 5000× to about 10,000×. Depth of sequencing can be the number of times a sequence (e.g., a genome) is sequenced. In some cases, the Lander/Waterman equation is used for computing coverage. The general equation can be: $C=LN/G$, where C=coverage; G=haploid genome length; L=read length; and N=number of reads.

In some cases, the methods described herein can be useful for enhancing sequence diversity in a sample. For example, the sample can be a sequencing library comprising polynucleotides sharing the same sequencing terminal 1, 2, or 3 bases before sequencing inserts. The polynucleotides can be fragments digested by MspI. 0, 1, 2, 3 diversity bases can be added before the shared sequencing terminal bases. For example, the diversity bases can be added between a sequencing primer and a sequencing insert. In some cases, the sequencing terminal bases of the polynucleotides are the diversity bases, not the shared bases. Thus, sequence diversity can be enhanced in the library. The library can be used in next generation sequencing. For example, when used for Illumina sequencing, the library with enhanced diversity can allow better cluster identification, phasing and color matrix calculation by the sequencer.

Figure 18C:
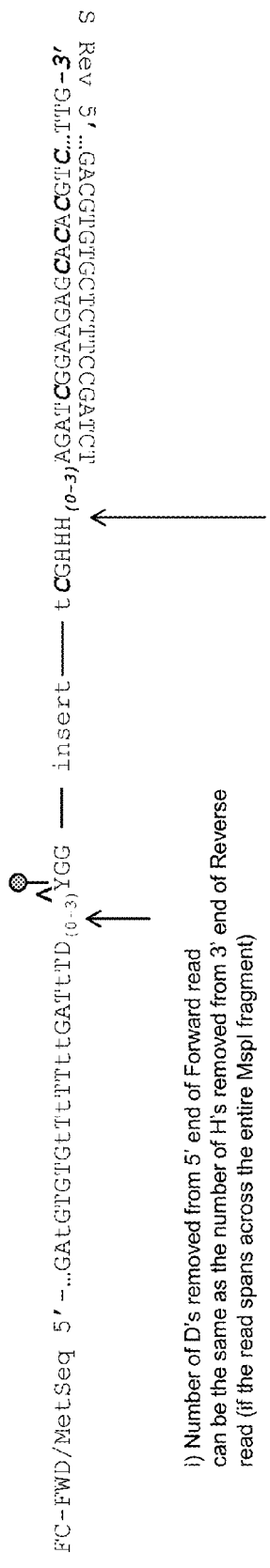

In some cases, the methods described herein can be useful for in silico analysis of sequence reads. In one aspect, computer-implemented software can be used to remove certain bases (e.g., bases added from an adaptor) from a sequence read. In some cases, Trim Galore (www.bioinformatics.babraham.ac.uk/projects/trim_galore) can be used to trim an adaptor sequence from a sequence read. In another case, python scriptscan be used to trim (i.e., remove) diversity bases from a sequence read. The computer implemented software can follow rules for removing certain bases from sequencing reads such as the rules shown in FIG. 18A-C. As shown in FIG. 18A, the rules can be used on library inserts that comprise adaptors (e.g., diversity adaptors or adaptors comprising extender sequence) on each end. The adaptors on each end can be different lengths (i.e., different numbers of nucleotides). As shown in FIG. 18A, the computer implemented software can be designed to look from a YGG triplet of bases at the 5' end of the sequence and trim or remove 0-2 D bases and/or an R base before the YGG triplet. The Y in the YGG triplet can be a cytosine (C) or thymine base (T). Within the 6 nucleotides at the 3' end of the forward read, the computer implemented software can look for a TCG triplet and trim it as well as the 0-3 "H" bases after it. Outside of the D, R, and H bases, the computer implemented software can be further designed to remove any additional adaptor sequence from or a plurality of sequence reads. In some cases, the MspI fragment can be larger than the read length and thus the software can look for TC at the 3' end and remove it. If TC is not found, then the software can look for a "T" and remove it. As shown in FIG. 18B, with regards to a reverse read, the computer-implemented software can look for a CGA triplet within the 6 nucleotides at the 5' end and trim the 0-3 D bases as well as the CGA triplet since this contains no genomic info other than the fact that it is an MspI site. Within the 6 nucleotides at the 3' end of the reverse reads, the computer implemented software can look for CCR and trim the 0-3 H bases after it. Again, the computer implemented software can be further designed to remove any additional adaptor sequence from or a plurality of sequence reads. With regards to the reverse read, if the software cannot find a CCR, the MspI fragment may be larger than the read length. In general, the number of D (or D and R base combination) removed from the 5' end of forward reads can be the same as the number of H bases removed from 3' end of the reverse read (if the read spans across the entire MspI fragment). Additionally, the number of H bases removed from the 3' end of a forward read (if the read spans across the entire MspI fragment) can be the same as the number of D bases (or D and R base combination) removed from the 3' end of the reverse read. In some cases, following trimming, a library insert can align with respect to MspI sites in a genome from which the insert was derived as shown in FIG. 18C.

In another aspect, the methods provided herein can be useful for removing duplicated sequence reads. In these cases, a stretch of nucleotides whose base compositions is selected at random is inserted within one or both ends of a nucleic acid library insert generated using the method provided herein. This stretch of nucleotides whose base compositions is selected at random can be inserted adjacent to another sequence element (e.g., a barcode) and can be located proximally to a sequence that is capable of binding a sequencing primer. An example of a library insert generated using the methods provided herein for generating an RRBS library that comprises this stretch of nucleotides whose base compositions is selected at random is shown in FIG. 32 and FIG. 37. This stretch of nucleotides whose base compositions is selected at random can be present in an adaptor or pool of adaptors comprising no or varying numbers of diversity bases (or extender sequence) and can be introduced to the end or ends of a polynucleotide upon introduction of the adaptor or pool of adaptors to the end or ends of the polynucleotide using the methods provided herein. This stretch of nucleotides whose base compositions is selected at random can be present in a primer or pool of primers comprising no or varying numbers of diversity bases (or extender sequence) and can be introduced to the end or ends of a polynucleotide upon introduction of the primer or pool of primers to the end or ends of the polynucleotide using the methods provided herein. This stretch of nucleotides whose base compositions is selected at random can be considered an additional sequence element as described herein. In some cases, this stretch of nucleotides whose base compositions is selected at random is introduced to the end or ends of a nucleic acid library insert during amplification of the nucleic acid library inserts using a primer or set of primers comprising the stretch of nucleotides whose base compositions is selected at random. The length of the stretch of nucleotides whose base compositions is selected at random can comprise 1, 2, 3, 4, 5, 6, 7, 8, 9, 9, 10, 11, or 12 bases. This random sequence can be common to each adaptor in a pool of adaptors or can be different between each adaptor within a pool of adaptors. This random sequence can be different between pools of adaptors. This random sequence can be common to each primer in a pool of primers or can be different between each primer within a pool of primers. This random sequence can be different between pools of primers. The presence of this random sequence can be utilized by computer-implemented software during the analysis of sequence reads. The computer-implemented software can be used to analyze the random sequence associated with all sequence reads that map to the same genomic location. Any reads that both map to the same genomic location and contain the same random sequence are considered duplicates, and all but one copy are removed.

In some cases, different barcodes can be added to polynucleotides in different samples (e.g., by using primers and/or adapters), and the different samples can be pooled and analyzed in a multiplexed assay. The barcode can allow the determination of the sample from which a polynucleotide originated.

The compositions, kits, and methods provided herein can be used to treat, prevent, diagnose, and/or prognose a variety of methylation related diseases. Such methylation related diseases can be cancer, mental retardation, neurodegenerative disorders, imprinting disorders, and syndromes involving chromosomal abnormalities. Such methylation related diseases can be Immunodeficiency-centromeric instability-facial anomalies syndrome (ICF), Rett syndrome, Beckwith-Wiedemann Syndrome (BWS), ATRX-linked mental retardation, fragile X syndrome. The cancer can be breast, ovarian, lung, head and neck, testicular, colon, or brain cancer. The cancer can be medulloblastoma, hepatoblastoma, uterine leiomyosarcomata, cervical carcinoma, renal cell carcinoma, rhadbomyosarcoma, gliomas, colorectal cancer, Wilm's tumour, Burkitt's lymphoma, or leukemia. In some cases, the methods described herein are used to determine the status of one or more genes associated with methylation related disorders. The status can include the presence or absence of a nucleic acid modification (i.e. methylation) at one or more bases in a nucleic acid sequence. In some cases, the methods disclosed herein are used to determine or recommend a course of treatment or administration of a therapy based on the status of one or more genes. The therapy can reduce one or more signs or symptoms of a methylation related disease. The therapy can prevent one or more signs or symptoms of any methylation related diseases. In some cases, the methods disclosed herein are used to determine the outcome or progress of a course of treatment or administration of a therapy based on the status of one or more genes. Genes associated with methylation related diseases can be, but are not limited to Socs1, Cdkn1c, Slc22a11, Bmp3b, Wit1, Rassf1a, Brca1, p16, Dapk, Mgmt, D4z4, Nbl2, H19, Igf2, G6pd, Rasgrf1 Sybl1, Ar, Pgk1, Dyz2, or Fmr1. In some cases, the status of 1, 2, 3, 4, 5, 6, 7, 8, 9, 10, 11, 12, 13, 14, 15, 16, 17, 18, 19, or 20 of any of the genes associated with methylation related diseases are analyzed.

The methods, kits, and compositions described herein can be used to prevent the development of one or more signs and/or symptoms of methylation related diseases or reduce the severity of one or more signs and/or symptoms of methylation related diseases. The severity of the sign and/or symptom can be reduced by about, or more than about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent. The severity of the sign or symptom can be decreased by about 1 percent to about 10 percent, about 1 percent to about 20 percent, about 1 percent to about 30 percent, about 1 percent to about 50 percent, about 1 percent to about 90 percent, about 1 percent to about 99 percent, about 10 percent to about 20 percent, about 10 percent to about 30 percent, about 10 percent to about 50 percent, about 50 percent to about 75 percent, about 75 percent to about 90 percent, about 75 percent to about 99 percent. The severity of the sign and/or symptom can be reduced by about, more than about, or at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 200-fold, 300-fold, 400-fold, 500-fold, 600-fold, 700-fold, 800-fold, 900-fold, or 1000-fold. The severity of the sign and/or symptom can be reduced by about 2-fold to 10-fold, about 2-fold to about 50-fold, about 2-fold to about 100-fold, about 10-fold to about 20-fold, about 10-fold to about 50-fold, about 10-fold to about 75-fold, about 10-fold to about 100-fold, about 50-fold to about 75-fold, about 50-fold to about 100-fold, about 100-fold to about 500-fold, about 100-fold to about 1000-fold, or about 500-fold to about 1000-fold.

The methods, kits, and compositions described herein can be used to decrease the likelihood that a subject will develop one or more signs and/or symptoms of methylation related diseases. The decrease in likelihood can be about, or more than about, or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent. The decrease in likelihood can be about 1 percent to about 10 percent, about 1 percent to about 20 percent, about 1 percent to about 30 percent, about 1 percent to about 50 percent, about 1 percent to about 90 percent, about 1 percent to about 99 percent, about 10 percent to about 20 percent, about 10 percent to about 30 percent, about 10 percent to about 50 percent, about 50 percent to about 75 percent, about 75 percent to about 90 percent, about 75 percent to about 99 percent. The decrease in likelihood can be about, more than about, or at least about 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 200-fold, 300-fold, 400-fold, 500-fold, 600-fold, 700-fold, 800-fold, 900-fold, or 1000-fold. The decrease in likelihood can be about 2-fold to 10-fold, about 2-fold to about 50-fold, about 2-fold to about 100-fold, about 10-fold to about 20-fold, about 10-fold to about 50-fold, about 10-fold to about 75-fold, about 10-fold to about 100-fold, about 50-fold to about 75-fold, about 50-fold to about 100-fold, about 100-fold to about 500-fold, about 100-fold to about 1000-fold, or about 500-fold to about 1000-fold.

A diagnosis and/or prognosis of a methylation associated neurological in a subject can be made by a health care provider, e.g., a developmental-behavioral pediatrician, a neurologist, a pediatric psychologist, or a psychiatrist. A diagnosis and/or prognosis of a neurological condition can be made or supported by a genetic test performed by a diagnostic laboratory. In some cases, a neurological assessment is administered to a subject by an individual trained and certified to administer a neurological assessment.

In some cases, a procedure can be performed to diagnose a methylation associated neurological condition in a subject, e.g., angiography, biopsy, a brain scan (e.g., computed tomography (CT), magnetic resonance imaging (MRI), positron emission tomography (PET)), cerebrospinal fluid analysis (by, e.g., lumbar puncture or spinal tap), discography, intrathecal contrast-enhanced CT scan (cisternograhpy), electronencephalography (EEG), electromyography (EMG), nerve conduction velocity (NCV) test, electronystagmography (ENG), evoked potentials (evoked response; e.g., auditory evoked potentials, visual evoked potentials, somatosensory evoked potentials), myelography, polysomnogram, single photon emission computed tomography (SPECT), thermography, or ultrasound imaging (e.g., neurosonography, transcranial Doppler ultrasound). One or more procedures that can diagnose a neurological condition can be performed on a subject.

Instruments that can be used in neurological examination can include, e.g., a tuning fork, flashlight, reflex hammer, ophthalmoscope, X-ray, fluoroscope, or a needle.

The methods, kits, and compositions provided herein can be used to treat, prevent, diagnose, and/or prognose a methylation associate disease or condition in a subject. The subject can be a male or female. The subject can have, or be suspected of having, a methylation associated disease. The subject can have a relative (e.g., a brother, sister, monozygotic twin, dizygotic twin, father, mother, cousin, aunt, uncle, grandfather, grandmother) that was diagnosed with a methylation associate disease. The subject can be, for example, a newborn (birth to about 1 month old), an infant (about 1 to 12 months old), a child (about 1 year old to 12 years old), a teenager (about 13 years old to 19 years old), an adult (about 20 years old to about 64 years old), or an elderly person (about 65 years old and older). The subject can be, for example, about 1 day to about 120 years old, about 1 day to about 110 years old, about 1 day to about 100 years old, about 1 day to about 90 years old, about 1 day to about 80 years old, about 1 day to about 70 years old, about 1 day to about 60 years old, about 1 day to about 50 years old, about 1 day to about 40 years old, about 1 day to about 30 years old, about 1 day to about 20 years old, about 1 day to about 15 years old, about 1 day to about 10 years old, about 1 day to about 9 years old, about 1 day to about 8 years old, about 1 day to about 7 years old, about 1 day to about 6 years old, about 1 day to about 5 years old, about 1 day to about 4 years old, about 1 day to about 3 years old, about 1 year to about 2 years old, about 3 years to about 15 years old, about 3 years to about 10 years old, about 3 years to about 7 years old, or about 3 years to about 5 years old. The subject can be about, more than about, at least about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old.

The methods for generating polynucleotide libraries as described herein can be used for detecting the presence of fetal DNA in a maternal sample. In some cases, the method comprises: (a) generating bisulfite treated DNA libraries as described herein using a sample obtained from a pregnant woman comprising maternal and fetal DNA; (b) detecting the methylation status of DNA sequence of one or more genes from the sample comprising maternal and fetal DNA; and (c) comparing the methylation status the one or more genes from the sample comprising maternal and fetal DNA to a reference maternal DNA sample comprising only maternal DNA. In some cases, step (b) of the method comprises an amplification process. In some cases, the amplification process is a polymerase chain reaction (PCR), such as real-time PCR. In other embodiments, step (b) determines the quantity of the DNA sequence. In some cases, the methods provided herein can be used to determine the Rhesus D (RhD) blood group compatibility between a pregnant woman and a fetus. In some cases, the methods for generating directional polynucleotide libraries as described herein can be used for diagnosing, monitoring, or risk assessment of a number of prenatal conditions. For example, the prenatal conditions can include, but are not limited to, beta-thalassemia, cystic fibrosis, congenital adrenal hyperplasia, chromosomal aneuploidies, preeclampsia, preterm labor, and intrauterine growth retardation (IUGR). In some cases, the method comprises (a) generating directional, bisulfite treated DNA libraries as described herein using a sample obtained from a pregnant woman comprising maternal and fetal DNA; (b) detecting the amount of DNA sequence of one or more genes from the sample comprising maternal and fetal DNA; and (c) comparing the amount of the DNA sequence with a standard control, wherein an increase from the control indicates the presence of or an increased risk for developing the pregnancy-associated condition. In some cases, step (b) of the method comprises an amplification process, which can be accomplished by various means, including polymerase chain reaction (PCR), such as real-time PCR. The one or more genes can be RASSF1A, APC, CASP8, RARB, SCGB3A1, DAB2IP, PTPN6, THY1, TMEFF2, or PYCARD. The sample can be whole blood, plasma, serum, urine, or saliva. The DNA can be cell-free DNA and/or DNA derived from maternal and fetal cells present in the sample from the pregnant woman. "Standard control value" as used herein refers to a predetermined amount of a genomic sequence that is originated from a fetus and is present in an established sample. The standard control value is suitable for the use of a method described herein, in order for comparing the amount of a gene of interest (or a non-coding sequence) that is present in a test sample. The standard control can provide an average amount of a fetal gene of interest that is typical for a defined time (e.g., first trimester) during pregnancy in the blood of an average, healthy pregnant woman carrying a normal fetus, both of whom are not at risk of developing any pregnancy-associated disorders or complications. A standard control value can vary depending on the genomic sequence of interest and the nature of the sample.

The methods for generating polynucleotide libraries as described herein can be combined with one or more methods for measuring DNA methylation at specific genomic loci. For example, the methods for measuring DNA methylation can include, but are not limited to, immunoprecipitation of methylated DNA, methyl-binding protein enrichment of methylated fragments, and/or digestion with methylation-sensitive restriction enzymes.

The methods for generating polynucleotide libraries as described herein can be combined with one or more methods for profiling methylation status of the whole genome, i.e. the methylome. For example, the methods provided herein can be combined with reduced representation bisulfite sequencing (RRBS). RRBS involves digestion of a DNA sample with a methylation-insensitive restriction endonuclease that has CpG dinucleotide as a part of its recognition site, followed by bisulfite sequencing of the selected fragments (Meissner et al., *Nucleic Acids Res.* 33(18):5868-5877, 2005).

VIII. Compositions and Reaction Mixtures

The present methods further provide one or more compositions or reaction mixtures. In some cases, the reaction mixture comprises: (a) a pool of duplex adaptors comprising duplex adaptors comprising 0, 1, 2, or 3 diversity bases in a ligation strand, wherein the ligation strand comprises cytosine analogs resistant to bisulfite treatment and a non-ligation strand wherein the non-ligation strand is blocked at the 3' and 5' ends and is enzymatically unreactive; (b) a strand displacing polymerase; (c) unmodified dNTPs; and (d) bisulfite. The duplex adaptors in the pool can be partial duplex adaptors comprising a long strand and a short strand as provided herein, wherein the long strand comprises the ligation strand, while the short strand comprises the non-ligation strand. In some cases, the strand displacing polymerase in the reaction mixture is substituted with a polymerase comprising exonuclease activity (e.g., Taq polymerase). In some cases, the reaction mixture further comprises (e) amplification primers directed to unique priming sites created at each end of the DNA fragments following bisulfite treatment. In some cases, at least one of the amplification primers is directed against adaptor sequence following bisulfite treatment, whereby cytosine residues have been converted to uracil residues. In some cases, the reaction mixture further comprises (f) sequencing primers directed against sequences present in the adaptor sequence. In some cases, at least one of the sequencing primers is directed against adaptor sequence following bisulfite treatment, whereby cytosine residues have been converted to uracil residues and subsequently replaced with thymine residues following amplification.

In some cases, the reaction mixture comprises: (a) a pool of duplex adaptors comprising duplex adaptors comprising 0, 1, 2, or 3 diversity bases in a ligation strand and a non-ligation strand wherein the non-ligation strand is blocked at the 3' and 5' ends and is enzymatically unreactive; (b) a strand displacing polymerase; (c) modified dCTP (i.e. 5-methyl-dCTP, 5-hydroxymethyl-dCTP, or 5-propynyl-dCTP); (d) dATP, dGTP, and dTTP; and (e) bisulfite. The duplex adaptors in the pool can be partial duplex adaptors comprising a long strand and a short strand as provided herein, wherein the long strand comprises the ligation strand, while the short strand comprises the non-ligation strand. In some cases, the strand displacing polymerase in the reaction mixture is substituted with a polymerase comprising exonuclease activity (e.g., Taq polymerase). In some cases, the reaction mixture further comprises (f) amplification primers directed to unique priming sites created at each end of the DNA fragments following bisulfite treatment. In some cases, at least one of the amplification primers is directed against adaptor sequence following bisulfite treatment, whereby cytosine residues have been converted to uracil residues. In some cases, the reaction mixture further comprises (g) sequencing primers directed against sequences present in the adaptor sequence. In some cases, at least one of the sequencing primers is directed against adaptor sequence following bisulfite treatment, whereby cytosine residues have been converted to uracil residues and subsequently replaced with thymine residues following amplification.

IX. Kits

Any of the compositions described herein may be comprised in a kit. In a non-limiting example, the kit, in a suitable container, comprises: an adaptor or several adaptors, one or more of oligonucleotide primers and reagents for ligation, primer extension and amplification. In some cases, the adaptors are diversity adaptors. The diversity adaptors can be any adapter has generated by the method depicted in FIG. 2B. The diversity adaptors can be any adaptor that comprises a partial duplex as depicted in FIG. 3. The adapters can be the adapters depicted in FIG. 3. The kit may also comprise means for purification, such as a bead suspension, and nucleic acid modifying enzymes.

The containers of the kits can include at least one vial, test tube, flask, bottle, syringe or other containers, into which a component may be placed, and preferably, suitably aliquotted. Where there is more than one component in the kit, the kit also can contain a second, third or other additional container into which the additional components may be separately placed. Various combinations of components may be comprised in a container.

When the components of the kit are provided in one or more liquid solutions, the liquid solution can be an aqueous solution. The components of the kit may be provided as dried powder(s). When reagents and/or components are provided as a dry powder, the powder can be reconstituted by the addition of a suitable solvent.

The present methods provide kits containing one or more compositions described herein and other suitable reagents suitable for carrying out the methods described herein. The methods described herein provide, e.g., diagnostic kits for clinical or criminal laboratories, or nucleic acid amplification or analysis kits for general laboratory use. The present methods thus include kits which include some or all of the reagents to carry out the methods described herein, e.g., sample preparation reagents, oligonucleotides, binding molecules, stock solutions, nucleotides, polymerases, enzymes, positive and negative control oligonucleotides and target sequences, test tubes or plates, fragmentation reagents, detection reagents, purification matrices, and an instruction manual. In some cases, the kit comprises a binding molecule, wherein the binding molecule is a nucleotide analog binding protein. In some cases, the nucleotide analog binding protein comprises a methylcytosine binding protein. In some cases, the methylcytosine binding protein comprises an anti-5-methylcytosine antibody. In some cases, the kit contains a modified nucleotide. Suitable modified nucleotides include any nucleotides provided herein including but not limited to a nucleotide analog. In some cases, the nucleotide analog can be a cytosine analog. In some cases, the cytosine analogs can be 5-methyl dCTP, 5-hydroxymethyl dCTP, and/or 5-propynl dCTP. In some cases, the kit comprises a converting agent. In some cases, the converting agent is bisulfite or its equivalent.

In some cases, the kit can contain one or more reaction mixture components, or one or more mixtures of reaction mixture components. In some cases, the reaction mixture components or mixtures thereof can be provided as concentrated stocks, such as 1.1×, 1.5×, 2×, 2.5×, 3×, 4×, 5×, 6×, 7×, 10×, 15×, 20×, 25×, 33×, 50×, 75×, 100× or higher concentrated stock. The reaction mixture components can include any of the compositions provided herein including but not limited to buffers, salts, divalent cations, azeotropes, chaotropes, dNTPs, labeled nucleotides, modified nucleotides, dyes, fluorophores, biotin, enzymes (such as endonucleases, exonucleases, glycosylases), or any combination thereof.

In some cases, the kit can contain one or more oligonucleotide primers, such as the oligonucleotide primers described herein. The oligonucleotide primers can be one or more primers comprising diversity bases or extender sequence as described herein. In some cases, the kit comprises a pool of primers, wherein some of the primers comprise no diversity bases, while the remaining primers in the pool of primers comprise a variable number of diversity bases. The primers can comprise 1, 2, 3, 4, 5, 6, 7, 8, 9, 10, 11, 12, 13, 14, 15, 16, 17, 18, 19, 20 or more diversity bases. In some cases, the pool of primers is used to generate RRBS libraries such that the base composition of the diversity base is chosen so as not to recreate the YGG (Y is cytosine or thymine) motif at the 5' end of a nucleic insert in the RRBS library. The kit can contain one or more oligonucleotide primers comprising sequence directed against the ligation strand of an adapter or its complement and/or sequence directed against the ligation strand of an adapter or its complement whose sequence is altered by treatment with a converting agent. In some cases, the converting agent is bisulfite. In some cases the kit can contain tailed primers comprising a 3'-portion hybridizable to the target nucleic acid and a 5'-portion which is not hybridizable to the target nucleic acid. In some cases, the kit can contain chimeric primers comprising an RNA portion and a DNA portion. In some cases, the 5' portion of the tailed primers comprises one or more barcodes or other identifier sequences. In some cases, the identifier sequences comprise flow cell sequences, TruSeq primer sequence, and/or second read barcode sequences. In some cases, the identifier sequence is a stretch of random sequences such that the random sequences are read during an index or barcode read and are used as mark to facilitate identification and removal of PCR duplicates during subsequent in silico analysis of sequencing reads.

In some cases, the kit can contain one or more polymerases or mixtures thereof. In some cases, the one or more polymerases or mixtures thereof can comprise strand displacement activity and/or exonuclease activity. Suitable polymerases include any of the polymerases provided herein. The kit can further contain one or more polymerase substrates such as for example dNTPs, non-canonical or modified nucleotides, or nucleotide analogs.

In some cases, the kit can contain one or more means for purification of the nucleic acid products, removing of the fragmented products from the desired products, or combination of the above. Suitable means for the purification of the nucleic acid products include but are not limited to single stranded specific exonucleases, affinity matrices, nucleic acid purification columns, spin columns, ultrafiltration or dialysis reagents, or electrophoresis reagents including but not limited acrylamide or agarose, or any combination thereof.

In some cases, the kit can contain one or more reagents for producing blunt ends. For example, the kit can contain one or more of single stranded DNA specific exonucleases including but not limited to exonuclease 1 or exonuclease 7; a single stranded DNA specific endonucleases such as mung bean exonuclease or S1 exonuclease, one or more polymerases such as for example T4 DNA polymerase or Klenow polymerase, or any mixture thereof. Alternatively, the kit can contain one or more single stranded DNA specific exonucleases, endonucleases and one or more polymerases, wherein the reagents are not provided as a mixture. Additionally, the reagents for producing blunt ends can comprise dNTPs.

In some cases, the kit can contain one or more reagents for preparing the double stranded products for ligation to adapter molecules. For example, the kit can contain dATP, dCTP, dGTP, dTTP, or any mixture thereof. In some cases, the kit can contain a polynucleotide kinase, such as for example T4 polynucleotide kinase. Additionally, the kit can contain a polymerase suitable for producing a 3' extension from the blunt ended double stranded DNA fragments. Suitable polymerases can be included, for example, exo-Klenow polymerase.

In some cases, the kit can contain one or more adaptor molecules such as any of the adapter molecules provided herein. Suitable adapter molecules include single or double stranded nucleic acid (DNA or RNA) molecules or derivatives thereof, stem-loop nucleic acid molecules, forked nucleic acid molecules, double stranded molecules comprising one or more single stranded overhangs of 1, 2, 3, 4, 5, 6, 7, 8, 9, 10 bases or longer, proteins, peptides, aptamers, organic molecules, small organic molecules, or any adapter molecules known in the art that can be covalently or non-covalently attached, such as for example by ligation, to the double stranded DNA fragments. In some cases, the adapters can be duplex adapters wherein one strand comprises nucleotide analogs resistant to conversion by a converting agent, while the other strand comprises a 5' and 3' block. In some cases, the adapters can be duplex adapters wherein both strands comprise nucleotide analogs resistant to conversion by a converting agent. In some cases, the adapters can be duplex adapters wherein both strands comprise nucleotides sensitive to conversion by a converting agent. In a further embodiment, the duplex adapter is a partial duplex adapter. In some cases, the partial duplex adapter comprises a long strand comprising nucleotide analogs resistant to conversion by a converting agent, and a short strand comprising a 5' and 3' block. In some cases, the partial duplex adapter comprises a long strand comprising nucleotides sensitive to conversion by a converting agent, and a short strand comprising a 5' and 3' block. In some cases, the nucleotide analog is a cytosine analog. In some cases, the nucleotides sensitive to a converting agent is dCTP. In some cases, the cytosine analogs present in the adapter can be 5-methylcytosine, 5-hydroxymethylcytosine, and/or 5-propynlcytosine. In some cases, the 5' block comprises a biotin moiety. In some cases, the 3' block is blocked with a terminal dideoxycytosine. In some cases, one or more adaptors in the kit comprise one or more diversity bases or extender sequence as described herein.

In some cases, the kit can contain one or more reagents for performing nick or fill-in repair on the ligation complex formed between the adaptors and the double stranded products of the methods described herein. The kit can contain a polymerase suitable for performing nick repair. Suitable polymerases can be included, for example, Taq DNA polymerase.

The kit can further contain instructions for the use of the kit. For example, the kit can contain instructions for generating RRBS libraries, directional cDNA libraries or directional cDNA libraries representing the methylome or the methylation status of a specific genomic region or locus useful for large scale analysis of including but not limited to e.g., pyrosequencing, sequencing by synthesis, sequencing by hybridization, single molecule sequencing, nanopore sequencing, and sequencing by ligation, high density PCR, digital PCR, massively parallel Q-PCR, and characterizing amplified nucleic acid products generated by the methods described herein, or any combination thereof. The kit can further contain instructions for mixing the one or more reaction mixture components to generate one or more reaction mixtures suitable for the methods described herein. The kit can further contain instructions for hybridizing the one or more oligonucleotide primers to a nucleic acid template. The kit can further contain instructions for extending the one or more oligonucleotide primers with for example a polymerase and/or nucleotide analogs. The kit can further contain instructions for treating the DNA products with a converting agent. In some cases, the converting agent is bisulfite. The kit can further contain instructions for purification of any of the products provided by any of the steps of the methods provided herein. The kit can further contain instructions for producing blunt ended fragments, for example by removing single stranded overhangs or filling in single stranded overhangs, with for example single stranded DNA specific exonucleases, polymerases, or any combination thereof. The kit can further contain instructions for phosphorylating the 5' ends of the double stranded DNA fragments produced by the methods described herein. The kit can further contain instructions for ligating one or more adapter molecules to the double stranded DNA fragments. The kit can further contain instructions for analysing sequence reads obtained from libraries generated using the methods provided herein and subsequently sequenced. The instructions can describe how to trim diversity bases present in sequence reads in silico. The instructions can describe how to remove duplicates present in sequence reads in silico.

A kit will can include instructions for employing, the kit components as well the use of any other reagent not included in the kit. Instructions can include variations that can be implemented.

Unless otherwise specified, terms and symbols of genetics, molecular biology, biochemistry and nucleic acid used herein follow those of standard treatises and texts in the field, e.g. Kornberg and Baker, *DNA Replication*, Second Edition (W.H. Freeman, New York, 1992); Lehninger, *Biochemistry*, Second Edition (Worth Publishers, New York, 1975); Strachan and Read, Human *Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

EXAMPLES

Example 1: Generation of a RRBS Library Using Diversity Adapters

Figure 9A:
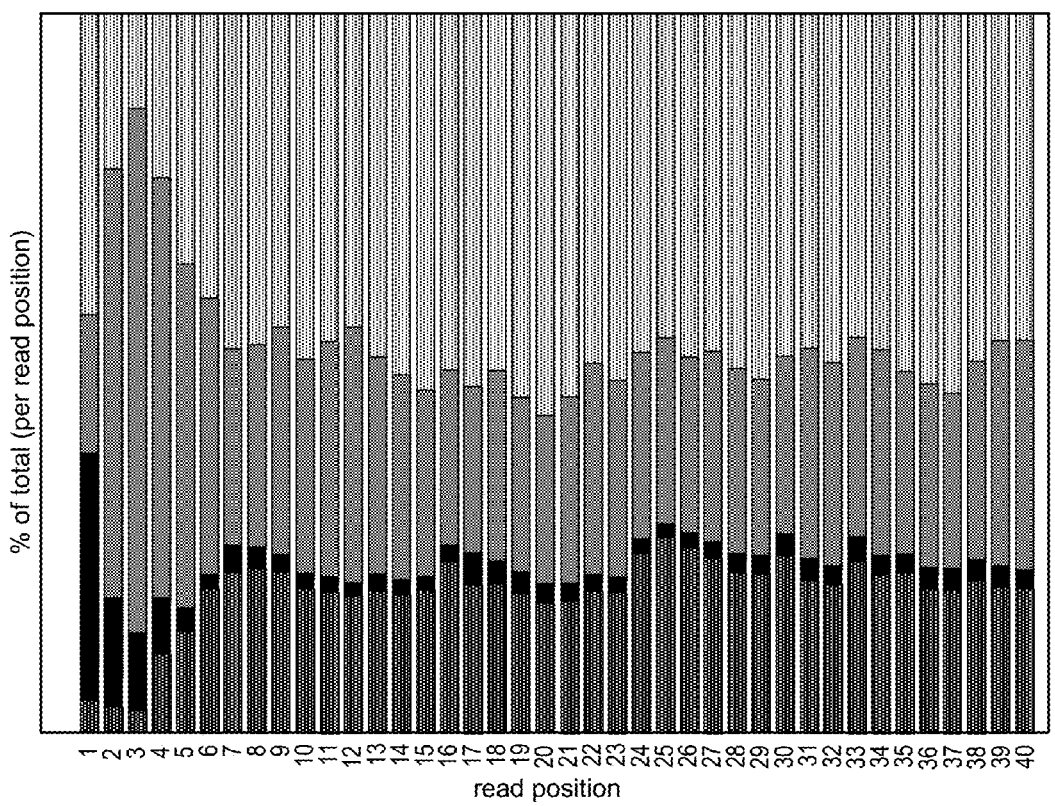
FIG. 9A-B illustrates the sequencing results of forward reads (FIG. 9A) and reverse reads (FIG. 9B) for sequencing an RRBS library with a pool of diversity-adapters comprising a variable number of "D" bases.
Figure 9B:
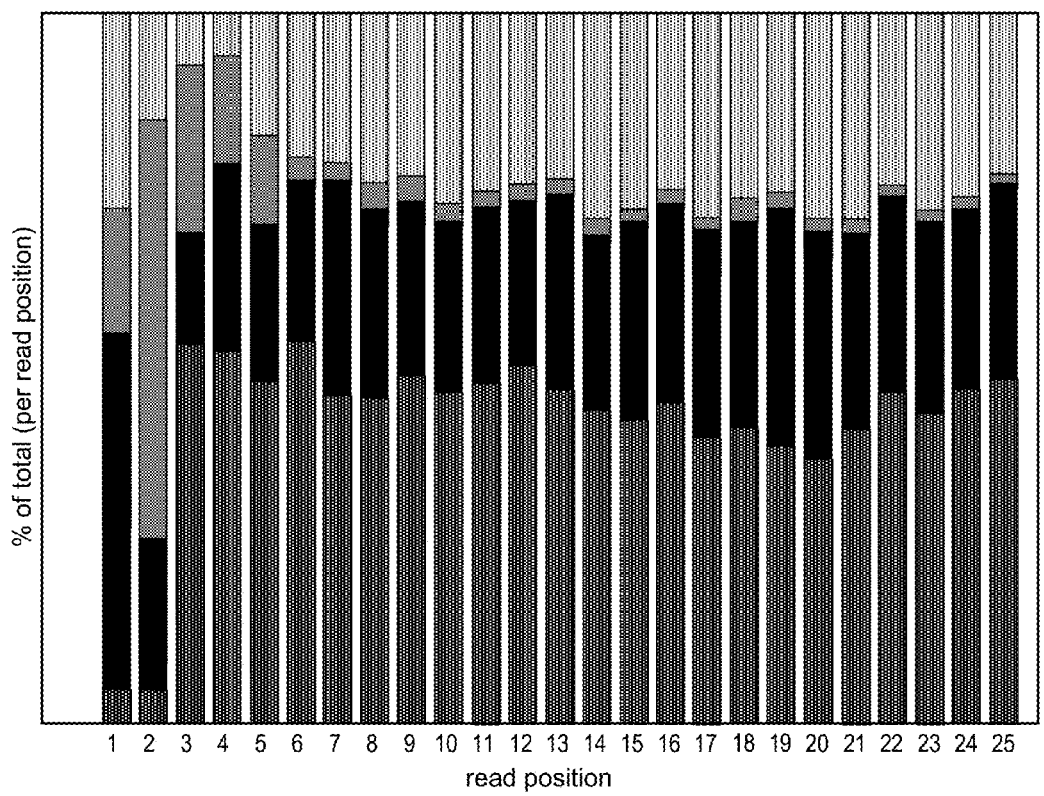

In this example, an RRBS library was generated using the diversity adapters shown in FIG. 2A-B and the sequencing results were subsequently analyzed. As shown in FIG. 2A-B, the diversity adapters can be partial duplex adapters comprising a long strand (e.g., R01446 in FIG. 2A), hybridized with a short strand (e.g., Ben383, 384, 385, or 381 in FIG. 2A) in such a manner that both ends of the partial duplex comprise a 5' overhang. The 5' overhang comprising sequence from the short strand of the partial duplex comprises a 5' terminal GC sequence with a Biosg label on the terminal cytosine residue, while the 3' terminus comprises a terminal 3' dideoxy cytosine residue. As can be seen in FIG. 2A-B, the 5' overhang comprising short strand sequence contains either no (D0, e.g., Ben341 in FIG. 2A), 1 (D1, e.g., Ben385 in FIG. 2A), 2 (D2, e.g., Ben384 in FIG. 2A), or 3 ((D3, e.g., Ben383 in FIG. 2A) "H" bases. The "H" bases can be either an adenosine, cytosine or thymine residue, but cannot be a guanine residue. As shown in FIG. 2A-B, for use in the methods provided herein as well as this Example, the partial duplex adapter is subjected to an extension reaction using a dNTP mix containing only dATP, dGTP, and dTTP (i.e., no dCTP), whereby a partial duplex adapter comprising a 5' overhang comprising at least one "H" (e.g., R01446 hybridized to Ben 383, 384, or 385) is extended to produce a partial duplex adapter containing a two base 5' overhang with the sequence GC at one end. In this Example, 5 ng of human gDNA was digested with MspI and the resulting fragments were separated into different diversity adaptor pools as shown in FIG. 2A-B, wherein a first pool was ligated to the D0 diversity adaptors, a second pool was ligated to the D1 diversity adapters, a third pool was ligated the D2 diversity adapters, a fourth pool was ligated to the D3 adapters, and a fifth pool was ligated to a mixture of the D0, D1, D2, and D3 diversity adapters. The ligations and all subsequent steps were performed according to the protocol for the NuGEN Ovation® Ultralow Methyl-Seq Library System, which is herein incorporated by reference in its entirety. Briefly, following digestion of the gDNA with MspI to produce DNA fragments, the DNA fragments are combined with a master mix containing the appropriate diversity adapters comprising 0, 1, 2, or 3 diversity "D" bases (i.e., D3, D2, D1, D0, or a mix of D0-D3 in FIGS. 4A-B, 5A-B, 6A-B, 7A-B, and 9A-B, respectively), ligation buffer, water and ligation enzyme mix, placed in a thermal cycler and run through a program on the thermal cycler that comprised of a single cycle comprising incubations at 25 C for 30 minutes, 70 C for 10 minutes, and then holding the mixture at 4 C. Following ligation, the ligation complexes were subjected to a post-ligation purification followed by a final repair reaction entailing incubation of the ligation complexes with a DNA repair enzyme in a thermal cycler programmed for a single cycle of 60 C incubation for 10 minutes. Following final repair, the samples were subjected to bisulfite conversion, wherein 20 uL of the products from the final repair reactions were inputted directly into a Qiagen EpiTect Fast DNA Bisulfite Kit according to manufacturer protocols and subjected to two cycles of 95 C for 5 minutes, and 60 C for 20 minutes on a thermal cycler followed by elution of the purified, bisulfite converted DNA libraries. The bisulfite converted DNA libraries were then PCR amplified and purified. Following library amplification and purification, the libraries were pooled and sequenced on an Illumina MiSeq sequencer according to manufacturer instructions with a 40 nucleotide forward read, 6 nucleotide index read, and 25 nucleotide reverse read. FIGS. 4A-B, 5A-B, 6A-B, 7A-B, 8, and 9A-B show a high correlation between the expected forward and reverse sequencing reads and the actual nucleotide distributions at read positions 1-40 in the forward reads (FIGS. 4A, 5A, 6A, 7A, and 9A) and 1-25 in the reverse reads (FIGS. 4B, 5B, 6B, 7B, and 9B) for nucleic acid fragments appended with diversity adapters with three diversity "D" bases (FIG. 4A-B), diversity adapters with 2 diversity "D" bases (FIG. 5A-B), diversity adapters with 1 diversity "D" base (FIG. 6A-B), diversity adapters with no diversity bases (FIG. 7A-B), and the mix of diversity adapters comprising zero, 1, 2, or 3 diversity "D" bases (FIGS. 8 & 9A-B). In some cases, the diversity base in the 5' position of a diversity adaptor comprising three diversity bases can be an "R" base while the remaining 2 diversity bases can be "D" bases as shown in FIG. 35. The "R" base can be either an adenine or a guanine nucleotide base, while the "D" bases can be either an adenine, guanine, or thymine nucleotide base as shown in FIG. 35 and as described herein. In some cases, an "R" base is substituted for a "D" base in a pool of diversity adaptors such that library inserts generated using the methods described herein for generating an RRBS library following MspI digestion using the pool of diversity adaptors with an "R" base comprise an "R" base as the first base read in a forward sequence read (e.g., FIG. 35).

Figure 11:
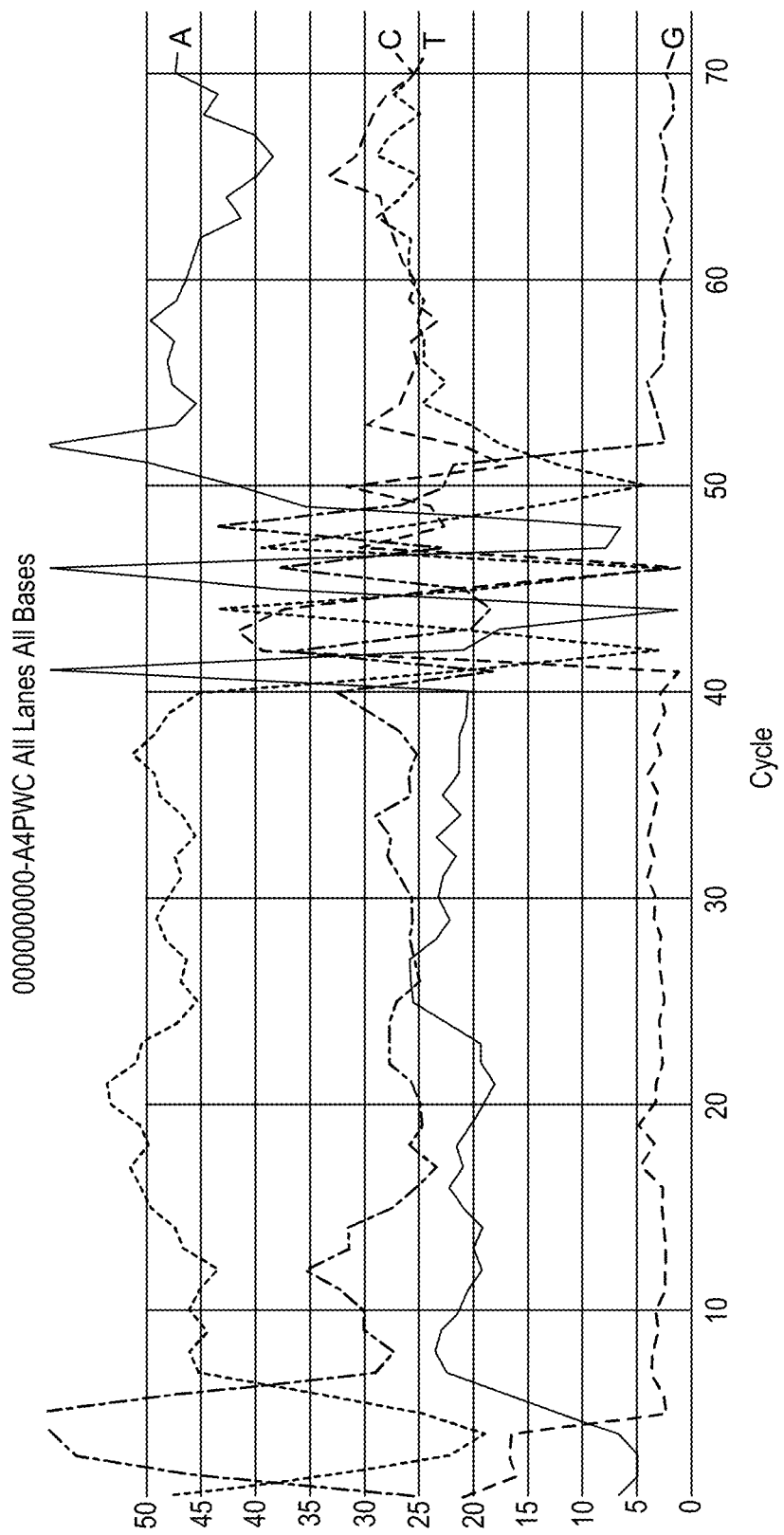
FIG. 11 illustrates the % base for each cycle for the sequencing reactions performed in FIG. 10.
Figure 12:
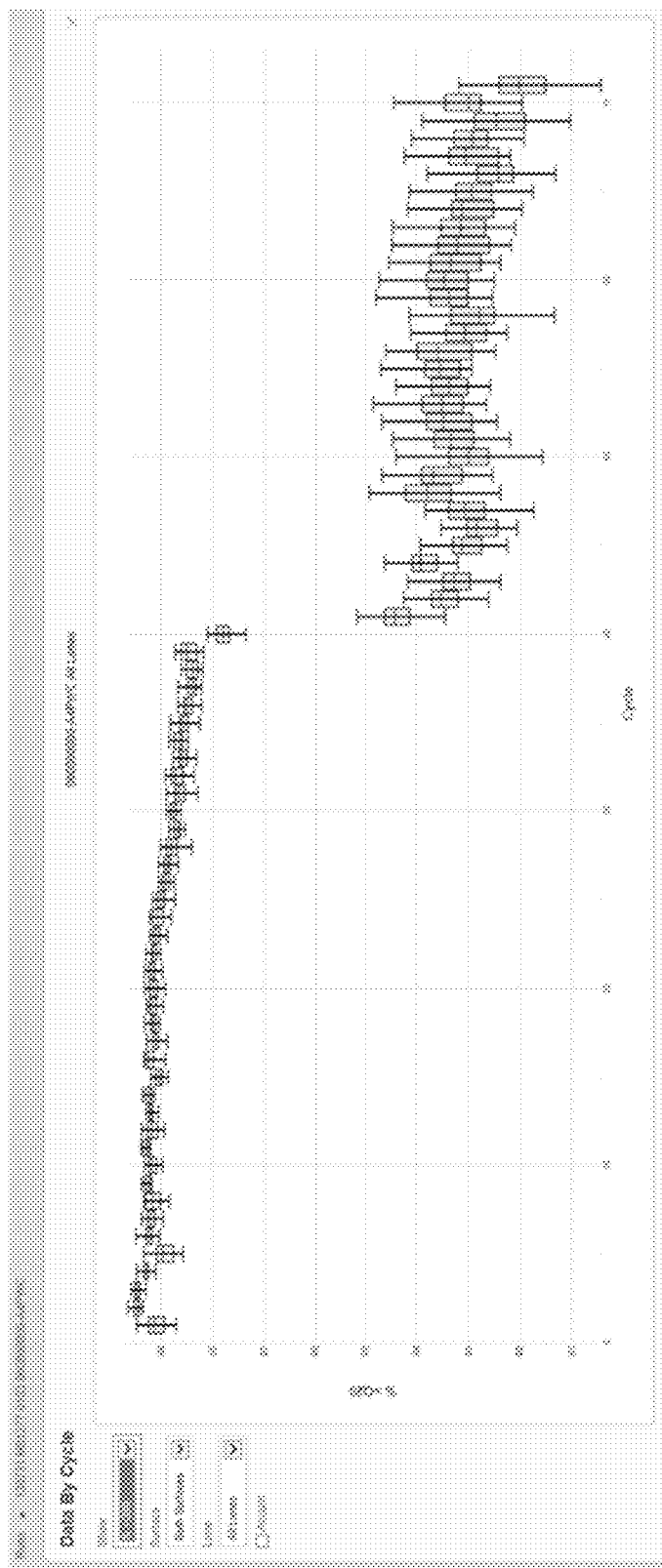
FIG. 12 illustrates the %>Q20 score for each cycle for the sequencing reactions performed in FIG. 10.
Figure 13:
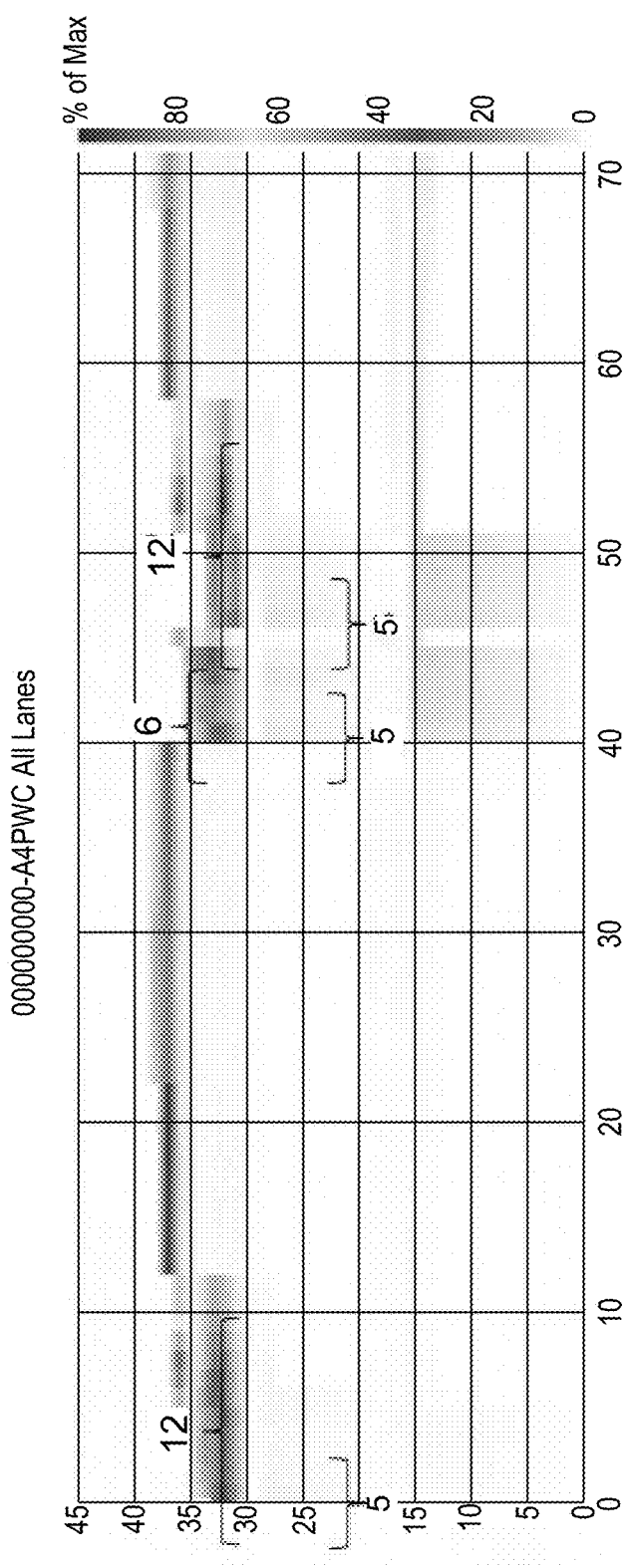
FIG. 13 illustrates a Q-score heat map for the sequencing reactions performed in FIG. 10.
Figure 16:
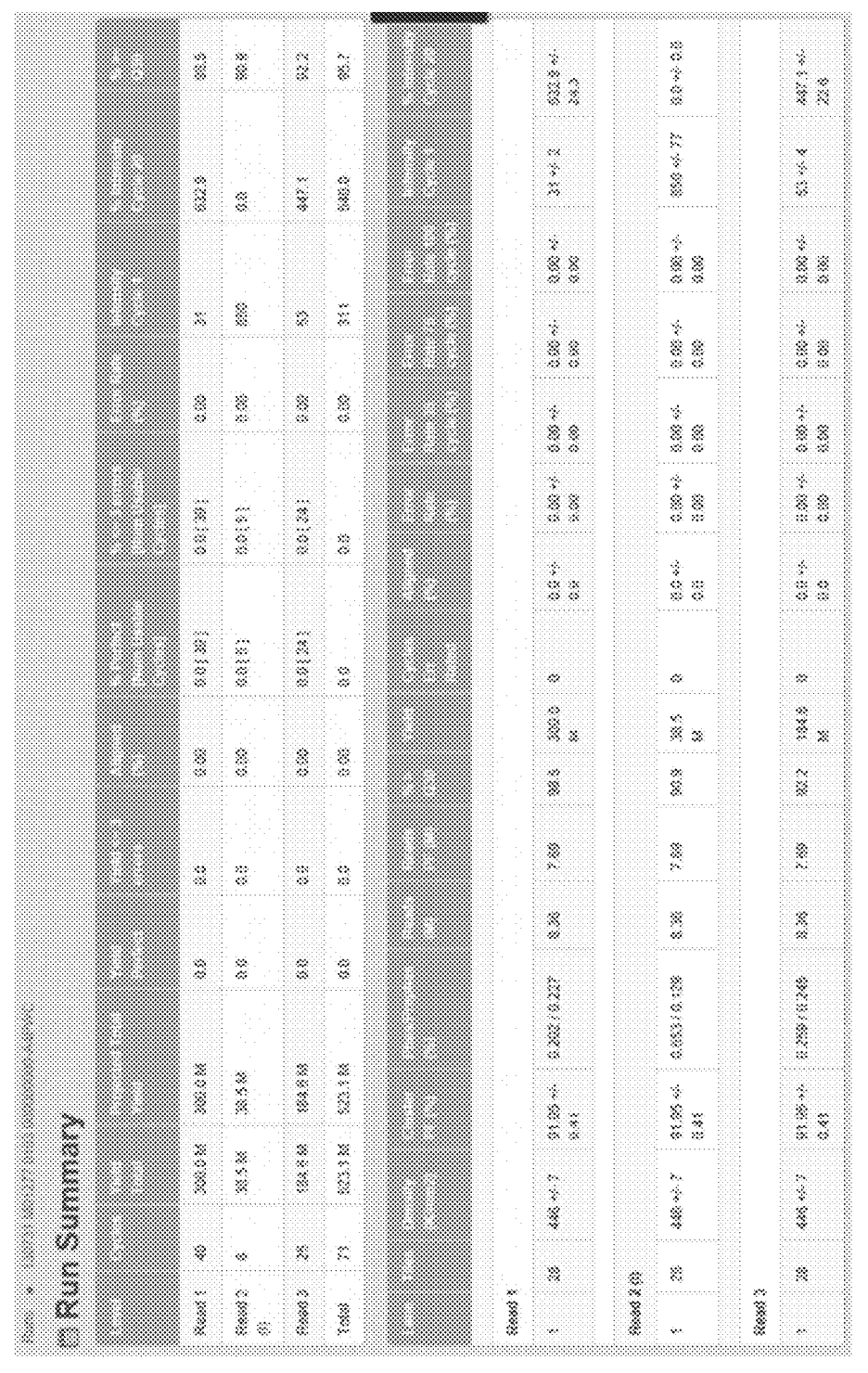

Example 2: Sequencing of RRBS Library Generated Using Diversity Adapters without Phi X Control In this example, RRBS libraries were generated using diversity adapters as described in Example 1; however, sequencing of the RRBS libraries generated using diversity adapters with a 40 nucleotide forward read, 6 nucleotide index read, and 25 nucleotide reverse read was conducted without running a dedicated control high diversity Phi X control lane. As can be seen in FIGS. 10-12, the RRBS library sequenced without a PhiX control showed a Q-score distribution whereby >95% of the Q-scores were >30 (FIG. 10), an anticipated distribution of bases (FIGS. 10 and 11) whereby a diversity of bases existed at the start of the sequencing read while roughly equal numbers of "A" and "G" bases were reported further into the read, and the percentage of >Q20 scores being above 95% at PCR amplification cycles of less than 40 (FIG. 12), which indicated a low probability of an incorrect base calling. FIG. 13 shows a Q-score heatmap over 71 sequencing cycles that include 40 forward read cycles, 6 index read cycles, and 25 reverse read sequencing cycles. FIG. 16 shows a summary of the run for this Example showing a high percentage (>95%) of total reads with a Q score above 30, with a forward read (read 1) having a Q 30 score of 95%, an index read (read 2) having a Q 30 score of >90%, and a reverse read (read 3) having a Q30 score of >90%. In summary, the use of the diversity adapters in generating RRBS libraries with diversity adaptors comprising D bases as described in Example 1 produced high quality sequencing reads with or without the use of PhiX control libraries.

Figure 15:
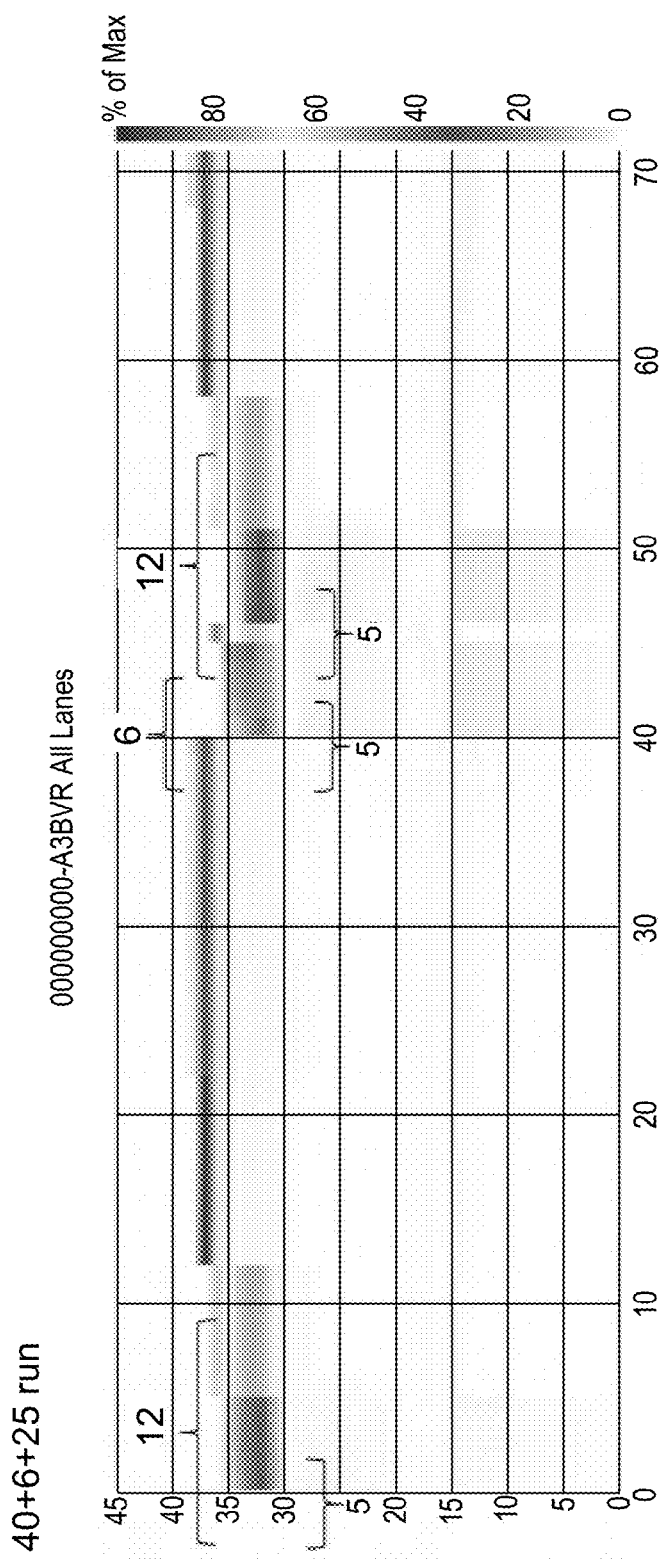
FIG. 15 illustrates a Q-score heat map for the sequencing reactions performed in FIG. 14.
Figure 17:
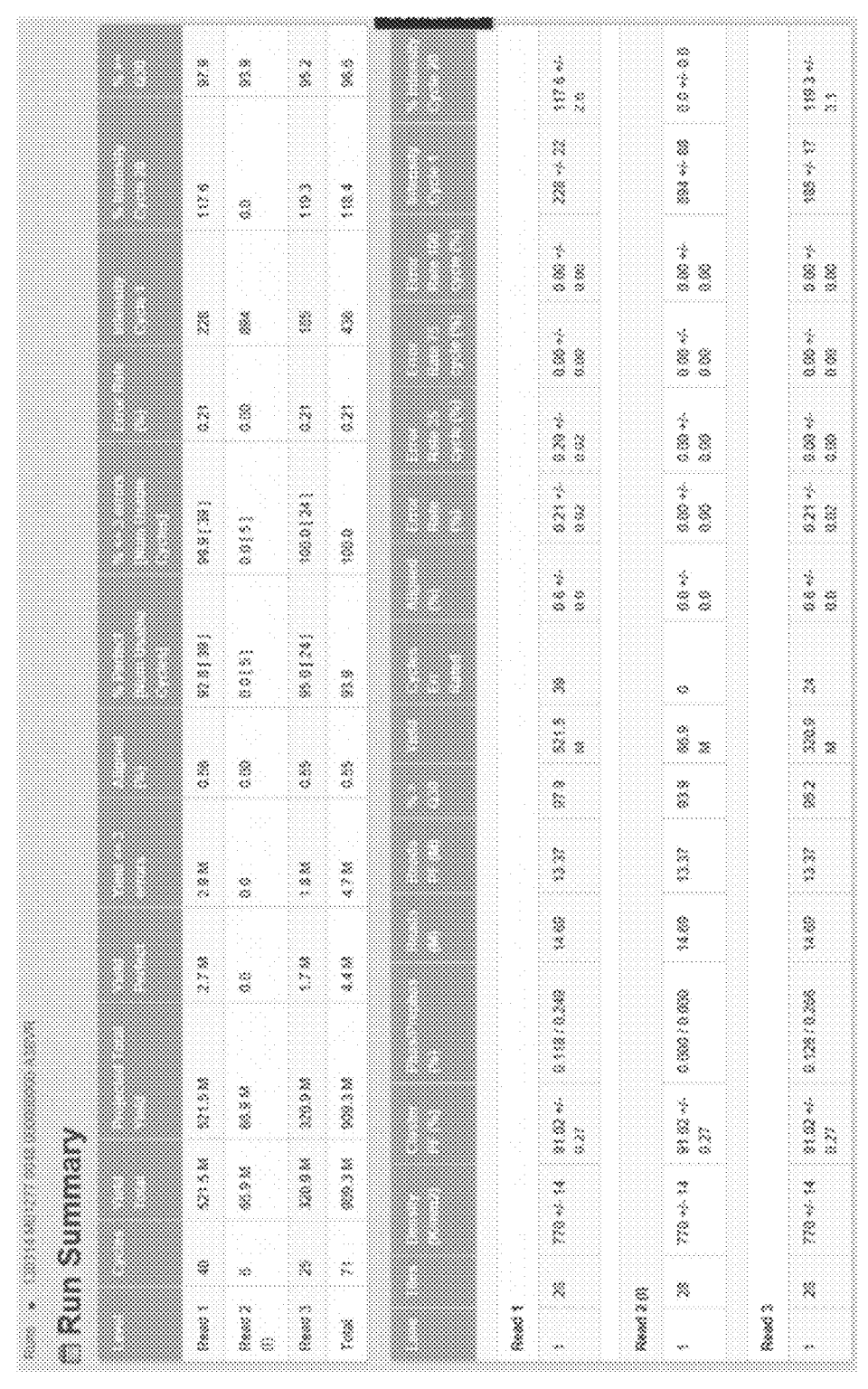

As a comparison, inserts from a Human Blood RNA sequencing library generated for 100 ng of total RNA from adult human whole blood according to the manufacturer's instructions for the NuGEN Ovation® Human Blood RNA-Seq Library System, which is herein incorporated by reference in its entirety, were sequenced with a 40 nucleotide forward read, 6 nucleotide index read, and 25 nucleotide reverse read. Briefly, ~100 ng of total RNA from adult human whole blood was subjected to first strand synthesis using random primers, followed by second strand synthesis in the presence of a non-canonical nucleotide (i.e., dUTP), fragmented using the Covaris sonication, end repaired, ligated with adapters marked with a non-canonical nucleotide (i.e., dUTP) and comprising barcode sequences, strand selected, adapter cleavage to remove unwanted sequences (e.g., rRNA and Globin RNA), and finally, library amplification using PCR with primers directed against the adapter sequences, thereby allowing for 16-plex sequencing capability. FIGS. 14 and 15 show intensity by cycle, cluster density, Q-score distribution and heat-map data from the 40 cycle forward read by 6 cycle index read by 25 cycle reverse read run performed on the Blood-Seq library that was similar to the data obtained from the 40 cycle forward read by 6 cycle index read by 25 cycle reverse read run performed on the RRBS library generated without Phi X controls (see FIGS. 10 and 13). FIG. 17 shows the run summary for the 40 cycle forward read by 6 cycle index read by 25 cycle reverse read run performed on the Blood-Seq library. A comparison between FIGS. 16 and 17 showed that sequencing of the RRBS library generated with diversity adapters as described in Example 1 produced high quality sequencing data without requiring a Phi X high diversity control.

Example 3: Comparison of the CpGs Analyzed by Sequencing a RRBS Library Generated Using Diversity Adapters Vs. Whole Genome Bisulfite Sequencing (WGBS)

In this example, a comparison of the CpGs analyzed by sequencing a RRBS library generated by the methods provided herein vs. WGBS was conducted. The RRBS library was generated from MspI fragmented genomic DNA (gDNA) from IMR90 human cell line was ligated to a mixture of D0-D3 diversity adapters as described in Example 1 using either 400, 100, 25, 6.25, or 1.56 ng of gDNA as input for generation of the RRBS library. The library used for WGBS was generated by first subjecting 50 ng of human gDNA to Covaris sonication to an average size of 200 bp, and then generating a library for WGBS using the fragmented gDNA as input into the NuGEN Ovation® Ultralow Methyl-Seq Library System, wherein the library for WGBS was generated as directed by the manufacturer. The RRBS and WGBS libraries were each separately sequenced on an Illumina GAIIx sequencer with a 40 nucleotide single end (40 nt SE) and 6 nucleotide index read. For the RRBS sequences, the D1-D3 adaptor sequences were trimmed off, and the resulting reads, which started with "YGG", were analyzed with the Bismark program for mapping bisulfite treated sequencing reads. Mapped reads were further analyzed by grouping into categories of CpG islands, CpG shores, and promoters. FIG. 20 shows that the total CpGs analyzed using as little as 1.56 ng of starting gDNA was considerably greater than the total CpGs analyzed by WGBS. Moreover, the average CpG per read and average CpG per uniquely aligned read were at least 6× and 7× greater than WGBS, respectively (FIG. 21). FIG. 22 shows that the feature coverage (i.e., CpG Islands and Shores, as well as Promoters) using RRBS libraries generated using the methods provided herein are very close to the theoretical maximum predicted by an in silico analysis for a 40 nt SE read for a RRBS library (FIGS. 22 and 25). Overall, RRBS libraries generated using diversity adapters as provided herein can be easily sequenced (e.g., with commercially available NGS sequencers such Illumina systems), and provide CpG-dense data.

Example 4: Kit Components

A kit can be used for RRBS library formation.
A. Reagents
The kit can comprise the components in Table 1:

TABLE 1

| Reagents |
| --- |
| MspI Buffer Mix |
| MspI Enzyme Mix |
| Ligation Buffer Mix |
| Ligation Adaptor Mixes |
| Ligation Enzyme Mix |
| Final Repair Buffer Mix |
| Final Repair Enzyme Mix |
| Amplification Primer Mix |
| Amplification Enzyme Mix |
| 25 µM Sequencing Primer |
| Nuclease-free Water |
| Agencourt RNAClean XP Beads |
| DNA Resuspension Buffer |

B. Additional Equipment, Reagents and Labware
Additional materials that can be used include the following Equipment, Reagents, and Labware.
Equipment includes: Agilent 2100 Bioanalyzer, High Sensitivity DNA Kit or materials and equipment for electrophoretic analysis of nucleic acids; Qubit® 2.0 Fluorometer and dsDNA HS Assay Kit (Life Technologies); microcentrifuge for individual 1.5 mL and 0.5 mL tubes; 0.5-10 µL pipette, 2-20 µL pipette, 20-200 µL pipette, 200-1000 µL pipette; vortexer; thermal cycler with 0.2 mL tube heat block, heated lid, and 100 µL reaction capacity.
Reagents include: EpiTect Fast DNA Bisulfite Kit (QIAGEN Cat. #59824 for 50 preps or Cat. #59826 for 200 preps); Ethanol (Sigma-Aldrich, Cat. #E7023), for purification steps; OPTIONAL: EvaGreen® Dye, 20× in water (Biotium, Cat. #31000).
Supplies and Labware include: Nuclease-free pipette tips; 1.5 mL and 0.5 mL RNase-free microcentrifuge tubes; 0.2 mL individual thin-wall PCR tubes or 8×0.2 mL strip PCR tubes or 0.2 mL thin-wall PCR plates; magnetic separation device for the Bead Purification of the Amplified Material protocol; disposable gloves; kimwipes; ice bucket; cleaning solutions such as DNA-OFF™ (MP Biomedicals, Cat. #QD0500); OPTIONAL: PhiX Control (Illumina, Cat. Cat. #FC-110-3001); OPTIONAL: Real-time PCR system.

Example 5: Planning an Experiment

A. Input DNA
Methods, compositions, and kits provided herein can work with inputs of 100 ng of intact human genomic DNA. Quantitation of gDNA by a dsDNA assay, such as PicoGreen® or the Qubit System, can be performed. In some cases, OD260 readings for quantitation of input material are not relied upon. DNA samples can be free of contaminating proteins, RNA, organic solvents (including phenol and ethanol) and salts. A commercially available system for gDNA isolation can be used. The A260:A280 ratio for DNA samples can be in excess of 1.8. Using DNA samples with lower ratios can compromise results. RRBS libraries can be generated from less than 100 ng of gDNA, or from degraded gDNA, such as DNA extracted from formalin fixed, paraffin embedded (FFPE) specimens. If such samples are used, library amplification can require additional cycles of PCR. One additional cycle of PCR can be used for each two fold decrease in starting material. To accurately determine the number of PCR cycles to perform, the optional real-time PCR protocol in Example 7. An increase in adaptor artifacts can be observed, as well as decreased library complexity, in libraries made from less than 100 ng or degraded samples, and additional cycles of PCR amplification can be performed. Adaptor artifacts can appear as a peak of approximately 145 bp. These artifacts can be reduced by performing a second bead purification. One volume of beads can be added to the purified library.

Signs of reduced complexity can be monitored by sequencing unique 6 random bases appended to the index on each adaptor molecule, then a Duplicate Marking tool can be used to identify true PCR duplicates. The Duplicate Marking tool utilizes information provided by the unique 6 random bases sequence to discriminate between true PCR duplicates and independent adaptor ligation events to fragments with the same start site resulting in the recovery of more usable data. The Duplicate Marking tool and instructions for use can be obtained by contacting NuGEN Technical Support (techserv@nugen.com). After removing true PCR duplicates, a reliable measure of library complexity can be made. Sequencing the additional 6 bases after the 6-base barcode can be useful when attempting RRBS on rare or degraded samples. See Example 7 for information on index structure and sequencing.

B. Using Compositions and Kits Described Herein on Illumina NGS Platforms

Methods described herein can use the same approach to multiplexing found in the standard Illumina method. These libraries can be sequenced using the Illumina protocol for multiplex sequencing. The dedicated read (DR) barcode sequences, found in Table 2, can be entered into the Illumina software prior to analysis.

Barcode sequences and multiplex guidelines for adaptors used herein can be found in Table 2. These 6-nucleotide barcode sequences can be input into the Illumina Sequencing System prior to parsing of the data. You may combine anywhere from 2-16 barcoded libraries to allow for a range of multiplex sequencing. The barcodes can be chosen for their ability to parse properly and for color balancing and can have strict pairing requirements when performing 2-plex multiplexing. Users wishing to perform greater than a 2-plex multiplexing can choose a Duplex Set (as defined in Table 9), combined with any of the remaining barcoded libraries. The barcode sequences can be separated by an edit distance of three. For further details on the barcode design strategy, please refer to Faircloth B C and Glenn T C (2012). *PLoS ONE* 7 (8): e42543. doi:10.1371/journal.pone.0042543, which is herein incorporated by reference in its entirety. NuGEN RRBS libraries can be mixed with other libraries if the barcodes are compatible (i.e. can be parsed). One mismatch allowed can be parsed with if the spike in library barcodes are an edit distance of 3 or greater from the RRBS barcodes used in that lane. The PhiX library from Illumina does not contain an index. As a result, the sequencer can produce a low-quality index read from PhiX clusters. To remove PhiX reads prior to parsing, filter by index read quality and remove reads with quality less than 20.

Barcode sequences for dedicated read (DR) adaptors used in herein can be found in Table 2.

TABLE 2

Barcode sequences for dedicated read (DR) adaptors

| 6 NT BARCODE SEQUENCE AS READ BY THE SEQUENCER | BARCODE PAIRING (2-PLEX) |
|---|---|
| AACCAG TGGTGA | Duplex Set 1 |
| AGTGAG GCACTA | Duplex Set 2 |
| ACCTCA GTGCTT | Duplex Set 3 |
| AAGCCT GTCGTA | Duplex Set 4 |
| AAGAGG GGAGAA | Duplex Set 5 |
| AGCATG GAGTCA | Duplex Set 6 |
| CGTAGA TCAGAG | Duplex Set 7 |
| CACAGT TTGGCA | Duplex Set 8 |

One of the duplex sets can be used in combination with any of the other remaining 14 individual barcodes.

The barcode sequences used can be chosen for their ability to parse properly and for color balancing.

Libraries generated using methods, compositions, and kits described herein can be sequenced using a custom Read 1 sequencing primer, e.g., MetSeq Primer 1, which can be included in a kit at a concentration of 25 μM. The Standard Read 1 Primer can be used when multiplexing with PhiX or other libraries. The standard primers provided in the Illumina sequencing kit can be sufficient for sequencing the barcodes and, if desired, the reverse read.

Methods, compositions, and kits provided herein can be used to produce directional bisulfite-converted libraries. The Read 1 sequencing primer can sequence the C-to-T converted strand and the overall nucleotide balance for the Read 1 sequencing primer can show a low proportion of C bases. Illumina can recommend how to obtain high-quality base calls from libraries containing unbalanced nucleotide ratios. These recommendations can differ by instrument. Illumina software can produce higher-quality reads from low-diversity samples such as RRBS. High quality results can be made if the sequencing instrument is running the following versions or later:

HiSeq—HCS v2.2.38 (includes RTA v1.18.61)
MiSeq—RTA v1.17.28

These software upgrades, in combination with the sequence diversity incorporated in the adaptors described herein, can produce high-quality RRBS reads without the need to spike in balanced library such as PhiX. However, spiking in 5% PhiX or another, previously characterized high-quality library can be useful for troubleshooting purposes in the event of a failed run, but can reduce the data output by 5%. Such a control can be used to tell if the sequencing run failed in general, or if there is a problem specific to the particular RRBS library being sequenced.

The first base of the read RRBS method contains a CpG methylation measurement. In principle, reads need only be long enough to accurately map them to the genome. However, mapping rates can be directly affected by sequence read length, and use of longer reads can potentially lead to more uniquely mapping reads and coverage of a greater number of CpG loci. Table 3 lists the percent of MspI fragments 40-300 nt in length that are uniquely or non-uniquely mappable to the hg19 reference genome. In this theoretical analysis, the 1,545,560 MspI fragments of hg19 that are 40-300 nt in length are bisulfite-converted in silico (assuming 0% methylation and 100% bisulfite conversion), trimmed to the indicated read length, then mapped using Bismark (www.bioinformatics.bbsrc.ac.uk/projects/bismark/).

TABLE 3

Percent of MspI fragments 40-300 nt in length that are uniquely or nonuniquely mappable to the hg19 reference genome

| | SINGLE END READ LENGTH | | |
|---|---|---|---|
| | 40 nt | 50 nt | 100 nt |
| Sequences mapping uniquely | 65.2% | 69.6% | 83.9% |
| Sequences mapping non-uniquely | 34.8% | 30.4% | 16.1% |

In addition to mappability, how read length affects CpG loci coverage can be considered. Many MspI fragments contain internal CpG's, so longer reads can sequence more CpGs. However, many MspI fragments can be smaller than 100 bp, and even smaller than 50 bp. For these fragments, long sequencing reads, or paired end reads, can provide no additional CpG data. Table 4 lists the number of CpG loci that can be expected to be covered by various sequencing protocols.

TABLE 4

Number of CpG loci expected to be covered by various sequencing protocols

| | SINGLE END READ LENGTH | | |
|---|---|---|---|
| | 40 nt | 50 nt | 100 nt |
| CpG loci covered | 2,649,855 | 3,281,511 | 5,916,268 |

C. Amplified Library Storage

Amplified libraries can be stored at −20° C.

D. Data Analysis and Parsing Multiplex Libraries

The sequences of the barcodes can be entered prior to parsing (the sequences are listed in Table 3). With bisulfite-converted libraries, a slightly higher rate of unmatched barcodes relative to non-bisulfite-converted libraries can be observed. The methods can use edit distance 3 barcodes, which can allow one mismatch during parsing. This can significantly reduce the fraction of unmatched barcode reads.

The Duplicate Marking feature mentioned above can built into the NuGEN RRBS system, by adding an additional 6 nt to the index read. See Example 7 for more information on this feature.

Once the data have been parsed according to sample index, the reads can be trimmed before attempting alignment. Trimming can be done in two steps. First, any low-quality bases and adaptor sequences can be removed, then the sequence diversity provided by adaptors described herein can be removed. Example 8 contains detailed recommendations on trimming. At this point reads can be ready for downstream analysis, such as mapping to the genome and determining methylation status.

Example 6: Protocol

A. Overview

As shown in FIG. 38, an RRBS library preparation process can be performed in five stages: 1. DNA digestion with MspI: 1.0 hour; 2. Adaptor ligation: 0.75 hours; 3. final repair: 0.25 hours; 4. bisulfite conversion: 3.0 hours; 5. amplification and purification: 1.5 hours. Total time to prepare amplified library: 6.5 hours.

Components in a kit can be color coded, with each color linked to a specific stage of the process. Performing each stage can involve making a master mix, then adding it to the reaction, followed by incubation. Master mixes can be prepared by mixing components provided for that stage.

Each library can be produced independently when performing multiplex sequencing. In some cases, adaptors are not mixed during the actual library construction protocol. Multiplexing can be achieved by mixing the amplified libraries prior to cluster formation. The barcode sequences in can be carefully chosen for their ability to parse properly and for color balancing.

B. Protocol Notes

Water provided with a kit or an alternate source of nuclease-free water can be used. In some cases, DEPC-treated water is used; in some cases, DEPC-treated water is not used. A minimum of four reactions can be set up at a time to avoid pipetting very small volumes. Components used in each step can be thawed and immediately placed on ice. In some cases, all reagents at not thawed once. Thawed reagents and reaction tubes can be kept on ice. After thawing and mixing buffer mixes, if any precipitate is observed, it can be re-dissolved completely prior to use. The buffer mix can be gently warmed for 2 minutes at room temperature followed by brief vortexing. In some cases, any enzyme, primer, or adaptor mixes is not warmed.

Small amounts of reagents can be placed into a reaction mix, pipetted up and down several times to ensure complete transfer from the pipet tip into the reaction mix. Pipetting a mix can involve gently aspirating and dispensing a volume that is at least half of the total volume of the reaction mix.

The thermal cycler can be allowed to reach the initial incubation temperature prior to placing the tubes or plates in the block. Fresh ethanol stocks can be used make 70% ethanol for the purification protocols. The ethanol mixes can be made fresh, carefully measuring both the ethanol and water with pipettes. Lower concentrations of ethanol in wash solutions can result in loss of yield as the higher aqueous content will dissolve the DNA and wash it off the beads or column.

C. Agencourt® RNAClean® XP Purification Beads

The bead purification processes can include 1. binding of DNA to RNAClean XP beads; 2. magnetic separation of beads from supernatant; 3. ethanol wash of bound beads to remove salts, etc.; 4. elution of bound DNA from beads. Beads can be removed from 4° C. and left at room temperature for at least 15 minutes before use. Beads can completely reach room temperature before using. Cold beads can reduce recovery. Beads can be fully resuspended by vortexing before adding to sample. The ratio of Agencourt RNAClean XP bead volume to sample volume can vary among different steps in the protocol. Furthermore, the bead:sample ratios used can differ from the standard Agencourt protocol. The beads can separate on the magnet for a full 5 minutes. Removing binding buffer before the beads have completely separated can impact DNA yields. After completing the binding step, bead loss can be minimized when removing the binding buffer. With the samples placed on the magnet, the amount of the binding buffer specified at each of the individual purification steps can be removed. Some liquid can remain at the bottom of the tube, helping to minimize bead loss at this step. Bead loss can be minimized throughout the procedure to maximize DNA yield. An ethanol wash can be freshly prepared from fresh ethanol stocks at the indicated concentration. Lower percent ethanol mixes can reduce recovery. During the ethanol washes, the samples can be kept on the magnet. Dispersion of the beads can be avoided. The magnet can keep the beads on the walls of sample wells or tubes. All residual ethanol can be removed prior to continuing with the next step. When removing the final ethanol wash, most of the ethanol can be removed first, then excess ethanol is collected at the bottom of the tube before removing the remaining ethanol. This process can reduce the required bead air drying time. After drying the beads for the time specified in the protocol, each tube can be carefully inspected to determine whether all the ethanol has evaporated before proceeding.

Strip tubes or partial plates can be firmly placed within the magnetic plate. Individual tubes can be difficult to position stably on the magnetic plates.

D. Programming the Thermal Cycler

A thermal cycler with a heat block designed for 0.2 mL tubes can be used, equipped with a heated lid, and with a capacity of 100 μL reaction volume. The programs can be prepared as shown in Table 5, following the operating instructions provided by the thermal cycler manufacturer. For thermal cyclers with an adjustable heated lid, the lid temperature can be set to 100° C. when sample temperature reaches above 30° C. For thermal cyclers with a fixed temperature heated lid (e.g., ABI GeneAmp® PCR 9600 and 9700 models), default settings can be used (e.g., 100° C. to 105° C.).

TABLE 5

Thermal cycler programming

| Program 1 (MspI Digestion) | 37° C.-60 min, hold at 4° C. |
|---|---|
| Program 2 (Ligation) | 25° C.-30 min, 70° C.-10 min, hold at 4° C. |
| Program 3 (Final Repair) | 60° C.-10 min, 70° C.-10 min, hold at 4° C. |
| Program 4 (Bisulfite Conversion) | 2 cycles of (95° C.-5 min, 60° C.-20 min) hold at 20° C. |
| Program 5 (Library Amplification) | 95° C.-2 min, 12 cycles of (95° C.-15 sec, 60° C.-1 min, 72° C.-30 sec), hold at 10° C. |

If less than 100 ng of intact gDNA is used, or if DNA is severely degraded (such as with FFPE), more than 12 cycles of PCR may be performed. As an estimate, one additional cycle of PCR for each two-fold reduction of input can be performed. For example, for 25 ng of intact gDNA, 14 cycles of PCR can be used.

E. MspI Digestion

The MspI Buffer Mix, MspI Enzyme Mix, and Nuclease-free Water can be removed from −20° C. storage. Contents of MspI Enzyme Mix can be spun down and placed on ice. MspI buffer mix and nuclease-free water can be thawed at room temperature. MspI buffer mix can be mixed by vortexing, spun and placed on ice. Each 100 ng gDNA sample can be adjusted to 8.5 μL with nuclease-free water. A master mix can be prepared by combining MspI buffer mix and MspI enzyme mix in a 0.5 mL capped tube, according to the volumes shown in Table 6.

TABLE 6

MspI Master Mix (volumes listed are for a single reaction)

| MspI Buffer Mix | MspI Enzyme Mix |
|---|---|
| 1.0 μL | 0.5 μL |

1.5 μL of the MspI master mix can be added to each sample tube. Mixing can be by pipetting; tubes can be capped, spun and placed on ice. Tubes can be placed in a thermal cycler programmed to run Program 1 (MspI Digestion; see Table 5): 37° C.—60 min, hold at 4° C. Tubes can be removed from the thermal cycler, spin to collect condensation and place on ice.

F. Ligation

A Ligation Buffer Mix, Ligation Adaptor Mixes, and Ligation Enzyme Mix can be removed from −20° C. storage. Ligation Enzyme mix can be spun down and placed on ice. Ligation Buffer Mix (L1) and Ligation Adaptor Mixes (L2) can be thawed at room temperature. The solution can be mixed by vortexing, spun and placed on ice. The Ligation Buffer Mix (L1) can be extremely viscous. Care can be taken to ensure it is well mixed after thawing (it can be helpful to alternately vortex the tube right-side up and upside down). In some cases, Ligation Adaptor mixes are not warmed above room temperature. Heating can degrade performance.

Three μL of appropriate L2 Ligation Adaptor Mix can be added to each sample and mixed thoroughly by pipetting. Prior to use, a master mix can be made by combining nuclease-free water, L1, Ligation Enzyme Mix in a 0.5 mL capped tube according to the volumes in Table 7. The solutions can be mixed by pipetting slowly, without introducing bubbles, spun and placed on ice. The mix can be used immediately.

The L1 Ligation Buffer Mix can be very viscous. This reagent can be pipetted slowly, and care can be taken to ensure that the Ligation Master Mix and the ligation reactions are well mixed (visually observe that the solutions become homogeneous).

TABLE 7

Ligation Master Mix (volumes listed are for a single reaction)

| WATER | 2.0 μL |
|---|---|
| LIGATION BUFFER MIX | 4.0 μL |
| LIGATION ENZYME MIX | 1.0 μL |

7 μL Ligation Master Mix can be added to each reaction tube. The solution can be mixed thoroughly by pipetting slowly, gently spun and placed on ice. Incubation can be preceded immediately. Tubes can be placed in a pre-warmed thermal cycler programmed to run Program 2 (Ligation; see Table 5): 25° C.—30 min, 70° C.—10 min, hold at 4° C. The tubes can be removed from the thermal cycler, spun to collect condensation, and placed on ice.

G. Final Repair

The Final Repair Buffer Mix (FR1) and Final Repair Enzyme Mix (FR2) can be removed from −20° C. storage. Contents of FR2 can be spun down and placed on ice. FR1 can be thawed at room temperature. The solutions can be mixed by vortexing, spun and placed on ice. A master mix can be prepared by combining FR1 and FR2 in a 0.5 mL capped tube, according to the volumes shown in Table 8.

TABLE 8

Final Repair Master Mix (volumes listed are for a single reaction)

| FINAL REPAIR BUFFER MIX | FINAL REPAIR ENZYME MIX | WATER |
|---|---|---|
| 6.0 µL | 0.5 µL | 13.5 µL |

The solutions can be mixed by pipetting slowly, without introducing bubbles, spun for 2 seconds and place on ice. The mix can be used immediately. 20 µL of the Final Repair Master Mix can be added to each of the 20 µL ligation reactions. The solution can be mixed by pipetting. The tubes can be capped, and spun, and placed on ice. The tubes can then be placed in a thermal cycler pre-heated to 60° C. and programmed to run Program 3 (Final Repair; see Table 5): 60° C.—10 min, 70° C.—10 min, hold at 4° C. The tubes can be removed from the thermal cycler, spun to collect condensation and placed on ice.

H. Bisulfite Conversion

1. QIAGEN EpiTect Fast DNA Bisulfite Kit (QIAGEN Cat. #59824 for 50 preps or Cat. #59826 for 200 preps) can be used for bisulfite conversion. Other commercial bisulfite conversion kits can also be used. The 40 µL product of the Final Repair reaction can be input directly into the bisulfite conversion kit. The input can be performed using the QIAGEN EpiTect Fast protocol "Bisulfite Conversion of Unmethylated Cytosines in DNA", on page 19, following the guidelines for 1-500 ng in a maximum volume of 40 µL (low concentration). 40 µL of input and 15 µL of DNA Protect Buffer can be used. The following thermal cycler conditions can be used: 95° C.—5 min, 60° C.—20 min, 95° C. 5 min, 60° C.—20 min, hold at 20° C. After thermal cycling, a blue ring at the meniscus can be observed. This can be normal and may not affect the results. The rest of the QIAGEN protocol can then be followed. Carrier RNA in the BL Buffer can be used. The purified, bisulfite-converted DNA can be eluted in 23 µL of EB. This can yield 20 µL of bisulfite-converted DNA ready for amplification. If necessary, the final eluted volume of bisulfite-converted DNA can be adjusted to 20 µL with nuclease-free water.

I. Library Amplification

The real-time protocol in Example 7 can be consulted to determine the number of cycles of PCR to perform (such as when starting with degraded DNA or significantly less than 100 ng of high-quality DNA). The Amplification Primer Mix (P2) and Amplification Enzyme Mix (P3)m can be removed from −20° C. storage. P3 can be spun and placed on ice. P2 can be thawed at room temperature. The solutions can be mixed by vortexing, spun and placed on ice. The 20 µL product from the Bisulfite Conversion protocol can be obtained. A master mix can be made by combining P2 and P3 in an appropriately sized capped tube according to the volumes shown in Table 9. The solutions can be mixed by pipetting (care can be taken to avoid bubbles), spun and placed on ice.

TABLE 9

Amplification Master Mix (volumes listed are for a single reaction)

| AMP PRIMER MIX (P2) | AMP ENZYME MIX (P3) |
|---|---|
| 5 µL | 25 µL |

On ice, 30 µL of the Amplification Master Mix can be added to each sample. Tubes can be placed in a pre-warmed thermal cycler programmed to run Program 5 (Library Amplification; see Table 5): 95° C.—2 min, 12 cycles of (95° C.—15 sec, 60° C.—1 min, 72° C.—30 sec), hold at 10° C. If less than 100 ng of intact gDNA is used, or if the DNA is severely degraded (such as with FFPE), more than 12 cycles of PCR can be performed. Methods provided in Example 8 can be used in such situations. Tubes can be removed from the thermal cycler, spun to collect condensation and placed on ice.

J. Amplified Library Purification

The Agencourt RNAClean XP Beads and 70% ethanol set aside previously can be used if they are still at room temperature. The beads can be resuspended by vortexing the tube and added to the sample. In some cases, the beads are not spun after resuspending. At room temperature, 50 µL (1 volume) of the bead suspension can be added to each reaction. The bead suspension can be quite viscous; therefore slow pipetting can be performed to enhance accuracy. The solutions can be mixed thoroughly by pipetting 10 times. A multichannel pipettor can be used to make the incubation times uniform. The mixture can be incubated at room temperature for 10 minutes. The tubes can be transferred to the magnet and let stand 5 minutes to clear the solution of beads. 90 µL of the binding buffer can be carefully removed and discarded. Some of the volume can be left behind to reduce bead loss at this step. In some cases, the beads are not disperse; instead, they can stay on the walls of the tubes. Significant loss of beads at this stage will impact the amount of purified DNA, so in some cases, beads are not removed with the binding buffer or the wash. The 70% ethanol wash in the library purification step can involve removing samples from the magnet, fully resuspending the beads in the 70% ethanol wash, and re-magnetizing until the beads have cleared from the solution. The beads can be washed in following steps: the plate can be removed from the magnet, 150 µL of freshly prepared 70% ethanol can be added and the mixture can be pipetted to resuspend the beads; the beads can be cleared by re-magnetizing and a 70% ethanol wash can be performed using a pipette. The washing steps can be repeated twice. In some cases, the ethanol can be removed as much as possible with the final wash. At least 2 pipetting steps can be performed to allow excess ethanol to collect at the bottom of the tubes after removing most of the ethanol in the first pipetting step. The beads can be air dried on the magnet for a minimum of 10 minutes. In some cases each tube can be carefully to ensure that all the ethanol has evaporated. All residual ethanol can be removed prior to continuing. The tubes can then be removed from the magnet. 20 µL DNA Resuspension Buffer can be added to the dried beads. The beads can be resuspended by thorough mixing. The tubes can be transferred to the magnet and let stand for 5 minutes. 18 µL, of the eluate can be carefully removed, ensuring as few beads as possible are carried over, and transferred to a fresh set of tubes. When pipetting any portion of this eluted library downstream, the library can be let stand briefly on a magnet to reduce bead carryover. The eluate can then be used to quantitatively and qualitatively assess the library. After quantitation, barcoded libraries that will be run in the same flow cell can be mixed in equimolar ratios prior to processing on the flow cell, cBot or Cluster Station.

K. Quantitative and Qualitative Assessment of the Library

Figure 28:
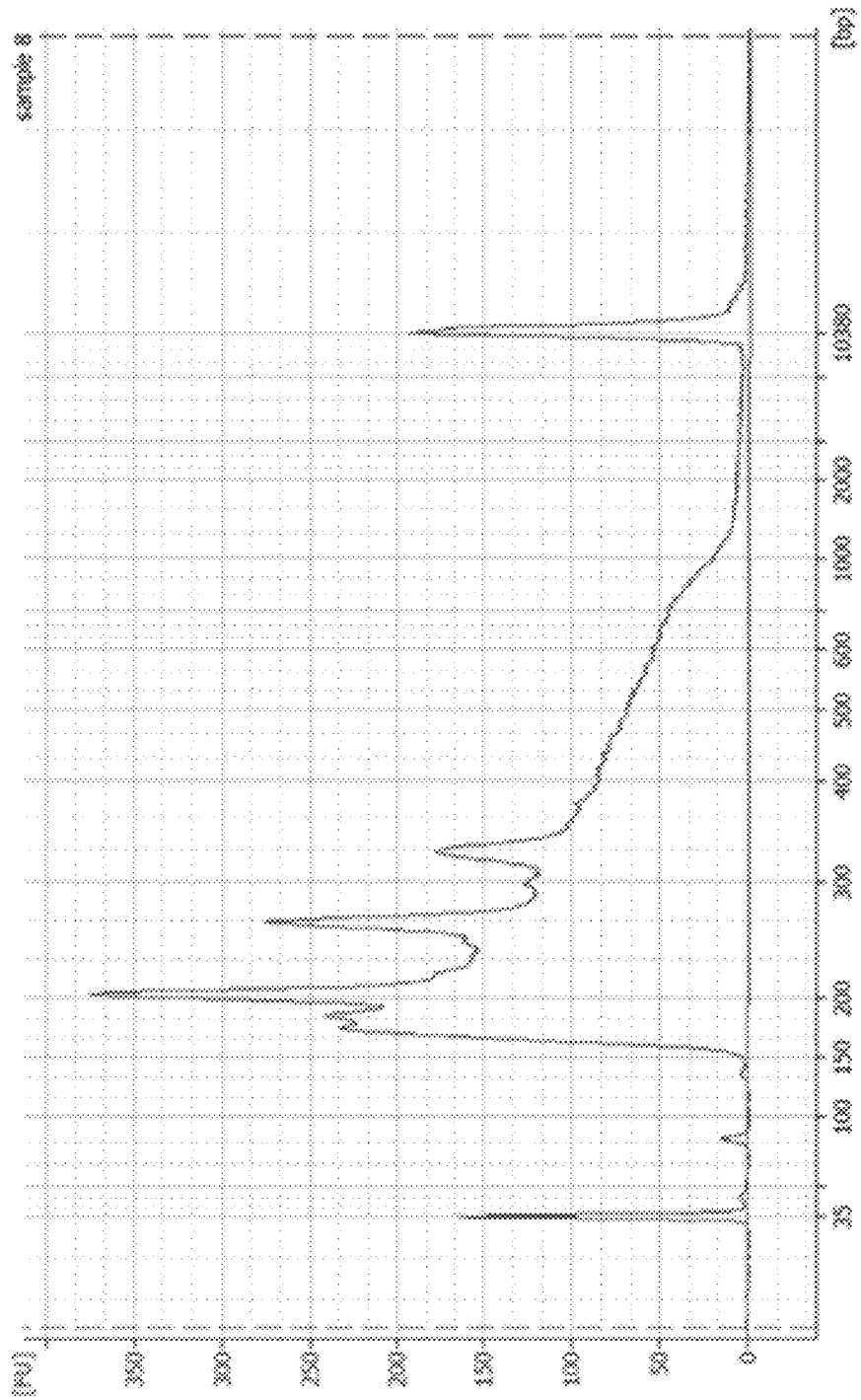
FIG. 28 illustrates library size distribution on Bioanalyzer High Sensitivity DNA Chip.

Samples can be diluted 1:3 with water. 1 µL, of the diluted sample can be loaded on the Bioanalyzer High Sensitivity DNA Chip. In some cases, fragment distribution can be as shown in FIG. 28. The three peaks at 200 bp, 265 bp, and 330 bp are due to MspI-containing micro-satellite repeats, and are characteristic of RRBS libraries made from human DNA. For qPCR for quantification, 250 bp can be used as library size for calculations.

Figure 29:
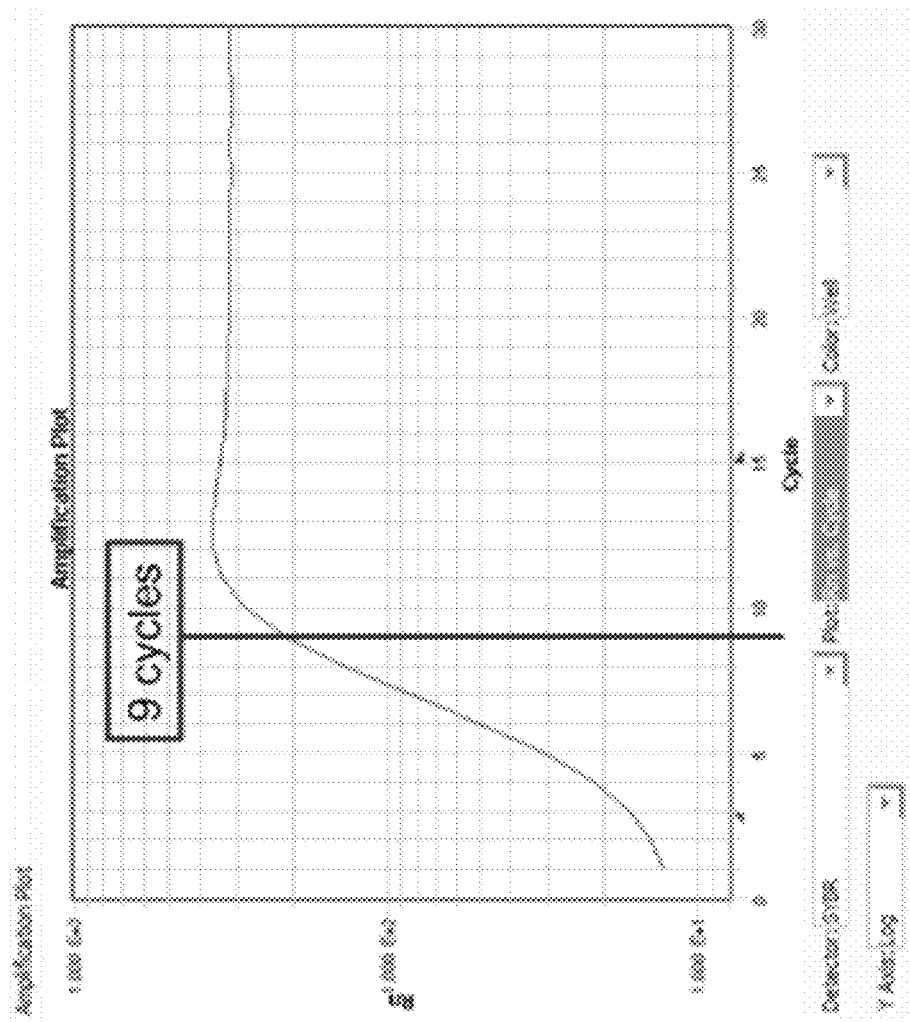
FIG. 29 illustrates determination of the number of PCR cycles to perform during the library amplification.

Example 7—PCR Amplification when Using Degraded DNA or Less than 100 ng of High-Quality DNA Standard RRBS libraries can be generated using 100 ng of high-quality, MspI-digested genomic DNA. Library Amplification can be performed by preparing an Amplification Master Mix and adding 30 µL, of this to 20 µL, of bisulfite-converted sample for a total PCR volume of 50 µL. In some cases, the following two options can be used for degraded DNA or less than 100 ng of high-quality DNA: A) If high-quality DNA is used and the amount of DNA is known, the number of PCR cycles can be adjusted to obtain sufficient material for analysis and sequencing. One additional cycle of PCR can be performed for each two-fold reduction of input. For example, for 25 ng of intact gDNA, 14 cycles of PCR can be used. B) If degraded DNA is used or if the amount and/or quality of the DNA is unknown, a ⅕ scale real-time PCR with an aliquot of your sample can be performed as follows: A master mix can be made by combining P2 and P3 in an appropriately sized capped tube according to the volumes shown in Table 10. P3 Enzyme Mix can be added at the last moment and mixed well by pipetting taking care to avoid bubbles, spun and placed on ice. EvaGreen (Biotium, Cat. #31000) is less inhibitory to PCR than SYBR Green®, however SYBR Green can also be used at a 1× final concentration in the real-time PCR reaction. For each library, 6 µL, of the Amplification Master Mix can be aliquoted into a well of on a real-time PCR plate. 4 µL, of sample can be added to each well (after bisulfite conversion but before PCR amplification) for a total real-time PCR volume of 10 µL. Real-time PCR can be performed with the following cycling conditions: 95° C.—2 min, 30 cycles of (95° C.—15 sec, 60° C.—1 min, 72° C.—30 sec). The SYBR Green channel can be monitored. In some cases, ROX normalization is not used. After thermal cycling is complete, the amplification plot can be examined for each sample to determine the number of PCR cycles to perform during the Library Amplification step. A cycle in the late exponential phase can be selected. For example, in the amplification plot shown in FIG. 29, cycle 9 was chosen. This provides sufficient amplification without entering the plateau phase.

TABLE 10

Amplification Master Mix (volumes listed are for a single reaction)

| AMP PRIMER MIX (P2) | 20X EVAGREEN | AMP ENZYME MIX (P3) |
|---|---|---|
| 1.0 µL | 0.5 µL | 4.5 µL |

Figure 30:
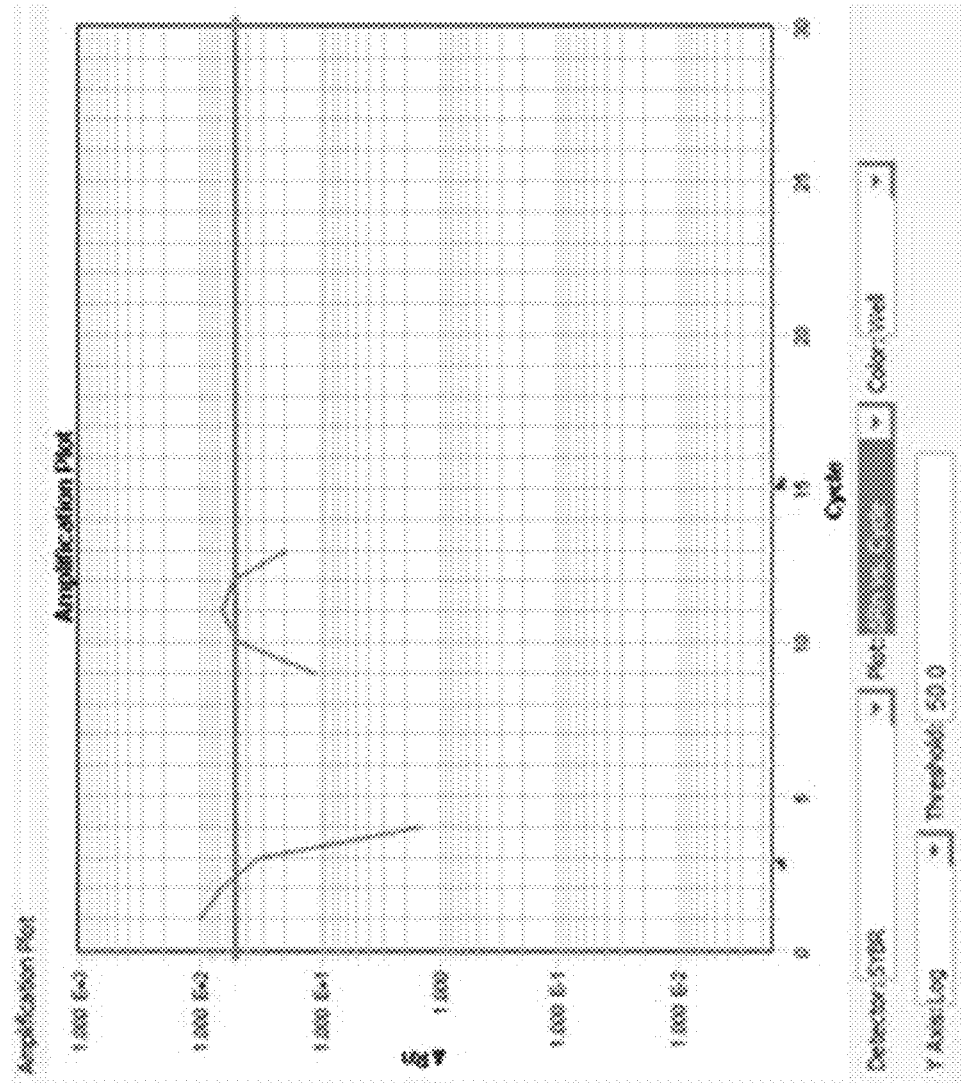
FIG. 30 illustrates results from selecting Plot>deltaRn vs. Cycle

If using an Applied Biosystems real-time PCR instrument, Plot>Rn vs. Cycle, not Plot>deltaRn vs. Cycle is selected. Selecting Plot>deltaRn vs. Cycle may give unexpected results similar to those shown in FIG. 30.

After determining the optimal number of PCR cycles to perform, the remaining 16 µL of bisulfite-converted library can be amplified as follows: A master mix can be made by combining P2 and P3 in an appropriately sized capped tube according to the volumes shown in Table 11. P3 Enzyme Mix can be added at the last moment and mix well by pipetting taking care to avoid bubbles, spun and placed on ice. For each library, 24 µL of the Amplification Master Mix can be aliquoted into a well of on a real-time PCR plate. 16 µL of sample can be added to each well. PCR can be performed with the following cycling conditions, where N=number of cycles determined from the above real-time PCR assay: 95° C.—2 min, N cycles of (95° C.—15 sec, 60° C.—1 min, 72° C.—30 sec, hold at 10° C. Proceed with the Amplified Library Purification protocol in Example 6, Section J, by adding 1 volume (40 µL) of Agencourt RNAClean XP Beads to each amplified sample and following the remaining steps of the purification protocol.

TABLE 11

Amplification Master Mix (volumes listed are for a single reaction)

| AMP PRIMER MIX (P2) | AMP ENZYME MIX (P3) |
|---|---|
| 4.0 µL | 20 µL |

Example 8—Index Structure and Index Read Recommendations

The 6-base barcodes can be used for sample multiplexing. In addition to the 6-base barcode, the adaptor can contain 6 random bases immediately following the 6-base barcode, for a total of 12 bases. The additional 6 bases can be used for duplicate read determination using the Duplicate Marking Tool. The libraries can be sequenced using 12 cycles for the index read. The 6-base barcode sequences can be found in Table 2. In some cases, the MiSeq and HiSeq instruments do not provide a simple way to obtain the sequence information contained in the 12-base pair index read including the 6 random bases that can be necessary for duplicate read determination. Several methods can be used to generate the necessary index fastq file are provided below.

MiSeq Instrument

Parsing multiplex runs using the MiSeq built-in Illumina software can replace the barcode sequence from each library with a numerical substitute, which removes the duplicate information provided by the N6 sequence present after the barcode. To retrieve this information using the MiSeq instrument, one of the options can be used: Option 1: contact Illumina Technical Support and request a modification of the MiSeq config file to allow generation of an index fastq file during data analysis. Option 2: Modify the MiSeq config file to allow generation of an index fastq file during data analysis: 1. Stop the MiSeq Reporter process. 2. Locate the "MiSeq Reporter.exe.config" file located in C:/Illumina/MiSeq Reporter. 3. Open config file and search for a line that reads:

<add key="CreateFastqForIndexReads" value="0"/>

1. If this line is present, change the value from "0" to "1".
2. If this line is not present, add the line to the config file using the add keys function under the app Settings tab with the value set as "1".

4. Restart the MiSeq reporter process. 5. Re-queue the run for data analysis if required. The 6-base barcodes followed by NNNNNN can be entered into the sample sheet to enable proper multiplex library parsing.

HiSeq Instrument

When setting up the HiSeq run, 12 bases of index sequencing (no sample sheet is required) can be specified. However, if a sample sheet to be included, the 6 bases of the actual barcode can be specified. In some cases, the N6 in your sample sheet is not included. The method described below can be used to parse and generate the N6 index fastq files for HiSeq using CASAVA: 1. Browse to the location of the run folder (called "RunFolder" in this example). 2. Open the "Data" folder in your run (/RunFolder/Data). 3. Run CASAVA. Use the "--use-bases-mask Y*, I6Y*" option to generate an Index fastq file along with the forward read (for paired end reads use "--use-bases-mask Y*,I6Y*, Y*"). For example:

"/illumina/pipeline/CASAVA-1.8.2/bin/configureBclTo-Fastq.pl--input-dir/data/Runs/RunFolder/Data/Intensities/Basecalls/--fastq-cluster-count 0--use-basesmask Y*,I6Y*--ignore-missing-control".

To generate the read and index fastq files without parsing, the -usebases- mask option to "--use-bases-mask Y*,Y*" can be modified. The generated fastq files can then be parsed using alternative software. 4. Open /RunFolder/Unaligned. 5. Type "nohup make -j 12" (this command will produce the actual fastq files, the 12 indicates how many threads to use). 6. The fastq files will be located in /RunFolder/Unaligned/Project_UniqueID Example 9—Diversity Trimming Following sequencing and parsing, adaptors can be trimmed and the additional sequence added by the diversity adaptors to the 5' and 3' ends of the insert can be removed before downstream analysis.

Removing Adaptor Sequences

To accurately identify the diversity sequence and MspI (CACGG) site, adaptor sequences present on the 3' end of your reads can be trimmed. Trim Galore (www.bioinformatics.babraham.ac.uk/projects/trim_galore/) can be used for this purpose. Other programs can also be used. Trim Galore may also trim some or all of a read due to low quality. In some cases, the program is run with default parameters, and the --RRBS option is not used. Single end reads can be trimmed with the following command:

trim_galore sampleR1.fq

Paired end reads can be trimmed with the following command:

trim_galore --adaptor2 AAATCAAAAAAAC (SEQ ID NO: 1) sampleR1.fq sampleR2.fq

Diversity Trimming and Filtering

Additional filtering and trimming can be performed by a custom python script provided by NuGEN. The script can be obtained from NuGEN Technical Support at techserv@nugen.com. The script removes reads that do not contain an MspI site signature (YGG) at the 5' end. For paired end data an MspI site signature can be required at the 5' end of both sequences. The script will generate new file(s) with "_trimmed.fq" appended to the filename. In it, all reads have been trimmed at the 5' end to remove the diversity sequence (0-3 bases), and all reads can begin with YGG, where Y is C or T. On the 3' end, 5 bases are trimmed from every read (6 bases are trimmed for paired-end to prevent alignment issues).

Examples of Trimming the 5' Ends of Forward Reads

Underlined bases denote sequence derived from the adaptor. In this example, the fragment is derived from the genomic sequence, starting and ending with MspI sites:

```
5' CCGGAGTT . . . AAGGGCCGG 3'
3' GGCCTCAA . . . TTCCCGGCC 5'
```

After MspI digestion:

```
5' CGGAGTT . . . AAGGGC 3'
3'   CTCAA . . . TTCCCGGC 5'
```

After ligation to adaptors, both with three bases of diversity:

```
                                (SEQ ID NOS 2 and 3)
5' RDDCGGAGTT . . . AAGGGCCGHHY 3'

(SEQ ID NOS 4 and 5)
3' YHHGCCTCAA . . . TTCCCGGCDDR 5'
```

After bisulfite conversion and PCR amplification of the top strand:

```
                                (SEQ ID NOS 6 and 7)
5' RDDYGGAGTT . . . AAGGGTCGHHY 3'

(SEQ ID NOS 8 and 9)
3' YHHRCCTCAA . . . TTCCCAGCDDR 5'
```

Assuming the insert is smaller than the read length, the forward read after Trim Galore is used to trim the adaptor from the 3' end will be:

```
                                (SEQ ID NOS 6 and 7)
5' RDDYGGAGTT . . . AAGGGTCGHHY 3'
```

The result of the NuGEN diversity trim of the forward read (if it's a single-end read) will be:

```
5' YGGAGTT . . . AAGGGT 3'
```

The reverse read after Trim Galore is used will be:

```
                                (SEQ ID NOS 10 and 11)
5' RDDCGACCCTT . . . AACTCCRHHY 3'
```

The result of the NuGEN diversity trim of the reverse read:

```
5' ACCCTT . . . AACT 3'
```

The adaptor can contain between 0 and 3 bases of diversity.

Tables 12-15 show how the script trims all types of adaptor variation.

TABLE 12

Trimming of the 5' ends of forward reads

| READ BEFORE TRIMMING | READ AFTER TRIMMING |
|---|---|
| 5' YGGAGTT . . . | 5' YGGAGTT . . . |
| 5' DYGGAGTT . . . | 5' YGGAGTT . . . |

TABLE 12-continued

Trimming of the 5' ends of forward reads

| READ BEFORE TRIMMING | READ AFTER TRIMMING |
|---|---|
| 5' DDYGGAGTT . . . | 5' YGGAGTT . . . |
| 5' RDDYGGAGTT . . .<br>(SEQ ID NO: 6) | 5' YGGAGTT . . . |

Note: If YGG is not found in the first 6 bases, the read is discarded.

TABLE 13

Trimming of the 3' ends of forward reads

| READ BEFORE TRIMMING | READ AFTER TRIMMING |
|---|---|
| 5' . . . AAGGGTCG | 5' . . . AAG |
| 5' . . . AAGGGTCGH | 5' . . . AAGG |
| 5' . . . AAGGGTCGHH<br>(SEQ ID NO: 12) | 5' . . . AAGGG |
| 5' . . . AAGGGTCGHHY<br>(SEQ ID NO: 7) | 5' . . . AAGGGT |

TABLE 14

Trimming of the 5' ends of reverse reads

| READ BEFORE TRIMMING | READ AFTER TRIMMING |
|---|---|
| 5' CGACCCTT . . . | 5' ACCCTT . . . |
| 5' DCGACCCTT . . . | 5' ACCCTT . . . |
| 5' DDCGACCCTT . . .<br>(SEQ ID NO: 13) | 5' ACCCTT . . . |
| 5' RDDCGACCCTT . . .<br>(SEQ ID NO: 6) | 5' ACCCTT . . . |

Note: If CGR is not found in the first 6 bases, the read is discarded.

TABLE 15

Trimming of the 3' ends of reverse reads

| READ BEFORE TRIMMING | READ AFTER TRIMMING |
|---|---|
| 5' . . . AACTCCRHHY<br>(SEQ ID NO: 8) | 5' . . . AACTC |
| 5' . . . AACTCCRHH | 5' . . . AACT |
| 5' . . . AACTCCRH | 5' . . . AAC |
| 5' . . . AACTCCR | 5' . . . AA |

The script accepts as input one or two fastq file strings, given either as complete filenames or as a pattern in quotes. When a pattern is given, the script will find all the filenames matching a specified pattern according to the rules used by the Unix shell (*,?).

Example usage for single end reads with a complete filename:
    python    trimRRBSdiversityAdaptCustomers.py    -1 sample_R1.fq
with a pattern:
    python    trimRRBSdiversityAdaptCustomers.py    -1 "s_R1_1_edit3_6bp_BC??.fq"

Example usage for paired end reads with a complete filename:
    python    trimRRBSdiversityAdaptCustomers.py    -1 sample_R1.fq -2 sample_R2.fq
with a pattern:
    python    trimRRBSdiversityAdaptCustomers.py    -1 "s_R1*.fq"-2"s_R2*.fq"

The help option of this script can be accessed for more details (-h). The script outputs a trimmed fastq file that can be used for downstream analysis including Bismark.

Following trimming, an additional algorithm can be used to remove sequencing duplicates. The Duplicate Marking tool can utilize information provided by the unique N6 sequence to discriminate between true PCR duplicates and independent adaptor ligation events to fragments with the same start site resulting in the recovery of more usable data. Using the index sequence reads, the Duplicate Marking tool can utilize the N6 random sequence found adjacent to the barcode sequence (as shown in FIGS. 32 and 37) in the sequence appended to nucleic acid inserts generated using the methods outlined in Example 4-8 to unambiguously identify other PCR duplicates comprising the same N6-barcode sequence and removing all but one of these reads.

Example 10—A Simplified Workflow for Reduced Representation Bisulfite Sequencing RRBS can be used to obtain quantitative DNA methylation information across many features of the genome with approximately 50-fold fewer sequencing reads than can be needed with whole genome bisulfite sequencing which can result in substantial sequencing cost reduction. The methods described herein can be used for generating RRBS libraries in less than one day, without gel purification. The methods can entail digesting samples, ligating adaptors, performing a final repair, bisulfite converting, and PCR amplifying to generate libraries ready for NGS sequencing platforms such as Illumina. Additional benefits of the methods provided herein can include improved sequencing performance without the need for PhiX spike in, and the ability to mark PCR duplicates.

DNA methylation can be a central component of epigenetic regulation, and can play a role in development, environmental exposure, and diseases including cancer. In humans, the predominant form of DNA methylation can be 5-methyl cytosine. When present, 5-mC can occur in the context of the CpG sequence motif. RRBS can utilize the restriction enzyme MspI, which can recognize and cleave the sequence CCGG regardless of the methylation state of the central CpG.

Reducing Representation to ~2%

After digestion with MspI, ~2% of the genome can be represented in fragments under 500 bp. However, many of these fragments can be from CpG-rich regions. By focusing RRBS sequencing on small fragments, the methylation status of these regions can be determined with much less sequencing than would be required using a whole genome bisulfite sequencing approach.

Challenges with Sequencing RRBS Libraries

On sequencers such as provided by Illumina, cluster identification as well as phasing and color matrix calculations can be negatively impacted by a lack of sequence complexity in the sample. RRBS libraries all begin with YGG (Y=C or T), which can make these libraries challenging to sequence. These issues can be mitigated by reducing cluster density and/or mixing in a high diversity library, such as a PhiX control library. This approach can reduce the number of useful reads as PhiX levels of 40% or higher may be needed to ensure a successful run.

Adding Diversity to RRBS Reads

The challenges described above can be overcome by adding diversity in the form of 0 to 3 bases of sequence between the sequencing primer and the insert. This can ensure all 4 bases are present during the first few cycles of sequencing. In addition, the YGG signature can be de-phased so that no cycle contains only G across all clusters.

Figure 34:
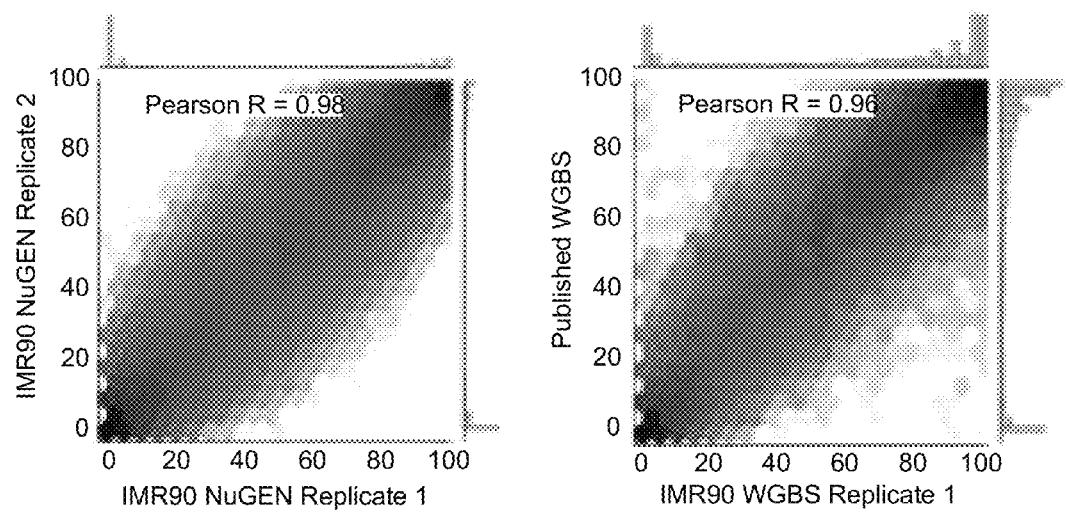
FIG. 34 illustrates concordance in methylation levels. Concordance for CpG's covered at 20× or greater depth between NuGEN RRBS technical replicates (left) or between NuGEN RRBS (30 M reads) and published whole genome bisulfite sequencing (WGBS) from Lister et al., *Nature*, 2009, 462:315-322 (1180 M reads), which is herein incorporated by reference in its entirety.

The methods described herein can be multiplexed up to 16 samples per lane, can require no gel purification steps, and can have many advantages, including: simplified workflow that can be completed in a single day; adaptor features (i.e., sequence diversity) which can provide enhanced sequence quality without PhiX spike in, the ability to identify and remove PCR duplicates; and highly reproducible data that can displays excellent concordance with published methylation profiles such as shown in FIG. 34.

Example 11—Generation of and Analysis of Reduced Representation Bisulfite Sequencing Library from IMR-90 Human Genomic DNA Using Diversity Adaptors In this example, an RRBS nucleic acid library from 25 ng of genomic DNA (gDNA) from the IMR-90 human cell line was generated using the kit, protocol, considerations, and analytical software outlined and described in Examples 4-9. Briefly, following digestion of 25 ng of gDNA from IMR-90 human cells with MspI to produce DNA fragments, the DNA fragments are combined with a master mix containing the appropriate diversity adapters (i.e., D0, D1, D2, D3, or a mix of D0-D3), ligation buffer, water and ligation enzyme mix, placed in a thermal cycler and run through a program on the thermal cycler that comprised of a single cycle comprising incubations at 25 C for 30 minutes, 70 C for 10 minutes, and then holding the mixture at 4 C. Following ligation, the ligation complexes were subjected to a post-ligation purification followed by a final repair reaction entailing incubation of the ligation complexes with a DNA repair enzyme in a thermal cycler programmed for a single cycle of 60 C incubation for 10 minutes. Following final repair, the samples were subjected to bisulfite conversion, wherein 20 uL of the products from the final repair reactions were inputted directly into a Qiagen EpiTect Fast DNA Bisulfite Kit according to manufacturer protocols and subjected to two cycles of 95 C for 5 minutes, and 60 C for 20 minutes on a thermal cycler followed by elution of the purified, bisulfite converted DNA libraries. The bisulfite converted DNA libraries were then PCR amplified and purified. Following library amplification and purification, the libraries were pooled and sequenced on an Illumina MiSeq sequencer according to manufacturer instructions with a 40 nucleotide forward read, 6 nucleotide index read, and 25 nucleotide reverse read. The sequence reads were analyzed using the in silico diversity trimming and duplicate marking computer programs described in Example 9. This procedure was repeated two more times to generate technical replicates. The sequencing analysis was then compared between the replicates.

Figure 33:
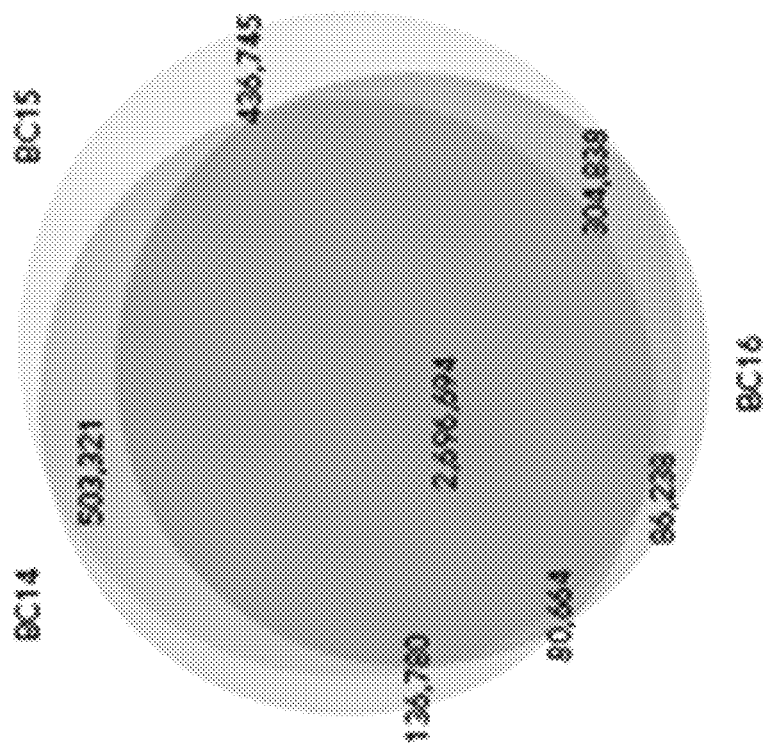
FIG. 33 illustrates high coverage overlap between three NuGEN RRBS technical replicates, each made from 25 ng of IMR90 gDNA. CpG's covered at 10× or greater are shown, after PCR duplicate removal.

Following sequencing and in silico analysis of sequence reads obtained from the sequencing, a high coverage overlap can be seen between the three RRBS technical replicates as shown in FIG. 33. Moreover, as shown in Table 16, each of the technical replicates produced similar high levels of total mapping, as well as other measures.

TABLE 16

Replicate RRBS libraries from 25 ng IMR90 gDNA

|  | Replicate 1 | Replicate 2 | Replicate 3 |
| --- | --- | --- | --- |
| Uniquely Mapping | 67.60% | 67.47% | 66.98% |
| Non-Uniquely Mapping | 23.12% | 22.70% | 23.93% |
| Total Mapping | 90.72% | 90.18% | 90.91% |
| Methyl CG | 44.05% | 44.14% | 43.17% |
| Methyl CHG | 0.37% | 0.37% | 0.36% |
| Methyl CHH | 0.31% | 0.31% | 0.30% |

Additionally, FIG. 34 shows a concordance in methylation levels between IMR-90 RRBS replicates (left) and IMR-90 whole genome bisulfite sequencing (WGBS) libraries (right).

While preferred embodiments are shown and described herein, it will be obvious to those skilled in the art that such embodiments are provided by way of example only. Numerous variations, changes, and substitutions will now occur to those skilled in the art without departing from the instant disclosure. It should be understood that various alternatives to the embodiments described herein may be employed in practicing the disclosure. It is intended that the following claims define the scope of the invention and that methods and structures within the scope of these claims and their equivalents be covered thereby.

What is claimed is:

1. A method for generating a bisulfite converted library, the method comprising:
   a) ligating a first oligonucleotide sequence from a pool of oligonucleotide sequences to a 5' end of a first polynucleotide from a plurality of polynucleotides from a sample to generate a first oligonucleotide-polynucleotide complex,
      wherein following the ligating of a), a 3' end of the first oligonucleotide sequence is immediately adjacent to a 5' end of the first polynucleotide from the plurality of polynucleotides;
   b) ligating a second oligonucleotide sequence from the pool of oligonucleotide sequences to a 5' end of a second polynucleotide from the plurality of polynucleotides to generate a second oligonucleotide-polynucleotide complex, wherein the second oligonucleotide sequence terminates at its 3' end with one random base, wherein following the ligating of b), the one random base at the 3' end of the second oligonucleotide sequence is immediately adjacent to the 5' end of the second polynucleotide from the plurality of polynucleotides;
   c) ligating a third oligonucleotide sequence from the pool of oligonucleotide sequences to a 5' end of a third polynucleotide from the plurality of polynucleotides to generate a third oligonucleotide-polynucleotide complex, wherein the third oligonucleotide sequence terminates at its 3' end with two random bases, wherein following the ligating of c), a 3' most base of the two random bases at the 3' end of the third oligonucleotide sequence is immediately adjacent to the 5' end of the third polynucleotide from the plurality of polynucleotides;
   d) ligating a fourth oligonucleotide sequence from the pool of oligonucleotide sequences to a 5' end of a fourth polynucleotide from the plurality of polynucleotides to generate a fourth oligonucleotide-polynucleotide complex, wherein the fourth oligonucleotide sequence terminates at its 3' end with three random bases, wherein following the ligating of d), a 3' most base of the three random bases at the 3' end of the fourth oligonucleotide sequence is immediately adjacent to a 5' end of the fourth polynucleotide from the plurality of polynucleotides;
   e) treating the first, second, third, and fourth oligonucleotide-polynucleotide complexes with bisulfite, thereby generating a bisulfite converted polynucleotide library.

2. The method of claim 1, further comprising fragmenting the plurality of polynucleotides prior to steps a), b), c), d), and e).

3. The method of claim 2, wherein the fragmenting comprises contacting the plurality of polynucleotides with an enzyme.

4. The method of claim 3, wherein the enzyme is a methylation insensitive restriction enzyme.

5. The method of claim 4, wherein the methylation insensitive restriction enzyme is MspI.

6. The method of claim 5, wherein the one random base of the second oligonucleotide sequence comprises an adenine, a thymine, or a guanine base.

7. The method of claim 5, wherein each of the two random bases of the third oligonucleotide sequence comprises an adenine, a thymine, or a guanine base.

8. The method of claim 5, wherein a 5' most base of the three random bases of the fourth oligonucleotide sequence comprises an adenine or a guanine base, and each of the two other bases of the three random bases of the fourth oligonucleotide sequence comprises an adenine, a thymine, or a guanine base.

9. The method of claim 1, wherein each oligonucleotide sequence in the pool of oligonucleotide sequences is within a strand of a duplexed adaptor.

10. The method of claim 9, wherein the plurality of polynucleotides are double-stranded nucleic acids, wherein each 5' end of the double-stranded nucleic acids comprises a ligation end and each 3' end of the double-stranded nucleic acids comprises a non-ligation end.

11. The method of claim 9, wherein the duplexed adaptor comprises a ligation strand and a non-ligation strand, wherein the ligation strand is capable of ligating to a ligation end of the plurality of polynucleotides, and wherein a nick is formed between the non-ligation strand and a non-ligation end of the plurality of polynucleotides.

12. The method of claim 11, further comprising an extending step prior to step e), wherein the non-ligation end of the plurality of polynucleotides is extended using a polymerase in the presence of a mixture of dNTPs using the ligation strand of the duplexed adaptor as template.

13. The method of claim 12, wherein the ligation strand of the duplexed adaptor comprises one or more cytosine bases sensitive to bisulfite treatment and the mixture of dNTPs comprises dATP, dTTP, dGTP, and a dCTP analog resistant to bisulfite treatment.

14. The method of claim 13, wherein the dCTP analog resistant to bisulfite treatment comprises 5-methylcytosine, 5-hydroxymethylcytosine, or 5-propynylcytosine.

15. The method of claim 1, further comprising amplifying the first, second, third, and fourth oligonucleotide-polynucleotide complexes to generate amplified oligonucleotide-polynucleotide complexes.

16. The method of claim 15, wherein the amplifying comprises solid-phase nucleic acid amplification to generate a plurality of clusters, wherein different clusters of the plurality of clusters comprise a plurality of copies of the first, second, third, and fourth oligonucleotide-polynucleotide complexes.

17. The method of claim 16, further comprising sequencing each of the plurality of clusters, wherein the sequencing comprises hybridizing a sequencing primer to a sequence complementary to the sequencing primer in the amplified oligonucleotide-polynucleotide complexes, and conducting sequencing by synthesis.

18. The method of claim 17, wherein the sequencing comprises imaging.

19. The method of claim 1, wherein the first oligonucleotide sequence further comprises a sequence element, wherein the sequence element comprises a barcode, a universal sequence, a linker sequence, or a random sequence.

20. The method of claim 1, wherein the second oligonucleotide sequence further comprises sequence complementary to a sequencing primer.

21. The method of claim 20, wherein the sequence complementary to a sequencing primer is immediately adjacent to the one random base at the 3' end of the second oligonucleotide sequence.

\* \* \* \* \*